(12) United States Patent
Nazare et al.

(10) Patent No.: US 7,067,665 B2
(45) Date of Patent: Jun. 27, 2006

(54) OXYBENZAMIDE DERIVATIVES USEFUL FOR INHIBITING FACTOR XA OR VLLA

(75) Inventors: Marc Nazare, Eppstein (DE); David William Will, Kriftel (DE); Anuschirwan Peyman, Kelkheim (DE); Hans Matter, Langenselbold (DE); Gerhard Zoller, Schoeneck (DE); Uwe Gerlach, Hattersheim (DE)

(73) Assignee: Sanofi-Aventis Deutschland GmbH, Frankfurt Ammain (DE)

( * ) Notice: Subject to any disclaimer, the term of this patent is extended or adjusted under 35 U.S.C. 154(b) by 90 days.

(21) Appl. No.: 11/039,107

(22) Filed: Jan. 19, 2005

(65) Prior Publication Data
US 2005/0165058 A1    Jul. 28, 2005

Related U.S. Application Data

(62) Division of application No. 10/023,933, filed on Dec. 21, 2001.

(30) Foreign Application Priority Data

Dec. 23, 2000 (EP) .................................. 00128477

(51) Int. Cl.
*C07D 401/04* (2006.01)
*A61K 31/505* (2006.01)
(52) U.S. Cl. ...................... 544/331; 514/275
(58) Field of Classification Search ................ 544/331; 514/275
See application file for complete search history.

(56) References Cited

U.S. PATENT DOCUMENTS

| | | | |
|---|---|---|---|
| 4,309,212 A | 1/1982 | Takemoto et al. | ............. 71/120 |
| 4,428,874 A | 1/1984 | Svendsen | ................. 280/112.5 |
| 4,568,636 A | 2/1986 | Svendsen | ..................... 434/13 |
| 5,753,659 A | 5/1998 | Mills | |

FOREIGN PATENT DOCUMENTS

| | | | |
|---|---|---|---|
| DE | 0019589 | | 11/1980 |
| GB | 2011892 | | 7/1979 |
| WO | 00/59893 | * | 10/2000 |

OTHER PUBLICATIONS

Nomoto et al, Chem. Pharm. Bull., 38(11), 3014-3019, 1990.*
Baiey, et al., *Angewandte Chemie*, 39: 506-508;(2000).
Campillo, et al., *Journal Medicinal Chemistry*, 42: 3279-3288 (1999).
Choi-Stedeski, et al., Bioorganic and Medicinal Chemistry Letters, 9: 2539-2544 (1999).
European Search report dated Oct. 29, 2001, foir European Patent Application No. 00/128477.
Fujio, et al., *Bloorganic and Medicinal Chemistry Letters*, 10: 2457-2481 (2000).
Hanessian, et al., *Bloorganic and Medicinal Chemistry Letters*, 10; 243-247 (2000).
He, et al., *Bioorganic and Medicinal Chemistry Letters*, 10: 1737-1739 (2000).
Herron, et al., *J. Med. Chem.*, 43: 859-872 (2000).
Hoekstra, et al., *J. Med. Chem.*, 42: 5254-5285 (1999).
Maignan, et al., *J. Med. Chem.*, 43: 3226-3232 (2000).
Ogino, et al, *Bioorganic and Medicinal Chemistry Letters*, 8:75-80 (1998).
Okade, et al., *Bioorganic and Medicinal Chemistry Letters*, 10: 2217-2221 (2000).
Pitts, et al., *J. Med. Chem.*, 43: 27-40 (2000).
Rehse, et al., *Archiv der Pharmazie*, 333: 157-161 (2000).
Roussel, et al., *Tetrahedron*, 55; 6219-6230 (1999).
Walser, et al., *J. Med. Chem.*, 34; 1209-1221 (1991).

* cited by examiner

*Primary Examiner*—Shailendra Kumar
(74) *Attorney, Agent, or Firm*—Joseph D. Rossi

(57) ABSTRACT

The present invention relates to compounds comprising the following formula:

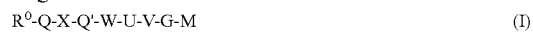

$$R^0-Q-X-Q'-W-U-V-G-M \qquad (I)$$

These compounds are useful as pharmacologically active compounds. They exhibit an antithrombotic effect and are suitable, for example, for the therapy and prophylaxis of cardiovascular disorders such as thromboembolic diseases or restenoses. These compounds are reversible inhibitors of the blood clotting enzymes factor Xa (FXa) and/or factor VIIa (FVIIa), and can generally be used to treat, prevent, or cure conditions in which an undesired activity of factor Xa and/or factor VIIa is present, or where inhibition of factor Xa and/or factor VIIa is intended. The invention further relates to processes for the preparation of these compounds, methods of their use (e.g., as active ingredients in pharmaceuticals), and pharmaceutical preparations comprising them.

16 Claims, No Drawings

OXYBENZAMIDE DERIVATIVES USEFUL FOR INHIBITING FACTOR XA OR VLLA

RELATED APPLICATIONS

This application is a divisional application of U.S. patent application Ser. No. 10/023,933, filed Dec. 21, 2001, which claims priority under 35 U.S.C. § 119(a) to European Patent Application No. 00128477.7, filed on Dec. 23, 2000, the entirety of which is incorporated herein by reference.

The present invention relates to compounds of the formula I,

in which $R^0$, Q, X, Q', W, U, V, G, and M have the meanings indicated below. The compounds of formula I are useful as pharmacologically active compounds. They exhibit a strong antithrombotic effect and are suitable, for example, for the therapy and prophylaxis of cardiovascular disorders such as thromboembolic diseases or restenoses. These compounds are reversible inhibitors of the blood clotting enzymes factor Xa (FXa) and/or factor VIIa (FVIIa), and can generally be used to treat, prevent, or cure conditions in which an undesired activity of factor Xa and/or factor VIIa is present or where inhibition of factor Xa and/or factor VIIa is intended. The invention furthermore relates to processes for the preparation of compounds of the formula I, their use (e.g., as active ingredients in pharmaceuticals), and pharmaceutical preparations comprising them.

Normal haemeostasis is the result of a complex balance between the processes of clot initiation, formation and clot dissolution. The complex interactions between blood cells, specific plasma proteins and the vascular surface maintain the fluidity of blood unless injury and blood loss occurs (EP-A-987274). Many significant disease states are related to abnormal haemeostasis. For example, local thrombus formation due to rupture of atheroslerotic plaque is a major cause of acute myocardial infarction and unstable angina. Treatment of an occlusive coronary thrombus by either thrombolytic therapy or percutaneous angioplasty may be accompanied by acute thrombolytic reclosure of the affected vessel.

There continues to be a need for safe and effective therapeutic anticoagulants to limit or prevent thrombus formation. Such agents may inhibit coagulation without directly inhibiting thrombin. Instead of inhibiting thrombin, they may inhibit other steps in the coagulation cascade like factor Xa and/or factor VIIa activity. It is now believed that inhibitors of factor Xa carry a lower bleeding risk than thrombin inhibitors (A. E. P. Adang & J. B. M. Rewinkel, Drugs of the Future 2000, 25, 369–383).

Low molecular weight, factor Xa-specific blood clotting inhibitors that are effective but do not cause unwanted side effects have been described, for example, in WO-A-95/29189. However, besides being effective factor Xa-specific blood clotting inhibitors, it is desirable that such inhibitors also have further advantageous properties; such properties include, for instance, stability in plasma and liver and selectivity versus other serine proteases whose inhibition is not intended, such as thrombin. Thus, there is an ongoing need in the art for new low molecular weight factor-Xa specific blood clotting inhibitors, which are effective and also have one or more of the above noted advantages.

Specific inhibition of the factor VIIa/tissue factor catalytic complex using monoclonal antibodies (WO-A-92/06711), or a protein such as chloromethyl ketone inactivated factor VIIa (WO-A-96/12800, WO-A-97/47651), is an extremely effective means of controlling thrombus formation caused by acute arterial injury or the thrombotic complications related to bacterial septicaemia. There is also experimental evidence suggesting that inhibition of factor VIIa/tissue factor activity inhibits restenosis following balloon angioplasty. Bleeding studies conducted in baboons indicate that inhibition of the factor VIIa/tissue factor complex has the widest safety window with respect to therapeutic effectiveness and bleeding risk of any anticoagulant approach tested including thrombin, platelet and factor Xa inhibition. Certain inhibitors of factor VIIa have been described. For example, EP-A-987274 describes compounds containing a tripeptide unit that inhibit factor VIIa. However, the property profile of these compounds is less than ideal, and there remains an ongoing need for further low molecular weight factor VIIa-specific blood clotting inhibitors.

The present invention satisfies the above needs by providing novel compounds of formula I, which exhibit factor Xa and/or factor VIIa inhibitory activity and are favourable agents for inhibiting unwanted blood clotting and thrombus formation.

Thus, the present invention relates to compounds of the formula I,

wherein
$R^0$ is
1. a monocyclic or bicyclic 5- to 14-membered aryl, wherein aryl is unsubstituted or mono-, di- or trisubstituted independently of one another by $R^2$, or
2. a monocyclic or bicyclic 5- to 14-membered heteroaryl, containing zero, one, two, three or four heteroatoms chosen from nitrogen, sulphur or oxygen, wherein heteroaryl is unsubstituted or mono-, di- or trisubstituted independently of one another by $R^2$, $R^2$ is halogen, —$NO_2$, —CN, —C(O)—$NH_2$, —OH, —$NH_2$, —NH—C(O)—, —NH—C(O)—$(C_1$–$C_8)$-alkyl, —NH—C(O)—$(C_1$–$C_8)$-alkyl, —$(C_1$–$C_8)$-alkyl, wherein alkyl in each case is unsubstituted or mono-, di- or trisubstituted independently of one another by halogen, $NH_2$, —OH or a methoxy residue, or —$(C_1$–$C_8)$-alkyloxy, wherein alkyloxy is unsubstituted or mono-, di- or trisubstituted independently of one another by halogen, $NH_2$, —OH or a methoxy residue, Q and Q' are independently of one another identical or different and are a direct bond, —$(CH_2)_r$—O—$(CH_2)_s$—, wherein r and s are independently from each other the integers zero, 1, 2 or 3, —C(O)—; —O—, —$NR^{10}$—, —C(O)—$NR^{10}$—, —$NR^{10}$—C(O)—, —S—, —S(O)—, —$SO_2$—, —$NR^{10}$—$SO_2$—, —$SO_2$—$NR^{10}$—, —$(C_1$–$C_6)$-alkylene, wherein alkylene is unsubstituted or mono-, di- or trisubstituted independently of one another by halogen, $NH_2$ or —OH; or —$(C_3$–$C_6)$-cycloalkylene, wherein cycloalkylene is unsubstituted or mono-, di- or trisubstituted independently of one another by halogen, —$NH_2$ or —OH;

X is a direct bond, a 3- to 7-membered heteroaryl, —$(C_1$–$C_6)$-alkylene, wherein alkylene is unsubstituted or mono-, di- or trisubstituted independently of one another by halogen, —$NH_2$ or —OH; or —$(C_3$–$C_6)$-cycloalkylene, wherein cycloalkylene is unsubstituted or mono-, di- or trisubstituted independently of one another by halogen, —$NH_2$ or —OH;

provided that when Q or Q' is —$(C_1$–$C_6)$-alkylene then X is —O—, —S—, —$NR^{10}$—, —C(O)—, —C(O)—$NR^{10}$—, —$NR^{10}$—C(O)—, —S(O)—, —$SO_2$—, —$NR^{10}$—$SO_2$— or —$SO_2$—$NR^{10}$—; with the proviso that if X is a direct bond, the fragment -Q-X-Q'- is not O—O, O—S, S—O, S—S, $SO_2$—$SO_2$, SO—SO, SO—$SO_2$, $SO_2$—SO, S—$SO_2$, SO—S, S—SO; with the proviso that if X is oxygen atom or sulphur atom, then Q and Q' are not oxygen atom or sulphur atom; and with the further proviso that if X is S(O) or $SO_2$, then Q and Q' are not oxygen atom or sulphur atom;

W is
1. a 5- to 14-membered aryl, wherein aryl is unsubstituted or mono-, di- or trisubstituted independently of one another by $R^1$,
2. a 5- to 14-membered heteroaryl, wherein heteroaryl is unsubstituted or mono-, di- or trisubstituted independently of one another by $R^1$,
3. a 4- to 15 membered mono- or polycyclic group, wherein said mono- or polycyclic group is unsubstituted or mono-, di- or trisubstituted independently of one another by $R^1$, or
4. a 4- to 15 membered mono- or polycyclic group, containing one, two, three or four heteroatoms, such as nitrogen, sulphur or oxygen, wherein said mono- or polycyclic group is unsubstituted or mono-, di- or trisubstituted independently of one another by $R^1$, provided that if W is a six membered aryl or heteroaryl group, then Q' and U are not in an ortho position with respect to each other;

$R^1$ is
1. halogen,
2. —$NO_2$,
3. —CN,
4. —$NR^4R^5$ wherein $R^4$ and $R^5$ are defined below,
5. —O—($C_1$–$C_8$)-alkyl, wherein alkyl is unsubstituted or mono-, di- or trisubstituted independently of one another by $R^{13}$,
6. —OH,
7. —$SO_2$—$NH_2$,
8. ($C_1$–$C_8$)-alkyloxy-, wherein alkyl is unsubstituted or mono-, di- or trisubstituted independently of one another by $R^{13}$,
9. ($C_6$–$C_{14}$)-aryl, wherein aryl is unsubstituted or mono-, di- or trisubstituted independently of one another by $R^{13}$,
10. ($C_1$–$C_8$)-alkyl-, wherein alkyl is unsubstituted or mono-, di- or trisubstituted independently of one another by $R^{13}$,
11. hydroxycarbonyl-($C_1$–$C_8$)-alkylureido-, wherein alkyl is unsubstituted or mono-, di- or trisubstituted independently of one another by $R^{13}$,
12. ($C_1$–$C_8$)-alkyloxycarbonyl-($C_1$–$C_8$)-alkylureido-, wherein alkyl is unsubstituted or mono-, di- or trisubstituted independently of one another by $R^{13}$,
13. ($C_1$–$C_8$)-alkylsulfonyl-, wherein alkyl is unsubstituted or mono-, di- or trisubstituted independently of one another by $R^{13}$,
14. —NH—C(O),
15. —NH—C(O)—($C_1$–$C_8$)-alkyl,
16. —NH—C(O)—($C_1$–$C_8$)-alkyl,
17. —C(O)—$NR^4R^5$, wherein $R^4$ and $R^5$ are defined below,
18. —COOH;
19. —C(O)—($C_1$–$C_6$)-alkyl, wherein alkyl is unsubstituted or mono-, di- or trisubstituted independently of one another by $R^{13}$,
20. —C(O)—O—($C_1$–$C_4$)-alkyl, wherein alkyl is unsubstituted or mono-, di- or trisubstituted independently of one another by $R^{13}$,
21. —C(O)—$NR^{11}R^{12}$,
22. —C(NH)—$NH_2$,
23. —NH—C(O)—$NH_2$,
24. —S—($C_1$–$C_8$)-alkyl, wherein alkyl is unsubstituted or mono-, di- or trisubstituted independently of one another by $R^{13}$,
25. —($C_1$–$C_8$)-alkylthio, wherein alkyl is unsubstituted or mono-, di- or trisubstituted independently of one another by $R^{13}$, or
26. $R^{11}R^{12}N$—, or
two $R^1$ residues bonded to adjacent ring carbon atoms together with the carbon atoms to which they are bonded form a dioxalane ring or an aromatic ring condensed to W, where the ring formed by the two $R^1$ residues is unsubstituted or mono-, di- or trisubstituted independently of one another by $R^{13}$, $R^{11}$ and $R^{12}$ together with the nitrogen atom to which they are bonded form a saturated or unsaturated 5- to 6-membered monocyclic heterocyclic ring which, in addition to the nitrogen atom carrying $R^{11}$ and $R^{12}$, can contain one or two identical or different ring heteroatoms chosen from oxygen, sulphur and nitrogen, and in which one or two of the ring carbon atoms can be substituted by oxygen to form —C(O)— residue(s), $R^{13}$ is halogen, —$NO_2$, —CN, —OH, —($C_1$–$C_8$)-alkyl, —($C_1$–$C_8$)-alkyloxy, —$CF_3$, —C(O)—$NH_2$, —$NH_2$ or the residue V-G-M, wherein V, G and M are as defined below, $R^{10}$ is hydrogen atom or —($C_1$–$C_4$)-alkyl, U and G are independently of one another identical or different and are a direct bond, —$(CH_2)_m$—, —$(CH_2)_m$—O—$(CH_2)_n$—, —$(CH_2)_m$—C(O)—$NR^{10}$—$(CH_2)_n$—, —$(CH_2)$—$SO_2$—$(CH_2)_n$—, —$(CH_2)_m$—$NR^{10}$—C(O)—$NR^{10}$—$(CH_2)_n$—, —$(CH_2)_m$—$NR^{10}$—C(O)—$(CH_2)_n$—, —$(CH_2)$—S—$(CH_2)_n$—, —$(CH_2)_m$—C(O)—$(CH_2)_n$—, —$(CH_2)_m$—$SO_2$—$NR^{10}$—$(CH_2)_n$—, —$(CH_2)_m$—$NR^{10}$—$SO_2$—$(CH_2)_n$—, —$(CH_2)_m$—$NR^{10}$—$SO_2$—$NR^{10}$—$(CH_2)_n$—, —$(CH_2)_m$—CH(OH)—$(CH_2)_n$—, —$(CH_2)_m$—O—C(O)—$NR^{10}$—$(CH_2)_n$— or —$(CH_2)_m$—$NR^{10}$—C(O)—O—$(CH_2)_n$—, n and m are independently of one another identical or different and are the integers zero, 1, 2, 3, 4, 5 or 6, wherein the alkylene residues that are formed by —$(CH_2)_m$— or —$(CH_2)_n$— are unsubstituted or mono-, di- or trisubstituted independently of one another by —($C_1$–$C_4$)-alkyl; —C(O)—OH, —C(O)—O—($C_1$–$C_4$)-alkyl, —C(O)—$NR^4R^5$, —$SO_2$, —$NR^4R^5$ or —($C_1$–$C_8$)-alkylsulfonyl, $R^4$ and $R^5$ are independently of one another identical or different and are hydrogen atom, —($C_1$–$C_8$)-alkyl, wherein alkyl is unsubstituted or mono-, di- or tri-substituted independently of one another by $R^{13}$, —($C_6$–$C_{14}$)-aryl-($C_1$–$C_4$)-alkyl-, wherein alkyl and aryl independently from one another are unsubstituted or mono-, di- or trisubstituted by $R^{13}$, —($C_6$–$C_{14}$)-aryl-, wherein aryl is unsubstituted or mono-, di- or trisubstituted independently of one another by $R^{13}$, —($C_6$–$C_{14}$)-heteroaryl, wherein heteroaryl is unsubstituted or mono-, di- or trisubstituted independently of one another by $R^{13}$ or —($C_6$–$C_{14}$)-heteroaryl-($C_1$–$C_4$)-alkyl-, wherein alkyl and heteroaryl independently from one another are unsubstituted or mono-, di- or trisubstituted by $R^{13}$, or $R^4$ and $R^5$ together with the nitrogen atom to which they are bonded form a saturated 5- to 7-membered monocyclic heterocyclic ring which, in addition to the nitrogen atom carrying $R^4$ and $R^5$ can contain one or two identical or different ring heteroatoms chosen from oxygen, sulphur and nitrogen; wherein said heterocyclic ring is unsubstituted or mono-, di- or trisubstituted independently of one another by $R^{13}$, V is
1. a direct bond,
2. —($C_1$–$C_6$)-alkylene, which is branched or unbranched and which is unsubstituted or mono-, di- or trisubstituted independently of one another by halogen, =O, —CN, —OH, —$NR^4R^5$, —C(O)—OH, —C(O)—O—($C_1$–$C_4$)-alkyl, —$SO_2$—$NR^4R^5$, —C(O)—$NR^4R^5$ or —($C_1$–$C_8$)-alkylsulfonyl,
3. a 3- to 7-membered cyclic group, containing up to 1, 2, 3 or 4 heteroatoms chosen from nitrogen, sulphur or oxygen, wherein said cyclic group is unsubstituted or mono-, di- or trisubstituted independently of one another by $R^{14}$,
4. a 6- to 14-membered aryl, wherein aryl is unsubstituted or mono-, di- or trisubstituted independently of one another by $R^{14}$, or
5. a heteroaryl, wherein said heteroaryl is unsubstituted or mono-, di- or trisubstituted independently of one another by $R^{14}$, $R^{14}$ is $R^1$, halogen, —OH, —$NR^4R^5$, =O, —($C_1$–$C_4$)-alkyl, —($C_1$–$C_4$)-alkoxy, —$NO_2$ —C(O)—OH, —CN, —C(O)—O—($C_1$–$C_4$)-alkyl, —C(O)—$NR^4R^5$, —($C_1$–$C_8$)-alkylsulfonyl, —O-heteroary —$NR^{10}$—C(O)—NH—($C_1$–$C_8$)-alkyl, —$NR^{10}$—C(O)—NH—[($C_1$–$C_8$)-alkyl]$_2$, —$SO_2$—$NR^4R^{5,}$ —$SR^4$, or —$SO_2$, wherein $R^4$, $R^5$ and $R^{10}$ are as defined above, and M is
1. a hydrogen atom,
2. —($C_1$–$C_8$)-alkyl, wherein alkyl is unsubstituted or mono-, di- or trisubstituted independently of one another by $R^{14}$,
3. —C(O)—$NR^4R^5$,
4. —($C_6$–$C_{14}$)-aryl, wherein aryl is unsubstituted or mono-, di- or trisubstituted independently of one another by $R^{14}$,
5. —($C_6$–$C_{14}$)-heteroaryl, wherein heteroaryl is unsubstituted or mono-, di- or trisubstituted independently of one another by $R^{14}$,
6. a 3- to 7-membered cyclic group, wherein said cyclic group is unsubstituted or mono-, di- or trisubstituted independently of one another by $R^{14}$,
7. a 3- to 7-membered cyclic group, containing up to 1, 2, 3 or 4 heteroatoms chosen from nitrogen, sulphur or oxygen, wherein said cyclic group is unsubstituted or mono-, di- or trisubstituted independently of one another by $R^{14}$, wherein $R^{14}$ is defined above,
8. —NH—CH($NA^1$)($NA^2$), wherein $A^1$ and $A^2$ are independently of one another identical or different and are a hydrogen atom or —($C_1$–$C_8$)-alkyl, or $A^1$ and $A^2$ together with the nitrogen atom to which they are each bonded form a saturated 5- or 6-membered monocyclic heterocyclic ring, which is saturated or aromatic, or
9. —CH($NA^1$)($NA^2$), wherein $A^1$ and $A^2$ are independently of one another identical or different and are hydrogen atom or —($C_1$–$C_8$)-alkyl, or $A^2$ together with the nitrogen atom to which it is bonded forms a saturated 5- or 6-membered monocyclic heterocyclic ring, which contains 2 nitrogen atoms and is saturated or aromatic, in all its stereoisomeric forms and mixtures thereof in any ratio, polymorph forms and mixtures thereof in any ratio and its physiologically tolerable salts.

In one embodiment, the compounds of formula I are defined as follows:
$R^0$ is phenyl, wherein phenyl is unsubstituted or mono-, di- or trisubstituted independently of one another by $R^2$,
  pyridyl, wherein pyridyl is unsubstituted or mono-, di- or trisubstituted independently of one another by $R^2$,
  pyrimidyl, wherein pyrimidyl is unsubstituted or mono-, di- or trisubstituted independently of one another by $R^2$, or
  naphthyl, wherein naphthyl is unsubstituted or mono-, di- or trisubstituted independently of one another by $R^2$,
$R^2$ is as defined above and wherein the alkyl- or alkyloxy residue is unsubstituted or mono-, di- or trisubstituted independently of one another by an amino residue or a methoxy residue,
Q and Q' are as defined above and wherein the alkylene- or cycloalkylene residue is unsubstituted or mono-, di- or trisubstituted independently of one another by —$NH_2$ or —OH;
X is as defined above,
W is phenyl, pyridyl, pyrimidyl, benzoxazole, benzthiazole, indole, benzo[1,3]dioxole, or naphthyl, wherein W is unsubstituted or mono-, di- or trisubstituted independently of one another by $R^1$, provided that if W is a six membered aryl or heteroaryl group, Q' and U are not in an ortho position with respect to each other;
$R^1$, $R^{10}$, $R^{11}$, $R^{12}$ and $R^{13}$ are as defined above,
U and G are independently of one another identical or different and are a direct bond, —(CH$_2$)$_m$, —(CH$_2$)$_m$—O—(CH$_2$)$_n$—, —(CH$_2$)$_m$—C(O)—$NR^{10}$—(CH$_2$)$_n$, —(CH$_2$)$_m$—$NR^{10}$—C(O)—$NR^{10}$—(CH$_2$)$_n$, —(CH$_2$)$_m$—$NR^{10}$—C(O)—(CH$_2$)$_n$, —(CH$_2$)$_m$—C(O)—(CH$_2$)$_n$, —(CH$_2$)—S—(CH$_2$)$_n$, —(CH$_2$)$_m$—$SO_2$—$NR^{10}$—(CH$_2$)$_n$, —(CH$_2$)$_m$—$NR^{10}$—$SO_2$—(CH$_2$)$_n$, —(CH$_2$)$_m$—$NR^{10}$—$SO_2$—$NR^{10}$—(CH$_2$)$_n$ or —(CH$_2$)$_m$—CH(OH)—(CH$_2$)$_n$,
wherein n, m, $R^4$ and $R^5$ are as defined above,
V and M are as defined above, in all its stereoisomeric forms and mixtures thereof in any ratio, and its physiologically tolerable salts.

In another embodiment, the compounds of formula I are defined as follows:
$R^0$ is phenyl, wherein phenyl is unsubstituted or mono-, di- or trisubstituted independently of one another by $R^2$,
  pyridyl, wherein pyridyl is unsubstituted or mono-, di- or trisubstituted independently of one another by $R^2$,
  pyrimidyl, wherein pyrimidyl is unsubstituted or mono-, di- or trisubstituted independently of one another by $R^2$, or
  naphthyl, wherein naphthyl is unsubstituted or mono-, di- or trisubstituted independently of one another by $R^2$,
$R^2$ is halogen, —CN, —$NH_2$, —C(O)—$NH_2$, —($C_1$–$C_4$)-alkyl, or —($C_1$–$C_4$)-alkyloxy, wherein the alkyl- or alkyloxy residue is unsubstituted or mono-, di- or trisubstituted independently of one another by an amino residue or a methoxy residue,
Q and Q' are independently of one another identical or different and are a direct bond, —C(O)—; —O—, —$NR^{10}$—, —C(O)—$NR^{10}$—, —$NR^{10}$—C(O)—, —$SO_2$—, —$NR^{10}$—$SO_2$—, —$SO_2$—$NR^{10}$—, —($C_1$–$C_4$)-alkylene, wherein alkylene is unsubstituted or mono-, di- or trisubstituted independently of one another by halogen; or —($C_3$–$C_6$)-cycloalkylene, wherein cycloalkylene is unsubstituted or mono-, di- or trisubstituted independently of one another by halogen;

X is a direct bond, —($C_1$–$C_3$)-alkylene, wherein alkylene is unsubstituted or mono-, di- or trisubstituted independently of one another by halogen; or —($C_3$–$C_6$)-cycloalkylene, wherein cycloalkylene is unsubstituted or mono-, di- or trisubstituted independently of one another by halogen;

provided that when Q or Q' is —($C_1$–$C_3$)-alkylene then X is —O—, —$NR^{10}$—, —C(O)—, —C(O)—$NR^{10}$—, —$NR^{10}$—C(O)—, —$SO_2$—, —$NR^{10}$—$SO_2$— or —$SO_2$—$NR^{10}$—;

with the proviso that if X is a direct bond, the fragment -Q-X-Q'- is not O—O, $SO_2$—$SO_2$, or SO—$SO_2$; and with the proviso that if X is oxygen atom, then Q and Q' are not oxygen atom or sulphur atom; and with the further proviso that if X is $SO_2$, then Q and Q' are not oxygen atom or sulphur atom;

W is phenyl, pyridyl, pyrimidyl, benzoxazole, benzthiazole, indole, benzo[1,3]dioxole, or naphthyl, wherein W is unsubstituted or mono-, di- or trisubstituted independently of one another by $R^1$, provided that if W is a six membered aryl or heteroaryl group, Q' and U are not in an ortho position with respect to each other;

$R^1$ is
1. halogen,
2. —$NO_2$,
3. —CN,
4. —$NH_2$,
5. ($C_1$–$C_6$)-alkylamino-, wherein alkyl is unsubstituted or mono-, di- or trisubstituted independently of one another by $R^{13}$,
6. —OH,
7. —$SO_2$—$NH_2$,
8. ($C_1$–$C_6$)-alkyloxy-, wherein alkyl is unsubstituted or mono-, di- or trisubstituted independently of one another by $R^{13}$,
9. ($C_6$–$C_{14}$)-aryl, wherein aryl is unsubstituted or mono-, di- or trisubstituted independently of one another by $R^{13}$,
10. ($C_1$–$C_6$)-alkyl-, wherein alkyl is unsubstituted or mono-, di- or trisubstituted independently of one another by $R^{13}$,
11. hydroxycarbonyl-($C_1$–$C_6$)-alkylureido-, wherein alkyl is unsubstituted or mono-, di- or trisubstituted independently of one another by $R^{13}$,
12. ($C_1$–$C_6$)-alkyloxycarbonyl-($C_1$–$C_6$)-alkylureido-, wherein alkyl is unsubstituted or mono-, di- or trisubstituted independently of one another by $R^{13}$,
13. ($C_1$–$C_6$)-alkylsulfonyl-, wherein alkyl is unsubstituted or mono-, di- or trisubstituted independently of one another by $R^{13}$,
14. bis[($C_1$–$C_6$)-alkyl]amino, wherein alkyl is unsubstituted or mono-, di- or trisubstituted independently of one another by $R^{13}$,
15. —C(O)—$NH_2$,
16. —C(O)—OH,
17. —C(O)—($C_1$–$C_6$)-alkyl, wherein alkyl is unsubstituted or mono-, di- or trisubstituted independently of one another by $R^{13}$,
18. —C(O)—NH—($C_1$–$C_6$)-alkyl, wherein alkyl is unsubstituted or mono-, di- or trisubstituted independently of one another by $R^{13}$,
19. —C(O)—NH—[($C_1$–$C_6$)-alkyl]$_2$, wherein alkyl is unsubstituted or mono-, di- or trisubstituted independently of one another by $R^{13}$,
20. —C(NH)—$NH_2$,
21. ureido,
22. —($C_1$–$C_6$)-alkylthio, wherein alkyl is unsubstituted or mono-, di- or trisubstituted independently of one another by $R^{13}$, or
23. $R^{11}R^{12}N$—, or two $R^1$ residues bonded to adjacent ring carbon atoms together with the carbon atoms to which they are bonded form an aromatic ring condensed to W, where the ring formed by the two $R^1$ residues is unsubstituted or mono-, di- or trisubstituted independently of one another by $R^{13}$, $R^{11}$ and $R^{12}$ together with the nitrogen atom to which they are bonded form a saturated or unsaturated 5- to 6-membered monocyclic heterocyclic ring which, in addition to the nitrogen atom carrying $R^{11}$ and $R^{12}$ can contain one or two identical or different ring heteroatoms chosen from oxygen, sulphur and nitrogen, and in which one or two of the ring carbon atoms can be substituted by oxygen to form —C(O)—residue(s), $R^{13}$ is halogen, —CN, —($C_1$–$C_6$)-alkyl, —($C_1$–$C_6$)-alkyloxy, —$CF_3$, —C(O)—$NH_2$ or —$NH_2$, $R^{10}$ is hydrogen atom or —($C_1$–$C_4$)-alkyl, U and G are independently of one another identical or different and are a direct bond, —$(CH_2)_m$, —$(CH_2)_m$—O—$(CH_2)_n$—, —$(CH_2)_m$—C(O)—$NR^{10}$—$(CH_2)_n$, —$(CH_2)_m$—$NR^{10}$—C(O)—$NR^{10}$—$(CH_2)_n$, —$(CH_2)_m$—$NR^{10}$—C(O)—$(CH_2)_n$, —$(CH_2)_m$—C(O)—$(CH_2)_n$, —$(CH_2)_m$—S—$(CH_2)_n$, —$(CH_2)_m$—$SO_2$—$NR^{10}$—$(CH_2)_n$, —$(CH_2)_m$—$NR^{10}$—$SO_2$—$(CH_2)_n$, or —$(CH_2)_m$—$NR^{10}$—$SO_2$—$NR^{10}$—$(CH_2)_n$, n and m are independently of one another identical or different and are the integers zero, 1, 2 or 3, wherein the alkylene residues are unsubstituted or mono-, di- or trisubstituted independently of one another by —($C_1$–$C_4$)-alkyl; —C(O)—OH, —C(O)—O—($C_1$–$C_4$)-alkyl, —C(O)—$NR^4R^5$, —$SO_2$, —$NR^4R^5$ or —($C_1$–$C_8$)-alkylsulfonyl, $R^4$ and $R^5$ are independently of one another identical or different and are hydrogen atom, —($C_1$–$C_6$)-alkyl, wherein alkyl is unsubstituted or mono-, di- or trisubstituted independently of one another by $R^{13}$, —($C_6$–$C_{14}$)-aryl-($C_1$–$C_4$)-alkyl-, wherein alkyl and aryl independently from one another are unsubstituted or mono-, di- or trisubstituted by $R^{13}$, —($C_6$–$C_{14}$)-aryl-, wherein aryl is unsubstituted or mono-, di- or trisubstituted independently of one another by $R^{13}$, —($C_6$–$C_{14}$)-heteroaryl, wherein heteroaryl is unsubstituted or mono-, di- or trisubstituted independently of one another by $R^{13}$ or —($C_6$–$C_{14}$)-heteroaryl-($C_1$–$C_4$)-alkyl-, wherein alkyl and heteroaryl independently from one another are unsubstituted or mono-, di- or trisubstituted by $R^{13}$, or $R^4$ and $R^5$ together with the nitrogen atom to which they are bonded form a saturated 5- to 7-membered monocyclic heterocyclic ring, which in addition to the nitrogen atom carrying $R^4$ and $R^5$ can contain one or two identical or different ring heteroatoms chosen from oxygen, sulphur and nitrogen; wherein said heterocyclic ring is unsubstituted or mono-, di- or trisubstituted independently of one another by $R^{13}$, V is
1. a direct bond,
2. —($C_1$–$C_4$)-alkylene, which is branched or unbranched and which is unsubstituted or mono-, di- or trisubstituted independently of one another by halogen, =O, —CN, —OH, —NR4R$^5$, —C(O)—OH, —C(O)—O—($C_1$–$C_4$)-alkyl, —$SO_2$, —NR$^4$R$^5$, —C(O)—NR$^4$R$^5$ or —($C_1$–$C_8$)-alkylsulfonyl,
3. a 5- to 7-membered cyclic group, containing up to 1, 2, 3 or 4 heteroatoms chosen from nitrogen, sulphur or oxygen, wherein said cyclic group is unsubstituted or mono-, di- or trisubstituted independently of one another by R$^{14}$,
4. a 6- to 14-membered aryl, wherein aryl is unsubstituted or mono-, di- or trisubstituted independently of one another by R$^{14}$, or
5. a heteroaryl, wherein said heteroaryl is unsubstituted or mono-, di- or trisubstituted independently of one another by R$^{14}$, R$^{14}$ is halogen, —OH, —NR$^4$R$^5$, =O, —($C_1$–$C_4$)-alkyl, —($C_1$–$C_4$)-alkoxyl, —$NO_2$, —C(O)—OH, —CN, —C(O)—O—($C_1$–$C_4$)-alkyl, —C(O)—NR$^4$R$^5$, —($C_1$–$C_8$)-alkylsulfonyl, —C(O)—NR$^4$R$^5$, —$SO_2$—NR$^4$R$^5$, —C(O)—NH—($C_1$–$C_8$)-alkyl, —C(O)—NH—[($C_1$–$C_8$)-alkyl]$_2$, —NR$^{10}$—C(O)—NH—($C_1$–$C_8$)-alkyl, —C(O)—NH$_2$ or —NR$^{10}$—C(O)—NH—[($C_1$–$C_8$)-alkyl]$_2$, wherein R$^4$, R$^5$ and R$^{10}$ are as defined above, and M is
1. a hydrogen atom,
2. —($C_1$–$C_8$)-alkyl, wherein alkyl is unsubstituted or mono-, di- or trisubstituted independently of one another by R$^{14}$,
3. —C(O)—NR$^4$R$^5$,
4. —($C_6$–$C_{14}$)-aryl, wherein aryl is unsubstituted or mono-, di- or trisubstituted independently of one another by R$^{14}$,
5. —($C_6$–$C_{14}$)-heteroaryl, wherein heteroaryl is unsubstituted or mono-, di- or trisubstituted independently of one another by R$^{14}$,
6. a 5- to 7-membered cyclic group, wherein said cyclic group is unsubstituted or mono-, di- or trisubstituted independently of one another by R$^{14}$, or
7. a 5- to 7-membered cyclic group, containing up to 1, 2, 3 or 4 heteroatoms chosen from nitrogen, sulphur or oxygen, wherein said cyclic group is unsubstituted or mono-, di- or trisubstituted independently of one another by R$^{14}$, wherein R$^{14}$ is defined above, in all its stereoisomeric forms and mixtures thereof in any ratio, and its physiologically tolerable salts.

In yet another embodiment, the compounds of formula I are defined as follows:

R$^0$ is phenyl, wherein phenyl is unsubstituted or mono-, di- or trisubstituted independently of one another by R$^2$, or pyridyl, wherein pyridyl is unsubstituted or mono-, di- or trisubstituted independently of one another by R$^2$, R$^2$ is halogen, —CN, —C(O)—NH$_2$, —($C_1$–$C_4$)-alkyl, or —($C_1$–$C_4$)-alkyloxy, wherein the alkyl- or alkyloxy residue is unsubstituted or mono-, di- or trisubstituted independently of one another by an amino residue or a methoxy residue, Q and Q' are independently of one another identical or different and are a direct bond, —C(O)—; —O—, —NR$^{10}$—, —C(O)—NR$^{10}$—, —NR$^{10}$—C(O)—, —$SO_2$—, —NR$^{10}$—$SO_2$—NR$^{10}$—, or —($C_1$–$C_4$)-alkylene, X is a direct bond or —($C_1$–$C_3$)-alkylene, provided that when Q or Q' is —($C_1$–$C_3$)-alkylene then X is —O—, —NR$^{10}$—, —C(O)—, —C(O)—NR$^{10}$—, —NR$^{10}$—C(O)—, —$SO_2$—, —NR$^{10}$—$SO_2$— or —$SO_2$—NR$^{10}$—;

with the proviso that if X is a direct bond, the fragment -Q-X-Q'- is not O—O or $SO_2$—$SO_2$;

and with the proviso that if X is oxygen atom, then Q and Q' are not oxygen atom or sulphur atom; and with the further proviso that if X is $SO_2$, then Q and Q' are not oxygen atom or sulphur atom;

W is phenyl, pyridyl or pyrimidyl, wherein W is unsubstituted or mono-, di- or trisubstituted independently of one another by R$^1$, provided that Q' and U are not in an ortho position with respect to each other;

R$^1$ is
1. halogen,
2. —$NO_2$,
3. —CN,
4. —NH$_2$,
5. ($C_1$–$C_4$)-alkylamino-, wherein alkyl is unsubstituted or mono-, di- or trisubstituted independently of one another by R$^{13}$,
6. —OH,
7. —$SO_2$—NH$_2$,
8. ($C_1$–$C_4$)-alkyloxy-, wherein alkyl is unsubstituted or mono-, di- or trisubstituted independently of one another by R$^{13}$,
9. ($C_6$–$C_{14}$)-aryl, wherein aryl is unsubstituted or mono-, di- or trisubstituted independently of one another by R$^{13}$,
10. ($C_1$–$C_4$)-alkyl-, wherein alkyl is unsubstituted or mono-, di- or trisubstituted independently of one another by R$^{13}$,
11. hydroxycarbonyl-($C_1$–$C_4$)-alkylureido-, wherein alkyl is unsubstituted or mono-, di- or trisubstituted independently of one another by R$^{13}$,
12. ($C_1$–$C_4$)-alkyloxycarbonyl-($C_1$–$C_4$)-alkylureido-, wherein alkyl is unsubstituted or mono-, di- or trisubstituted independently of one another by R$^{13}$,
13. ($C_1$–$C_4$)-alkylsulfonyl-, wherein alkyl is unsubstituted or mono-, di- or trisubstituted independently of one another by R$^{13}$,
14. bis[($C_1$–$C_4$)-alkyl]amino, wherein alkyl is unsubstituted or mono-, di- or trisubstituted independently of one another by R$^{13}$,
15. —C(O)—NH$_2$,
16. —C(O)—OH,
17. —C(O)—($C_1$–$C_4$)-alkyl, wherein alkyl is unsubstituted or mono-, di- or trisubstituted independently of one another by R$^{13}$,
18. —C(O)—NH—($C_1$–$C_4$)-alkyl, wherein alkyl is unsubstituted or mono-, di- or trisubstituted independently of one another by R$^{13}$,
19. —C(O)—NH—[($C_1$–$C_4$)-alkyl]$_2$, wherein alkyl is unsubstituted or mono-, di- or trisubstituted independently of one another by R$^{13}$,
20. —C(NH)—NH$_2$,
21. ureido,
22. —($C_1$–$C_4$)-alkylthio, wherein alkylthio is unsubstituted or mono-, di- or trisubstituted independently of one another by R$^{13}$, or
23. R$^{11}$R$^{12}$N—, or
two R$^1$ residues bonded to adjacent ring carbon atoms together with the carbon atoms to which they are bonded form an aromatic ring condensed to W, where the ring formed by the two R$^1$ residues is unsubstituted or mono-, di- or trisubstituted independently of one another by R$^{13}$, R$^{11}$ and R$^{12}$ together with the nitrogen atom to which they are bonded form a saturated or unsaturated 5- to 6-membered monocyclic heterocyclic ring which, in addition to the nitrogen atom carrying $R^{11}$ and $R^{12}$, can contain one or two identical or different ring heteroatoms chosen from oxygen, sulphur and nitrogen, $R^{13}$ is halogen, —CN, —$(C_1$–$C_4)$-alkyl, —$(C_1$–$C_4)$-alkyloxy, —$CF_3$, —C(O)—$NH_2$ or —$NH_2$, $R^{10}$ is hydrogen atom or —$(C_1$–$C_4)$-alkyl, U and G are independently of one another identical or different and are a direct bond, —$(CH_2)_m$—, —$(CH_2)_m$—C(O)—$NR^{10}$—$(CH_2)_n$, —$(CH_2)_m$—$NR^{10}$—C(O)—$NR^{10}$—$(CH_2)_n$, —$(CH_2)_m$—$NR^{10}$—C(O)—$(CH_2)_n$, —$(CH_2)_m$—C(O)—$(CH_2)_n$, —$(CH_2)_m$—$SO_2$—$NR^{10}$—$(CH_2)_n$, or —$(CH_2)_m$—$NR^{10}$—$SO_2$—$(CH_2)_n$, n and m are are independently of one another identical or different and are the integers zero, 1, 2 or 3, wherein the alkylene residues are unsubstituted or mono-, di- or trisubstituted independently of one another by —$(C_1$–$C_4)$-alkyl; —C(O)—OH, —C(O)—O—$(C_1$–$C_4)$-alkyl or —C(O)—$NR^4R^5$, $R^4$ and $R^5$ are independently of one another identical or different and are hydrogen atom, —$(C_1$–$C_6)$-alkyl, wherein alkyl is unsubstituted or mono-, di- or trisubstituted independently of one another by $R^{13}$, —$(C_6$–$C_{14})$-aryl-$(C_1$–$C_4)$-alkyl-, wherein alkyl and aryl independently from one another are unsubstituted or mono-, di- or trisubstituted by $R^{13}$, —$(C_6$–$C_{14})$-aryl-, wherein aryl is unsubstituted or mono-, di- or trisubstituted independently of one another by $R^{13}$, —$(C_6$–$C_{14})$-heteroaryl, wherein heteroaryl is unsubstituted or mono-, di- or trisubstituted independently of one another by $R^{13}$ or —$(C_6$–$C_{14})$-heteroaryl-$(C_1$–$C_4)$-alkyl-, wherein alkyl and heteroaryl independently from one another are unsubstituted or mono-, di- or trisubstituted by $R^{13}$, or $R^4$ and $R^5$ together with the nitrogen atom to which they are bonded form a saturated 5- to 7-membered monocyclic heterocyclic ring which, in addition to the nitrogen atom carrying $R^4$ and $R^5$ can contain one or two identical or different ring heteroatoms chosen from oxygen, sulphur and nitrogen; wherein said heterocyclic ring is unsubstituted or mono-, di- or trisubstituted independently of one another by $R^{13}$, V is
1. a direct bond,
2. —$(C_1$–$C_4)$-alkylene, which is branched or unbranched and which is unsubstituted or mono-, di- or trisubstituted independently of one another by halogen, =O, —CN, —OH, —$NR^4R^5$, —C(O)—OH, —C(O)—O—$(C_1$–$C_4)$-alkyl, —$SO_2$—$NR^4R^5$, —C(O)—$NR^4R^5$ or —$(C_1$–$C_4)$-alkylsulfonyl,
3. a 5- to 7-membered cyclic group, containing up to 1, 2, 3 or 4 heteroatoms chosen from nitrogen, sulphur or oxygen, wherein said cyclic group is unsubstituted or mono-, di- or trisubstituted independently of one another by $R^{14}$,
4. a 6- to 14-membered aryl, wherein aryl is unsubstituted or mono-, di- or trisubstituted independently of one another by $R^{14}$, or
5. a 6- to 14-membered heteroaryl, wherein said heteroaryl is unsubstituted or mono-, di- or trisubstituted independently of one another by $R^{14}$, $R^{14}$ is halogen, —OH, —$NR^4R^5$, =O, —$(C_1$–$C_4)$-alkyl, —$(C_1$–$C_4)$-alkoxyl, —$NO_2$, —C(O)—OH, —CN, —C(O)—O—$(C_1$–$C_4)$-alkyl, —C(O)—$NR^4R^5$, —$(C_1$–$C_8)$-alkylsulfonyl, —C(O)—$NR^4R^5$, —$SO_2$—$NR^4R^5$, —C(O)—NH—$(C_1$–$C_8)$-alkyl, —C(O)—NH—[$(C_1$–$C_8)$-alkyl]$_2$, —$NR^{10}$—C(O)—NH—$(C_1$–$C_8)$-alkyl, —C(O)—$NH_2$ or —$NR^{10}$—C(O)—NH—[$(C_1$–$C_8)$-alkyl]$_2$, wherein $R^4$, $R^5$ and $R^{10}$ are as defined above, and M is
1. a hydrogen atom,
2. —$(C_1$–$C_8)$-alkyl, wherein alkyl is unsubstituted or mono-, di- or trisubstituted independently of one another by $R^{14}$,
3. —C(O)—$NR^4R^5$,
4. —$(C_6$–$C_{14})$-aryl, wherein aryl is unsubstituted or mono-, di- or trisubstituted independently of one another by $R^{14}$,
5. —$(C_6$–$C_{14})$-heteroaryl, wherein heteroaryl is unsubstituted or mono-, di- or trisubstituted independently of one another by $R^{14}$,
6. a 5- to 7-membered cyclic group, wherein said cyclic group is unsubstituted or mono-, di- or trisubstituted independently of one another by $R^{14}$, or
7. a 5- to 7-membered cyclic group, containing up to 1, 2, 3 or 4 heteroatoms chosen from nitrogen, sulphur or oxygen, wherein said cyclic group is unsubstituted or mono-, di- or trisubstituted independently of one another by $R^{14}$, wherein $R^{14}$ is defined above, in all its stereoisomeric forms and mixtures thereof in any ratio, and its physiologically tolerable salts.

In another embodiment, the compounds of formula I are defined as follows:

$R^0$ is phenyl, wherein phenyl is unsubstituted or mono- or disubstituted independently of one another by $R^2$, or pyridyl, wherein pyridyl is unsubstituted or mono-, disubstituted independently of one another by $R^2$, $R^2$ is halogen, —CN, —C(O)—$NH_2$, —$(C_1$–$C_3)$-alkyl, or —$(C_1$–$C_3)$-alkyloxy, wherein the alkyl- or alkyloxy residue is unsubstituted or mono-, di- or trisubstituted independently of one another by an amino residue or a methoxy residue, Q and Q' are independently of one another identical or different and are a direct bond, —C(O)—; —O—, —$NR^{10}$—, —C(O)—$NR^{10}$—, —$NR^{10}$—C(O)—, —$SO_2$—, —$NR^{10}$—$SO_2$—, —$SO_2$—$NR^{10}$—, or —$(C_1$–$C_4)$-alkylene, X is a direct bond or —$(C_1$–$C_3)$-alkylene, provided that when Q or Q' is —$(C_1$–$C_3)$-alkylene then X is —O—, —$NR^{10}$—, —C(O)—, —C(O)—$NR^{10}$—, —$NR^{10}$—C(O)—, —$SO_2$—, —$NR^{10}$—$SO_2$— or —$SO_2$—$NR^{10}$—;

with the proviso that if X is a direct bond, the fragment -Q-X-Q'- is not O—O or $SO_2$—$SO_2$;

and with the proviso that if X is oxygen atom, then Q and Q' are not oxygen atom or sulphur atom; and with the further proviso that if X is $SO_2$, then Q and Q' are not oxygen atom or sulphur atom;

W is phenyl, pyridyl or pyrimidyl, wherein W is unsubstituted or mono-, di- or trisubstituted independently of one another by $R^1$, provided that Q' and U are not in an ortho position with respect to each other;

$R^1$ is
1. halogen,
2. —$NO_2$,
3. —CN,
4. —$NH_2$,
5. $(C_1$–$C_4)$-alkylamino-, wherein alkyl is unsubstituted or mono-, di- or trisubstituted independently of one another by $R^{13}$,
6. —OH,
7. —$SO_2$—$NH_2$, 8. $(C_1$–$C_4)$-alkyloxy-, wherein alkyl is unsubstituted or mono-, di- or trisubstituted independently of one another by $R^{13}$,
9. $(C_6$–$C_{14})$-aryl, wherein aryl is unsubstituted or mono-, di- or trisubstituted independently of one another by $R^{13}$,
10. $(C_1$–$C_4)$-alkyl-, wherein alkyl is unsubstituted or mono-, di- or trisubstituted independently of one another by $R^{13}$,
11. $(C_1$–$C_4)$-alkylsulfonyl-, wherein alkyl is unsubstituted or mono-, di- or trisubstituted independently of one another by $R^{13}$,
12. bis[$(C_1$–$C_4)$-alkyl]amino, wherein alkyl is unsubstituted or mono-, di- or trisubstituted independently of one another by $R^{13}$,
13. —C(O)—NH$_2$,
14. —C(O)—OH,
15. —C(O)—$(C_1$–$C_4)$-alkyl, wherein alkyl is unsubstituted or mono-, di- or trisubstituted independently of one another by $R^{13}$,
16. —C(O)—NH—$(C_1$–$C_4)$-alkyl, wherein alkyl is unsubstituted or mono-, di- or trisubstituted independently of one another by $R^{13}$,
17. —C(O)—NH—[$(C_1$–$C_4)$-alkyl]$_2$, wherein alkyl is unsubstituted or mono-, di- or trisubstituted independently of one another by $R^{13}$,
18. —C(NH)—NH$_2$,
19. ureido,
20. —$(C_1$–$C_4)$-alkylthio, wherein alkylthio is unsubstituted or mono-, di- or trisubstituted independently of one another by $R^{13}$, or
21. $R^{11}R^{12}N$—, or two $R^1$ residues bonded to adjacent ring carbon atoms together with the carbon atoms to which they are bonded form an aromatic ring condensed to W, where the ring formed by the two $R^1$ residues is unsubstituted or mono-, di- or trisubstituted independently of one another by $R^{13}$, $R^{11}$ and $R^{12}$ together with the nitrogen atom to which they are bonded form a saturated or unsaturated 5- to 6-membered monocyclic heterocyclic ring which, in addition to the nitrogen atom carrying $R^{11}$ and $R^{12}$, can contain one or two identical or different ring heteroatoms chosen from oxygen or nitrogen, $R^{13}$ is halogen, —CN, —$(C_1$–$C_4)$-alkyl, —$(C_1$–$C_4)$-alkyloxy, —CF$_3$, —C(O)—NH$_2$ or —NH$_2$, $R^{10}$ is hydrogen atom or —$(C_1$–$C_4)$-alkyl, U is a direct bond, —(CH$_2$)$_m$—, —(CH$_2$)$_m$—C(O)—NR$^{10}$—(CH$_2$)$_n$—, —(CH$_2$)$_m$—NR$^{10}$—C(O)—(CH$_2$)$_n$—, —(CH$_2$)$_m$—C(O)—(CH$_2$)$_n$—, —(CH$_2$)$_m$—SO$_2$—NR$^{10}$—(CH$_2$)$_n$, or —(CH$_2$)$_m$—NR$^{10}$—SO$_2$—(CH$_2$)$_n$, n and m are independently of one another identical or different and are the integers zero, 1, 2 or 3, wherein the alkylene residues are unsubstituted or mono-, di- or trisubstituted independently of one another by —$(C_1$–$C_4)$-alkyl; —C(O)—OH, —C(O)—O—$(C_1$–$C_4)$-alkyl or —C(O)—NR$^4$R$^5$, $R^4$ and $R^5$ are independently of one another identical or different and are hydrogen atom, —$(C_1$–$C_6)$-alkyl, wherein alkyl is unsubstituted or mono-, di- or trisubstituted independently of one another by $R^{13}$, —$(C_6$–$C_{14})$-aryl-$(C_1$–$C_4)$-alkyl-, wherein alkyl and aryl independently from one another are unsubstituted or mono-, di- or trisubstituted by $R^{13}$, —$(C_6$–$C_{14})$-aryl-, wherein aryl is unsubstituted or mono-, di- or trisubstituted independently of one another by $R^{13}$, —$(C_6$–$C_{14})$-heteroaryl, wherein heteroaryl is unsubstituted or mono-, di- or trisubstituted independently of one another by $R^{13}$ or —$(C_6$–$C_{14})$-heteroaryl-$(C_1$–$C_4)$-alkyl-, wherein alkyl and heteroaryl independently from one another are unsubstituted or mono-, di- or trisubstituted by $R^{13}$, or $R^4$ and $R^5$ together with the nitrogen atom to which they are bonded form a saturated 5- to 7-membered monocyclic heterocyclic ring which, in addition to the nitrogen atom carrying $R^4$ and $R^5$, can contain one or two identical or different ring heteroatoms chosen from oxygen, sulphur and nitrogen; wherein said heterocyclic ring is unsubstituted or mono-, di- or trisubstituted independently of one another by $R^{13}$, G is a direct bond, —(CH$_2$)$_m$, —(CH$_2$)$_m$—O—(CH$_2$)$_n$—, —(CH$_2$)$_m$—C(O)—NR$^{10}$—(CH$_2$)$_n$, —(CH$_2$)$_m$—NR$^{10}$—C(O)—NR$^{10}$—(CH$_2$)$_n$, —(CH$_2$)$_m$—NR$^{10}$—C(O)—(CH$_2$)$_n$, —(CH$_2$)$_m$—C(O)—(CH$_2$)$_n$, —(CH$_2$)—S—(CH$_2$)$_n$, —(CH$_2$)$_m$—SO$_2$—NR$^{10}$—(CH$_2$)$_n$, —(CH$_2$)$_m$—NR$^{10}$—SO$_2$—(CH$_2$)$_n$, —(CH$_2$)$_m$—NR$^{10}$—SO$_2$—NR$^{10}$—(CH$_2$)$_n$ or —(CH$_2$)$_m$—SO$_2$—(CH$_2$)$_n$, wherein n, m, and $R^{10}$ are as defined above V is 1. a direct bond,
2. —$(C_1$–$C_4)$-alkylene, which is branched or unbranched and which is unsubstituted or mono-, di- or trisubstituted independently of one another by halogen, =O, —CN, —NR$^4$R$^5$, —C(O)—OH, —C(O)—O—$(C_1$–$C_4)$-alkyl, —SO$_2$—NR$^4$R$^5$, —C(O)—NR$^4$R$^5$ or —$(C_1$–$C_4)$-alkylsulfonyl,
3. a 5- to 7-membered cyclic group, containing up to 1, 2, 3 or 4 heteroatoms chosen from nitrogen, sulphur or oxygen, wherein said cyclic group is unsubstituted or mono-, di- or trisubstituted independently of one another by $R^{14}$,
4. a 6- to 14-membered aryl, wherein aryl is unsubstituted or mono-, di- or trisubstituted independently of one another by $R^{14}$, or
5. a 6- to 14-membered heteroaryl, wherein said heteroaryl is unsubstituted or mono-, di- or trisubstituted independently of one another by $R^{14}$, $R^{14}$ is halogen, —OH, —NR$^4$R$^5$, =O, —$(C_1$–$C_4)$-alkyl, —$(C_1$–$C_4)$-alkoxyl, —NO$_2$, —C(O)—OH, —CN, —C(O)—O—$(C_1$–$C_4)$-alkyl, —C(O)—NR$^4$R$^5$, —$(C_1$–$C_8)$-alkylsulfonyl, —C(O)—NR$^4$R$^5$, —SO$_2$—NR$^4$R$^5$, —C(O)—NH—$(C_1$–$C_8)$-alkyl, —C(O)—NH—[$(C_1$–$C_8)$-alkyl]$_2$, —NR$^{10}$—C(O)—NH—$(C_1$–$C_8)$-alkyl, —C(O)—NH$_2$, or —NR$^{10}$—C(O)—NH—[$(C_1$–$C_8)$-alkyl]$_2$, wherein $R^4$, $R^5$ and $R^{10}$ are as defined above, and M is 1. a hydrogen atom,
2. —$(C_1$–$C_4)$-alkyl, wherein alkyl is unsubstituted or mono-, di- or trisubstituted independently of one another by $R^{14}$,
3. —C(O)—NR$^4$R$^5$,
4. —$(C_6$–$C_{14})$-aryl, wherein aryl is unsubstituted or mono-, di- or trisubstituted independently of one another by $R^{14}$,
5. —$(C_6$–$C_{14})$-heteroaryl, wherein heteroaryl is unsubstituted or mono-, di- or trisubstituted independently of one another by $R^{14}$,
6. a 5- to 7-membered cyclic group, wherein said cyclic group is unsubstituted or mono-, di- or trisubstituted independently of one another by $R^{14}$, or
7. a 5- to 7-membered cyclic group, containing up to 1, 2, 3 or 4 heteroatoms chosen from nitrogen, sulphur or oxygen, wherein said cyclic group is unsubstituted or mono-, di- or trisubstituted independently of one another by $R^{14}$, wherein $R^{14}$ is defined above, in all its stereoisomeric forms and mixtures thereof in any ratio, and its physiologically tolerable salts.

In another embodiment, compounds of formula I are defined as follows:

$R^0$ is phenyl, wherein phenyl is unsubstituted or mono- or disubstituted independently of one another by $R^2$, or pyridyl, wherein pyridyl is unsubstituted or mono-, disubstituted independently of one another by $R^2$, $R^2$ is halogen, —CN, —C(O)—$NH_2$, —($C_1$–$C_3$)-alkyl, or —($C_1$–$C_3$)-alkyloxy, wherein the alkyl- or alkyloxy residue is unsubstituted or mono-, di- or trisubstituted independently of one another by an amino residue or a methoxy residue, Q and Q' are independently of one another identical or different and are a direct bond, —C(O)—; —O—, —$NR^{10}$—, —C(O)—$NR^{10}$—, —$NR^{10}$—C(O)—, —$SO_2$—, —$NR_{10}$—$SO_2$——$SO_2$—$NR^{10}$—, or —($C_1$–$C_4$)-alkylene, X is a direct bond or —($C_1$–$C_3$)-alkylene, provided that when Q or Q' is —($C_1$–$C_3$)-alkylene then X is —O—, —$NR_{10}$—, —C(O)—, —C(O)—$NR^{10}$—, —$NR^{10}$—C(O)—, —$SO_2$—, —$NR^{10}$—$SO_2$— or —$SO_2$—$NR^{10}$—;

with the proviso that if X is a direct bond, the fragment -Q-X-Q'- is not O—O or $SO_2$—$SO_2$;

and with the proviso that if X is oxygen atom, then Q and Q' are not oxygen atom or sulphur atom; and with the further proviso that if X is $SO_2$, then Q and Q' are not oxygen atom or sulphur atom;

W is phenyl or pyridyl, wherein W is unsubstituted or mono-, di- or trisubstituted independently of one another by $R^1$, provided that Q' and U are not in an ortho position with respect to each other;

$R^1$ is
1. halogen,
2. —$NO_2$,
3. —CN,
4. —$NH_2$,
5. ($C_1$–$C_4$)-alkylamino-, wherein alkyl is unsubstituted or mono-, di- or trisubstituted independently of one another by $R^{13}$,
6. —OH,
7. —$SO_2$—$NH_2$,
8. ($C_1$–$C_4$)-alkyloxy-, wherein alkyl is unsubstituted or mono-, di- or trisubstituted independently of one another by $R^{13}$,
9. ($C_6$–$C_{14}$)-aryl, wherein aryl is unsubstituted or mono-, di- or trisubstituted independently of one another by $R^{13}$,
10. ($C_1$–$C_4$)-alkyl-, wherein alkyl is unsubstituted or mono-, di- or trisubstituted independently of one another by $R^{13}$,
11. ($C_1$–$C_4$)-alkylsulfonyl-, wherein alkyl is unsubstituted or mono-, di- or trisubstituted independently of one another by $R^{13}$,
12. bis[($C_1$–$C_4$)-alkyl]amino, wherein alkyl is unsubstituted or mono-, di- or trisubstituted independently of one another by $R^{13}$,
13. —C(O)—$NH_2$,
14. —C(O)—OH,
15. —C(O)—($C_1$–$C_4$)-alkyl, wherein alkyl is unsubstituted or mono-, di- or trisubstituted independently of one another by $R^{13}$,
16. —C(O)—NH—($C_1$–$C_4$)-alkyl, wherein alkyl is unsubstituted or mono-, di- or trisubstituted independently of one another by $R^{13}$,
17. —C(O)—NH—[($C_1$–$C_4$)-alkyl]$_2$, wherein alkyl is unsubstituted or mono-, di- or trisubstituted independently of one another by $R^{13}$,
18. —C(NH)—$NH_2$,
19. ureido,
20. —($C_1$–$C_4$)-alkylthio, wherein alkylthio is unsubstituted or mono-, di- or trisubstituted independently of one another by $R^{13}$, or
21. $R^{11}R^{12}N$—, or two $R^1$ residues bonded to adjacent ring carbon atoms together with the carbon atoms to which they are bonded form an aromatic ring condensed to W, where the ring formed by the two $R^1$ residues is unsubstituted or mono-, di- or trisubstituted independently of one another by $R^{13}$, $R^{11}$ and $R^{12}$ together with the nitrogen atom to which they are bonded form a saturated or unsaturated 5- to 6-membered monocyclic heterocyclic ring which, in addition to the nitrogen atom carrying $R^{11}$ and $R^{12}$, can contain one or two identical or different ring heteroatoms chosen from oxygen or nitrogen, $R^{13}$ is halogen, —CN, —($C_1$–$C_4$)-alkyl, —($C_1$–$C_4$)-alkyloxy, —$CF_3$, —C(O)—$NH_2$ or —$NH_2$, $R^{10}$ is hydrogen atom or —($C_1$–$C_4$)-alkyl, U is a direct bond, —$(CH_2)_m$—, —$(CH_2)_m$—C(O)—$NR^{10}$—$(CH_2)_n$—, —$(CH_2)_m$—$NR^{10}$—C(O)—$(CH_2)_n$—, —$(CH_2)_m$—C(O)—$(CH_2)_n$—, —$(CH_2)_m$—$SO_2$—$NR^{10}$—$(CH_2)_n$—, or —$(CH_2)_m$—$NR^{10}$—$SO_2$—$(CH_2)_n$—, n and m are are independently of one another identical or different and are the integers zero, 1, 2 or 3, wherein the alkylene residues are unsubstituted or mono-, di- or trisubstituted independently of one another by —($C_1$–$C_4$)-alkyl; —C(O)—OH, —C(O)—O—($C_1$–$C_4$)-alkyl or —C(O)—$NR^4R^5$, $R^4$ and $R^5$ are independently of one another identical or different and are hydrogen atom, —($C_1$–$C_6$)-alkyl, wherein alkyl is unsubstituted or mono-, di- or trisubstituted independently of one another by $R^{13}$, —($C_6$–$C_{14}$)-aryl-($C_1$–$C_4$)-alkyl-, wherein alkyl and aryl independently from one another are unsubstituted or mono-, di- or trisubstituted by $R^{13}$, —($C_6$–$C_{14}$)-aryl-, wherein aryl is unsubstituted or mono-, di- or trisubstituted independently of one another by $R^{13}$, —($C_6$–$C_{14}$)-heteroaryl, wherein heteroaryl is unsubstituted or mono-, di- or trisubstituted independently of one another by $R^{13}$ or —($C_6$–$C_{14}$)-heteroaryl-($C_1$–$C_4$)-alkyl-, wherein alkyl and heteroaryl independently from one another are unsubstituted or mono-, di- or trisubstituted by $R^{13}$, or $R^4$ and $R^5$ together with the nitrogen atom to which they are bonded form a saturated 5- to 7-membered monocyclic heterocyclic ring which, in addition to the nitrogen atom carrying $R^4$ and $R^5$, can contain one or two identical or different ring heteroatoms chosen from oxygen, sulphur and nitrogen; wherein said heterocyclic ring is unsubstituted or mono-, di- or trisubstituted independently of one another by $R^{13}$, G is a direct bond, —$(CH_2)_m$, —$(CH_2)_m$—O—$(CH_2)_n$—, —$(CH_2)_m$—C(O)—$NR^{10}$—$(CH_2)_n$, —$(CH_2)_m$—$NR^{10}$—C(O)—$NR^{10}$—$(CH_2)_n$, —$(CH_2)_m$—$NR^{10}$—C(O)—$(CH_2)_n$, —$(CH_2)_m$—C(O)—$(CH_2)_n$, —$(CH_2)_m$—S—$(CH_2)_n$, —$(CH_2)_m$—$SO_2$—$NR^{10}$—$(CH_2)_n$, —$(CH_2)_m$—$NR^{10}$—$SO_2$—$(CH_2)_n$, —$(CH_2)_m$—$NR^{10}$—$SO_2$—$NR^{10}$—$(CH_2)_n$ or —$(CH_2)_m$—$SO_2$—$(CH_2)_n$, wherein n, m, and $R^{10}$ are as defined above V is
1. a direct bond, 2. —($C_1$–$C_4$)-alkylene, which is branched or unbranched and which is unsubstituted or mono-, di- or trisubstituted independently of one another by halogen, =O, —CN, —NR$^4$R$^5$, —C(O)—OH, —C(O)—O—($C_1$–$C_4$)-alkyl, —SO$_2$—NR$^4$R$^5$, —C(O)—NR$^4$R$^5$ or —($C_1$–$C_4$)-alkylsulfonyl,
3. a 5- to 7-membered cyclic group, containing up to 1, 2, 3 or 4 heteroatoms chosen from nitrogen, sulphur or oxygen, wherein said cyclic group is unsubstituted or mono-, di- or trisubstituted independently of one another by R$^{14}$,
4. a 6- to 14-membered aryl, wherein aryl is unsubstituted or mono-, di- or trisubstituted independently of one another by R$^{14}$, or
5. a 6- to 14-membered heteroaryl, wherein said heteroaryl is unsubstituted or mono-, di- or trisubstituted independently of one another by R$^{14}$, R$^{14}$ is halogen, —OH, —NR$^4$R$^5$, =O, —($C_1$–$C_4$)-alkyl, —($C_1$–$C_4$)-alkoxyl, —NO$_2$, —C(O)—OH, —CN, —C(O)—O—($C_1$–$C_4$)-alkyl, —C(O)—NR$^4$R$^5$, —($C_1$–$C_8$)-alkylsulfonyl, —C(O)—NR$^4$R$^5$, —SO$_2$—NR$^4$R$^5$, —C(O)—NH—($C_1$–$C_8$)-alkyl, —C(O)—NH—[($C_1$–$C_8$)-alkyl]$_2$, —NR$^{10}$—C(O)—NH—($C_1$–$C_8$)-alkyl, —C(O)—NH$_2$ or —NR$^{10}$—C(O)—NH—[($C_1$–$C_8$)-alkyl]$_2$, wherein R$^4$, R$^5$ and R$^{10}$ are as defined above, and M is
1. a hydrogen atom,
2. —($C_1$–$C_4$)-alkyl, wherein alkyl is unsubstituted or mono-, di- or trisubstituted independently of one another by R$^{14}$,
3. —C(O)—NR$^4$R$^5$,
4. —($C_6$–$C_{14}$)-aryl, wherein aryl is unsubstituted or mono-, di- or trisubstituted independently of one another by R$^{14}$,
5. —($C_6$–$C_{14}$)-heteroaryl, wherein heteroaryl is unsubstituted or mono-, di- or trisubstituted independently of one another by R$^{14}$,
6. a 5- to 7-membered cyclic group, wherein said cyclic group is unsubstituted or mono-, di- or trisubstituted independently of one another by R$^{14}$, or
7. a 5- to 7-membered cyclic group, containing up to 1, 2, 3 or 4 heteroatoms chosen from nitrogen, sulphur or oxygen, wherein said cyclic group is unsubstituted or mono-, di- or trisubstituted independently of one another by R$^{14}$, wherein R$^{14}$ is defined above, in all its stereoisomeric forms and mixtures thereof in any ratio, and its physiologically tolerable salts.

In another embodiment, compounds of formula I are defined as follows:

R$^0$ is —($C_6$–$C_{14}$)-aryl, wherein aryl is chosen from the group phenyl, naphthyl, biphenylyl, fluorenyl and anthracenyl and is unsubstituted or mono- or disubstituted independently of one another by R$^2$, or
—($C_6$–$C_{14}$)-heteroaryl, wherein heteroaryl is chosen from the group aziridine, oxirane, azetidine, pyrrole, furan, thiophene, dioxole, imidazole, pyrazole, oxazole, isoxazole, thiazole, isothiazole, 1,2,3-triazole, 1,2,4-triazole, tetrazole, pyridine, pyran, thiopyran, pyridazine, pyrimidine, pyrazine, 1,2-oxazine, 1,3-oxazine, 1,4-oxazine, 1,2-thiazine, 1,3-thiazine, 1,4-thiazine, 1,2,3-triazine, 1,2,4-triazine, 1,3,5-triazine, azepine, 1,2-diazepine, 1,3-diazepine, 1,4-diazepine, indole, isoindole, benzofuran, benzothiophene, 1,3-benzodioxole, indazole, chromane, benzimidazole, benzoxazole, benzothiazole, quinoline, isoquinoline, isochromane, cinnoline, quinazoline, quinoxaline, phthalazine, pteridine pyridyl, pyridopyridines, pyridoimidazoles, pyridopyrimidines and purine and is unsubstituted or mono- or disubstituted independently of one another by R$_2$, R$^2$ is halogen, —CN, —C(O)—NH$_2$, —($C_1$–$C_3$)-alkyl, or —($C_1$–$C_3$)-alkyloxy, wherein the alkyl- or alkyloxy residue is unsubstituted or mono-, di- or trisubstituted independently of one another by an amino residue or a methoxy residue, Q is a direct bond,
Q' is —O—
X is —($C_1$–$C_3$)-alkylene,
W is —($C_6$–$C_{14}$)-aryl, wherein aryl is chosen from the group phenyl, naphthyl, biphenylyl, fluorenyl and anthracenyl, or
—($C_6$–$C_{14}$)-heteroaryl, wherein heteroaryl is chosen from the group aziridine, oxirane, azetidine, pyrrole, furan, thiophene, dioxole, imidazole, pyrazole, oxazole, isoxazole, thiazole, isothiazole, 1,2,3-triazole, 1,2,4-triazole, tetrazole, pyridine, pyran, thiopyran, pyridazine, pyrimidine, pyrazine, 1,2-oxazine, 1,3-oxazine, 1,4-oxazine, 1,2-thiazine, 1,3-thiazine, 1,4-thiazine, 1,2,3-triazine, 1,2,4-triazine, 1,3,5-triazine, azepine, 1,2-diazepine, 1,3-diazepine, 1,4-diazepine, indole, isoindole, benzofuran, benzothiophene, 1,3-benzodioxole, indazole, chromane, benzimidazole, benzoxazole, benzothiazole, quinoline, isoquinoline, isochromane, cinnoline, quinazoline, quinoxaline, phthalazine, pteridine pyridyl, pyridopyridines, pyridoimidazoles, pyridopyrimidines and purine, wherein W is unsubstituted or mono-, di- or trisubstituted independently of one another by R$^1$, provided that Q' and U are in a 1,2- or 1,3-substitution relationship with respect to each other; and further provided that if Q' and U are in a 1,3-substitution relationship, the 2 position is unsubstituted;

R$^1$ is
1. halogen,
2. —NO$_2$,
3. —CN,
4. —NH$_2$,
5. ($C_1$–$C_4$)-alkylamino-, wherein alkyl is unsubstituted or mono-, di- or trisubstituted independently of one another by R$^{13}$,
6. —OH,
7. —SO$_2$—NH$_2$,
8. ($C_1$–$C_4$)-alkyloxy-, wherein alkyl is unsubstituted or mono-, di- or trisubstituted independently of one another by R$^{13}$,
9. ($C_6$–$C_{14}$)-aryl, wherein aryl is chosen from the group phenyl, naphthyl, biphenylyl, fluorenyl and anthracenyl, and is unsubstituted or mono-, di- or trisubstituted independently of one another by R$^{13}$,
10. ($C_1$–$C_4$)-alkyl-, wherein alkyl is unsubstituted or mono-, di- or trisubstituted independently of one another by R$^{13}$,
11. ($C_1$–$C_4$)-alkylsulfonyl-, wherein alkyl is unsubstituted or mono-, di- or trisubstituted independently of one another by R$^{13}$,
12. bis[($C_1$–$C_4$)-alkyl]amino, wherein alkyl is unsubstituted or mono-, di- or trisubstituted independently of one another by R$^{13}$,
13. —C(O)—NH$_2$,
14. —C(O)—OH,
15. —C(O)—($C_1$–$C_4$)-alkyl, wherein alkyl is unsubstituted or mono-, di- or trisubstituted independently of one another by R$^{13}$, 16. —C(O)—NH—($C_1$–$C_4$)-alkyl, wherein alkyl is unsubstituted or mono-, di- or trisubstituted independently of one another by $R^{13}$,
17. —C(O)—NH—[($C_1$–$C_4$)-alkyl]$_2$, wherein alkyl is unsubstituted or mono-, di- or trisubstituted independently of one another by $R^{13}$,
18. —C(NH)—NH$_2$,
19. ureido,
20. —($C_1$–$C_4$)-alkylthio, wherein alkylthio is unsubstituted or mono-, di- or trisubstituted independently of one another by $R^{13}$, or
21. $R^{11}R^{12}N$—, $R^{11}$ and $R^{12}$ together with the nitrogen atom to which they are bonded form a residue chosen from the group piperidine, morpholine, piperazine, thiomorpholine, pyrrolidine, pyrrolidinone, and ketopiperazine;

$R^{13}$ is halogen, —CN, —($C_1$–$C_4$)-alkyl, —($C_1$–$C_4$)-alkyloxy, —CF$_3$, —C(O)—NH$_2$ or —NH$_2$, $R^{10}$ is hydrogen atom or —($C_1$–$C_4$)-alkyl, U is —(CH$_2$)$_m$—C(O)—NR$^{10}$—(CH$_2$)$_n$, wherein n and m are independently of one another identical or different and are the integers zero, 1 or 2, $R^4$ and $R^5$ are independently of one another identical or different and are hydrogen atom, —($C_1$–$C_6$)-alkyl, wherein alkyl is unsubstituted or mono-, di- or trisubstituted independently of one another by $R^{13}$, —($C_6$–$C_{14}$)-aryl-($C_1$–$C_4$)-alkyl-, wherein aryl is as defined for W and alkyl and aryl independently from one another are unsubstituted or mono-, di- or trisubstituted by $R^{13}$, —($C_6$–$C_{14}$)-aryl-, wherein aryl is as defined for W and is unsubstituted or mono-, di- or trisubstituted independently of one another by $R^{13}$, —($C_6$–$C_{14}$)-heteroaryl, wherein heteroaryl is as defined for W and is unsubstituted or mono-, di- or trisubstituted independently of one another by $R^{13}$ or —($C_6$–$C_{14}$)-heteroaryl-($C_1$–$C_4$)-alkyl-, wherein heteroaryl is as defined for W and alkyl and heteroaryl independently from one another are unsubstituted or mono-, di- or trisubstituted by $R^{13}$, or $R^4$ and $R^5$ together with the nitrogen atom to which they are bonded form a residue chosen from the group aziridine, oxirane, azetidine, pyrrole, furan, thiophene, dioxole, imidazole, pyrazole, oxazole, isoxazole, thiazole, isothiazole, 1,2,3-triazole, 1,2,4-triazole, tetrazole, pyridine, pyran, thiopyran, pyridazine, pyrimidine, pyrazine, 1,2-oxazine, 1,3-oxazine, 1,4-oxazine, 1,2-thiazine, 1,3-thiazine, 1,4-thiazine, 1,2,3-triazine, 1,2,4-triazine, 1,3,5-triazine, azepine, 1,2-diazepine, 1,3-diazepine, and 1,4-diazepine, wherein said residue is unsubstituted or mono-, di- or trisubstituted independently of one another by $R^{13}$, G is a direct bond, —(CH$_2$)$_m$, —(CH$_2$)$_m$—O—(CH$_2$)$_n$—, —(CH$_2$)$_m$—C(O)—NR$^{10}$—(CH$_2$)$_n$, —(CH$_2$)$_m$—NR$^{10}$—C(O)—NR$^{10}$—(CH$_2$)$_n$, —(CH$_2$)$_m$—NR$^{10}$—C(O)—(CH$_2$)$_n$, —(CH$_2$)$_m$—C(O)—(CH$_2$)$_n$, —(CH$_2$)$_m$—SO$_2$—NR$^{10}$—(CH$_2$)$_n$, —(CH$_2$)$_m$—NR$^{10}$—SO$_2$—(CH$_2$)$_n$, —(CH$_2$)$_m$—SO$_2$—(CH$_2$)$_n$ or —(CH$_2$)$_m$—NR$^{10}$—SO$_2$—NR$^{10}$—(CH$_2$)$_n$, wherein n, m, and $R^{10}$ are as defined above V is
1. a 5- to 7-membered cyclic group chosen from the group pyrroline, pyrrolidine, tetrahydrofuran, tetrahydrothiophene, dihydropyridine, tetrahydropyridine, piperidine, 1,3-dioxolane, 2-imidazoline, imidazolidine, 4,5-dihydro-1,3-oxazol, 1,3-oxazolidine, 4,5-dihydro-1,3-thiazole, 1,3-thiazolidine, perhydro-1,4-dioxane, piperazine, perhydro-1,4-oxazine (morpholine), perhydro-1,4-thiazine (thiomorpholine), perhydroazepine, indoline, isoindoline, 1,2,3,4-tetrahydroquinoline, and 1,2,3,4-tetrahydroisoquinoline, wherein said cyclic group is unsubstituted or mono-, di- or trisubstituted independently of one another by $R^{14}$,
2. —($C_6$–$C_{14}$)-aryl, wherein aryl is chosen from the group phenyl, naphthyl, biphenylyl, fluorenyl and anthracenyl and is unsubstituted or mono-, di- or trisubstituted independently of one another by $R^{14}$, or
3. —($C_6$–$C_{14}$)-heteroaryl, wherein heteroaryl is chosen from the group aziridine, oxirane, azetidine, pyrrole, furan, thiophene, dioxole, imidazole, pyrazole, oxazole, isoxazole, thiazole, isothiazole, 1,2,3-triazole, 1,2,4-triazole, tetrazole, pyridine, pyran, thiopyran, pyridazine, pyrimidine, pyrazine, 1,2-oxazine, 1,3-oxazine, 1,4-oxazine, 1,2-thiazine, 1,3-thiazine, 1,4-thiazine, 1,2,3-triazine, 1,2,4-triazine, 1,3,5-triazine, azepine, 1,2-diazepine, 1,3-diazepine, 1,4-diazepine, indole, isoindole, benzofuran, benzothiophene, 1,3-benzodioxole, indazole, chromane, benzimidazole, benzoxazole, benzothiazole, quinoline, isoquinoline, isochromane, cinnoline, quinazoline, quinoxaline, phthalazine, pteridine pyridyl, pyridopyridines, pyridoimidazoles, pyridopyrimidines and purine, wherein said heteroaryl is unsubstituted or mono-, di- or trisubstituted independently of one another by $R^{14}$, $R^{14}$ is halogen, —OH, —NR$^4$R$^5$, =O, —($C_1$–$C_4$)-alkyl, —($C_1$–$C_4$)-alkoxyl, —NO$_2$, —C(O)—OH, —CN, —C(O)—O—($C_1$–$C_4$)-alkyl, —C(O)—NR$^4$R$^5$, —($C_1$–$C_8$)-alkylsulfonyl, —C(O)—NH$_2$, —SO$_2$—NR$^4$R$^5$, —C(O)—NH—($C_1$–$C_8$)-alkyl, —C(O)—NH—[($C_1$–$C_8$)-alkyl]$_2$, —NR$^{10}$—C(O)—NH—($C_1$–$C_8$)-alkyl, —C(O)—NH$_2$ or —NR$^{10}$—C(O)—NH—[($C_1$–$C_8$)-alkyl]$_2$, wherein $R^4$, $R^5$ and $R^{10}$ are as defined above, and M is
1. a hydrogen atom,
2. —($C_1$–$C_4$)-alkyl, wherein alkyl is unsubstituted or mono-, di- or trisubstituted independently of one another by $R^{14}$,
3. —C(O)—NR$^4$R$^5$,
4. a 5- to 7-membered cyclic group chosen from the group pyrroline, pyrrolidine, tetrahydrofuran, tetrahydrothiophene, dihydropyridine, tetrahydropyridine, piperidine, 1,3-dioxolane, 2-imidazoline, imidazolidine, 4,5-dihydro-1,3-oxazol, 1,3-oxazolidine, 4,5-dihydro-1,3-thiazole, 1,3-thiazolidine, perhydro-1,4-dioxane, piperazine, perhydro-1,4-oxazine (morpholine), perhydro-1,4-thiazine (thiomorpholine), perhydroazepine, indoline, isoindoline, 1,2,3,4-tetrahydroquinoline, and 1,2,3,4-tetrahydroisoquinoline, wherein said cyclic group is unsubstituted or mono-, di- or trisubstituted independently of one another by $R^{14}$,
5. —($C_6$–$C_{14}$)-aryl, wherein aryl is chosen from the group phenyl, naphthyl, biphenylyl, fluorenyl and anthracenyl and is unsubstituted or mono-, di- or trisubstituted independently of one another by $R^{14}$, or
6. —($C_6$–$C_{14}$)-heteroaryl, wherein heteroaryl is chosen from the group aziridine, oxirane, azetidine, pyrrole, furan, thiophene, dioxole, imidazole, pyrazole, oxazole, isoxazole, thiazole, isothiazole, 1,2,3-triazole, 1,2,4-triazole, tetrazole, pyridine, pyran, thiopyran, pyridazine, pyrimidine, pyrazine, 1,2-oxazine, 1,3-oxazine, 1,4-oxazine, 1,2-thiazine, 1,3-thiazine, 1,4-thiazine, 1,2,3-triazine, 1,2,4-triazine, 1,3,5-triazine, azepine, 1,2-diazepine, 1,3-diazepine, 1,4-diazepine, indole, isoindole, benzofuran, benzothiophene, 1,3-benzodioxole, indazole, chromane, benzimidazole, benzoxazole, benzothiazole, quinoline, isoquinoline, isochromane, cinnoline, quinazoline, quinoxaline, phthalazine, pteridine pyridyl, pyridopyridines, pyridoimidazoles, pyridopyrimidines and purine, wherein said heteroaryl is unsubstituted or mono-, di- or trisubstituted independently of one another by $R^{14}$, in all its stereoisomeric forms and mixtures thereof in any ratio, and its physiologically tolerable salts.

In still another embodiment, the compounds of formula I are defined as follows:

$R^0$ is phenyl, wherein phenyl is unsubstituted or mono- or disubstituted independently of one another by $R^2$, or
pyridyl, wherein pyridyl is unsubstituted or mono-, disubstituted independently of one another by $R^2$, $R^2$ is halogen or —CN, Q is a direct bond Q' is —O—, X is ethylene, W is phenyl or pyridyl, wherein W is unsubstituted or mono-, di- or trisubstituted independently of one another by $R^1$, provided that Q' and U are in a 1,2- or 1,3-substitution relationship with respect to each other and the 2 position is unsubstituted;

$R^1$ is halogen, —$NO_2$, —CN, —$NH_2$, ($C_1$–$C_4$)-alkylamino-, wherein alkyl is unsubstituted or mono-, di- or trisubstituted independently of one another by $R^{13}$, —OH, —$SO_2$—$NH_2$, ($C_1$–$C_4$)-alkyloxy-, wherein alkyl is unsubstituted or mono-, di- or trisubstituted independently of one another by $R^{13}$, ($C_6$–$C_{14}$)-aryl, wherein aryl is chosen from the group phenyl, naphthyl, biphenylyl, fluorenyl and anthracenyl and is unsubstituted or mono-, di- or trisubstituted independently of one another by $R^{13}$, ($C_1$–$C_4$)-alkyl-, wherein alkyl is unsubstituted or mono-, di- or trisubstituted independently of one another by $R^{13}$, ($C_1$–$C_4$)-alkylsulfonyl-, wherein alkyl is unsubstituted or mono-, di- or trisubstituted independently of one another by $R^{13}$, bis[($C_1$–$C_4$)-alkyl]amino, wherein alkyl is unsubstituted or mono-, di- or trisubstituted independently of one another by $R^{13}$, —C(O)—$NH_2$, —C(O)—OH, —C(O)—($C_1$–$C_4$)-alkyl, wherein alkyl is unsubstituted or mono-, di- or trisubstituted independently of one another by $R^{13}$, —C(O)—NH—($C_1$–$C_4$)-alkyl, wherein alkyl is unsubstituted or mono-, di- or trisubstituted independently of one another by $R^{13}$, —C(O)—NH—[($C_1$–$C_4$)-alkyl]$_2$, wherein alkyl is unsubstituted or mono-, di- or trisubstituted independently of one another by $R^{13}$, —C(NH)—$NH_2$, ureido, —($C_1$–$C_4$)-alkylthio, wherein alkylthio is unsubstituted or mono-, di- or trisubstituted independently of one another by $R^{13}$, or $R^{11}R^{12}N$—, $R^{11}$ and $R^{12}$ together with the nitrogen atom to which they are bonded form a residue chosen from the group piperidine, morpholine, piperazine, thiomorpholine, pyrrolidine, pyrrolidinone, and ketopiperazine, $R^{13}$ is halogen, —CN, —($C_1$–$C_4$)-alkyl, —($C_1$–$C_4$)-alkyloxy, —$CF_3$, —C(O)—$NH_2$ or —$NH_2$, $R^{10}$ is hydrogen atom or methyl, U is —$(CH_2)_m$—C(O)—$NR^{10}$—$(CH_2)_n$, wherein n is zero, 1 or 2, m is zero or 1, $R^4$ and $R^5$ are independently of one another identical or different and are hydrogen atom, —($C_1$–$C_6$)-alkyl, wherein alkyl is unsubstituted or mono-, di- or trisubstituted independently of one another by $R^{13}$, —($C_6$–$C_{14}$)-phenyl-($C_1$–$C_4$)-alkyl-, wherein alkyl and phenyl independently from one another are unsubstituted or mono-, di- or trisubstituted by $R^{13}$, —($C_6$–$C_{14}$)-phenyl-, wherein phenyl is unsubstituted or mono-, di- or trisubstituted independently of one another by $R^{13}$, —($C_6$–$C_{14}$)-heteroaryl, wherein heteroaryl is chosen from the group aziridine, oxirane, azetidine, pyrrole, furan, thiophene, dioxole, imidazole, pyrazole, oxazole, isoxazole, thiazole, isothiazole, 1,2,3-triazole, 1,2,4-triazole, tetrazole, pyridine, pyran, thiopyran, pyridazine, pyrimidine, pyrazine, 1,2-oxazine, 1,3-oxazine, 1,4-oxazine, 1,2-thiazine, 1,3-thiazine, 1,4-thiazine, 1,2,3-triazine, 1,2,4-triazine, 1,3,5-triazine, azepine, 1,2-diazepine, 1,3-diazepine, and 1,4-diazepine and is unsubstituted or mono-, di- or trisubstituted independently of one another by $R^{13}$ or —($C_6$–$C_{14}$)-heteroaryl-($C_1$–$C_4$)-alkyl-, wherein alkyl and heteroaryl are as defined above and independently from one another are unsubstituted or mono-, di- or trisubstituted by $R^{13}$, or $R^4$ and $R^5$ together with the nitrogen atom to which they are bonded form a residue chosen from the group aziridine, oxirane, azetidine, pyrrole, furan, thiophene, dioxole, imidazole, pyrazole, oxazole, isoxazole, thiazole, isothiazole, 1,2,3-triazole, 1,2,4-triazole, tetrazole, pyridine, pyran, thiopyran, pyridazine, pyrimidine, pyrazine, 1,2-oxazine, 1,3-oxazine, 1,4-oxazine, 1,2-thiazine, 1,3-thiazine, 1,4-thiazine, 1,2,3-triazine, 1,2,4-triazine, 1,3,5-triazine, azepine, 1,2-diazepine, 1,3-diazepine, and 1,4-diazepine, wherein said residue is unsubstituted or mono-, di- or trisubstituted independently of one another by $R^{13}$, G is a direct bond, —$(CH_2)_m$—, —$(CH_2)_m$—C(O)—$NR^{10}$—$(CH_2)_n$, —$(CH_2)_m$—$NR^{10}$—C(O)—$NR^{10}$—$(CH_2)_n$, —$(CH_2)_m$—$NR^{10}$—C(O)—$(CH_2)_n$, —$(CH_2)_m$—C(O)—$(CH_2)_n$, —$(CH_2)_m$—$SO_2$—$NR^{10}$—$(CH_2)_n$, or —$(CH_2)_m$—$NR^{10}$—$SO_2$—$(CH_2)_n$ wherein n, m, and $R^{10}$ are as defined above V is
1. a 5- to 7-membered cyclic group chosen from the group pyrroline, pyrrolidine, tetrahydrofuran, tetrahydrothiophene, dihydropyridine, tetrahydropyridine, piperidine, 1,3-dioxolane, 2-imidazoline, imidazolidine, 4,5-dihydro-1,3-oxazol, 1,3-oxazolidine, 4,5-dihydro-1,3-thiazole, 1,3-thiazolidine, perhydro-1,4-dioxane, piperazine, perhydro-1,4-oxazine (morpholine), perhydro-1,4-thiazine (thiomorpholine), perhydroazepine, indoline, isoindoline, 1,2,3,4-tetrahydroquinoline, and 1,2,3,4-tetrahydroisoquinoline, wherein said cyclic group is unsubstituted or mono-, di- or trisubstituted independently of one another by $R^{14}$,
2. —($C_6$–$C_{14}$)-aryl, wherein aryl is chosen from the group phenyl, naphthyl, biphenylyl, fluorenyl and anthracenyl and is unsubstituted or mono-, di- or trisubstituted independently of one another by $R^{14}$, or
3. —($C_6$–$C_{14}$)-heteroaryl, wherein heteroaryl is chosen from the group aziridine, oxirane, azetidine, pyrrole, furan, thiophene, dioxole, imidazole, pyrazole, oxazole, isoxazole, thiazole, isothiazole, 1,2,3-triazole, 1,2,4-triazole, tetrazole, pyridine, pyran, thiopyran, pyridazine, pyrimidine, pyrazine, 1,2-oxazine, 1,3-oxazine, 1,4-oxazine, 1,2-thiazine, 1,3-thiazine, 1,4-thiazine, 1,2,3-triazine, 1,2,4-triazine, 1,3,5-triazine, azepine, 1,2-diazepine, 1,3-diazepine, 1,4-diazepine, indole, isoindole, benzofuran, benzothiophene, 1,3-benzodioxole, indazole, chromane, benzimidazole, benzoxazole, benzothiazole, quinoline, isoquinoline, isochromane, cinnoline, quinazoline, quinoxaline, phthalazine, pteridine pyridyl, pyridopyridines, pyridoimidazoles, pyridopyrimidines and purine, wherein said heteroaryl is unsubstituted or mono-, di- or trisubstituted independently of one another by $R^{14}$, $R^{14}$ is halogen, —OH, —$NR^4R^5$, =O, —($C_1$–$C_4$)-alkyl, —($C_1$–$C_4$)-alkoxyl, —C(O)—OH, —CN, —C(O)—O—

$(C_1-C_4)$-alkyl, —C(O)—NR$^4$R$^5$, —$(C_1-C_8)$-alkylsulfonyl, —C(O)—NH$_2$, —SO$_2$—NR$^4$R$^5$, —C(O)—NH—$(C_1-C_8)$-alkyl, —C(O)—NH—[$(C_1-C_8)$-alkyl]$_2$, wherein R$^4$ or R$^5$ are as defined above, and M is
1. a hydrogen atom,
2. —$(C_1-C_4)$-alkyl, wherein alkyl is unsubstituted or mono-, di- or trisubstituted independently of one another by R$^{14}$,
3. —C(O)—NR$^4$R$^5$,
4. a 5- to 7-membered cyclic group chosen from the group pyrroline, pyrrolidine, tetrahydrofuran, tetrahydrothiophene, dihydropyridine, tetrahydropyridine, piperidine, 1,3-dioxolane, 2-imidazoline, imidazolidine, 4,5-dihydro-1,3-oxazol, 1,3-oxazolidine, 4,5-dihydro-1,3-thiazole, 1,3-thiazolidine, perhydro-1,4-dioxane, piperazine, perhydro-1,4-oxazine (morpholine), perhydro-1,4-thiazine (thiomorpholine), perhydroazepine, indoline, isoindoline, 1,2,3,4-tetrahydroquinoline, and 1,2,3,4-tetrahydroisoquinoline, wherein said cyclic group is unsubstituted or mono-, di- or trisubstituted independently of one another by R$^{14}$.
5. —$(C_6-C_{14})$-aryl, wherein aryl is chosen from the group phenyl, naphthyl, biphenylyl, fluorenyl and anthracenyl and is unsubstituted or mono-, di- or trisubstituted independently of one another by R$^{14}$, or
6. —$(C_6-C_{14})$-heteroaryl, wherein heteroaryl is chosen from the group aziridine, oxirane, azetidine, pyrrole, furan, thiophene, dioxole, imidazole, pyrazole, oxazole, isoxazole, thiazole, isothiazole, 1,2,3-triazole, 1,2,4-triazole, tetrazole, pyridine, pyran, thiopyran, pyridazine, pyrimidine, pyrazine, 1,2-oxazine, 1,3-oxazine, 1,4-oxazine, 1,2-thiazine, 1,3-thiazine, 1,4-thiazine, 1,2,3-triazine, 1,2,4-triazine, 1,3,5-triazine, azepine, 1,2-diazepine, 1,3-diazepine, 1,4-diazepine, indole, isoindole, benzofuran, benzothiophene, 1,3-benzodioxole, indazole, chromane, benzimidazole, benzoxazole, benzothiazole, quinoline, isoquinoline, isochromane, cinnoline, quinazoline, quinoxaline, phthalazine, pteridine pyridyl, pyridopyridines, pyridoimidazoles, pyridopyrimidines and purine, wherein said heteroaryl is unsubstituted or mono-, di- or trisubstituted independently of one another by R$^{14}$, in all its stereoisomeric forms and mixtures thereof in any ratio, and its physiologically tolerable salts.

In a another embodiment, the compounds of formula I are defined as follows:

R$^0$ is phenyl, wherein phenyl is unsubstituted or mono- or disubstituted independently of one another by R$^2$, or pyridyl, wherein pyridyl is unsubstituted or mono-, disubstituted independently of one another by R$^2$, R$^2$ is chlorine, Q is a direct bond Q' is —O—, X is ethylene, W is phenyl or pyridyl, wherein W is unsubstituted or mono-, di- or trisubstituted independently of one another by R$^1$, provided that Q' and U are in a 1,2- or 1,3-substitution relationship with respect to each other and the 2 position is unsubstituted;

R$^1$ is halogen, —NO$_2$, —CN, —NH$_2$, $(C_1-C_4)$-alkylamino-, wherein alkyl is unsubstituted or mono-, di- or trisubstituted independently of one another by R$^{13}$, —OH, —SO$_2$—NH$_2$, $(C_1-C_4)$-alkyloxy-, wherein alkyl is unsubstituted or mono-, di- or trisubstituted independently of one another by R$^{13}$, phenyl, wherein phenyl is unsubstituted or mono-, di- or trisubstituted independently of one another by R$^{13}$, $(C_1-C_4)$-alkyl-, wherein alkyl is unsubstituted or mono-, di- or trisubstituted independently of one another by R$^{13}$, $(C_1-C_4)$-alkylsulfonyl-, wherein alkyl is unsubstituted or mono-, di- or trisubstituted independently of one another by R$^{13}$, bis [$(C_1-C_4)$-alkyl]amino, wherein alkyl is unsubstituted or mono-, di- or trisubstituted independently of one another by R$^{13}$, —C(O)—NH$_2$, —C(O)—OH, —C(O)—$(C_1-C_4)$-alkyl, wherein alkyl is unsubstituted or mono-, di- or trisubstituted independently of one another by R$^{13}$, —C(O)—NH—$(C_1-C_4)$-alkyl, wherein alkyl is unsubstituted or mono-, di- or trisubstituted independently of one another by R$^{13}$, —C(O)—NH—[$(C_1-C_4)$-alkyl]$_2$, wherein alkyl is unsubstituted or mono-, di- or trisubstituted independently of one another by R$^{13}$, —C(NH)—NH$_2$, ureido, —$(C_1-C_4)$-alkylthio, wherein alkylthio is unsubstituted or mono-, di- or trisubstituted independently of one another by R$^{13}$, or R$^{11}$R$^{12}$N—, R$^{11}$ and R$^{12}$ together with the nitrogen atom to which they are bonded form a residue chosen from the group pyridine, phenyl, pyrazine, pyrimidine, pyran, triazole, tetrahydropyridine, pyrrolidine, tetrazole, imidazole, imidazolin, furopyridine, cyclic guanidinium, pyrrolopyridine, and oxadiazole, R$^{13}$ is halogen, —CN, —$(C_1-C_4)$-alkyl, —$(C_1-C_4)$-alkyloxy, —CF$_3$, —C(O)—NH$_2$, R$^{10}$ is hydrogen atom or methyl, U is —(CH$_2$)$_m$—C(O)—NR$^{10}$—(CH$_2$)$_n$, wherein n is zero, 1 or 2, m is zero or 1, R$^4$ and R$^5$ are independently of one another identical or different and are hydrogen atom, —$(C_1-C_6)$-alkyl, wherein alkyl is unsubstituted or mono-, di- or trisubstituted independently of one another by R$^{13}$, —$(C_6-C_{14})$-phenyl-$(C_1-C_4)$-alkyl-, wherein alkyl and phenyl independently from one another are unsubstituted or mono-, di- or trisubstituted by R$^{13}$, —$(C_6-C_{14})$-phenyl-, wherein phenyl is unsubstituted or mono-, di- or trisubstituted independently of one another by R$^{13}$, heteroaryl chosen from the group pyridine, pyrazine, pyrimidine, pyran, triazole, tetrahydropyridine, pyrrolidine, tetrazole, imidazole, imidazolin, furopyridine, cyclic guanidinium, pyrrolopyridine, and oxadiazole, wherein heteroaryl is unsubstituted or mono-, di- or trisubstituted independently of one another by R$^{13}$, or R$^4$ and R$^5$ together with the nitrogen atom to which they are bonded form a residue chosen from the group aziridine, oxirane, azetidine, pyrrole, furan, thiophene, dioxole, imidazole, pyrazole, oxazole, isoxazole, thiazole, isothiazole, 1,2,3-triazole, 1,2,4-triazole, tetrazole, pyridine, pyran, thiopyran, pyridazine, pyrimidine, pyrazine, 1,2-oxazine, 1,3-oxazine, 1,4-oxazine, 1,2-thiazine, 1,3-thiazine, 1,4-thiazine, 1,2,3-triazine, 1,2,4-triazine, 1,3,5-triazine, azepine, 1,2-diazepine, 1,3-diazepine, and 1,4-diazepine, wherein said residue is unsubstituted or mono-, di- or trisubstituted independently of one another by R$^{13}$, G is a direct bond, —(CH$_2$)$_m$, —(CH$_2$)$_m$—C(O)—NR$^{10}$—(CH$_2$)$_n$, —(CH$_2$)$_m$—C(O)—(CH$_2$)$_n$, —(CH$_2$)$_m$—NR$^{10}$—C(O)—NR$^{10}$—(CH$_2$)$_n$, —(CH$_2$)$_m$—NR$^{10}$—C(O)—(CH$_2$)$_n$, —(CH$_2$)$_m$—SO$_2$—NR$^{10}$—(CH$_2$)$_n$ or —(CH$_2$)$_m$—NR$^{10}$—SO$_2$—(CH$_2$)$_n$, wherein n, m, and R$^{10}$ are as defined above;

V is tetrahydropyridine, piperidine, phenyl, or piperazine, wherein said groups are unsubstituted or mono-, di- or trisubstituted independently of one another by R$^{14}$;

$R^{14}$ is halogen, —OH, —NR$^4$R$^5$, =O, —(C$_1$–C$_4$)-alkyl, —(C$_1$–C$_4$)-alkoxyl, —C(O)—OH, —CN, —C(O)—O—(C$_1$–C$_4$)-alkyl, —C(O)—NR$^4$R$^5$, —(C$_1$–C$_8$)-alkylsulfonyl, —C(O)—NH$_2$, —SO$_2$—NR$^4$R$^5$, —C(O)—NH—(C$_1$–C$_8$)-alkyl, —C(O)—NH—[(C$_1$–C$_8$)-alkyl]$_2$, wherein $R^4$ or $R^5$ are as defined above, and M is
1. a hydrogen atom,
2. —(C$_1$–C$_4$)-alkyl, wherein alkyl is unsubstituted or mono-, di- or trisubstituted independently of one another by $R^{14}$,
3. —C(O)—NR$^4$R$^5$, or
4. or a residue chosen from the group pyridine, phenyl, pyrazine, pyrimidine, pyran, triazole, tetrahydropyridine, pyrrolidine, tetrazole, imidazole, imidazolin, furopyridine, cyclic guanidinium, pyrrolopyridine, and oxadiazole, in all its stereoisomeric forms and mixtures thereof in any ratio, and its physiologically tolerable salts.

In another embodiment, the invention includes compounds of formula II that are defined as follows:

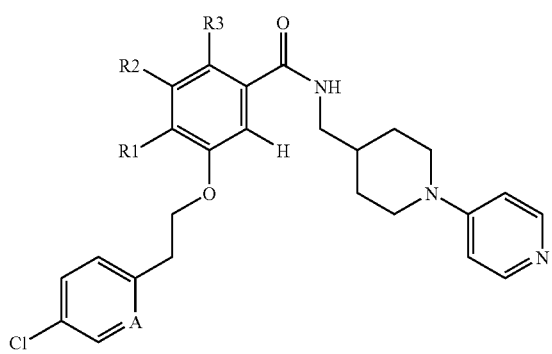

(II)

wherein A is carbon or nitrogen, wherein the carbon can be unsubstituted or substituted by Cl, F, or Br, and R1, R2, and R3 independent from each other are hydrogen, F, Cl, —O—CH$_3$, —CH$_3$, —C(O)—N(CH$_2$—CH$_3$)$_2$, —C(O)—NH$_2$, or —C(O)—NH—CH$_2$-piperidine-pyridine, in all its stereoisomeric forms and mixtures thereof in any ratio, and its physiologically tolerable salts.

In general, the meaning of any group, residue, heteroatom, number, etc. that may occur more than once in the compounds of the formula I, is independent of the meaning of this group, residue, heteroatom, number, etc. in any other occurrence. All groups, residues, heteroatoms, numbers etc. that may occur more than once in the compounds of the formula I may be identical or different.

As used herein, the term alkyl is to be understood in the broadest sense to mean hydrocarbon residues that can be linear, i.e., straight-chain, or branched and which can be acyclic or cyclic residues or comprise any combination of acyclic and cyclic subunits. Further, the term alkyl as used herein expressly includes saturated groups as well as unsaturated groups.

Unsaturated groups may contain one or more, for example one, two or three, double bonds and/or triple bonds, provided that the double bonds are not located within a cyclic alkyl group in such a manner that an aromatic system results. All these statements also apply if an alkyl group occurs as a substituent on another residue, for example in an alkyloxy, alkyloxycarbonyl, or arylalkyl residue. Examples of alkyl residues containing 1, 2, 3, 4, 5, 6, 7 or 8 carbon atoms are methyl, ethyl, propyl, butyl, pentyl, hexyl, heptyl or octyl residues, and the n-isomers of any of these residues, isopropyl, isobutyl, 1-methylbutyl, isopentyl, neopentyl, 2,2-dimethylbutyl, 2-methylpentyl, 3-methylpentyl, isohexyl, sec-butyl, tBu, tert-pentyl, sec-butyl, tert-butyl or tert-pentyl.

Unsaturated alkyl residues include, for example, alkenyl residues such as vinyl, 1-propenyl, 2-propenyl (=allyl), 2-butenyl, 3-butenyl, 2-methyl-2-butenyl, 3-methyl-2-butenyl, 5-hexenyl or 1,3-pentadienyl; or alkynyl residues such as ethynyl, 1-propynyl, 2-propynyl (=propargyl) or 2-butynyl. Alkyl residues can also be unsaturated when they are substituted.

Examples of cyclic alkyl residues are cycloalkyl residues containing 3, 4, 5 or 6 ring carbon atoms like cyclopropyl, cyclobutyl, cyclopentyl or cyclohexyl, which can also be substituted and/or unsaturated. Unsaturated cyclic alkyl groups and unsaturated cycloalkyl groups, e.g., cyclopentenyl or cyclohexenyl, can be bonded via any carbon atom.

Of course, a cyclic alkyl group has to contain at least three carbon atoms, and an unsaturated alkyl group has to contain at least two carbon atoms. Thus, a group like (C$_1$–C$_8$)-alkyl is to be understood as comprising, among others, saturated acyclic (C$_1$–C$_8$)-alkyl, (C$_3$–C$_6$)-cycloalkyl, and unsaturated (C$_2$–C$_8$)-alkyl like (C$_2$–C$_8$)-alkenyl or (C$_2$–C$_8$)-alkynyl. Similarly, a group like (C$_1$–C$_4$)-alkyl is to be understood as comprising, among others, saturated acyclic (C$_1$–C$_4$)-alkyl, and unsaturated (C$_2$–C$_4$)-alkyl like (C$_2$–C$_4$)-alkenyl or (C$_2$–C$_4$)-alkynyl.

Unless stated otherwise, the term alkyl may comprise acyclic saturated hydro-carbon residues that have from one to six carbon atoms and may be linear or branched. A typical group of saturated acyclic alkyl residues is formed by (C$_1$–C$_4$)-alkyl residues like methyl, ethyl, n-propyl, isopropyl, n-butyl, isobutyl, sec-butyl and tBu.

Unless stated otherwise, and irrespective of any specific substituents bonded to alkyl groups that are indicated in the definition of the compounds of the formula I, alkyl groups can generally be unsubstituted or substituted by one or more, for example one, two, or three, identical or different substituents. Any kind of substituents present in substituted alkyl residues can be present in any desired position provided that the substitution does not lead to an unstable molecule. Examples of substituted alkyl residues are alkyl residues in which one or more, for example 1, 2, or 3, hydrogen atoms are replaced with halogen atoms, e.g., fluorine atoms.

The term mono- or bicyclic 5- to 14-membered aryl group includes, for example, phenyl, biphenyl or napthyl.

The term mono- or bicyclic 5- to 14-membered heteroaryl refers to (C$_5$–C$_{14}$)-aryl in which one or more of the 5 to 10 ring carbon atoms are replaced by heteroatoms such as nitrogen, oxygen or sulphur. Examples include pyridyl; such as 2-pyridyl, 3-pyridyl or 4-pyridyl; pyrrolyl; such as 2-pyrrolyl and 3-pyrrolyl; furyl; such as 2-furyl and 3-furyl; thienyl; such as 2-thienyl and 3-thienyl; imidazolyl, pyrazolyl, oxazolyl, isoxazolyl, thiazolyl, isothiazolyl, tetrazolyl, pyridazinyl, pyrazinyl, pyrimidinyl, indolyl, isoindolyl, indazolyl, phthalazinyl, quinolyl, isoquinolyl or quinoxalinyl or phenylpyridyl.

The terms $R^{11}$ and $R^{12}$, together with the nitrogen atom to which they are bonded, form a saturated or unsaturated 5- to 6-membered monocyclic heterocyclic ring, and refer to, e.g., pyrrol, piperidine, pyrrolidine, morpholine, piperazine, pyridine, pyrimidine, imidazole or thiomorpholine.

The term aryl refers to a monocyclic or polycyclic hydrocarbon residue in which at least one carbocyclic ring is present that has a conjugated pi electron system. In a ($C_6$–$C_{14}$)-aryl residue, 6 to 14 ring carbon atoms are present. Examples of ($C_6$–$C_{14}$)-aryl residues include phenyl, naphthyl, biphenylyl, fluorenyl or anthracenyl. Unless stated otherwise, and irrespective of any specific substituents bonded to aryl groups that are indicated in the definition of the compounds of the formula I, aryl residues, (e.g., phenyl, naphthyl or fluorenyl), can in general be unsubstituted or substituted by one or more, for example one, two or three, identical or different substituents. Aryl residues can be bonded via any desired position, and in substituted aryl residues the substituents can be located in any desired position.

Unless stated otherwise, and irrespective of any specific substituents bonded to aryl groups that are indicated in the definition of the compounds of the formula I, substituents that can be present in substituted aryl groups are, for example, ($C_1$–$C_8$)-alkyl; ($C_1$–$C_4$)-alkyl, such as methyl, ethyl or tBu, hydroxyl; ($C_1$–$C_8$)-alkyloxy; ($C_1$–$C_4$)-alkyloxy, such as methoxy, ethoxy or tert-butoxy, methylenedioxy, ethylenedioxy; F; Cl; Br; I; cyano; nitro; trifluoromethyl; trifluoromethoxy; hydroxymethyl; formyl; acetyl; amino; mono- or di-($C_1$–$C_4$)-alkylamino; (($C_1$–$C_4$)-alkyl) carbonylamino like acetylamino; hydroxycarbonyl; (($C_1$–$C_4$)-alkyloxy)carbonyl; carbamoyl; benzyl optionally substituted in the phenyl group; optionally substituted phenyl; optionally substituted phenoxy; or benzyloxy optionally substituted in the phenyl group. A substituted aryl group that is present in a specific position of the compounds of formula I can independently of other aryl groups be substituted by substituents chosen from any desired subgroup of the substituents listed before and/or in the specific definition of that group. For example, a substituted aryl group may be substituted by one or more identical or different substituents chosen from ($C_1$–$C_4$)-alkyl, hydroxyl, ($C_1$–$C_4$)-alkyloxy, F, Cl, Br, I, cyano, nitro, trifluoromethyl, amino, phenyl, benzyl, phenoxy and benzyloxy. In general, not more than two nitro groups are present in the compounds of the formula I.

In monosubstituted phenyl residues the substituent can be located in the 2-position, the 3-position or the 4-position, with the 3-position and the 4-position being commonly used. If a phenyl group carries two substituents, they can be located in 2,3-position, 2,4-position, 2,5-position, 2,6-position, 3,4-position or 3,5-position. In phenyl residues carrying three substituents the substituents can be located in 2,3,4-position, 2,3,5-position, 2,3,6-position, 2,4,5-position, 2,4,6-position, or 3,4,5-position. Naphthyl residues can be 1-naphthyl and 2-naphthyl. In substituted naphthyl residues the substituents can be located in any positions, for example, in monosubstituted 1-naphthyl residues in the 2-, 3-, 4-, 5-, 6-, 7-, or 8-position and in monosubstituted 2-naphthyl residues in the 1-, 3-, 4-, 5-, 6-, 7-, or 8-position. Biphenylyl residues can be 2-biphenylyl, 3-biphenylyl and 4-biphenylyl. Fluorenyl residues can be 1-, 2-, 3-, 4- or 9-fluorenyl. In monosubstituted fluorenyl residues bonded via the 9-position the substituent is typically present in the 1-, 2-, 3- or 4-position.

A 4–15 membered mono- or polycyclic group, which can contain, zero, one, two, three or four heteroatoms, such as nitrogen, sulphur, or oxygen, comprises groups containing 4 to 15 ring atoms in the parent monocyclic or bicyclic carbocyclic or heterocyclic ring system. In monocyclic groups, the carbocyclic or heterocyclic ring may be a 5-membered, 6-membered or 7-membered ring. In one embodiment, it is a 5-membered or 6-membered ring. In bicyclic groups, two fused rings may be present in which one is a 5-membered ring or 6-membered carbocyclic or heterocyclic ring, and the other is a 5-membered or 6-membered heterocyclic or carbocyclic ring (i.e., the bicyclic ring typically contains 8, 9 or 10 ring atoms, generally 9 or 10 ring atoms). It comprises saturated carbocyclic or heterocyclic ring systems that do not contain any double bonds within the rings, as well as mono-unsaturated and poly-unsaturated carbocyclic or heterocyclic ring systems that contain one or more, for example one, two, three, four or five, double bonds within the rings provided that the resulting system is stable. Unsaturated rings may be non-aromatic or aromatic, i.e., double bonds within the rings in this group may be arranged in such a manner that a conjugated pi electron system results. Aromatic rings in a group may be 5-membered or 6-membered rings, i.e., aromatic groups in a group contain 5 to 10 ring atoms. Aromatic rings in this group thus comprise 5-membered and 6-membered monocyclic carbocycles or heterocycles and bicyclic carbocycles or heterocycles composed of two 5-membered rings, one 5-membered ring and one 6-membered ring, or two 6-membered rings. In bicyclic aromatic groups one or both rings may contain heteroatoms. Aromatic groups may also be referred to by the customary term aryl or heteroaryl for which all the definitions and explanations above and below correspondingly apply.

Examples of carbocyclic groups include cyclopropyl, cyclobutyl, cyclopentyl, cyclohexyl, cycloheptyl and cyclooctyl, decahydronaphthaline, twistan (=tricyclo [4.4.0.0$^{3,8}$]decan), adamantane (=tricyclo[3.3.1.1$^{3,7}$]decan), noradamantane (=tricyclo[3.3.1.0$^{3,7}$]nonane), tricyclo [2.2.1.0$^{2,6}$]heptane, tricyclo[5.3.2.0$^{4,9}$]dodecane, tricyclo [5.4.0.0$^{2,9}$]undecane or tricyclo[5.5.1.0$^{3,11}$]tridecane.

In heterocyclic groups, 1, 2, 3 or 4 identical or different ring heteroatoms chosen from nitrogen, oxygen and sulphur may be present. In these groups, one or two identical or different heteroatoms may be chosen from nitrogen, oxygen and sulphur. The ring heteroatoms may be present in any desired number and in any position with respect to each other provided that the resulting heterocyclic system is known in the art and is stable and suitable as a subgroup in a drug substance. Examples of parent structures of heterocycles from which the 4–15 membered mono- or polycyclic group can be derived are aziridine, oxirane, azetidine, pyrrole, furan, thiophene, dioxole, imidazole, pyrazole, oxazole, isoxazole, thiazole, isothiazole, 1,2,3-triazole, 1,2,4-triazole, tetrazole, pyridine, pyran, thiopyran, pyridazine, pyrimidine, pyrazine, 1,2-oxazine, 1,3-oxazine, 1,4-oxazine, 1,2-thiazine, 1,3-thiazine, 1,4-thiazine, 1,2,3-triazine, 1,2,4-triazine, 1,3,5-triazine, azepine, 1,2-diazepine, 1,3-diazepine, 1,4-diazepine, indole, isoindole, benzofuran, benzothiophene, 1,3-benzodioxole, indazole, benzimidazole, benzoxazole, benzothiazole, quinoline, isoquinoline, chromane, isochromane, cinnoline, quinazoline, quinoxaline, phthalazine, pyridoimidazoles, pyridopyridines, pyridopyrimidines, purine, pteridine etc. as well as ring systems that result from the listed heterocycles by fusion (or condensation) of a carbocyclic ring, for example benzo-fused, cyclopenta-fused, cyclohexa-fused or cyclohepta-fused derivatives of these heterocycles.

The fact that many of the before-listed names of heterocycles are the chemical names of unsaturated or aromatic ring systems does not imply that the, 4–15 membered mono- or polycyclic group could only be derived from the respective unsaturated ring system. The names here only serve to describe the ring systems by ring size, the number of the heteroatoms, and their relative positions.

As explained above, the 4–15 membered mono- or polycyclic groups can be saturated or partially unsaturated or aromatic, and can thus be derived not only from the beforelisted heterocycles themselves but also from all their partially or completely hydrogenated analogues, and their more highly unsaturated analogues if desired. As examples of completely or partially hydrogenated analogues of the before-listed heterocycles from which this group may be derived, the following are useful examples: pyrroline, pyrrolidine, tetrahydrofuran, tetrahydrothiophene, dihydropyridine, tetrahydropyridine, piperidine, 1,3-dioxolane, 2-imidazoline, imidazolidine, 4,5-dihydro-1,3-oxazol, 1,3-oxazolidine, 4,5-dihydro-1,3-thiazole, 1,3-thiazolidine, perhydro-1,4-dioxane, piperazine, perhydro-1,4-oxazine (=morpholine), perhydro-1,4-thiazine (=thiomorpholine), perhydroazepine, indoline, isoindoline, 1,2,3,4-tetrahydroquinoline, 1,2,3,4-tetrahydroisoquinoline, etc.

The 4–15 membered mono- or polycyclic group may be bonded via any ring carbon atom, and in the case of nitrogen heterocycles via any suitable ring nitrogen atom. Thus, for example, a pyrrolyl residue can be 1-pyrrolyl, 2-pyrrolyl or 3-pyrrolyl, a pyrrolidinyl residue can be pyrrolidin-1-yl (=pyrrolidino), pyrrolidin-2-yl or pyrrolidin-3-yl, a pyridinyl residue can be pyridin-2-yl, pyridin-3-yl or pyridin-4-yl, a piperidinyl residue can be piperidin-1-yl (=piperidino), piperidin-2-yl, piperidin-3-yl or piperidin-4-yl. Furyl can be 2-furyl or 3-furyl, thienyl can be 2-thienyl or 3-thienyl, imidazolyl can be imidazol-1-yl, imidazol-2-yl, imidazol-4-yl or imidazol-5-yl, 1,3-oxazolyl can be 1,3-oxazol-2-yl, 1,3-oxazol-4-yl or 1,3-oxazol-5-yl, 1,3-thiazolyl can be 1,3-thiazol-2-yl, 1,3-thiazol-4-yl or 1,3-thiazol-5-yl, pyrimidinyl can be pyrimidin-2-yl, pyrimidin-4-yl (=6-pyrimidinyl) or 5-pyrimidinyl, piperazinyl can be piperazin-1-yl (=piperazin-4-yl=piperazino) or piperazin-2-yl. Indolyl can be indol-1-yl, indol-2-yl, indol-3-yl, indol-4-yl, indol-5-yl, indol-6-yl or indol-7-yl. Similarly benzimidazolyl, benzoxazolyl and benzothiazol residues can be bonded via the 2-position and via any of the positions 4, 5, 6, and 7. Quinolinyl can be quinolin-2-yl, quinolin-3-yl, quinolin-4-yl, quinolin-5-yl, quinolin-6-yl, quinolin-7-yl or quinolin-8-yl, isoqinolinyl can be isoquinol-1-yl, isoquinolin-3-yl, isoquinolin-4-yl, isoquinolin-5-yl, isoquinolin-6-yl, isoquinolin-7-yl or isoquinolin-8-yl. In addition to being bonded via any of the positions indicated for quinolinyl and isoquinolinyl, 1,2,3,4-tetrahydroquinolinyl and 1,2,3,4-tetrahydroisoquinolinyl can also be bonded via the nitrogen atoms in 1-position and 2-position, respectively.

Unless stated otherwise, and irrespective of any specific substituents bonded to the 4–15 membered mono- or polycyclic group or any other heterocyclic groups that are indicated in the definition of the compounds of the formula I, the 4–15 membered mono- or polycyclic group can be unsubstituted or substituted on ring carbon atoms with one or more, for example one, two, three, four or five, identical or different substituents like $(C_1-C_8)$-alkyl, $(C_1-C_4)$-alkyl, $(C_1-C_8)$-alkyloxy, $(C_1-C_4)$-alkyloxy, $(C_1-C_4)$-alkylthio, halogen, nitro, amino $((C_1-C_4)$-alkyl)carbonylamino like acetylamino, trifluoromethyl, trifluoromethoxy, hydroxyl, oxo, hydroxy-$(C_1-C_4)$-alkyl such as, for example, hydroxymethyl, 1-hydroxyethyl, 2-hydroxyethyl, methylenedioxy, ethylenedioxy, formyl, acetyl, cyano, aminosulfonyl, methylsulfonyl, hydroxycarbonyl, aminocarbonyl, $(C_1-C_4)$-alkyloxycarbonyl, optionally substituted phenyl, optionally substituted phenoxy, benzyl optionally substituted in the phenyl group, benzyloxy optionally substituted in the phenyl group, etc. The substituents can be present in any desired position provided that a stable molecule results.

Of course an oxy group cannot be present in an aromatic ring. Each suitable ring nitrogen atom in the 4–15 membered mono- or polycyclic group can independently of each other be unsubstituted, (i.e. carry a hydrogen atom), or can be substituted, (i.e. carry a substituent like $(C_1-C_8)$-alkyl, for example $(C_1-C_4)$-alkyl such as methyl or ethyl, optionally substituted phenyl, phenyl-$(C_1-C_4)$-alkyl, for example benzyl, optionally substituted in the phenyl group, hydroxy-$(C_2-C_4)$-alkyl such as, for example 2-hydroxyethyl, acetyl or another acyl group, methylsulfonyl or another sulfonyl group, aminocarbonyl, $(C_1-C_4)$-alkyloxycarbonyl, etc.) In general, in the compounds of the formula I, nitrogen heterocycles can also be present as N-oxides or as quaternary salts. Ring sulphur atoms can be oxidized to the sulfoxide or to the sulfone. Thus, a tetrahydrothienyl residue, for example, may be present as S,S-dioxotetrahydrothienyl residue; or a thiomorpholinyl residue, such as thiomorpholin-4-yl, may be present as 1-oxo-thiomorpholin-4-yl or 1,1-dioxo-thiomorpholin-4-yl. A substituted 4–15 membered mono- or polycyclic group that can be present in a specific position of the compounds of formula I can independently of other groups be substituted by substituents chosen from any desired subgroup of the substituents listed before and/or in the definition of that group.

Examples for a 5 to 7-membered monocyclic heterocyclic ring, containing at least one nitrogen atom and which is optionally substituted by oxygen include piperidine, morpholine, piperazine, thiomorpholine, pyrrolidine, pyrrolidinone, and ketopiperazine.

A 3–7 membered monocyclic group, containing zero, one, two, three or four heteroatoms, such as nitrogen, sulphur or oxygen, comprises groups containing 3 to 7 ring atoms in the parent monocyclic carbocyclic or heterocyclic ring system. In one embodiment, the carbocyclic or heterocyclic ring is a 5-membered or a 6-membered ring.

The compounds may also comprise saturated carbocyclic or heterocyclic ring systems that do not contain any double bonds within the rings, as well as mono-unsaturated and poly-unsaturated carbocyclic or heterocyclic ring systems that contain one or more, (e.g., one, two or three double bonds within the ring) provided that the resulting ring system is stable.

Unsaturated rings may be non-aromatic or aromatic, i.e., double bonds within the rings in this group may be arranged in such a manner that a conjugated pi electron system results. Aromatic rings in this group comprise 5-membered and 6-membered monocyclic carbocycles or heterocycles. Aromatic groups may also be referred to by the customary term aryl or heteroaryl, for which all the definitions and explanations above and below correspondingly apply.

Examples of carbocyclic groups include cyclopropyl, cyclobutyl, cyclopentyl, cyclohexyl, cycloheptyl and cyclooctyl.

In heterocyclic groups, 1, 2, 3 or 4 identical or different ring heteroatoms chosen from nitrogen, oxygen and sulphur are present. In these groups, one or two identical or different heteroatoms chosen from nitrogen, oxygen and sulphur are present. The ring heteroatoms can be present in any desired number and in any position with respect to each other provided that the resulting heterocyclic system is known in the art and is stable and suitable as a subgroup in a drug substance. Examples of parent structures of heterocycles from which the 3–7 membered monocyclic group can be derived are aziridine, oxirane, azetidine, pyrrole, furan, thiophene, dioxole, imidazole, pyrazole, oxazole, isoxazole, thiazole, isothiazole, 1,2,3-triazole, 1,2,4-triazole, tetrazole, pyridine, pyran, thiopyran, pyridazine, pyrimidine, pyrazine, 1,2-oxazine, 1,3-oxazine, 1,4-oxazine, 1,2-thiazine, 1,3-thiazine, 1,4-thiazine, 1,2,3-triazine, 1,2,4-triazine, 1,3,5-triazine, azepine, 1,2-diazepine, 1,3-diazepine, 1,4-diazepine etc.

The fact that many of the before-listed names of heterocycles are the chemical names of unsaturated or aromatic ring systems does not imply that, the 3–7 membered monocyclic group can only be derived from the respective unsaturated ring system. The names here only serve to describe the ring system by ring size, the number of heteroatoms, and their relative positions. As explained above, the 3–7 membered monocyclic group can be saturated or partially unsaturated or aromatic; and can thus be derived not only from the before-listed heterocycles themselves but also from all their partially or completely hydrogenated analogues and also from their more highly unsaturated analogues, if desired. Completely or partially hydrogenated analogues of the before-listed heterocycles from which this group may be derived include: pyrroline, pyrrolidine, tetrahydrofuran, tetrahydrothiophene, dihydropyridine, tetrahydropyridine, piperidine, 1,3-dioxolane, 2-imidazoline, imidazolidine, 4,5-dihydro-1,3-oxazol, 1,3-oxazolidine, 4,5-dihydro-1,3-thiazole, 1,3-thiazolidine, perhydro-1,4-dioxane, piperazine, perhydro-1,4-oxazine (=morpholine), perhydro-1,4-thiazine (=thiomorpholine), perhydroazepine etc.

The 3–7 membered monocyclic group may be bonded via any ring carbon atom, and in the case of nitrogen heterocycles via any suitable ring nitrogen atom. Thus, for example, a pyrrolyl residue can be 1-pyrrolyl, 2-pyrrolyl or 3-pyrrolyl, a pyrrolidinyl residue can be pyrrolidin-1-yl (=pyrrolidino), pyrrolidin-2-yl or pyrrolidin-3-yl, a pyridinyl residue can be pyridin-2-yl, pyridin-3-yl or pyridin-4-yl, a piperidinyl residue can be piperidin-1-yl (=piperidino), piperidin-2-yl, piperidin-3-yl or piperidin-4-yl. Furyl can be 2-furyl or 3-furyl, thienyl can be 2-thienyl or 3-thienyl, imidazolyl can be imidazol-1-yl, imidazol-2-yl, imidazol-4-yl or imidazol-5-yl, 1,3-oxazolyl can be 1,3-oxazol-2-yl, 1,3-oxazol-4-yl or 1,3-oxazol-5-yl, 1,3-thiazolyl can be 1,3-thiazol-2-yl, 1,3-thiazol-4-yl or 1,3-thiazol-5-yl, pyrimidinyl can be pyrimidin-2-yl, pyrimidin-4-yl (=6-pyrimidinyl) or 5-pyrimidinyl, piperazinyl can be piperazin-1-yl (=piperazin-4-yl=piperazino) or piperazin-2-yl. Unless stated otherwise, and irrespective of any specific substituents bonded to the 3–7 membered monocyclic group or any other heterocyclic groups that are indicated in the definition of the compounds of the formula I, the 3–7 membered rings can be unsubstituted or substituted on ring carbon atoms with one or more, for example one, two, three, four or five, identical or different substituents like $(C_1-C_8)$-alkyl, $(C_1-C_4)$-alkyl, $(C_1-C_8)$-alkyloxy, $(C_1-C_4)$-alkyloxy, $(C_1-C_4)$-alkylthio, halogen, nitro, amino, $((C_1-C_4)$-alkyl)carbonylamino like acetylamino, trifluoromethyl, trifluoromethoxy, hydroxyl, oxo, hydroxy-$(C_1-C_4)$-alkyl such as, for example, hydroxymethyl or 1-hydroxyethyl or 2-hydroxyethyl, methylenedioxy, ethylenedioxy, formyl, acetyl, cyano, aminosulfonyl, methylsulfonyl, hydroxycarbonyl, aminocarbonyl, $(C_1-C_4)$-alkyloxycarbonyl, optionally substituted phenyl, optionally substituted phenoxy, benzyl optionally substituted in the phenyl group, benzyloxy optionally substituted in the phenyl group, etc. The substituents can be present in any desired position provided that a stable molecule results. Of course an oxy group cannot be present in an aromatic ring. Each suitable ring nitrogen atom in the 3–7 membered monocyclic group can independently of each other be unsubstituted (i.e. carry a hydrogen atom), or can be substituted, (i.e. carry a substituent like $(C_1-C_8)$-alkyl, for example $(C_1-C_4)$-alkyl such as methyl or ethyl, optionally substituted phenyl, phenyl-$(C_1-C_4)$-alkyl, for example benzyl, optionally substituted in the phenyl group, hydroxy-$(C_2-C_4)$-alkyl such as, for example 2-hydroxyethyl, acetyl or another acyl group, methylsulfonyl or another sulfonyl group, aminocarbonyl, $(C_1-C_4)$-alkyloxycarbonyl, etc.) In general, in the compounds of the formula I, nitrogen heterocycles can also be present as N-oxides or as quaternary salts. Ring sulphur atoms can be oxidized to the sulfoxide or to the sulfone. Thus, for example a tetrahydrothienyl residue may be present as a S,S-dioxotetrahydrothienyl residue; or a thiomorpholinyl residue like thiomorpholin-4-yl may be present as 1-oxo-thiomorpholin-4-yl or 1,1-dioxo-thiomorpholin-4-yl. A substituted 3–7 membered monocyclic group that can be present in a specific position of the compounds of formula I can independently of other groups be substituted by substituents chosen from any desired subgroup of the substituents listed before and/or in the definition of that group.

Halogen refers to fluorine, chlorine, bromine or iodine; typically, fluorine, chlorine or bromine is used. In one embodiment, the halogen is, chlorine or bromine.

Optically active carbon atoms present in the compounds of the formula I can independently of each other have R configuration or S configuration. The compounds of the formula I can be present in the form of pure enantiomers, pure diastereomers, or a mixture of enantiomers and/or diastereomers; for example, in the form of racemates. The present invention relates to pure enantiomers and mixtures of enantiomers as well as to pure diastereomers and mixtures of diastereomers. The invention comprises mixtures of two or more stereoisomers of the compounds of formula I; It also comprises all ratios of the stereoisomers in the mixtures. In case the compounds of formula I can be present as E isomers or Z isomers (or cis isomers or trans isomers) the invention relates both to pure E isomers, pure Z isomers, and to E/Z mixtures in all ratios. The invention also comprises all tautomeric forms of the compounds of the formula I.

Diastereomers, including E/Z isomers, can be separated into the individual isomers, for example, by chromatography. Racemates can be separated into the two enantiomers by customary methods, for example by chromatography on chiral phases or by resolution, for example by crystallisation of diastereomeric salts obtained with optically active acids or bases. Stereochemically uniform compounds of the formula I can also be obtained by employing stereochemically uniform starting materials or by using stereoselective reactions.

The choice of incorporating into a compound of the formula I a building block with R configuration or S configuration, or in the case of an amino acid unit present in a compound of the formula I of incorporating a building block designated as D-amino acid or L-amino acid, can depend, for example, on the desired characteristics of the compound of the formula I. For example, the incorporation of a D-amino acid building block can confer increased stability in vitro or in vivo. The incorporation of a D-amino acid building block also can achieve a desired increase or decrease in the pharmacological activity of the compound. In some cases it can be desirable to allow the compound to remain active for only a short period of time. In such cases, the incorporation of an L-amino acid building block in the compound can allow endogenous peptidases in an individual to digest the compound in vivo, thereby limiting the individual's exposure to the active compound. A similar effect may also be observed in the compounds of the invention by changing the configuration in another building block from S configuration to R configuration or vice versa. By taking into consideration the medical needs one skilled in the art can determine the desirable characteristics, for example a favourable stereochemistry, of the required compound of the invention.

Physiologically tolerable salts of the compounds of formula I are non-toxic salts that are physiologically acceptable, in particular pharmaceutically utilisable salts. Such salts of compounds of the formula I containing acidic groups, for example a carboxyl group COOH, are for example alkali metal salts or alkaline earth metal salts such as sodium salts, potassium salts, magnesium salts and calcium salts, and also salts with physiologically tolerable quaternary ammonium ions such as tetramethylammonium or tetraethylammonium, and acid addition salts with ammonia and physiologically tolerable organic amines, such as methylamine, dimethylamine, trimethylamine, ethylamine, triethylamine, ethanolamine or tris-(2-hydroxyethyl)amine. Basic groups contained in the compounds of the formula I, for example amino groups or guanidino groups, form acid addition salts, for example with inorganic acids such as hydrochloric acid, hydrobromic acid, sulphuric acid, nitric acid or phosphoric acid, or with organic carboxylic acids and sulfonic acids such as formic acid, acetic acid, oxalic acid, citric acid, lactic acid, malic acid, succinic acid, malonic acid, benzoic acid, maleic acid, fumaric acid, tartaric acid, methanesulfonic acid or p-toluenesulfonic acid. Compounds of the formula I, which simultaneously contain a basic group and an acidic group, for example, a guanidino group and a carboxyl group, can also be present as zwitterions (betaines), which are likewise included in the present invention.

Salts of compounds of the formula I can be obtained by customary methods known to those skilled in the art, for example by combining a compound of the formula I with an inorganic or organic acid or base in a solvent or dispersant, or from other salts by cation exchange or anion exchange. The present invention also includes all salts of the compounds of the formula I which, because of low physiologically tolerability, are not directly suitable for use in pharmaceuticals but are suitable, for example, as intermediates for carrying out further chemical modifications of the compounds of the formula I or as starting materials for the preparation of physiologically tolerable salts. The present invention furthermore includes all solvates of compounds of the formula I, for example hydrates or adducts with alcohols.

The invention also includes derivatives and modifications of the compounds of the formula I, for example prodrugs, protected forms, and other physiologically tolerable derivatives, as well as active metabolites of the compounds of the formula I. The invention relates, for example, to prodrugs and protected forms of the compounds of the formula I that can be converted into compounds of the formula I under physiological conditions. Suitable prodrugs for the compounds of the formula I, i.e. chemically modified derivatives of the compounds of the formula I having properties that are improved in a desired manner, for example with respect to solubility, bioavailability or duration of action, are known to those skilled in the art. More detailed information relating to prodrugs is found in standard literature (see, for example, Design of Prodrugs, H. Bundgaard (ed.), Elsevier, 1985, Fleisher et al., Advanced Drug Delivery Reviews 19 (1996) 115–130; or H. Bundgaard, Drugs of the Future 16 (1991) 443, which are all incorporated herein by reference). Suitable prodrugs for the compounds of the formula I include acyl prodrugs and carbamate prodrugs of acylatable, nitrogen-containing groups (such as amino guanidino groups), and ester prodrugs and amide prodrugs of carboxylic acid groups that may be present in compounds of the formula I. In the acyl prodrugs and carbamate prodrugs, one or more (for example one or two) hydrogen atoms on nitrogen atoms in such groups are replaced with an acyl group or a carbamate, such as a $(C_1-C_6)$-alkyloxycarbonyl group. Suitable acyl groups and carbamate groups for acyl prodrugs and carbamate prodrugs include, for example, the groups $R^{p1}$—CO— and $R^{p2}$O—CO—, in which $R^{p1}$ is hydrogen, $(C_1-C_{18})$-alkyl, $(C_3-C_8)$-cycloalkyl, $(C_3-C_8)$-cycloalkyl-$(C_1-C_4)$-alkyl-, $(C_6-C_{14})$-aryl, Het-, $(C_6-C_{14})$-aryl-$(C_1-C_4)$-alkyl- or Het-$(C_1-C_4)$-alkyl- and in which $R^{p2}$ has the meanings indicated for $R^{p1}$ with the exception of hydrogen.

The present invention also relates to processes of preparation by which the compounds of the formula I are obtainable, and which comprises carrying out one or more of the synthesis steps described below. The compounds of the formula I can generally be prepared using procedures described below, together with synthetic methods known to those skilled in the art of organic synthesis (see, e.g., J. March, Advanced Organic Chemistry, Fourth Edition, John Wiley & Sons, 1992), or variations thereon as appreciated by those skilled in the art. For example, in the course of a convergent synthesis, linkage of two or more fragments that can be derived retrosynthetically from the formula I and the synthesis of those fragments is known to those skilled in the art. In the course of the preparation of the compounds of the formula I it can generally be advantageous or necessary to introduce functional groups that could avoid undesired reactions or side reactions in the respective synthesis step, in the form of precursor groups that are later converted into the desired functional groups, or to temporarily block functional groups by a protective group strategy suited to the synthesis problem. Such strategies are well known to those skilled in the art (see, for example, Greene and Wuts, Protective Groups in Organic Synthesis, Wiley, 1991 or P. Kocienski, Protecting Groups, Thieme 1994). Examples of precursor groups include nitro groups and cyano groups, which can later be converted by reduction, for example by catalytic hydrogenation, into amino groups and aminomethyl groups, respectively. Protective groups can also have the meaning of a solid phase, and cleavage from the solid phase results in the removal of the protective group. The use of such techniques is known to those skilled in the art (Burgess K (Ed.) Solid Phase Organic Synthesis, New York: Wiley, 2000). For example, a phenolic hydroxyl group can be attached to a trityl-polystyrene resin, which serves as a protecting group, and the molecule may be cleaved from this resin by treatment with TFA at a later stage of the synthesis.

For example, for the preparation of one of the compounds of the formula I, in which W is phenyl, and in which U has the meaning of —$(CH_2)_0C(O)NR^{10}(CH_2)_1$—, a building block of the formula XI,

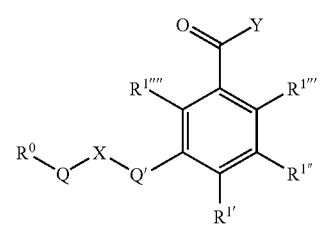

XI in which $R^0$, Q, Q', X, are as defined above for the compounds of the formula I but functional groups of the formula XI can optionally also be present in the form of precursor groups or can be protected by protective groups known to those skilled in the art, e.g. an amino group can be protected with a tert.-butyloxycarbonyl group or a benzyloxycarbonyl group. $R^{1'}$, $R^{1''}$, $R^{1'''}$, $R^{1''''}$, are defined as hydrogen or as $R^1$ which, has the same meaning as in formula I, but can optionally also be present in the form of precursor groups or can be protected by protective groups known to those skilled in the art, e.g., a hydroxyl group may be attached to a polystyrene resin, and Y is a nucleophilically substitutable leaving group or a hydroxyl group, which may also be attached to a polystyrene resin, is reacted with a fragment of the formula XII

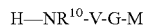 (XII)

in which $R^{10}$, V, G, and M are as defined above for the compounds of the formula I but functional groups of the formula XII can optionally also be present in the form of precursor groups or can be protected by protective groups.

The group COY in the formula XI may be the carboxylic acid group COOH or an activated carboxylic acid derivative. Y can thus be, for example, hydroxyl, halogen, such as chlorine or bromine, alkoxyl, such as methoxy or ethoxy, aryloxy, for example phenoxy or pentafluorophenoxy, phenylthio, methylthio, 2-pyridylthio or a residue of a nitrogen heterocycle bonded via a nitrogen atom. In one embodiment, Y is a residue of an azole, such as 1-imidazolyl. Y can furthermore be, for example, $((C_1–C_4)$-alkyl)—O—CO—O— or tolylsulfonyloxy and the activated acid derivative can thus be a mixed anhydride.

If Y is hydroxyl, then the carboxylic acid is expediently first activated, for example by one of the various methods used for peptide couplings that are well known to those skilled in the art. Examples of suitable activation agents are O-((cyano(ethoxycarbonyl) methylene)amino)-1,1,3,3-tetramethyluronium tetrafluoroborate (TOTU); (König et al., Proc. 21st Europ. Peptide Symp. 1990 (Eds. Giralt, Andreu), Escom, Leiden 1991, p. 143), O-(benzotriazol-1-yl)-1,1,3,3-tetramethyluronium hexafluorophosphate (HBTU), O-(7-azabenzotriazol-1-yl)-1,1,3,3-tetramethyluronium hexafluorophosphate (HATU) (L. A. Carpino, J. Am. Chem. Soc. 115 (1993) 4397), diethylphosphoryl cyanide (DEPC); bis-(2-oxo-3-oxazolidinyl)-phosphoryl chloride (BOP-Cl) or carbodiimides like dicyclohexylcarbodiimide or diisopropylcarbodiimide. The activation of the carboxylic acid function may also favourably be carried, for example, by conversion of the carboxylic acid group into the pentafluorophenyl ester using dicyclohexylcarbodiimide and pentafluorophenol. Another favourable method is the activation of the carboxylic acid group as a carbonylimidazolide with N,N-carbonyldiimidazole (CDI). A number of suitable methods for the preparation of activated carboxylic acid derivatives are also indicated with details of source literature in J. March, Advanced Organic Chemistry, Fourth Edition, John Wiley & Sons, 1992. The activation and the subsequent reaction with the compound of the formula III are usually carried in the presence of an inert solvent or diluent, for example DCM, chloroform, THF, diethyl ether, n-heptane, n-hexane, n-pentane, cyclohexane, diisopropyl ether, methyl tBu ether, acetonitrile, DMF, DMSO, dioxane, toluene, benzene, ethyl acetate or a mixture of these solvents, if appropriate, with addition of a base such as, for example, potassium tert-butoxide or tributylamine or triethylamine or diisopropyl-ethylamine.

The resulting product is a compound of the formula I in which functional groups can also be present in the form of precursor groups or can be protected by protective groups.

If any protective groups or precursor groups are present, they may then be removed by known methods (see Greene and Wuts, Protective Groups in Organic Synthesis, Wiley, 1991 or P. Kocienski, Protecting Groups, Thieme 1994), or converted into the desired final groups, respectively. For example, if a carboxylic acid group is protected as tBu ester, and the free carboxylic acid is to be prepared as the final compound, the protective group can be removed by reaction with trifluoroacetic acid or hydrochloric acid. If desired, the obtained compounds may be subject to further reactions carried out by standard processes. For example the compounds may be subjected to acylation reactions or esterification reactions, or the compounds can be converted into physiologically tolerable salts or prodrugs by standard processes known to those skilled in the art.

In one embodiment, the groups present in the compounds with the formula XI can be modified by a variety of reactions and thus the desired residues $R^{1'}$, $R^{1''}$, $R^{1'''}$ and $R^{1''''}$ may be obtained. For example, nitro groups can be reduced to amino groups with various reducing agents, such as sulphides, dithionites, and complex hydrides or by catalytic hydrogenation. A reduction of a nitro group may also be carried out at a later stage of the synthesis of a compound of the formula I, and a reduction of a nitro group to an amino group may also occur simultaneously with a reaction performed on another functional group, for example when reacting a group like a cyano group with hydrogen sulphide or when hydrogenating a group. Ester groups present in the benzene nucleus can be hydrolysed to the corresponding carboxylic acids, which after activation can then be reacted with amines or alcohols under standard conditions. Ether groups present at the benzene nucleus, for example benzyloxy groups or other easily cleavable ether groups, can be cleaved to give hydroxyl groups that then can be reacted with a variety of agents, for example etherification agents or activating agents allowing replacement of the hydroxyl group by other groups. Sulphur-containing groups can be reacted accordingly. In order to introduce the residues attached to compounds of the formula XI, amino groups can then be modified according to standard procedures for alkylation, for example by reaction with (substituted) alkyl halogenides or by reductive amination of carbonyl compounds, according to standard procedures for acylation, for example by reaction with activated carboxylic acid derivatives such as acid chlorides, anhydrides, activated esters or others or by reaction with carboxylic acids in the presence of an activating agent, or according to standard procedures for sulfonylation, for example by reaction with sulfonyl chlorides. Halogens or hydroxyl groups, (via the triflate or nonaflate) primary amines (via its diazonium salt), or boronic acid (after conversion to the corresponding stannane), present in the structure of formula I can be converted into a variety of other functional groups like for example —CN, —CF3, ethers, acids, amides, amines, alkyl- or aryl groups mediated by means of transition metals, namely palladium or nickel catalysts or copper salts and reagents referred in the literature cited below (F. Diederich, P. Stang, Metal-catalyzed Cross-coupling Reactions, Wiley-VCH, 1998; or M. Beller, C. Bolm, Transition Metals for Organic Synthesis, Wiley-VCH, 1998; J. Tsuji, Palladium Reagents and Catalysts, Wiley, 1996; J. Hartwig, Angew. Chem. 110 (1998) 2154; B. Yang, S. Buchwald, J. Organomet. Chem. 576 (1999) 125; S. Wagaw, S. Buchwald J. Org. Chem. 61 (1996) 7240; J. Wolfe, S. Buchwald J. Org. Chem. 65 (2000) 1144; D. Old, J. Wolfe, S. Buchwald J. Am. Chem. Soc. 120 (1998) 9722; J. Hartwig, M. Kawatsura, S. Hauck, K. Shaughnessy L. Alcazar-Roman, J. Org. Chem. 64 (1999) 5575, J. Wolfe, H.

Tomori, J. Sadighi, J. Yin, S. Buchwald, J. Org. Chem. 65 (2000) 1158; T. Sakamoto, K. Ohsawa, J. Chem. Soc. Perkin Trans I, (1999) 2323; D. Nichols, S. Frescas, D. Marona-Lewicka, X. Huang, B. Roth, G. Gudelsky, J. Med. Chem, 37 (1994) 4347; P. Lam, C. Clark, S. Saubern, J. Adams, M. Winters, D. Chan, A. Combs, Tetrahedron Lett., 39, (1998) 2941; D. Chan, K. Monaco, R. Wang, M. Winters, Tetrahedron Lett. 39, (1998) 2933; D. Su, J. Duan, Q. Chen, Tetrahedron Lett. 32 (1991) 7689; F. Qing, J. Fan, H. Sun, X. Yue, J. Chem. Perkin Trans. 1 (1997) 3053; V. Farina, V. Krishnamurthy, W. Scott, The Stille Reaction, Wiley, 1994).

To attach the groups $R^0$-Q-X-Q' to W in the formula XI, several standard methods are known to those skilled in the art of organic synthesis (see e.g. J. March, Advanced Organic Chemistry, Fourth Edition, John Wiley & Sons, 1992). For example, the Mitsunobu reaction may be a useful reaction (O. Mitsunobu, Synthesis 1981, 1), and further modified procedures may also be used (A. Tunoori, D. Dutta, G. Gunda, Tetrahedron Lett. 39 (1998) 8751; J. Pelletier, S. Kincaid, Tetrahedron Lett. 41 (2000) 797; D. L. Hughes, R. A. Reamer, J. J. Bergan, E. J. J. Grabowski, J. Am. Chem. Soc. 110 (1998) 6487; D. J. Camp, I. D. Jenkins, J. Org. Chem. 54 (1989) 3045; D. Crich, H. Dyker, R. J. Harris, J. Org. Chem. 54 (1989) 257).

In order to make modifications during the course of the synthesis or prepare the groups $R^0$-Q-X-Q' or Y attached to the benzene nucleus by application of parallel synthesis methodology, beside a variety of well-known reactions, palladium catalysis may be used. Such reactions like the Suzuki coupling, the Stille reaction, the Heck reaction, the Sonogashira coupling or the Buchwald-Hartwig amination are well known by those skilled in the art. (F. Diederich, P. Stang, Metal-catalyzed Cross-coupling Reactions, Wiley-VCH, 1998; or M. Beller, C. Bolm, Transition Metals for Organic Synthesis, Wiley-VCH, 1998; J. Tsuji, Palladium Reagents and Catalysts, Wiley, 1996; J. Hartwig, Angew. Chem. 110 (1998) 2154; B. Yang, S. Buchwald, J. Organomet. Chem. 576 (1999) 125; J. Wolfe, S. Buchwald J. Org. Chem. 65 (2000) 1144; D. Old, J. Wolfe, S. Buchwald J. Am. Chem. Soc. 120 (1998) 9722; J. Hartwig, M. Kawatsura, S. Hauck, K. Shaughnessy L. Alcazar-Roman, J. Org. Chem. 64 (1999) 5575, J. Wolfe, H. Tomori, J. Sadighi, J. Yin, S. Buchwald, J. Org. Chem. 65 (2000) 1185; P. Lam, C. Clark, S. Saubern, J. Adams, M. Winters, D. Chan, A. Combs, Tetrahedron Lett. 39 (1998) 2941; D. Chan, K. Monaco, R. Wang, M. Winters, Tetrahedron Lett. 39 (1998) 2933; J. Wolfe, H. Tomori, J. Sadight, J. Yin, S. Buchwald, J. Org. Chem. 65 (2000) 1158; V. Farina, V. Krishnamurthy, W. Scott, The Stille Reaction, Wiley, 1994).

If the residue Y in a compound of the formula I contains a primary or secondary nitrogen atom and is a residue in which functional groups within the residue Y are present in protected form or in the form of a precursor group, which have not already been introduced during a preceding step, these residues can, for example, be introduced at the nitrogen position by conventional literature procedures well known to one skilled in the art for N-alkylation, reductive amination, N-arylation, N-acylation or N-sulfonylation of nitrogen atoms. The starting compound that is to be employed in such a reaction carries a hydrogen atom at the nitrogen position. N-Alkylation of a nitrogen atom can, for example, be performed under standard conditions, which may include the presence of a base, using an alkylating compound containing a leaving group for example halogen like chlorine, bromine or iodine, or a sulfonyloxy group like tosyloxy, mesyloxy or trifluormethylsulfonyloxy. The leaving group may, for example, also be a hydroxyl group which, in order to achieve the alkylation reaction, is activated by a conventional activating agent. For the preparation of compounds of the formula I in which G is a direct linkage and an aromatic group is directly bonded to the nitrogen atom in Y, conventional standard arylation procedures can be used. For example aryl fluorides like alkyl fluorobenzoates or 4-fluorophenyl methyl sulfones can be employed as arylating agents. Moreover, arylation of nitrogen with heterocycles in compounds of the formula I is easily achieved by well known standard substitution reactions of the corresponding heteroaryl chlorides or triflates. Alternatively a wide variety of substituted aryl chlorides, aryl bromides, aryl iodides or aryl triflates can serve as arylating agents in a copper salt and/or palladium mediated reaction according to R. Sarges, H. Howard, K. Koe, A. Weissmann, J. Med. Chem, 32 (1989) 437; P. Unangst, D. Connor, R. Stabler, R. Weikert, J. Heterocycl. Chem, 24 (1987) 811; G. Tokmakov, I. Grandberg, Tetrahedron, 51 (1995) 2091; D. Old, M. Harris, S. Buchwald, Org. Lett. 2 (2000) 1403, G. Mann, J. Hartwig, M. Driver, C. Fernandez-Rivas, J. Am. Chem. Soc. 120 (1998) 827; J. Hartwig, M. Kawatsura, S. Hauk, K. Shaughnessy, L. J. Org. Chem. 64 (1999) 5575. Moreover such arylations can also be accomplished by reaction of a wide range of substituted aryl boronic acids as demonstrated for example by W. Mederski, M. Lefort, M. Germann, D. Kux, Tetrahedron 55 (1999) 12757; P. Lam, C. Clark, S. Saubern, J. Adams, M. Winters, D. Chan, A. Combs, Tetrahedron Lett. 39 (1998) 2941; D. Chan, K. Monaco, R. Wang, M. Winters, Tetrahedron Lett. 39 (1998) 2933.

Other compounds of the formula I can be prepared in a similar fashion as described above by coupling of a compound of the formula XIII with a compound of the formula XII.

$$R^0\text{-}Q\text{-}X\text{-}Q'\text{-}W\text{-}C(O)\text{-}Y \quad\quad\quad (XIII)$$

in which $R^0$, Q, Q', X, W and Y are as defined above for the compounds of the formula I, but functional groups can optionally also be present in the form of precursor groups or can be protected by protective groups known to those skilled in the art, e.g., an amino group can be protected with a tert-butyloxycarbonyl group or a benzyloxycarbonyl group or a hydroxyl group may be attached to a polystyrene resin.

The before-mentioned reactions for the conversion of functional groups are furthermore in general extensively described in textbooks of organic chemistry like M. Smith, J. March, March's Advanced Organic Chemistry, Wiley-VCH, 2001 and in treatises like Houben-Weyl, "Methoden der Organischen Chemie" (Methods of Organic Chemistry), Georg Thieme Verlag, Stuttgart, Germany, or "Organic Reactions", John Wiley & Sons, New York, or R. C. Larock, "Comprehensive Organic Transformations", Wiley-VCH, $2^{nd}$ ed (1999), B. Trost, I. Fleming (eds.) Comprehensive Organic Synthesis, Pergamon, 1991, in which details on the reactions and primary source literature can be found. Indeed, the compounds of the formula XI, XII and XIII are prepared by methods well known to those skilled in the art by application of various standard procedures. Due to the fact that in the present case the functional groups are attached to a highly functionalized system, it may in certain cases become necessary to specifically adapt reaction conditions or to choose specific reagents from a variety of reagents that can in principle be employed into a conversion reaction, or otherwise to take specific measures for achieving a desired conversion, for example to use protection group techniques.

However, finding out suitable reaction variants and reaction conditions in such cases does not cause any problems for one skilled in the art.

Suitable methods include, but are not limited to, those described in the examples.

The compounds of the present invention may be used as serine protease inhibitors, which inhibit the activity of the blood coagulation enzymes factor Xa and/or factor VIIa. In one embodiment, they are highly active inhibitors of factor Xa. They are generally specific serine protease inhibitors inasmuch as they do not substantially inhibit the activity of other proteases whose inhibition is not desired. The activity of the compounds of the formula I can be determined, for example, in the assays described below or in other assays known to those skilled in the art. With respect to factor Xa inhibition, one embodiment of the invention comprises compounds that have a $Ki \leq 1$ for factor Xa inhibition as determined in the assay described below, with or without concomitant factor VIIa inhibition, and does not substantially inhibit the activity of other proteases involved in coagulation and fibrinolysis whose inhibition is not desired (using the same concentration of the inhibitor). The compounds of the invention typically inhibit factor Xa catalytic activity either directly, within the prothrombinase complex or as a soluble subunit, or indirectly, by inhibiting the assembly of factor Xa into the prothrombinase complex.

The present invention also relates to the compounds of the formula I, and/or their physiologically tolerable salts, and/or their prodrugs for use as pharmaceuticals (or medicaments), and to the use of any such forms of the compounds for the production of pharmaceuticals useful for inhibiting factor Xa and/or factor VIIa, for influencing blood coagulation, inflammatory response or fibrinolysis, or for the therapy or prophylaxis of the diseases mentioned above or below. For example, the compounds may be used in pharmaceuticals for the therapy and prophylaxis of cardiovascular disorders, thromboembolic diseases or restenoses. The invention also relates to the use of the compounds of the formula I and/or their physiologically tolerable salts and/or their prodrugs for the inhibition of factor Xa and/or factor VIIa or for influencing blood coagulation or fibrinolysis or for the therapy or prophylaxis of the diseases mentioned above or below, for example for use in the therapy and prophylaxis of cardiovascular disorders, thromboembolic diseases or restenoses, and to methods of treatment aiming at such purposes including methods for said therapies and prophylaxis. The present invention also relates to pharmaceutical preparations (or pharmaceutical compositions) that contain an effective amount of at least one compound of the formula I and/or its physiologically tolerable salts and/or its prodrugs in addition to a customary pharmaceutically acceptable carrier, i.e., one or more pharmaceutically acceptable carrier substances or excipients and/or auxiliary substances or additives.

In one embodiment, the compounds are used in the treatment of disease states such as abnormal thrombus formation, acute myocardial infarction, unstable angina, thromboembolism, acute vessel closure associated with thrombolytic therapy or percutaneous transluminal coronary angioplasty, transient ischemic attacks, stroke, pathologic thrombus formation occurring in the veins of the lower extremities following abdominal, knee and hip surgery, a risk of pulmonary thromboembolism, or disseminated systemic intravascular coagulatopathy occurring in vascular systems during septic shock, certain viral infections or cancer.

The compounds of the formula I and their physiologically tolerable salts and their prodrugs can be administered to animals, such as mammals, and in particular to humans as pharmaceuticals for therapy or prophylaxis. They can be administered on their own, or in mixtures with one another or in the form of pharmaceutical preparations, which permit enteral or parenteral administration.

The pharmaceuticals can be administered orally, for example in the form of pills, tablets, lacquered tablets, coated tablets, granules, hard and soft gelatine capsules, solutions, syrups, emulsions, suspensions or aerosol mixtures. Administration, however, can also be carried out rectally, for example in the form of suppositories, or parentally, for example intravenously, intramuscularly or subcutaneously, in the form of injection solutions or infusion solutions, microcapsules, implants or rods, or percutaneously or topically, for example in the form of ointments, solutions or tinctures, or in other ways, for example in the form of aerosols or nasal sprays.

The pharmaceutical preparations according to the invention are prepared in a manner known and familiar to one skilled in the art; pharmaceutically acceptable inert inorganic and/or organic carriers may be used in addition to the compounds of the formula I and/or their physiologically tolerable salts and/or their prodrugs. For the production of pills, tablets, coated tablets and hard gelatine capsules it is possible to use, for example, lactose, cornstarch or derivatives thereof, talc, stearic acid or its salts, etc. Carriers for soft gelatin capsules and suppositories include, for example, fats, waxes, semisolid and liquid polyols, natural or hardened oils, etc.

Suitable carriers for the production of solutions, such as injection solutions, emulsions, or syrups include, for example, water, saline, alcohols, glycerol, polyols, sucrose, invert sugar, glucose, vegetable oils, etc. Suitable carriers for microcapsules, implants or rods include, for example, copolymers of glycolic acid and lactic acid. The pharmaceutical preparations normally contain about 0.5% to 90% by weight of the compounds of the formula I and/or their physiologically tolerable salts and/or their prodrugs. The amount of the active ingredient of the formula I and/or its physiologically tolerable salts and/or its prodrugs in the pharmaceutical preparations normally is from about 0.5 mg to about 1000 mg, In another embodiment, the active ingredient is present from about 1 mg to about 500 mg.

In addition to the active ingredients of the formula I, and/or their physiologically acceptable salts, and/or prodrugs, and carrier substances, the pharmaceutical preparations can contain additives such as, for example, fillers, disintegrants, binders, lubricants, wetting agents, stabilisers, emulsifiers, preservatives, sweeteners, colorants, flavourings, aromatizers, thickeners, diluents, buffer substances, solvents, solubilizers, agents for achieving a depot effect, salts for altering the osmotic pressure, coating agents or antioxidants. They can also contain two or more compounds of the formula I, and/or their physiologically tolerable salts, and/or their prodrugs. In case a pharmaceutical preparation contains two or more compounds of the formula I, the selection of the individual compounds can aim at a specific overall pharmacological profile of the pharmaceutical preparation. For example, a highly potent compound with a shorter duration of action may be combined with a long-acting compound of lower potency. The flexibility permitted with respect to the choice of substituents in the compounds of the formula I allows a great deal of control over the biological and physico-chemical properties of the compounds and thus allows the selection of such desired compounds. Furthermore, in addition to at least one compound of the formula I and/or its physiologically tolerable salts and/or its prodrugs, the pharmaceutical preparations can also contain one or more other therapeutically or prophylactically active ingredients.

As inhibitors of factor Xa and/or factor VIIa, the compounds of the formula I, their physiologically tolerable salts, and their prodrugs are generally suitable for the therapy and prophylaxis of conditions in which the activity of factor Xa and/or factor VIIa plays a role or has an undesired extent, or conditions that can favourably be influenced by inhibiting or decreasing the activity of factor Xa and/or factor VIIa. The compounds may be used in the prevention, alleviation or cure of these conditions by inhibiting or decreasing the activity of factor Xa and/or factor VIIa, as desired by a physician. As inhibition of factor Xa and/or factor VIIa influences blood coagulation and fibrinolysis, the compounds of the formula I and their physiologically tolerable salts and their prodrugs are generally suitable for reducing blood clotting, or for the therapy and prophylaxis of conditions in which the activity of the blood coagulation system plays a role or has an undesired extent, or which can favourably be influenced by reducing blood clotting. The compounds may be used in, the prevention, alleviation or cure of these conditions by decreasing activity of the blood coagulation system, as desired by a physician. A specific subject of the present invention thus is the reduction or inhibition of unwanted blood clotting in an individual by administering an effective amount of compound I, a physiologically tolerable salt thereof, a prodrug thereof, or a pharmaceutical preparation thereof.

Conditions in which a compound of the formula I can be favourably used include, for example, cardiovascular disorders, thromboembolic diseases or complications associated, for example, with infection or surgery. The compounds of the present invention can also be used to reduce an inflammatory response. Examples of specific disorders for the treatment or prophylaxis of which the compounds of the formula I can be used are coronary heart disease, myocardial infarction, angina pectoris, vascular restenosis, for example restenosis following angioplasty like PTCA, adult respiratory distress syndrome, multi-organ failure, stroke and disseminated intravascular clotting disorder. Examples of related complications associated with surgery are thromboses like deep vein and proximal vein thrombosis, which can occur following surgery. In view of their pharmacological activity, the compounds of the invention can replace or supplement other anticoagulant agents such as heparin. The use of a compound of the invention can result, for example, in a cost saving as compared to other anticoagulants.

When using the compounds of the formula I the dose can vary within wide limits and, as is customary and is known to the physician, may be suited to the individual conditions in each individual case. The dose may depend, for example, on the specific compound employed, on the nature and severity of the disease to be treated, on the mode and the schedule of administration, or on whether an acute or chronic condition is treated or whether prophylaxis is carried out. An appropriate dosage can be established using clinical approaches well known in the medical art. In general, the daily dose for achieving the desired results in an adult weighing about 75 kg is from 0.01 mg/kg to 100 mg/kg. In another embodiment, from 0.1 mg/kg to 50 mg/kg or, from 0.1 mg/kg to 10 mg/kg (in each case in mg per kg of body weight) is used. The daily dose can be divided in the case of the administration of relatively large amounts, for example, into several parts for administration. As usual, depending on individual behaviour, it may be necessary to deviate upwards or downwards from the daily dose indicated.

A compound of the formula I can also advantageously be used as an anticoagulant outside an individual. For example, an effective amount of a compound of the invention can be contacted with a freshly drawn blood sample to prevent coagulation of the blood sample. Further, a compound of the formula I and its salts can be used for diagnostic purposes, for example for in vitro diagnoses, and as an auxiliary in biochemical investigations. For example, a compound of the formula I can be used in an assay to identify the presence of factor Xa and/or factor VIIa, or to isolate factor Xa and/or factor VIIa, in a substantially purified form. A compound of the invention can be labelled with, for example, a radioisotope, and the labelled compound bound to factor Xa and/or factor VIIa is then detected using a routine method useful for detecting the particular label. Thus, a compound of the formula I or a salt thereof can be used as a probe to detect the location or amount of factor Xa and/or factor VIIa activity in vivo, in vitro, or ex vivo.

Furthermore, the compounds of the formula I can be used as synthesis intermediates for the preparation of other compounds, such as other pharmaceutical active ingredients, which are obtainable from the compounds of the formula I, for example, by introduction of substituents or modification of functional groups.

The general synthetic sequences for preparing the compounds useful in the present invention our outlined in the examples given below. Both an explanation of, and the actual procedure for, the various aspects of the present invention are described where appropriate. The following examples are intended to be merely illustrative of the present invention, and not limiting thereof in either scope or spirit. Those with skill in the art will readily understand that known variations of the conditions and processes described in the examples can be used to synthesise the compounds of the present invention.

It is understood that changes that do not substantially affect the activity of the various embodiments of this invention are included within the invention disclosed herein. Thus, the following examples are intended to illustrate but not limit the present invention.

EXAMPLES

Abbreviations Used:

| | |
|---|---|
| tert-Butyl | tBu |
| 2,2'-bis(diphenylphoshino-1,1'-binaphthyl | Binap |
| Bis-(oxo-3-oxazolidinyl)-phosphoryl chloride | BOP-Cl |
| dibenzylidenacetone | dba |
| Dichloromethane | DCM |
| Diethyl azodicarboxylate | DEAD |
| 4-Dimethyaminopyridine | DMAP |
| N,N-Dimethylformamide | DMF |
| Dimethylsulfoxide | DMSO |
| O-(7-Azabenzotriazol-1-yl)-N,N,N',N'-tetramethyluronium-hexafluorophosphate | HATU |
| N-Ethylmorpholine | NEM |
| Methanol | MeOH |
| Tetrahydrofuran | THF |
| Trifluoroacetic acid | TFA |
| O-((Ethoxycarbonyl)cyanomethyleneamino)-N,N,N',N'-tetramethyluronium tetrafluoroborate | TOTU |

When in the final step of the synthesis of a compound an acid such as trifluoroacetic acid or acetic acid was used, the compound was obtained partially or completely in the form of a salt of the acid used. For example, when trifluoroacetic acid was employed to remove a tBu group or when a compound was purified by chromatography using an eluent that contained such an acid, in some cases (depending on the work-up procedure such as, the particulars of a freeze-drying process), the resulting compound was obtained in the form of the acetic acid salt or trifluoroacetic acid salt or hydrochloric acid salt.

Example 1

{3-[2-(2,4-Dichlorophenyl)-ethoxy]-4-methoxy-phenyl}-(4-pyridin-4-ylmethyl-piperazin-1-yl)-methanone

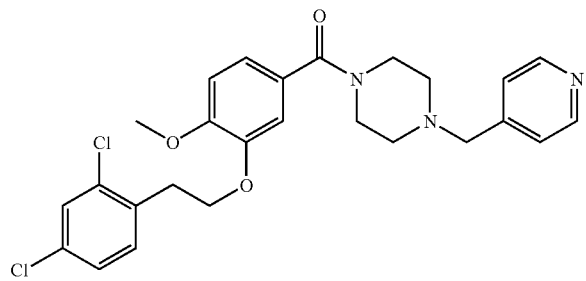

0.100 g (0.29 mmol) of 3-[2-(2,4-Dichloro-phenyl)-ethoxy]-4-methoxy-benzoic acid was dissolved in 2 ml of DMF and treated with 0.146 ml (1.16 mmol) of N-NEM and 51 mg (0.29 mmol) of 1-Pyridin-4-ylmethyl-piperazine and 0.098 g (0.3 mmol) of TOTU. The solution was stirred for 1 h at RT. The solvent was removed under reduced pressure, the residue was taken-up in DCM and the solution was washed three times with saturated aqueous sodium bicarbonate. The organic phase was dried with sodium sulphate, filtered and the solvent was removed under reduced pressure. The residue was chromatographed on silica gel eluting with n-heptane/ethyl acetate (1/1), ethyl acetate, and ethyl acetate/MeOH (10/1).

| Yield 102 mg. | MS (ES⁺): m/e = 500 (M⁺). |
|---|---|

Example 2

{3-[2-(2,4-Dichlorophenyl)-ethoxy]-4-methoxy-phenyl}-(4-pyridin-2-ylmethyl-piperazin-1-yl)-methanone

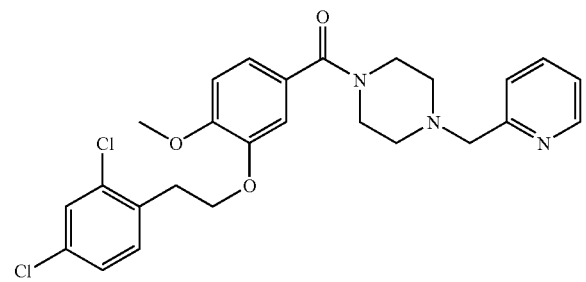

0.100 g (0.29 mmol) of 3-[2-(2,4-Dichloro-phenyl)-ethoxy]-4-methoxy-benzoic acid was dissolved in 2 ml of DMF and treated with 0.146 ml (1.16 mmol) of N-NEM and 51 mg (0.29 mmol) of 1-Pyridin-2-ylmethyl-piperazine and 0.098 g (0.3 mmol) of TOTU. The solution was stirred for 1 h at RT. The solvent was removed under reduced pressure, the residue was taken-up in DCM and the solution was washed three times with saturated aqueous sodium bicarbonate. The organic phase was dried with sodium sulphate, filtered and the solvent was removed under reduced pressure. The residue was chromatographed on silica gel eluting with n-heptane/ethyl acetate (1/1), ethyl acetate, and ethyl acetate/MeOH (10/1).

| Yield 93 mg. | MS (ES⁺): m/e = 500 (M⁺). |
|---|---|

Example 3

{3-[2-(2,4-Dichlorophenyl)-ethoxy]-4-methoxy-phenyl}-(4-pyridin-4-yl-piperazin-1-yl)-methanone

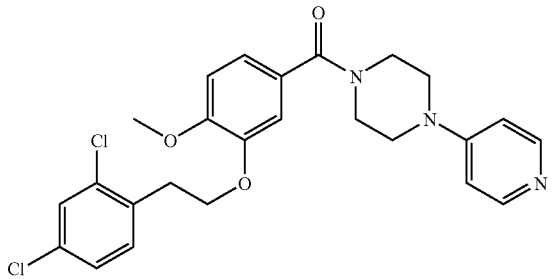

0.100 g (0.29 mmol) of 3-[2-(2,4-Dichloro-phenyl)-ethoxy]-4-methoxy-benzoic acid was dissolved in 2 ml of DMF and treated with 0.146 ml (1.16 mmol) of N-NEM and 47 mg (0.29 mmol) of 1-Pyridin-4-yl-piperazine and 0.098 g (0.3 mmol) of TOTU. The solution was stirred for 1 h at RT. The solvent was removed under reduced pressure, the residue was taken-up in DCM and the solution was washed three times with saturated aqueous sodium bicarbonate. The organic phase was dried with sodium sulphate, filtered and the solvent was removed under reduced pressure. The residue was chromatographed on silica gel eluting with n-heptane/ethyl acetate (1/1), ethyl acetate, and ethyl acetate/MeOH (10/1).

| Yield 40 mg. | MS (ES⁺): m/e = 486 (M⁺). |
|---|---|

Example 4

{3-[2-(2,4-Dichlorophenyl)-ethoxy]-4-methyl-phenyl}-(4-pyridin-4-ylmethyl-piperazin-1-yl)-methanone

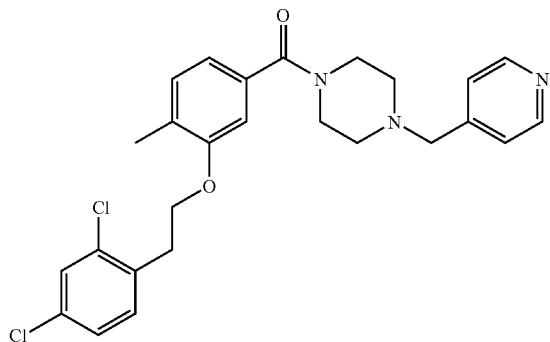

0.094 g (0.29 mmol) of 3-[2-(2,4-dichloro-phenyl)-ethoxy]-4-methyl-benzoic acid was dissolved in 2 ml of DMF and treated with 0.146 ml (1.16 mmol) of N-NEM and 51 mg (0.29 mmol) of 1-Pyridin-4-ylmethyl-piperazine and 0.098 g (0.3 mmol) of TOTU. The solution was stirred for 16 h at RT. The solvent was removed under reduced pressure, the residue was taken-up in DCM and the solution was washed three times with saturated aqueous sodium bicarbonate. The organic phase was dried with sodium sulphate, filtered and the solvent was removed under reduced pressure. The residue was chromatographed on silica gel eluting with DCM, and DCM/MeOH (20/1).

| Yield 82 mg. | MS (ES$^+$): m/e = 484 (M$^+$). |

Example 5

{3-[2-(2,4-Dichloro-phenyl)-ethoxy]-4,5-dimethoxy-phenyl}-(4-pyridin-4-ylmethyl-piperazin-1-yl)-methanone

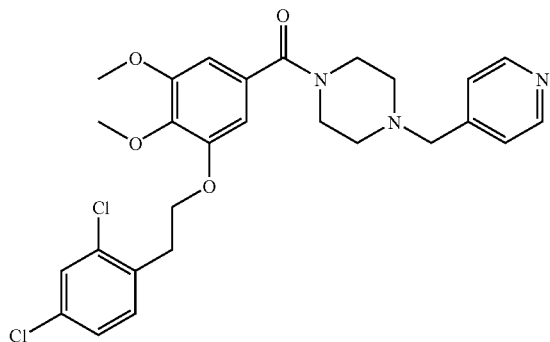

(i) 3-Hydroxy-4,5-dimethoxy-benzoic acid methyl ester 5 g (27.2 mmol) of 3-Hydroxy-4,5-dimethoxy-benzoic acid was added at 0° C. to 100 ml of a saturated solution of HCl in MeOH. The solution was stirred for 16 h at RT. The solvent was removed under reduced pressure. The residue was chromatographed on silica gel eluting with ethyl acetate/n-heptane (2/1).

| Yield 4.66 g. | MS (Cl$^+$): m/e = 212.2 (M$^+$). |

(ii) 3-[2-(2,4-Dichlorophenyl)-ethoxy]-4,5-dimethoxy-benzoic acid 2 g (9.42 mmol) of 3-Hydroxy-4,5-dimethoxy-benzoic acid methyl ester was dissolved in 100 ml of anhydrous tetrahydrofuran. To this solution was added 1.98 g (10.37 mmol) of 2-(2,4-Dichlorophenyl)-ethanol, 9.415 g (equivalent to 28.27 mmol PPh$_3$) of triphenylphosphine derivatized polystyrene and 4.924 g (28.27 mmol) of DEAD. The solution was shaken for 16 h at RT. The polymer was filtered off and washed with ethyl acetate. The solvent was removed under reduced pressure. The residue was taken-up in ethyl acetate and the solution was washed three times with water and twice with saturated aqueous sodium chloride. The organic phase was dried with magnesium sulphate, filtered and the solvent was removed under reduced pressure.

The residue was dissolved in 20 ml of dioxan. 1 ml of water was added to the solution followed by 2N aqueous NaOH to give a pH of 13. The reaction solution was heated at 60° C. for 10 hours. The solution was cooled to 0° C., 5 ml water was added, followed by concentrated hydrochloric acid to give a pH of 1 to 2, whereupon the product precipitated from solution. The product was filtered off and dried under reduced pressure.

| Yield 3.3 g. | MS (ES$^-$): m/e = 369 (M − H)$^-$. |

(iii) {3-[2-(2,4-Dichlorophenyl)-ethoxy]-4,5-dimethoxy-phenyl}-(4-pyridin-4-ylmethyl-piperazin-1-yl)-methanone 0.100 g (0.269 mmol) of 3-[2-(2,4-Dichlorophenyl)-ethoxy]-4,5-dimethoxy-benzoic acid was dissolved in 2 ml of DMF and treated with 0.124 g (1.08 mmol) of N-NEM and 0.0477 g (0.27 mmol) of 1-Pyridin-4-ylmethyl-piperazine and 0.088 g (0.269 mmol) of TOTU. The solution was stirred for 16 h at RT. The solvent was removed under reduced pressure, the residue was taken-up in ethyl acetate and the solution was washed twice with saturated aqueous sodium bicarbonate and once with saturated aqueous sodium chloride. The organic phase was dried with magnesium sulphate, filtered and the solvent was removed under reduced pressure. The residue was chromatographed on silica gel eluting with a gradient of 0–17% MeOH in DCM.

| Yield 23.8 mg. | MS (ES$^+$): m/e = 530 (M$^+$). |

Example 6

3-[2-(2,4-Dichlorophenyl)-ethoxy]-4,5-dimethoxy-N-(3,4,5,6-tetrahydro-2H-[1,4']bipyridinyl-4-ylmethyl)-benzamide

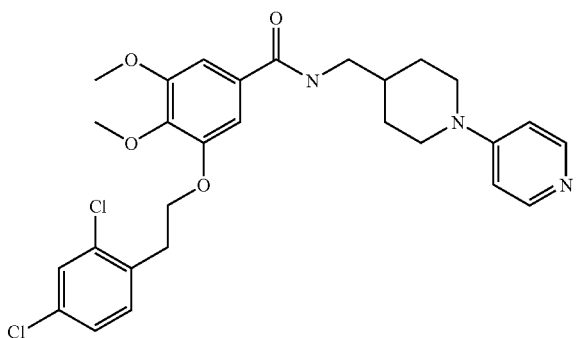

0.100 g (0.269 mmol) of 3-[2-(2,4-Dichlorophenyl)-ethoxy]-4,5-dimethoxy-benzoic acid was dissolved in 2 ml of DMF and treated with 0.372 g (3.23 mmol) of N-NEM and 0.144 mg (0.27 mmol) of C-(3,4,5,6-Tetrahydro-2H-[1,4']bipyridinyl-4-yl)-methylamine tris-trifluoroacetate salt and 0.088 g (0.269 mmol) of TOTU. The solution was stirred for 16 h at RT. The solvent was removed under reduced pressure, the residue was taken-up in ethyl acetate and the solution was washed twice with saturated aqueous sodium bicarbonate and once with saturated aqueous sodium chloride. The organic phase was dried with magnesium sulphate, filtered and the solvent was removed under reduced pressure. The residue was chromatographed on silica gel eluting with a gradient of 0–17% MeOH in DCM.

| Yield 19.2 mg. | MS (ES$^+$): m/e = 544 (M$^+$). |
|---|---|

Example 7

{3-[2-(2,4-Dichloro-phenyl)-ethoxy]-phenyl}-(4-pyridin-4-ylmethyl-piperazin-1-yl)-methanone

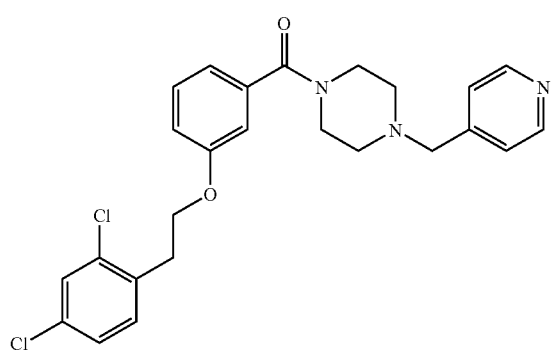

(i) 3-[2-(2,4-Dichlorophenyl)-ethoxy]-benzoic acid methyl ester 2 g (13.1 mmol) of 3-hydroxybenzoic acid methyl ester and 4.75 g (18.1 mmol) of triphenylphosphine were dissolved in 48 ml of anhydrous tetrahydrofuran. The solution was cooled to 0° C. and a solution of 3.04 g (17.5 mmol) DEAD in 7 ml of anhydrous tetrahydrofuran was added dropwise over 20 min. The solution was stirred at RT for 45 min. and a solution of 2.76 g (14.5 mmol) of 2-(2,4-Dichlorophenyl)-ethanol in 3 ml anhydrous tetrahydrofuran was added. The reaction was stirred for 16 h at RT. The solvent was removed under reduced pressure. The residue was chromatographed on silica gel eluting with ethyl acetate/n-heptane (4/1).

| Yield 2.6 g. | MS (CI$^+$): m/e = 325 (M$^+$). |
|---|---|

(ii) 3-[2-(2,4-Dichloro-phenyl)-ethoxy]-benzoic acid 1 g (3.07 mmol) of 3-[2-(2,4-Dichlorophenyl)-ethoxy]-benzoic acid methyl ester was dissolved in 20 ml of dioxan. 2N aqueous NaOH was added to the solution to give a pH of 13. The reaction solution was heated at 50° C. for 3 h, and stirred at RT for 16 h. 5 ml water was added, followed by concentrated hydrochloric acid to give a pH of 1 to 2, whereupon the product precipitated from solution. The suspension was stirred for 30 min, then the product was filtered off and dried under reduced pressure.

Yield 0.92 g. MS (CI$^+$): m/e=311 (M$^+$).

(iii) {3-[2-(2,4-Dichloro-phenyl)-ethoxy]-phenyl}-(4-pyridin-4-ylmethyl-piperazin-1-yl)-methanone 0.100 g (0.321 mmol) of 3-[2-(2,4-Dichlorophenyl)-ethoxy]-benzoic acid was dissolved in 2 ml of DMF and treated with 0.148 g (1.28 mmol) of N-NEM and 0.105 g (0.321 mmol) of TOTU and 0.0569 g (0.32 mmol) of 1-Pyridin-4-ylmethyl-piperazine. The solution was stirred for 16 h at RT. The solvent was removed under reduced pressure, the residue was taken-up in ethyl acetate and the solution was washed twice with saturated aqueous sodium bicarbonate and once with saturated aqueous sodium chloride. The organic phase was dried with magnesium sulphate, filtered and the solvent was removed under reduced pressure. The residue was chromatographed on silica gel eluting with a gradient of 0–17% MeOH in DCM.

| Yield 84 mg. | MS (ES$^+$): m/e = 470 (M$^+$). |
|---|---|

Example 8

3-[2-(2,4-Dichlorophenyl)-ethoxy]-N-(3,4,5,6-tetrahydro-2H-[1,4']bipyridinyl-4-ylmethyl)-benzamide

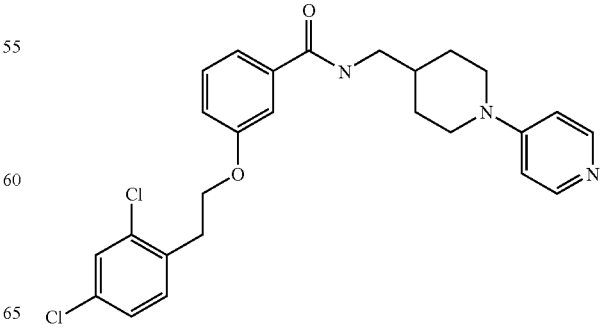

0.100 g (0.321 mmol) of 3-[2-(2,4-Dichlorophenyl)-ethoxy]-benzoic acid was dissolved in 2 ml of DMF and treated with 0.148 g (1.28 mmol) of N-NEM and 0.105 g (0.321 mmol) of TOTU and 0.123 g (0.64 mmol) of C-(3,4,5,6-Tetrahydro-2H-[1,4']bipyridinyl-4-yl)-methylamine. The solution was stirred for 16 h at RT. The solvent was removed under reduced pressure, the residue was taken-up in ethyl acetate and the solution was washed twice with saturated aqueous sodium bicarbonate and once with saturated aqueous sodium chloride. The organic phase was dried with magnesium sulphate, filtered and the solvent was removed under reduced pressure. The residue was chromatographed on silica gel eluting with a gradient of 0 to 17% MeOH in DCM.

| Yield 73 mg. | MS (ES$^+$): m/e = 484 (M$^+$). |
|---|---|

Example 9

{3-[2-(2,4-Dichloro-phenyl)-ethoxy]-4-ethoxy-phenyl}-(4-pyridin-4-ylmethyl-piperazin-1-yl)-methanone

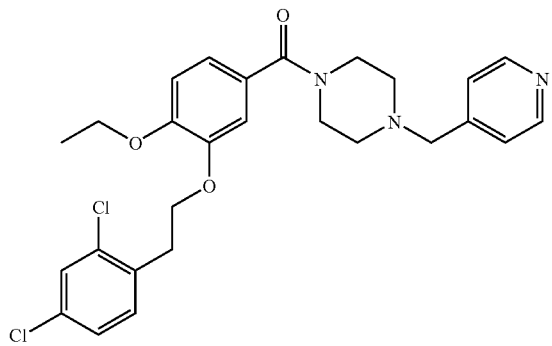

(i) 4-Ethoxy-3-hydroxy-benzoic acid ethyl ester 5 g (27.2 mmol) of 3,4-Dihydroxy-benzoic acid ethyl ester was dissolved in 100 ml DMF and 3.75 g (27.2 mmol) of potassium carbonate was added. The solution was cooled to 0° C. and a solution of 2.96 g (27.2 mmol) ethyl bromide in 10 ml DMF was added dropwise. The solution was stirred for 16 h at room temperature (RT). The solvent was removed under reduced pressure. The residue was taken-up in ethyl acetate and the solution was washed three times with water and twice with saturated aqueous sodium chloride. The organic phase was dried with magnesium sulphate, filtered and the solvent was removed under reduced pressure. The residue was chromatographed on silica gel eluting with ethyl acetate/n-heptane (1/4).

| Yield 1.84 g. | MS (Cl$^+$): m/e = 211.1 (M + H)$^+$. |
|---|---|

(ii) 3-[2-(2,4-Dichlorophenyl)-ethoxy]-4-ethoxy-benzoic acid ethyl ester 0.5 g (2.38 mmol) of 4-Ethoxy-3-hydroxy-benzoic acid ethyl ester was dissolved in 10 ml of anhydrous tetrahydrofuran. To this solution was added 0.5 g (2.62 mmol) of 2-(2,4-Dichlorophenyl)-ethanol, 2.38 g (equivalent to 7.13 mmol PPh$_3$) of triphenylphosphine derivatized polystyrene and 1.24 g (7.13 mmol) of DEAD. The solution was shaken for 16 h at RT. The polymer was filtered off and washed with ethyl acetate. The solvent was removed under reduced pressure. The residue was taken-up in ethyl acetate and the solution was washed three times with water and twice with saturated aqueous sodium chloride. The organic phase was dried with magnesium sulphate, filtered and the solvent was removed under reduced pressure. The residue was chromatographed on silica gel eluting with ethyl acetate/n-heptane (1/4).

| Yield 300 mg. | LC-MS (ES$^+$): m/e = 383 (M)$^+$ |
|---|---|

(iii) 3-[2-(2,4-Dichloro-phenyl)-ethoxy]-4-ethoxy-benzoic acid 0.300 g (0.78 mmol) of 3-[2-(2,4-Dichlorophenyl)-ethoxy]-4-ethoxy-benzoic acid ethyl ester was dissolved in 10 ml of dioxan. 2N aqueous NaOH was added to the solution to give a pH of 13. The reaction solution was heated at 60° C. for 10 h. 5 ml water was added, followed by concentrated hydrochloric acid to give a pH of 1–2, whereupon the product precipitated from solution. The suspension was stirred for 30 min, and then the product was filtered off and dried under reduced pressure.

| Yield 0.205 g. | MS (Cl$^+$): m/e = 355 (M$^+$). |
|---|---|

(iv) {3-[2-(2,4-Dichloro-phenyl)-ethoxy]-4-ethoxy-phenyl}-(4-pyridin-4-ylmethyl-piperazin-1-yl)-methanone 0.050 g (0.141 mmol) of 3-[2-(2,4-Dichloro-phenyl)-ethoxy]-4-ethoxy-benzoic acid was dissolved in 2 ml of DMF and treated with 0.065 g (0.564 mmol) of N-NEM and 0.046 g (0.141 mmol) of TOTU and 0.025 g (0.141 mmol) of 1-Pyridin-4-ylmethyl-piperazine. The solution was stirred for 16 h at RT. The solvent was removed under reduced pressure, the residue was taken-up in ethyl acetate and the solution was washed twice with saturated aqueous sodium bicarbonate and once with saturated aqueous sodium chloride. The organic phase was dried with magnesium sulphate, filtered and the solvent was removed under reduced pressure. The residue was purified by preparative RP-HPLC eluting with a gradient of 0–100% acetonitrile in water (+0.01% trifluoroacetic acid). After lyophilization the product was obtained as its trifluoroacetate salt.

| Yield 28.6 mg. | MS (ES$^+$): m/e = 514 (M$^+$). |
|---|---|

Example 10

3-[2-(2,4-Dichloro-phenyl)-ethoxy]-4-ethoxy-N-(3,4,5,6-tetrahydro-2H-[1,4']bipyridinyl-4-ylmethyl)-benzamide

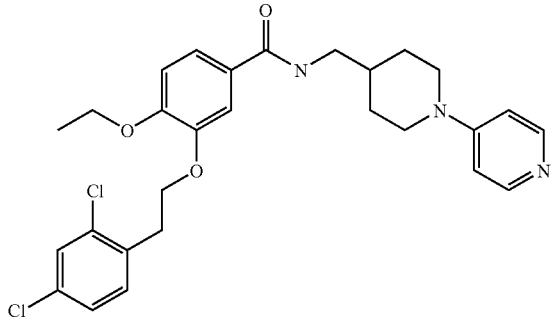

0.050 g (0.141 mmol) of 3-[2-(2,4-Dichloro-phenyl)-ethoxy]-4-ethoxy-benzoic acid was dissolved in 2 ml of DMF and treated with 0.163 g (1.41 mmol) of N-NEM and 0.046 g (0.141 mmol) of TOTU and 0.075 g (0.141 mmol) of C-(3,4,5,6-Tetrahydro-2H-[1,4']bipyridinyl-4-yl)-methylamine tris-trifluoroacetate salt. The solution was stirred for 16 h at RT. The solvent was removed under reduced pressure, the residue was taken-up in ethyl acetate and the solution was washed twice with saturated aqueous sodium bicarbonate and once with saturated aqueous sodium chloride. The organic phase was dried with magnesium sulphate, filtered and the solvent was removed under reduced pressure. The residue was purified by preparative RP-HPLC eluting with a gradient of 0 to 100% acetonitrile in water (+0.01% trifluoroacetic acid). After lyophilization the product was obtained as its trifluoroacetate salt.

| Yield 26.1 mg. | MS (ES$^+$): m/e = 528 (M$^+$). |
|---|---|

Example 11

4-(4-{3-[2-(2,4-Dichloro-phenyl)-ethoxy]-4-methoxy-benzoyl}-piperazin-1-ylmethyl)-benzonitrile

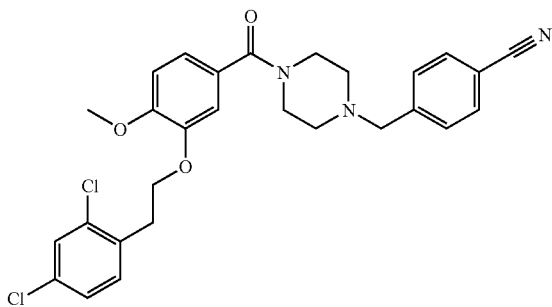

(i) 4-{3-[2-(2,4-Dichlorophenyl)-ethoxy]-4-methoxy-benzoyl}-piperazine-1-carboxylic acid tBu ester 3 g (9 mmol) of 3-[2-(2,4-Dichlorophenyl)-ethoxy]-4-methoxy-benzoic acid was dissolved in 30 ml DMF and treated with 4.6 ml (36 mmol) of N-NEM and 3.2 g (9.9 mmol) of TOTU and 1.67 g (9 mmol) of piperazine-1-carboxylic acid tBu ester. The solution was stirred for 40 min. at RT. The solvent was removed under reduced pressure, the residue was taken-up in DCM and the solution was washed three times with saturated aqueous sodium bicarbonate. The organic phase was dried with sodium sulphate, filtered and the solvent was removed under reduced pressure. The residue was chromatographed on silica gel eluting with n-heptane/ethyl acetate (1/1).

| Yield 4.2 g. | MS (ES$^+$): m/e = 509 (M$^+$). |
|---|---|

(ii) {3-[2-(2,4-Dichlorophenyl)-ethoxy]-4-methoxy-phenyl}-piperazin-1-yl-methanone, hydrochloride salt 4.2 g (8.2 mmol) of 4-{3-[2-(2,4-Dichlorophenyl)-ethoxy]-4-methoxy-benzoyl}-piperazine-1-carboxylic acid tBu ester was dissolved in 25 ml of MeOH. To this solution was added 100 ml of a saturated solution of HCl in MeOH. The solution was stirred for 30 min at RT. The solvent was removed under reduced pressure. The residue was treated twice with toluene, which was removed under reduced pressure.

| Yield 3.8 g. | MS (ES$^+$): m/e = 409 (M$^+$). |
|---|---|

(iii) 4-(4-{3-[2-(2,4-Dichlorophenyl)-ethoxy]-4-methoxy-benzoyl}-piperazin-1-ylmethyl)-benzonitrile 0.050 g (0.112 mmol) of {3-[2-(2,4-Dichlorophenyl)-ethoxy]-4-methoxy-phenyl}-piperazin-1-yl-methanone, hydrochloride salt was dissolved in 3 ml of DMF. 61.9 mg (0.448 mmol) of potassium carbonate was added to the solution, followed by 0.022 g (0.11 mmol) of 4-bromomethyl-benzonitrile. The reaction solution was shaken for 16 h at RT. The solvent was removed under reduced pressure, the residue was taken-up in ethyl acetate and the solution was washed twice with water and once with saturated aqueous sodium chloride. The organic phase was dried with magnesium sulphate, filtered and the solvent was removed under reduced pressure. The residue was chromatographed on silica gel eluting with n-heptane/ethyl acetate (1/1), and DCM/MeOH (10/1).

| Yield 33 mg. | MS (ES$^+$): m/e = 524 (M$^+$). |
|---|---|

Example 12

{3-[2-(2,4-Dichlorophenyl)-ethoxy]-4-methoxy-phenyl}-[4-(4-fluorobenzyl)-piperazin-1-yl]-methanone

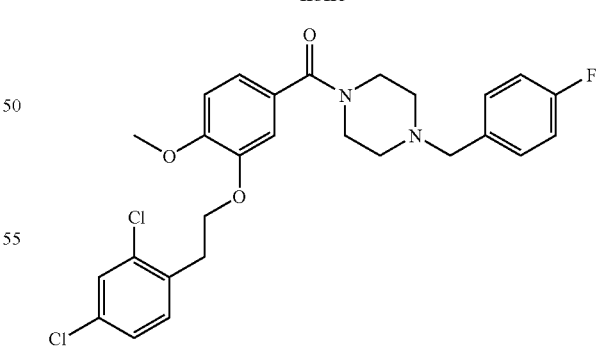

0.050 g (0.112 mmol) of {3-[2-(2,4-Dichlorophenyl)-ethoxy]-4-methoxy-phenyl}-piperazin-1-yl-methanone, hydrochloride salt was dissolved in 3 ml of DMF. 61.9 mg (0.448 mmol) of potassium carbonate was added to the solution, followed by 0.021 g (0.11 mmol) of 1-Bromomethyl-4-fluoro-benzene. The reaction solution was shaken for 16 h at RT. The solvent was removed under reduced pressure, the residue was taken-up in ethyl acetate and the

Example 13

2-(4-{3-[2-(2,4-Dichlorophenyl)-ethoxy]-4-methoxy-benzoyl}-piperazin-1-yl)-N,N-dimethyl-acetamide

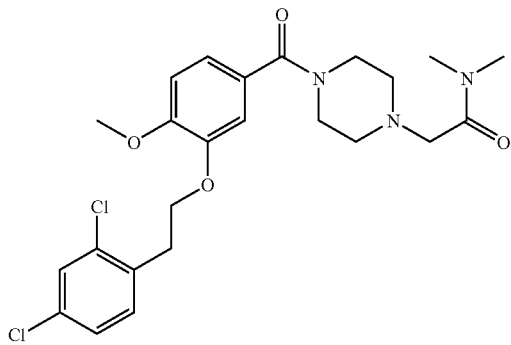

0.050 g (0.112 mmol) of {3-[2-(2,4-Dichlorophenyl)-ethoxy]-4-methoxy-phenyl}-piperazin-1-yl-methanone, hydrochloride salt was dissolved in 3 ml of DMF. 61.9 mg (0.448 mmol) of potassium carbonate was added to the solution, followed by 0.016 g (0.13 mmol) of 2-chloro-N,N-dimethyl-acetamide. The reaction solution was shaken for 32 h at RT. The solvent was removed under reduced pressure. The residue was chromatographed on silica gel eluting with a gradient of 0–17% MeOH in DCM, followed by additional purification by preparative RP-HPLC eluting with a gradient of 0 to 100% acetonitrile in water (+0.01% trifluoroacetic acid). After lyophilization the product was obtained as its trifluoroacetate salt.

| Yield 20.5 mg. | MS (ES+): m/e = 494 (M+). |

Example 14

2-(4-{3-[2-(2,4-Dichlorophenyl)-ethoxy]-4-methoxy-benzoyl}-piperazin-1-yl)-1-pyrrolidin-1-yl-ethanone

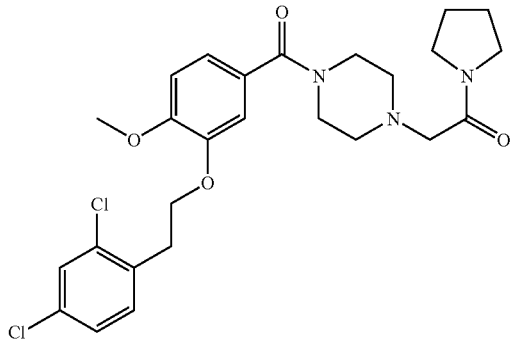

0.102 g (0.3 mmol) of 3-[2-(2,4-Dichlorophenyl)-ethoxy]-4-methoxy-benzoic acid was dissolved in 3 ml of DMF. 138.2 mg (1.2 mmol) of N-NEM and 0.098 g (0.3 mmol) TOTU were added to the solution, followed by 0.059 g (0.3 mmol) of 2-piperazin-1-yl-1-pyrrolidin-1-yl-ethanone. The reaction solution was stirred for 4 h at RT. The solvent was removed under reduced pressure. The solvent was removed under reduced pressure, the residue was taken-up in ethyl acetate and the solution was washed three times with saturated aqueous sodium bicarbonate. The organic phase was dried with sodium sulphate, filtered and the solvent was removed under reduced pressure. The residue was purified by preparative RP-HPLC eluting with a gradient of 0–100% acetonitrile in water (+0.01% trifluoroacetic acid). After lyophilization the product was obtained as its trifluoroacetate salt.

| Yield 74 mg. | MS (ES+): m/e = 520 (M+). |

Example 15

3-[2-(2,4-Dichlorophenyl)-ethoxy]-4-methoxy-N-(3-piperidin-1-yl-propyl)-benzamide

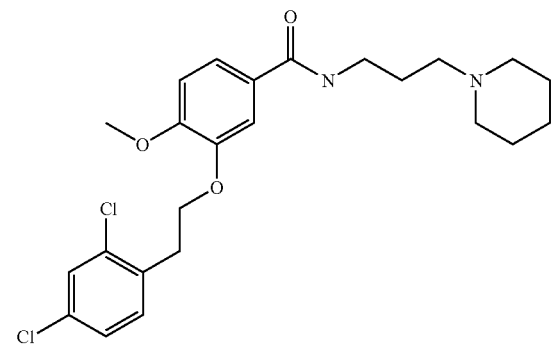

0.075 g (0.22 mmol) of 3-[2-(2,4-Dichlorophenyl)-ethoxy]-4-methoxy-benzoic acid was dissolved in 3 ml of DMF. 101.3 mg (0.88 mmol) of N-NEM and 0.072 g (0.22 mmol) TOTU were added to the solution, followed by 0.031 g (0.22 mmol) of 3-piperidin-1-yl-propylamine. The reaction solution was stirred for 4 h at RT. The solvent was removed under reduced pressure. The solvent was removed under reduced pressure, the residue was taken-up in ethyl acetate and the solution was washed three times with saturated aqueous sodium bicarbonate. The organic phase was dried with sodium sulphate, filtered and the solvent was removed under reduced pressure. The residue was purified by preparative RP-HPLC eluting with a gradient of 0–100% acetonitrile in water (+0.01% trifluoroacetic acid). After lyophilization the product was obtained as its trifluoroacetate salt.

| Yield 50 mg. | MS (ES+): m/e = 465 (M+). |

(Preceding Example 13, continued from previous page:)

solution was washed twice with water and once with saturated aqueous sodium chloride. The organic phase was dried with magnesium sulphate, filtered and the solvent was removed under reduced pressure. The residue was chromatographed on silica gel eluting with n-heptane/ethyl acetate (1/1), and DCM/MeOH (10/1).

| Yield 42.5 mg. | MS (ES+): m/e = 517 (M+). |

Example 16

3-[2-(2,4-Dichloro-phenyl)-ethoxy]-4-methoxy-N-(2-piperidin-1-yl-ethyl)-benzamide

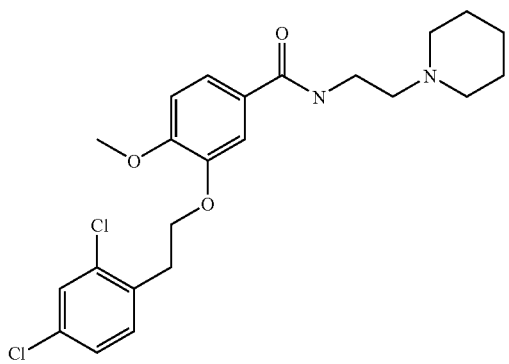

0.075 g (0.22 mmol) of 3-[2-(2,4-Dichlorophenyl)-ethoxy]-4-methoxy-benzoic acid was dissolved in 3 ml of DMF. 101.3 mg (0.88 mmol) of N-NEM and 0.072 g (0.22 mmol) TOTU were added to the solution, followed by 0.028 g (0.22 mmol) of 2-piperidin-1-yl-ethylamine. The reaction solution was stirred for 4 h at RT. The solvent was removed under reduced pressure. The solvent was removed under reduced pressure, the residue was taken-up in ethyl acetate and the solution was washed three times with saturated aqueous sodium bicarbonate. The organic phase was dried with sodium sulphate, filtered and the solvent was removed under reduced pressure. The residue was purified by preparative RP-HPLC eluting with a gradient of 0 to 100% acetonitrile in water (+0.01% trifluoroacetic acid). After lyophilization the product was obtained as its trifluoroacetate salt.

| Yield 50 mg. | MS (ES+): m/e = 451 (M+). |
|---|---|

Example 17

{3-[2-(2,4-Dichloro-phenyl)-ethoxy]-4-methyl-phenyl}-[4-(1-oxy-pyridin-4-ylmethyl)-piperazin-1-yl]-methanone

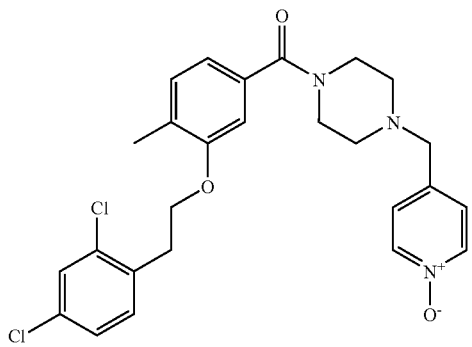

0.020 g (0.04 mmol) of {3-[2-(2,4-Dichlorophenyl)-ethoxy]-4-methyl-phenyl}-(4-pyridin-4-ylmethyl-piperazin-1-yl)-methanone was dissolved in 1 ml of DCM. To this solution was added 15.2 mg (0.06 mmol) meta-chloroperbenzoic acid. The reaction was stirred at RT for 16 h, and then the solvent was removed under reduced pressure. The residue was chromatographed on silica gel eluting with a gradient of 0 to 17% MeOH in DCM.

| Yield 5 mg. | MS (ES+): m/e = 500 (M+). |
|---|---|

Example 18

{3-[2-(2,4-Dichloro-phenyl)-ethoxy]-4-hydroxymethyl-phenyl}-[4-(1-oxy-pyridin-4-ylmethyl)-piperazin-1-yl]-methanone

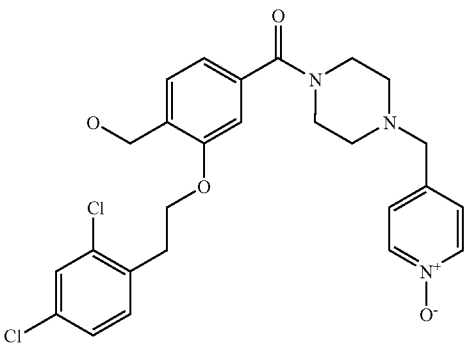

This compound was isolated by chromatography from the reaction described for the synthesis of example 17. Yield 2 mg. MS (ES+): m/e=516 (M+).

Example 19

{4-Bromo-3-[2-(2,4-dichlorophenyl)-ethoxy]-5-methoxyphenyl}-(4-pyridin-4-ylmethyl-piperazin-1-yl)-methanone

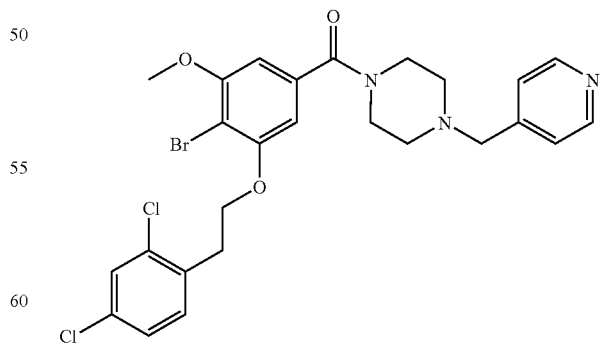

(i) 4-Bromo-3-[2-(2,4-dichlorophenyl)-ethoxy]-5-methoxy-benzoic acid 0.2 g (0.49 mmol) of 4-Bromo-3-[2-(2,4-dichlorophenyl)-ethoxy]-5-hydroxy-benzoic acid was dissolved in 5 ml DMF and 0.272 mg (1.97 mmol) of potassium carbonate was added. The solution was cooled to 0° C. and 0.699 g (4.9 mmol) methyl bromide was added. The solution was stirred for 16 h at RT. The solvent was removed under reduced pressure. The residue was chromatographed on silica gel eluting with ethyl acetate/n-heptane (1/1). The resulting compound was dissolved in 10 ml dioxan and 1 ml water. 2N aqueous NaOH was added to the solution to give a pH of 13. The reaction solution was heated at 60° C. for 4 h. 5 ml water was added, followed by concentrated hydrochloric acid to give a pH of 1–2, whereupon the product precipitated from solution. The suspension was stirred for 30 min, then the product was filtered off and dried under reduced pressure.

| Yield 120 mg. | MS (ES$^-$): m/e = 416.9 (M – H)$^-$. |
|---|---|

(ii) {4-Bromo-3-[2-(2,4-dichlorophenyl)-ethoxy]-5-methoxyphenyl}-(4-pyridin-4-ylmethyl-piperazin-1-yl)-methanone 0.05 g (0.119 mmol) of 4-Bromo-3-[2-(2,4-dichlorophenyl)-ethoxy]-5-methoxy-benzoic acid was dissolved in 2 ml of DMF and treated with 0.055 g (0.476 mmol) of N-NEM and 0.039 g (0.119 mmol) of TOTU and 0.021 g (0.12 mmol) of 1-Pyridin-4-ylmethyl-piperazine. The solution was stirred for 16 h at RT. The solvent was removed under reduced pressure, the residue was taken-up in acetonitrile and the residue was purified by preparative RP-HPLC eluting with a gradient of 0 to 100% acetonitrile in water (+0.01% trifluoroacetic acid). After lyophilization the product was obtained as its trifluoroacetate salt.

| Yield 35.5 mg. | MS (ES$^+$): m/e = 578 (M + H)$^+$. |
|---|---|

Example 20

4-Bromo-3-[2-(2,4-dichloro-phenyl)-ethoxy]-5-methoxy-N-(3,4,5,6-tetrahydro-2H-[1,4']bipyridinyl-4-ylmethyl)-benzamide

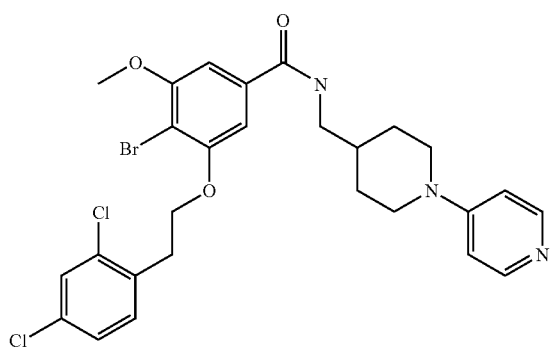

0.05 g (0.119 mmol) of 4-Bromo-3-[2-(2,4-dichlorophenyl)-ethoxy]-5-methoxy-benzoic acid was dissolved in 2 ml of DMF and treated with 0.055 g (0.476 mmol) of N-NEM and 0.039 g (0.119 mmol) of TOTU and 0.063 g (0.12 mmol) of C-(3,4,5,6-Tetrahydro-2H-[1,4']bipyridinyl-4-yl)-methylamine tris-trifluoroacetate salt. The solution was stirred for 16 h at RT. The solvent was removed under reduced pressure, the residue was taken-up in acetonitrile and the residue was purified by preparative RP-HPLC eluting with a gradient of 0 to 100% acetonitrile in water (+0.01% trifluoroacetic acid). After lyophilization the product was obtained as its trifluoroacetate salt.

| Yield 34.3 mg. | MS (ES$^+$): m/e = 592 (M + H)$^+$. |
|---|---|

Example 21

3-[2-(2,4-Dichloro-phenyl)-ethoxy]-4-methoxy-N-(2'-sulfamoyl-biphenyl-4-ylmethyl)-benzamide

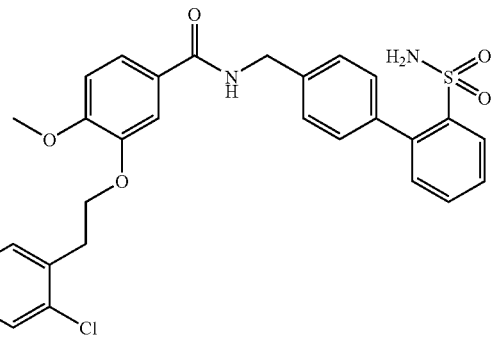

(i) 4'-Aminomethyl-biphenyl-2-sulfonic acid dimethylaminomethyleneamide 1.5 g of 4'-formyl-biphenyl-2-sulfonic acid dimethylaminomethyleneamide prepared according to H. Jendralla et al. (Liebigs Ann. 1995, 1253–7) in 15 ml MeOH were treated with 208.6 mg NaCNBH$_3$ and the reaction was stirred for 4 hours at RT. The pH was adjusted to 4.0, the reaction was filtered, the solvent was removed under reduced pressure and the residue was chromatographed on silica gel eluting with a gradient of 10–20% MeOH in DCM.

| Yield 912 mg. | MS (ES$^+$): m/e = 318 (M + H$^+$). |
|---|---|

(ii) 4'-Aminomethyl-biphenyl-2-sulfonic acid amide hydrochloride 400 mg of 4'-Aminomethyl-biphenyl-2-sulfonic acid dimethylaminomethyleneamide were treated with 10 ml MeOH and 4 ml conc. HCl and refluxed for 1 h. Solvent and HCl were evaporated and the product used without purification.

(iii) 3-[2-(2,4-Dichloro-phenyl)-ethoxy]-4-methoxy-N-(2'-sulfamoyl-biphenyl-4-ylmethyl)-benzamide 77 mg of 4'-aminomethyl-biphenyl-2-sulfonic acid amide hydrochloride were reacted with 100 mg of 3-[2-(2,4-dichloro-phenyl)-ethoxy]-4-methoxy-benzoic acid, 111 mg HATU and 0.2 ml DIPEA in 3 ml DMF for 1 h at RT. The pH was adjusted to 4.0, the solvent evaporated, the residue was dissolved in DCM and extracted with brine. After evaporation of the solvent, the product was purified by preparative RP-HPLC eluting with a gradient of 0–100% acetonitrile in water (+0.01% trifluoroacetic acid). After lyophilisation the product was obtained as its trifluoroacetate salt.

Yield: 33 mg. MS (ES$^+$): m/e=585.1; 587.0 (M+H$^+$).

Example 22

3-[2-(2,4-Dichloro-phenyl)-ethoxy]-4-methoxy-N-(1H-pyrrolo[3,2-c]pyridin-2-ylmethyl)-benzamide

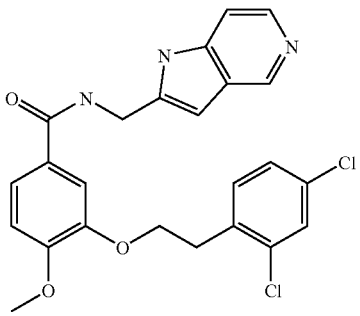

(i) 3-Hydroxy-4-methoxy-benzoic acid methyl ester 10 ml of thionyl chloride was added to 250 ml of MeOH at 0° C. The solution was stirred for 10 min. and 25 g of 3-hydroxy-4-methoxybenzoic acid was added. The reaction was stirred for 16 h at RT then heated to 50° C. for 3 h. The solvents were removed under reduced pressure. The residue was directly used in the next reaction.

(ii) 3-[2-(2,4-Dichlorophenyl)-ethoxy]-4-methoxy-benzoic acid methyl ester 20 g of triphenylphosphine and 10 g of 3-Hydroxy-4-methoxy-benzoic acid methyl ester were dissolved in 200 ml of anhydrous THF. The solution was cooled to 0° C. to 10° C. and a solution of 11.4 ml DEAD in 30 ml anhydrous THF was added dropwise over 20 min. The reaction was warmed to RT and stirred for 45 min. A solution of 11.3 ml 2-(2,4-Dichlorophenyl)-ethanol in 10 ml anhydrous THF was added with cooling. The reaction was stirred at RT for 16 h, and then the solvents were removed under reduced pressure. The residue was treated with n-heptane:ethyl acetate/1:1. The filtrate was dried under reduced pressure. The product was purified by silica gel chromatography, eluting with n-heptane:ethyl acetate/4:1, then n-heptane:ethyl acetate/3:1.

Yield 17 g.

(iii) 3-[2-(2,4-Dichlorophenyl)-ethoxy]-4-methoxy-benzoic acid 17 g of 3-[2-(2,4-Dichlorophenyl)-ethoxy]-4-methoxy-benzoic acid methyl ester were dissolved in 200 ml of MeOH:water/3:1. 4.1 g of lithium hydroxide monohydrate was added to the solution, and the reaction was stirred at RT for 16 h then at 90° C. for 2 h. The solution was cooled to RT, then acidified with half-concentrated hydrochloric acid. The solvents were removed under reduced pressure and the residue was washed twice with warm water to remove salts. The so obtained acid was used for the subsequent reaction without further purification.

(iv) 3-[2-(2,4-Dichloro-phenyl)-ethoxy]-4-methoxy-N-(1H-pyrrolo[3,2-c]pyridin-2-ylmethyl)-benzamide To a solution of 100 mg 3-[2-(2,4-Dichloro-phenyl)-ethoxy]-4-methoxy-benzoic acid in 1 ml DMF 53 mg carbonyldiimidazole were added. After stirring for 2 h at RT 48 mg of C-(1H-Pyrrolo[3,2-c]pyridin-2-yl)-methylamine tris-trifluoroacetate [prepared by adopting a procedure described by F. Ujjainwalla, D. Warner; Tertrahedron Lett. 1998, 39, 5355 and L. Xu, I. Lewis, S. Davidsen, J. Summers, Tertrahedron Lett. 1998, 39, 5159] were added and stirred over night after addition of 5 mg of DMAP. The solvent was removed under reduced pressure and the residue purified by preparative HPLC (C$_{18}$ reverse phase column, elution with a H$_2$O/MeCN gradient with 0.5% TFA) The fractions containing the product were evaporated and lyophilised. The product was obtained as its trifluoroacetate salt.

| Yield 48 mg. | MS (ESI+): 470, chloro pattern |
|---|---|

Example 23

3-[2-(2,4-Dichloro-phenyl)-ethoxy]-N-furo[3,2-c]pyridin-2-ylmethyl-4-methoxy-benzamide

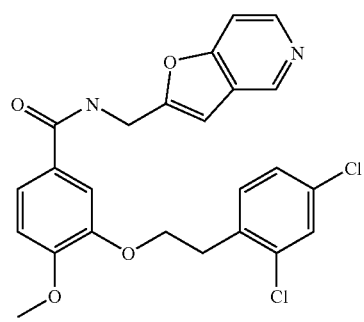

The title compound was prepared analogously to Example 22 with the difference that C-Furo[3,2-c]pyridin-2-yl-methylamine [prepared by adopting a procedure described by F. Ujjainwalla, D. Warner; Tertrahedron Lett. 1998, 39, 5355 and L. Xu, I. Lewis, S. Davidsen, J. Summers, Tertrahedron Lett. 1998, 39, 5159] was used instead of C-(1H-Pyrrolo[3,2-c]pyridin-2-yl)-methylamine. MS (ESI+): 471, chloro pattern

Example 24

3-[2-(2,4-Dichloro-phenyl)-ethoxy]-4-methoxy-N-(3-pyridin-4-yl-4,5-dihydro-isoxazol-5-ylmethyl)-benzamide

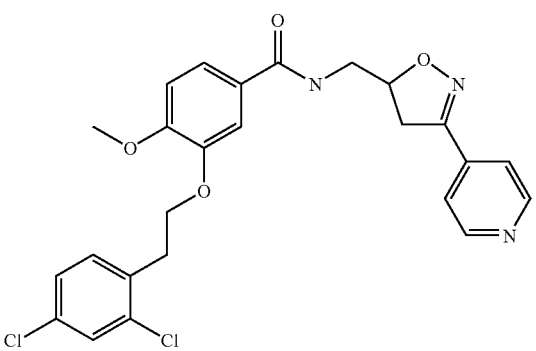

The title compound was prepared analogously to Example 22 with the difference that C-(3-Pyridin-4-yl-4,5-dihydro-isoxazol-5-yl)-methylamine was used instead of C-(1H-Pyrrolo[3,2-c]pyridin-2-yl)-methylamine. MS (ESI+): 500, chloro pattern

Example 25

3-[2-(2,4-Dichloro-phenyl)-ethoxy]-4-methoxy-N-(2-pyridin-4-yl-ethyl)-benzamide

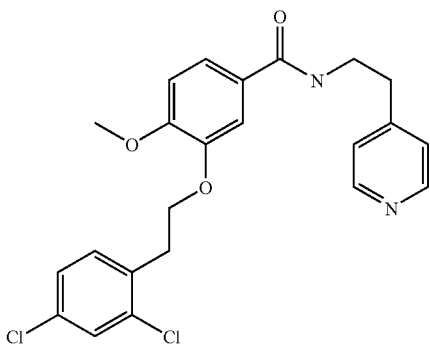

The title compound was prepared analogously to Example 22 with the difference that 2-Pyridin-4-yl-ethylamine was used instead of C-(1H-Pyrrolo[3,2-c]pyridin-2-yl)-methylamine. MS (ESI+): 445, chloro pattern

Example 26

3-[2-(2,4-Dichloro-phenyl)-ethoxy]-4-methoxy-N-(2-pyridin-2-yl-ethyl)-benzamide

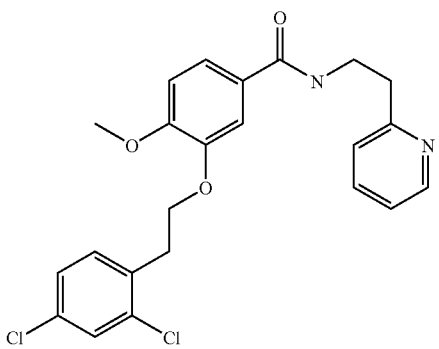

The title compound was prepared analogously to Example 22 with the difference that 2-Pyridin-2-yl-ethylamine was used instead of C-(1H-Pyrrolo[3,2-c]pyridin-2-yl)-methylamine. MS (ESI+): 445, chloro pattern

Example 27

3-[2-(2,4-Dichloro-phenyl)-ethoxy]-4-methoxy-N-piperidin-4-ylmethyl-benzamide

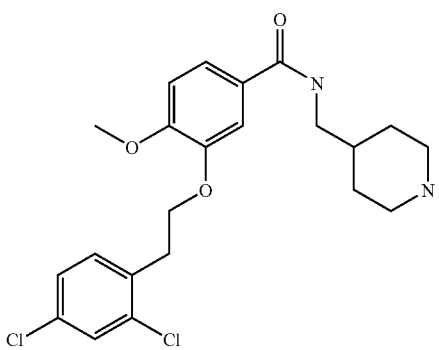

To a solution of 3 g 3-[2-(2,4-Dichloro-phenyl)-ethoxy]-4-methoxy-benzoic acid in 20 ml CH$_2$Cl$_2$ 4.5 ml N-NEM and subsequently 2.9 g TOTU were added. After stirring for 1 h at RT 2.8 g 4-Aminomethyl-piperidine-1-carboxylic acid tBu ester in 10 ml CH$_2$Cl$_2$ were added and the mixture was stirred for 2 h. The reaction mixture was then diluted with 50 ml CH$_2$Cl$_2$ and was washed with saturated aqueous NaHCO$_3$ solution. The organic layer was dried over Na$_2$SO$_4$. After removal of the solvent the white residue was recrystallized from ethyl acetate to yield 4.8 g of the BOC-protected derivative. This crystalline white solid was suspended in EtOH/HCl at RT. After 3 h a clear solution was obtained. Removal of the solvent under reduced pressure yielded a white foam.

Yield: 3.7 g    MS (ESI+) 437, chloro pattern

Alternatively the compound could be obtained by activation with carbonylimidazole and subsequent reaction of the activated intermediate with C-Piperidin-4-yl-methylamine.

Example 28

3-[2-(2,4-Dichloro-phenyl)-ethoxy]-N-[3-(1-hydroxy-pyridin-4-yl)-4,5-dihydro-isoxazol-5-ylmethyl]-4-methoxy-benzamide

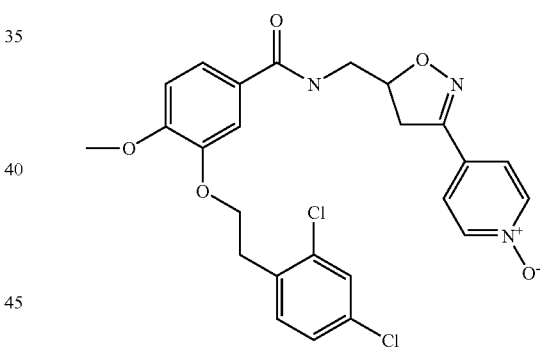

To a solution of 100 mg 3-[2-(2,4-Dichloro-phenyl)-ethoxy]-4-methoxy-N-(3-pyridin-4-yl-4,5-dihydro-isoxazol-5-ylmethyl)-benzamide in 5 ml CH$_2$Cl$_2$ 70 mg MCPBA were added at RT and stirred over night. The solvent was removed under reduced pressure and the residue purified by preparative HPLC (C$_{18}$ reverse phase column, elution with a H$_2$O/MeCN gradient with 0.5% TFA) The fractions containing the product were evaporated and lyophilised. The product was obtained as its trifluoroacetate salt.

Yield: 50 mg    MS (ESI+): 516, chloro pattern

Example 29

3-[2-(2,4-Dichloro-phenyl)-ethoxy]-N-[3-(1-methyl-pyridin-4-ium)-4,5-dihydro-isoxazol-5-ylmethyl]-4-methoxy-benzamidyl iodide

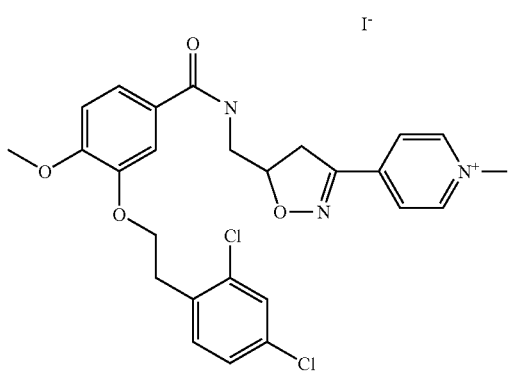

To a solution 30 mg (0.06 mmol) 3-[2-(2,4-Dichloro-phenyl)-ethoxy]-4-methoxy-N-(3-pyridin-4-yl-4,5-dihydro-isoxazol-5-ylmethyl)-benzamide in 5 ml acetone 0.3 ml MeI were added at RT and stirred for 2 d. The product precipitated from the solution as a yellow solid that was isolated by filtration.

| Yield. 25 mg | MS (ESI+): 515, chloro pattern |

Example 30

N-[5-(5-Chloro-thiophen-2-yl)-isoxazol-3-ylmethyl]-3-[2-(2,4-dichloro-phenyl)-ethoxy]4-methoxy-benzamide

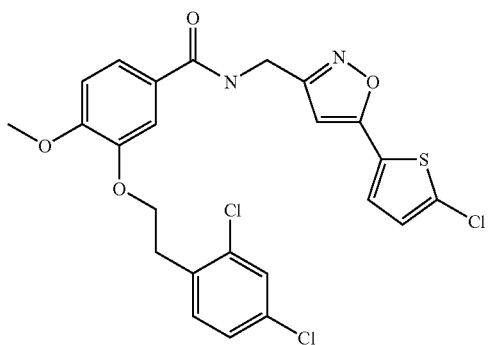

To a solution of 250 mg hexamethylenetetraamine (1.8 mmol) in 8 ml CHCl$_3$ 500 mg (1.8 mmol) 3-Bromomethyl-5-(5-chloro-thiophen-2-yl)-isoxazole [Ewing, William R.; Becker, Michael R.; Choi-Sledeski, Yong Mi; Pauls, Heinz W.; He, Wei; Condon, Stephen M.; Davis, Roderick S.; Hanney, Barbara A.; Spada, Alfred P.; Burns, Christopher J.; Jiang, John Z.; Li, Aiwen; Myers, Michael R.; Lau, Wan F.; Poli, Gregory B; PCT Int. Appl. (2001), 460 pp. WO 0107436 A2]. was added and the reaction mixture stirred at 50° C. for 1 h and kept for additional 3 h at RT. The solvent was removed under reduced pressure and the residue was taken up in 5 ml EtOH and 2 ml concentrated HCl. This solution was heated for 5 h at 50° C. and the precipitate collected by filtration. An aliquot (68 mg) of the obtained amine was then subsequently coupled with 100 mg (0.29 mmol) 3-[2-(2,4-Dichloro-phenyl)-ethoxy]4-methoxy-benzoic acid preactivated by addition of 95 mg TOTU and 150 mg N-NEM in 2 ml CH$_2$Cl$_2$. After stirring over night at RT the solvent was removed under reduced pressure an taken up in 3 ml saturated NaHCO$_3$ solution and filtered through a chem elut® cartridge by elution with ethyl acetate. After concentration under reduced pressure and purification by preparative HPLC (C$_{18}$ reverse phase column, elution with a H$_2$O/MeCN gradient with 0.5% TFA) the fractions containing the product were evaporated and lyophilised. The product was obtained as its trifluoroacetate salt. Yield 10 mg MS (ESI+): 537, chloro pattern

Example 31

N-(4-Aminomethyl-cyclohexylmethyl)-3-[2-(2,4-dichloro-phenyl)-ethoxy]-4-methoxy-benzamide

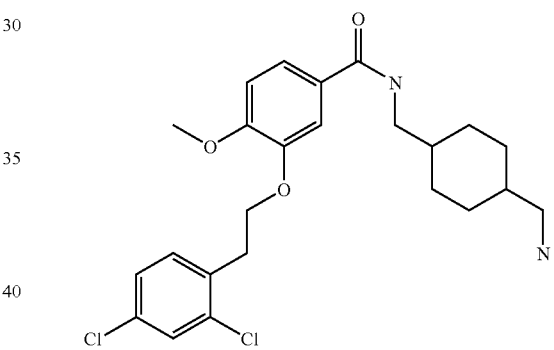

To a solution of 100 mg 3-[2-(2,4-Dichloro-phenyl)-ethoxy]-4-methoxy-benzoic acid in 2 ml CH$_2$Cl$_2$ 150 µl N-NEM and subsequently 96 mg TOTU were added. After stirring for 1 h at room temperature (RT) 83 mg C-(4-Aminomethyl-cyclohexyl)-methylamine in 1 ml CH$_2$Cl$_2$ were added and the mixture was stirred for additional 2 h followed by removal of the solvent under reduced pressure. The residue was taken up in 3 ml saturated NaHCO$_3$ solution and filtered through a chem elut® cartridge by elution with ethyl acetate. After concentration under reduced pressure and purification by preparative HPLC (C$_{18}$ reverse phase column, elution with a H$_2$O/MeCN gradient with 0.5% TFA) the fractions containing the product were evaporated and lyophilised. The product was obtained as its trifluoroacetate salt.

| Yield: 32 mg | MS (ESI+): 465, chloro pattern |

Example 32

3-[2-(2,4-Dichloro-phenyl)-ethoxy]-4-methoxy-N-(1-pyridin-4-ylmethyl-piperidin-4-ylmethyl)-benzamide

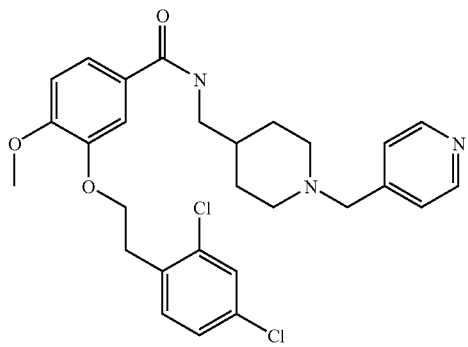

A suspension of 120 mg 3-[2-(2,4-Dichloro-phenyl)-ethoxy]-4-methoxy-N-piperidin-4-ylmethyl-benzamide, 50 mg 4-Picolylchloride hydrochloride and 110 mg $Cs_2CO_3$ in 2 ml DMF was stirred at RT over night. The reaction mixture was diluted with 2 ml water, filtered through a chem elut® cartridge by elution with ethyl acetate. After concentration under reduced pressure and purification by preparative HPLC ($C_{18}$ reverse phase column, elution with a $H_2O$/MeCN gradient with 0.5% TFA) the fractions containing the product were evaporated and lyophilised. The product was obtained as its trifluoroacetate salt.

| | |
|---|---|
| Yield 22 mg | MS (ESI+): 528, chloro pattern |

Analogously to example 32 the following compounds were prepared by a similar procedure

| Example | Structure | MS (ESI+) |
|---|---|---|
| 33 | 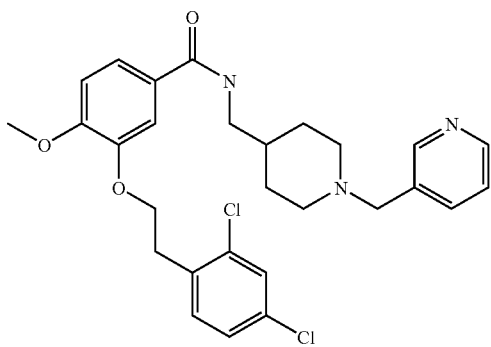 | 527, chloro pattern |
| 34 | 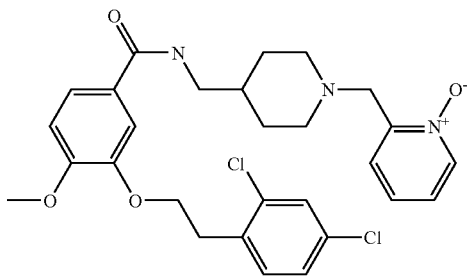 | 544, chloro pattern |

-continued
| Example | Structure | MS (ESI+) |
|---|---|---|
| 35 | 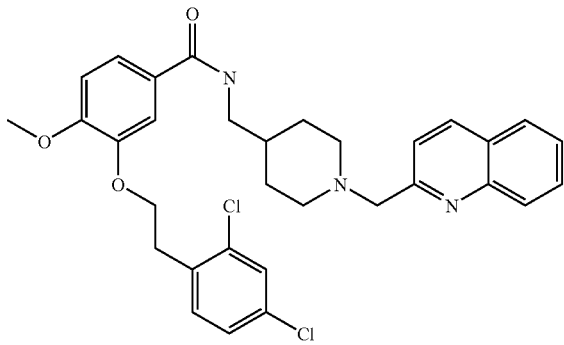 | 578, chloro pattern |
| 36 | 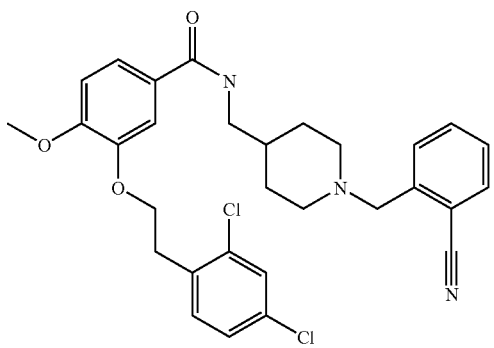 | 552, chloro pattern |
| 37 | 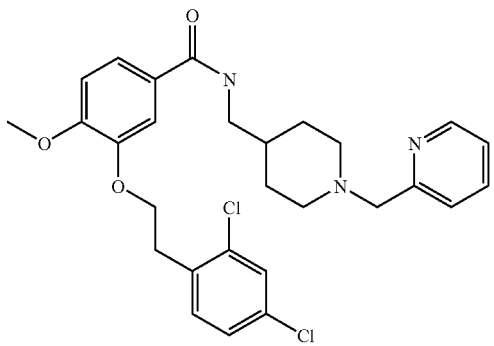 | 527, chloro pattern |
| 38 | 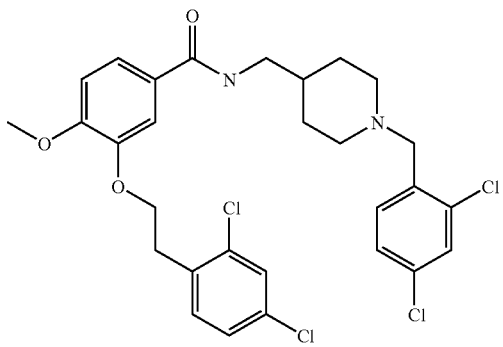 | 595, chloro pattern |

Example 39

3-[2-(2,4-Dichloro-phenyl)-ethoxy]-4-methoxy-N-(1-methyl-1H-benzoimidazol-5-yl)-benzamide

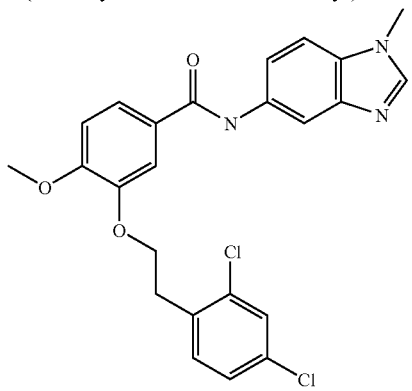

This compound was prepared analogously to example 31 employing 1-Methyl-1H-benzoimidazol-5-ylamine as amine component. MS (ESI+): 470, chloro pattern

Example 40

3-[2-(2,4-Dichloro-phenyl)-ethoxy]-4-methoxy-N-[4-(pyrimidin-2-ylsulfamoyl)-phenyl]-benzamide

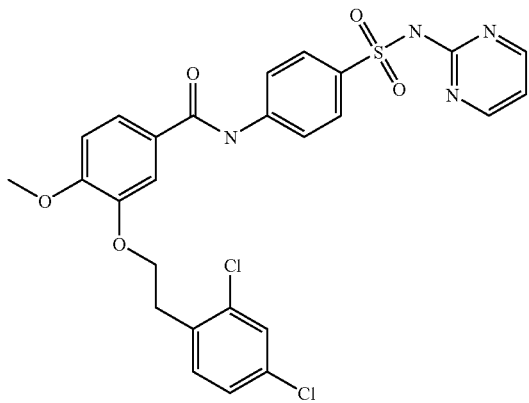

To a solution of 100 mg 3-[2-(2,4-Dichloro-phenyl)-ethoxy]-4-methoxy-benzoic acid in 2 ml CH$_2$Cl$_2$ 150 µl TEA and subsequently 77 mg TFFH were added. After stirring for 1 h at RT 87 mg 4-Amino-N-pyrimidin-2-yl-benzene-sulfonamide in 1 ml CH$_2$Cl$_2$ were added and the mixture was stirred over night followed by removal of the solvent under reduced pressure. The residue was taken up in 3 ml saturated NaHCO$_3$ solution and filtered through a chem elut® cartridge by elution with ethyl acetate. After concentration under reduced pressure and purification by preparative HPLC (C18 reverse phase column, elution with a H$_2$O/MeCN gradient with 0.5% TFA) the fractions containing the product were evaporated and lyophilised. The product was obtained as its trifluoroacetate salt.

| Yield 11 mg | MS (ESI+): 573, chloro pattern |

Example 41

N-[1-(5-Chloro-thiophene-2-sulfonyl)-piperidin-4-ylmethyl]-3-[2-(2,4-dichloro-phenyl)-ethoxy]-4-methoxy-benzamide

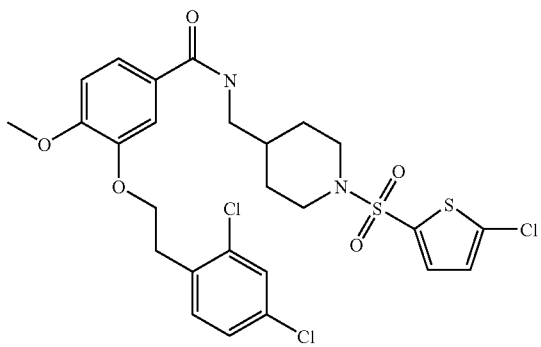

To a solution of 50 mg (0.14 mmol) 3-[2-(2,4-Dichloro-phenyl)-ethoxy]-4-methoxy-N-piperidin-4-ylmethyl-benzamide and 200 µl TEA in 3 ml DMF/CH$_2$Cl$_2$ 1:2, 73 mg 5-Chloro-thiophene-2-sulfonyl chloride were added at RT. The reaction mixture was stirred over night followed by concentration under reduced pressure. The residue was taken up in 1 ml (0.5M) NaOH solution and filtered through a chem elut® cartridge by elution with ethyl acetate. After concentration under reduced pressure and purification by preparative HPLC (C$_{18}$ reverse phase column, elution with a H$_2$O/MeCN gradient with 0.5% TFA) the fractions containing the product were evaporated and lyophilised. The product was obtained as its trifluoroacetate salt.

| Yield: 15 mg | MS (ESI+): 617, chloro pattern |

Analogously to example 42 the following compounds were prepared by a similar procedure:

| Example | Structure | MS (ESI+) |
|---|---|---|
| 43 | 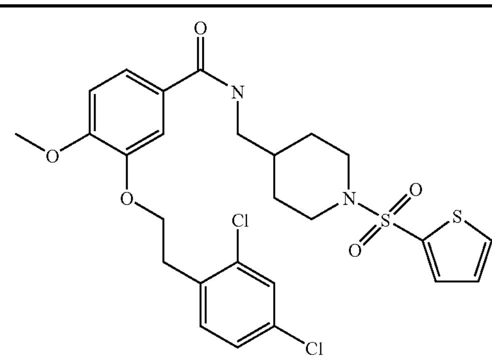 | 583, chloro pattern |

-continued
| Example | Structure | MS (ESI+) |
|---|---|---|
| 44 | 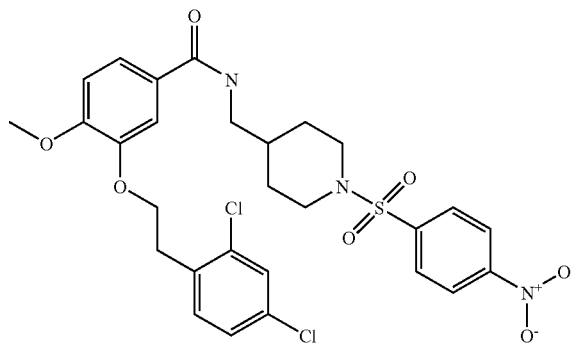 | 624, chloro pattern |
| 45 | 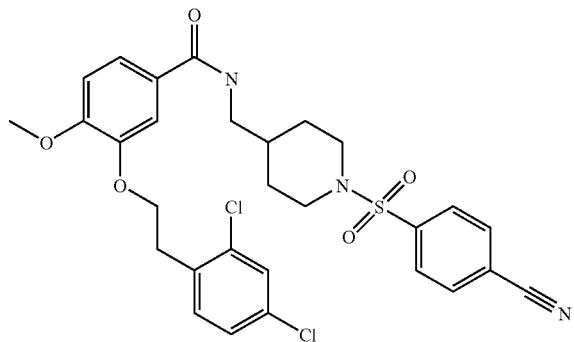 | 602, chloro pattern |
| 46 | 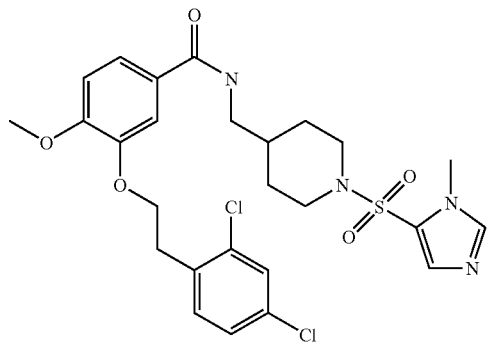 | 581, chloro pattern |
| 47 | 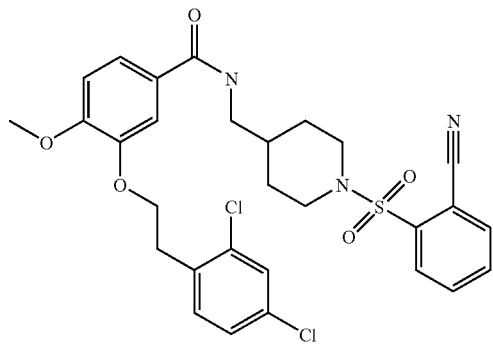 | 602, chloro pattern |

Example 48

3-[2-(2,4-Dichloro-phenyl)-ethoxy]-N-[1-(4-dimethylamino-benzoyl)-piperidin-4-ylmethyl]-4-methoxy-benzamide

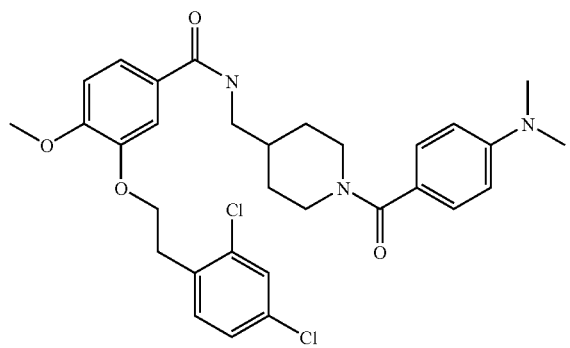

To a solution of 50 mg (0.14 mmol) 3-[2-(2,4-Dichloro-phenyl)-ethoxy]-4-methoxy-N-piperidin-4-ylmethyl-benzamide and 200 µl TEA in 3 ml DMF/CH$_2$Cl$_2$ 1:2, 61 mg 4-Dimethylamino-benzoyl chloride hydrochloride were added at RT. The reaction mixture was stirred over night followed by concentration under reduced pressure. The residue was taken up in 1 ml (0.5M) NaOH solution and filtered through a chem elut® cartridge by elution with ethyl acetate. After concentration under reduced pressure and purification by preparative HPLC (C18 reverse phase column, elution with a H$_2$O/MeCN gradient with 0.5% TFA) the fractions containing the product were evaporated and lyophilised. The product was obtained as its trifluoroacetate salt.

| Yield: 10 mg | MS (ESI+): 584, chloro pattern |
|---|---|

Example 49

N-[1-(2-Chloro-pyridine-4-carbonyl)-piperidin-4-ylmethyl]-3-[2-(2,4-dichloro-phenyl)-ethoxy]-4-methoxy-benzamide

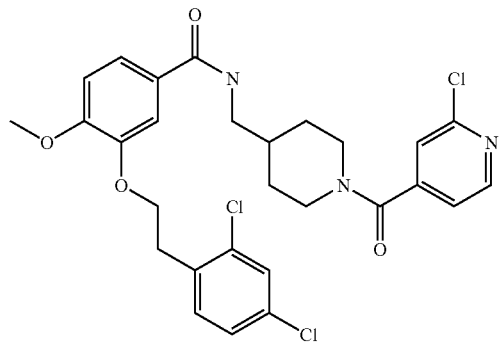

The title compound was prepared analogously to example 48 employing 2-Chloro-isonicotinoyl chloride hydrochloride as acylation component.
MS (ESI+): 576, chloro pattern

Example 50

3-[2-(2,4-Dichloro-phenyl)-ethoxy]-4-methoxy-N-[1-(pyridine-3-carbonyl)-piperidin-4-ylmethyl]-benzamide

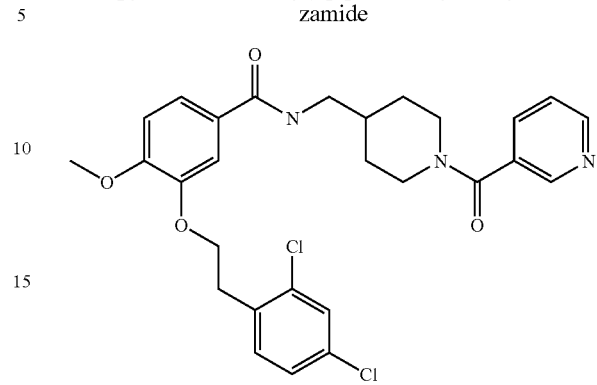

The title compound was prepared analogously to example 48 employing Nicotinoyl chloride hydrochloride as acylation component. MS (ESI+): 542, chloro pattern

Example 51

3-[2-(2,4-Dichloro-phenyl)-ethoxy]-N-[1-(2,2-dimethyl-propionyl)-piperidin-4-ylmethyl]-4-methoxy-benzamide

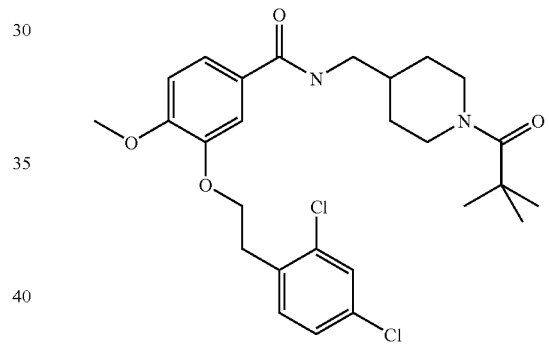

This compound was prepared analogously to example 48 employing pivalic anhydride as acylation component. MS (ESI+): 521, chloro pattern

Example 52

3-[2-(2,4-Dichloro-phenyl)-ethoxy]-N-[1-(6-hydroxy-pyridine-3-carbonyl)-piperidin-4-ylmethyl]-4-methoxy-benzamide

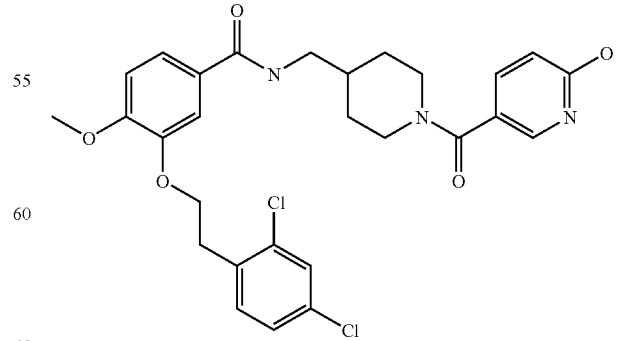

To a solution of 100 mg 3-[2-(2,4-Dichloro-phenyl)-ethoxy]-4-methoxy-N-piperidin-4-ylmethyl-benzamide in 2 ml CH$_2$Cl$_2$ 150 µl N-NEM and subsequently 150 mg TOTU were added. After stirring for 1 h at RT 70 mg 6-Hydroxy-nicotinic acid in 1 ml CH$_2$Cl$_2$ were added and the mixture was stirred for additional 2 h followed by removal of the solvent under reduced pressure. The residue was taken up in 3 ml saturated NaHCO$_3$ solution and filtered through a chem elut® cartridge by elution with ethyl acetate. After concentration under reduced pressure and purification by preparative HPLC (C$_{18}$ reverse phase column, elution with a H$_2$O/MeCN gradient with 0.5% TFA) the fractions containing the product were evaporated and lyophilised. The product was obtained as its trifluoroacetate salt.

| Yield: 45 mg | MS (ESI+): 558, chloro pattern |
|---|---|

Example 53

3-[2-(2,4-Dichloro-phenyl)-ethoxy]-4-methoxy-N-[1-(2-methoxy-pyridine-3-carbonyl)-piperidin-4-ylmethyl]-benzamide

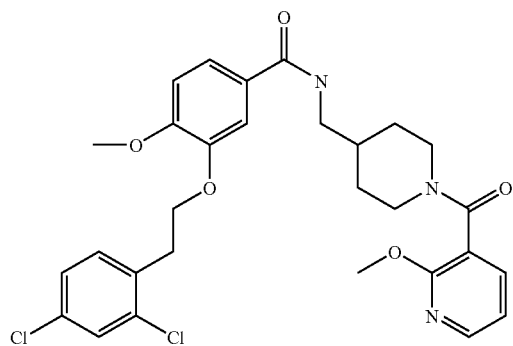

The title compound was prepared analogously to example 52 employing 2-Methoxy-nicotinic acid as acylation component MS (ESI+): 572, chloro pattern

Example 54

N-(1-Cyclopentyl-piperidin-4-ylmethyl)-3-[2-(2,4-dichloro-phenyl)-ethoxy]-4-methoxy-benzamide

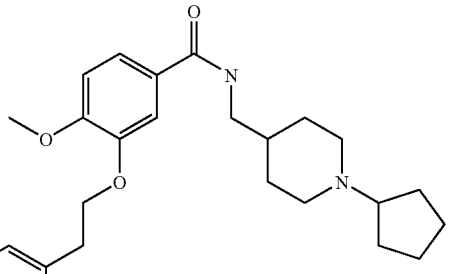

To a solution of 100 mg 3-[2-(2,4-Dichloro-phenyl)-ethoxy]-4-methoxy-N-piperidin-4-ylmethyl-benzamide and 35 mg cyclopentanone in 2 ml acetonitrile 27 mg Na(CN)BH$_3$ were introduced. After stirring at RT overnight the reaction mixture was heated to 80° C. for 4 h. After removal of the solvent under reduced pressure and purification by preparative HPLC (C$_{18}$ reverse phase column, elution with a H$_2$O/MeCN gradient with 0.5% TFA) the fractions containing the product were evaporated and lyophilised. The product was obtained as its trifluoroacetate salt.

| Yield: 47 mg | MS (ESI+): 505, chloro pattern |
|---|---|

Analogously to example 54 the following compounds were prepared by a similar procedure:

| Example | Structure | MS (ESI+) |
|---|---|---|
| 55 | 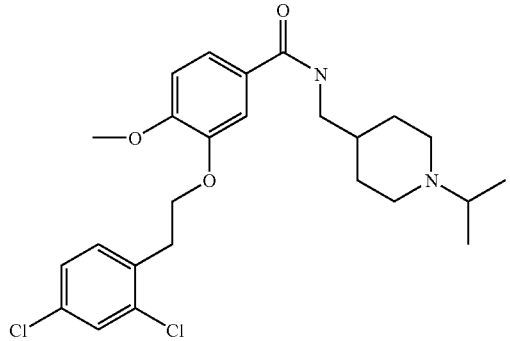 | 479, chloro pattern |

| Example | Structure | MS (ESI+) |
|---|---|---|
| 56 | 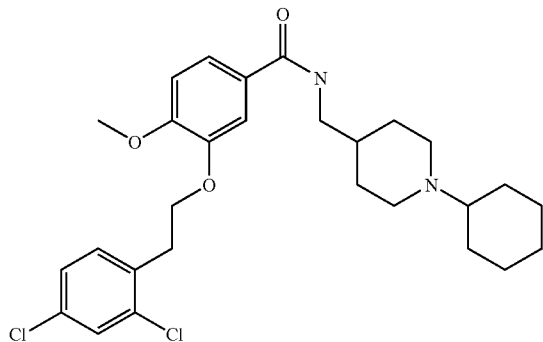 | 519, chloro pattern |
| 57 | 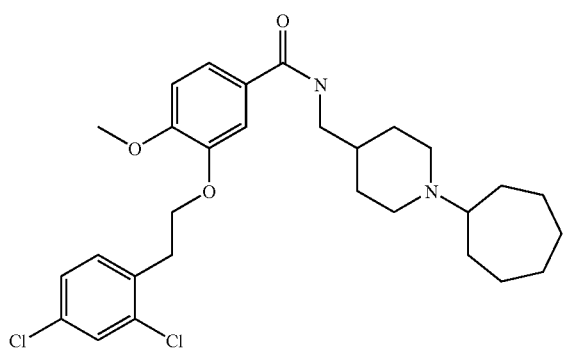 | 533, chloro pattern |
| 58 | 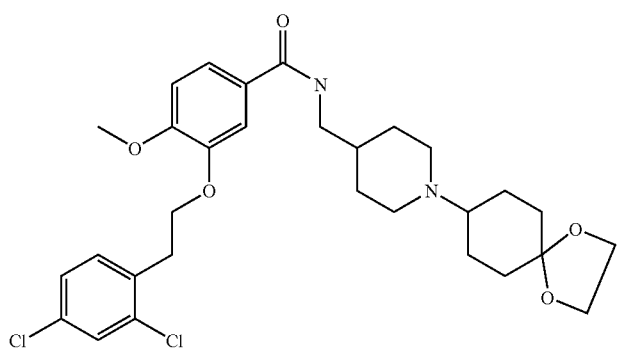 | 577, chloro pattern |
| 59 | 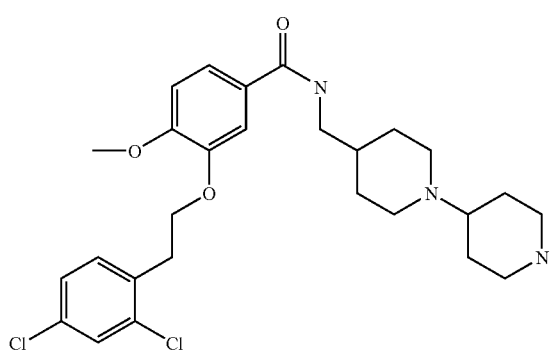 | 520, chloro pattern |

-continued

| Example | Structure | MS (ESI+) |
|---|---|---|
| 60 | 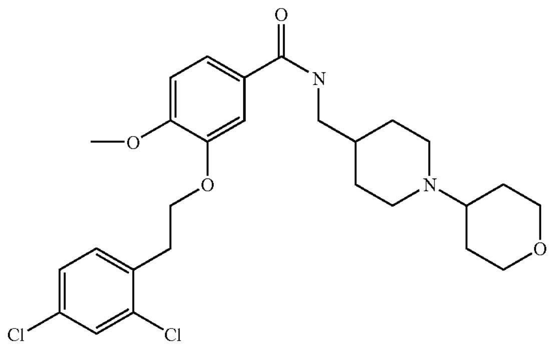 | 521, chloro pattern |

Example 61

3-[2-(2,4-Dichloro-phenyl)-ethoxy]-4-methoxy-N-(2'-methyl-3,4,5,6-tetrahydro-2H-[1,4']bipyridinyl-4-ylmethyl)-benzamide A solution of 100 mg 3-[2-(2,4-Dichloro-phenyl)-ethoxy]-4-methoxy-N-piperidin-4-ylmethyl-benzamide and 60 mg 4-Chloro-2-picoline in 6 ml n-BuOH/NEt₃ 5:1 was refluxed overnight. After subsequent removal of the solvent under reduced pressure and purification by preparative HPLC (C₁₈ reverse phase column, elution with a H₂O/MeCN gradient with 0.5% TFA) the fractions containing the product were evaporated and lyophilised. The product was obtained as its trifluoroacetate salt.

| Yield: 67 mg | MS (ESI+): 528, chloro pattern |
|---|---|

Analogously to example 61 the following compounds were prepared by a similar procedure:

| Example | Structure | MS (ESI+) |
|---|---|---|
| 62 | 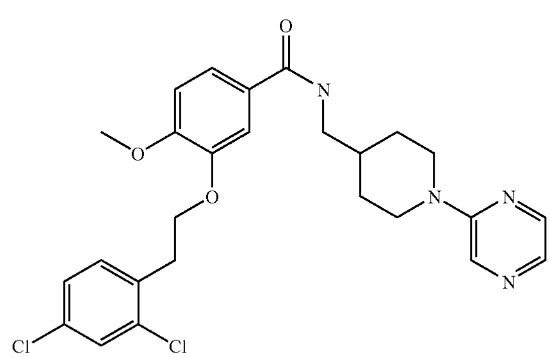 | 515, chloro pattern |

-continued
| Example | Structure | MS (ESI+) |
|---|---|---|
| 63 | 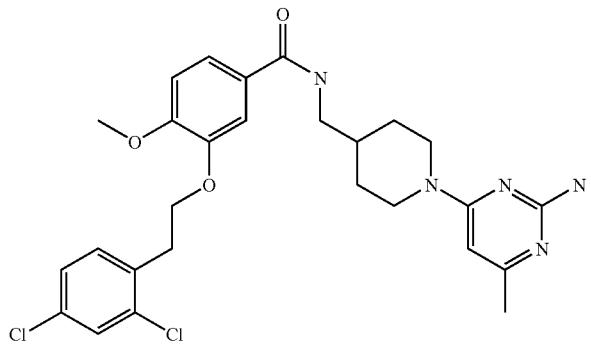 | 544, chloro pattern |
| 64 | 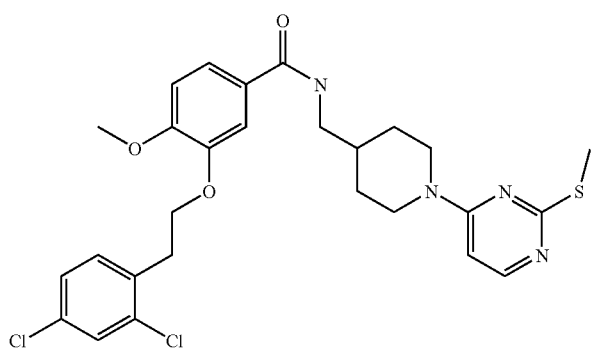 | 561, chloro pattern |
| 65 | 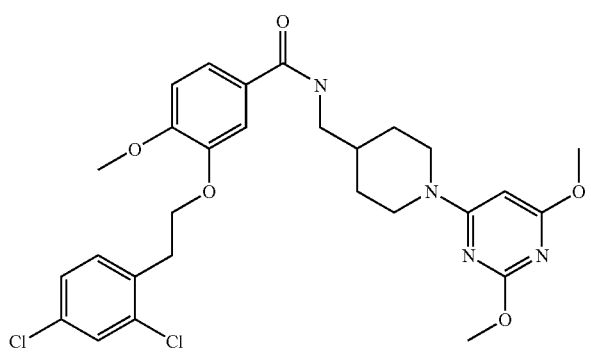 | 575, chloro pattern |
| 66 | 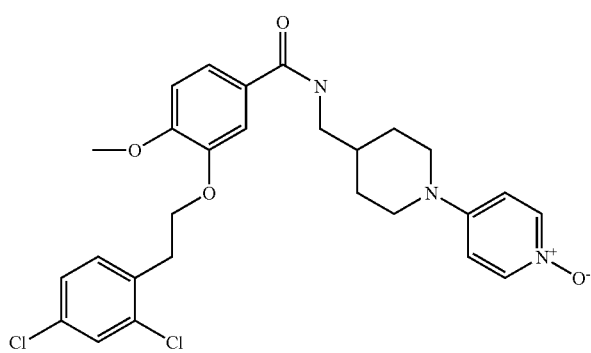 | 530, chloro pattern |

Example 67

3-[2-(2,4-Dichloro-phenyl)-ethoxy]-4-methoxy-N-(3,4,5,6-tetrahydro-2H-[1,4']bipyridinyl-4-ylm-ethyl)-benzamide

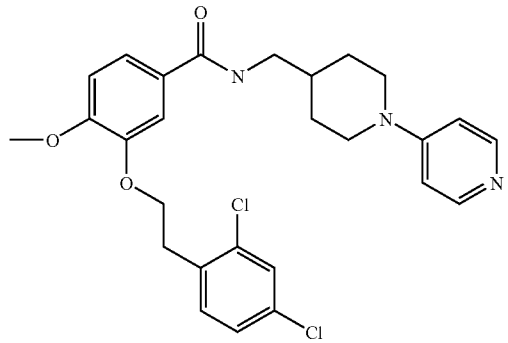

A mixture of 110 mg (0.25 mmol) 3-[2-(2,4-Dichloro-phenyl)-ethoxy]-4-methoxy-N-piperidin-4-ylmethyl-benzamide, 49 mg (0.49 mmol) 4-Bromopyridine hydrochloride, 57 mg sodium-t-butoxide in 5 ml THF were purged with argon for 10 min. Then 15 mg of (+)-R-Binap and 15 mg Pd(OAc)$_2$ were added under argon and the mixture refluxed overnight. The residue was taken up in 3 ml saturated NaHCO$_3$ solution and filtered through a chem elut® cartridge by elution with ethyl acetate. Subsequent removal of the solvent under reduced pressure and purification by preparative HPLC (C$_{18}$ reverse phase column, elution with a H$_2$O/MeCN gradient with 0.5% TFA) the fractions containing the product were evaporated and lyophilised. The product was obtained as its trifluoroacetate salt.

| Yield: 35 mg | MS (ESI+): 514, chloro pattern |

Example 68

3-[2-(2,4-Dichloro-phenyl)-ethoxy]-4-methoxy-N-(3,4,5,6-tetrahydro-2H-[1,2']bipyridinyl-4-ylm-ethyl)-benzamide

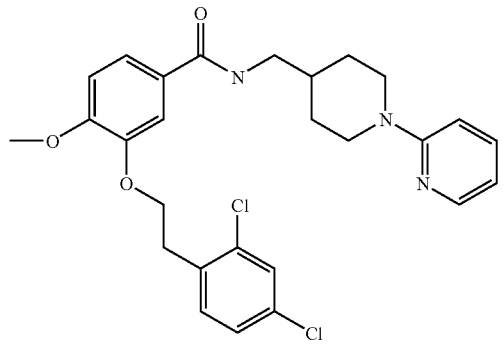

This compound was prepared analogously to example 67 employing 2-Bromopyridine hydrochloride coupling component. MS (ESI+): 514, chloro pattern

Example 69

N-[1-(4-Chloro-phenyl)-piperidin-4-ylmethyl]-3-[2-(2,4-dichloro-phenyl)-ethoxy]4-methoxy-benzamide

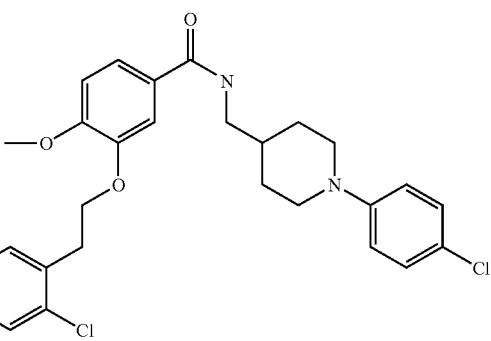

A mixture of 100 mg (0.2 mmol) 3-[2-(2,4-Dichloro-phenyl)-ethoxy]-4-methoxy-N-piperidin-4-ylmethyl-benzamide, 66 mg (0.34 mmol) 4-Bromochlorobenzene, 33 mg sodium-t-butoxide in 5 ml THF were purged with argon for 10 min. Then 37 mg of dppf and 5 mg Pd(OAc)$_2$ were added under argon and the mixture refluxed overnight. The residue was taken up in 3 ml saturated NaHCO$_3$ solution and filtered through a chem elut® cartridge by elution with ethyl acetate. Subsequent removal of the solvent under reduced pressure and purification by preparative HPLC (C18 reverse phase column, elution with a H$_2$O/MeCN gradient with 0.5% TFA) the fractions containing the product were evaporated and lyophilised. The product was obtained as its trifluoroacetate salt.

| Yield: 47 mg | MS (ESI+): 547, chloro pattern |

Analogously to example 69 the following compounds were prepared by a similar procedure:

| Example | Structure | MS (ESI+) |
|---|---|---|
| 70 | 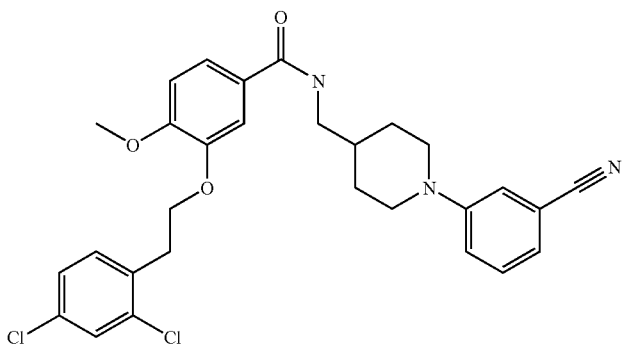 | 538, chloro pattern |
| 71 | 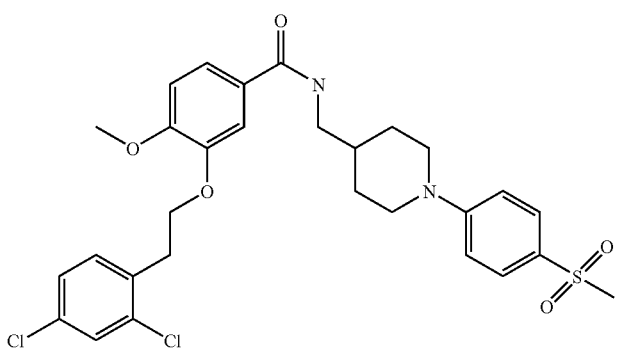 | 591, chloro pattern |
| 72 | 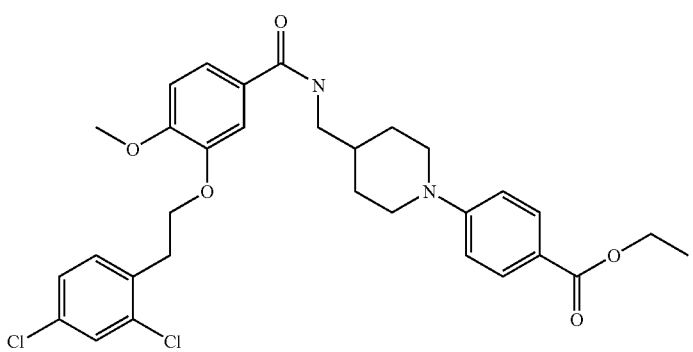 | 585, chloro pattern |
| 73 | 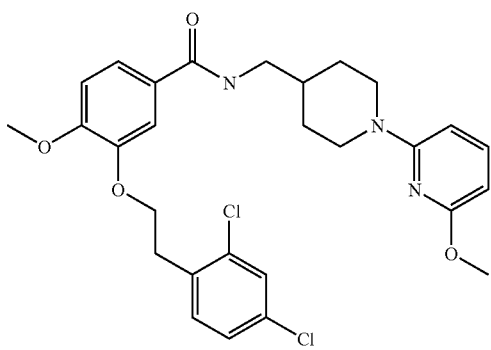 | 544, chloro pattern |

Example 74

3-[2-(2,4-Dichloro-phenyl)-ethoxy]-4-methoxy-N-(1-pyrimidin-5-yl-piperidin-4-ylmethyl)-benzamide

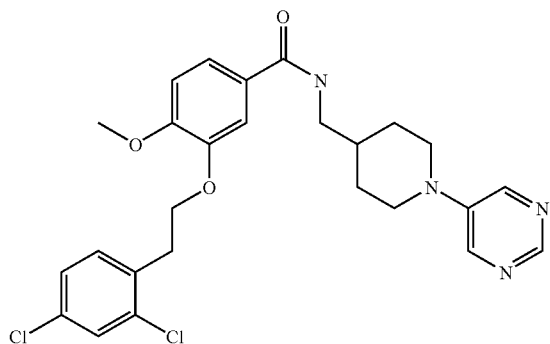

A mixture of 100 mg (0.2 mmol) 3-[2-(2,4-Dichlorophenyl)-ethoxy]-4-methoxy-N-piperidin-4-ylmethyl-benzamide, 50 mg (0.32 mmol) 4-Brompyrimidine, 70 mg sodium-t-butoxide in 5 ml dioxane were purged with argon for 10 min. Then 37 mg of 2-(Dicyclohexylphosphino)biphenyl and 20 mg $Pd_2(dba)_3$ were added under argon and the mixture refluxed overnight. The residue was taken up in 3 ml saturated $NaHCO_3$ solution and filtered through a chem elut® cartridge by elution with ethyl acetate. Subsequent removal of the solvent under reduced pressure and purification by preparative HPLC ($C_{18}$ reverse phase column, elution with a $H_2O$/MeCN gradient with 0.5% TFA) the fractions containing the product were evaporated and lyophilised. The product was obtained as its trifluoroacetate salt.

| Yield: 21 mg | MS (ESI+): 515, chloro pattern |
|---|---|

Example 75

3-[2-(2,4-Dichloro-phenyl)-ethoxy]-4-methoxy-N-(6'-methoxy-3,4,5,6-tetrahydro-2H-[1,3']bipyridinyl-4-ylmethyl)-benzamide

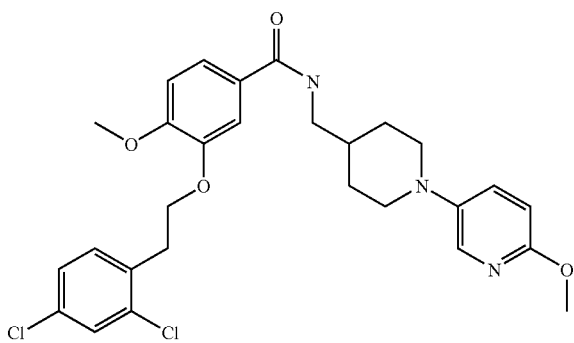

A mixture of 100 mg (0.2 mmol) 3-[2-(2,4-Dichlorophenyl)-ethoxy]-4-methoxy-N-piperidin-4-ylmethyl-benzamide, 55 mg (0.32 mmol) 5-Brom-2-methoxypyridine, 70 mg sodium-t-butoxide in 5 ml dioxane were purged with argon for 10 min. Then 37 mg of 2-(Dicyclohexylphosphino)biphenyl and 20 mg $Pd_2(dba)_3$ were added under argon and the mixture refluxed overnight. The residue was taken up in 3 ml saturated $NaHCO_3$ solution and filtered through a chem elut® cartridge by elution with ethyl acetate. Subsequent removal of the solvent under reduced pressure and purification by preparative HPLC ($C_{18}$ reverse phase column, elution with a $H_2O$/MeCN gradient with 0.5% TFA) the fractions containing the product were evaporated and lyophilised. The product was obtained as its trifluoroacetate salt.

| Yield: 52 mg | MS (ESI+): 544, chloro pattern |
|---|---|

Example 76

3-[2-(2,4-Dichloro-phenyl)-ethoxy]-4-methoxy-N-(1-phenyl-piperidin-4-ylmethyl)-benzamide

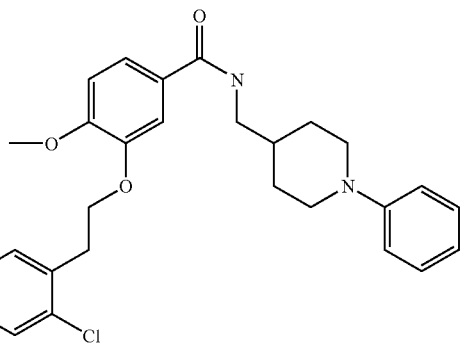

A mixture of 100 mg (0.2 mmol) 3-[2-(2,4-Dichlorophenyl)-ethoxy]-4-methoxy-N-piperidin-4-ylmethyl-benzamide, 50 mg (0.32 mmol) Bromobenzene, 70 mg sodium-t-butoxide in 5 ml dioxane were purged with argon for 10 min. Then 37 mg of 2-(Dicyclohexylphosphino)biphenyl and 20 mg $Pd_2(dba)_3$ were added under argon and the mixture refluxed overnight. The residue was taken up in 3 ml saturated $NaHCO_3$ solution and filtered through a chem elut® cartridge by elution with ethyl acetate. Subsequent removal of the solvent under reduced pressure and purification by preparative HPLC (C18 reverse phase column, elution with a $H_2O$/MeCN gradient with 0.5% TFA) the fractions containing the product were evaporated and lyophilised.

| Yield: 14 mg | MS (ESI+): 513, chloro pattern |
|---|---|

Example 77

4-Bromo-3-[2-(2,4-dichloro-phenyl)-ethoxy]-N-(3,4,5,6-tetrahydro-2H-[1,4']bipyridinyl-4-ylmethyl)-benzamide

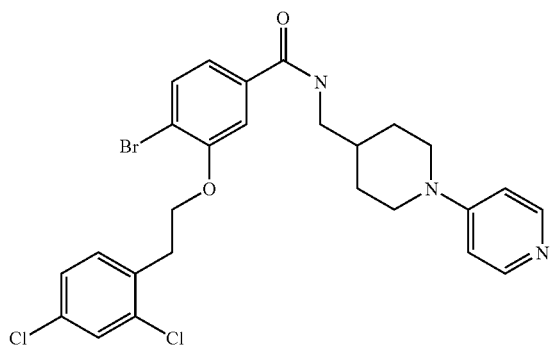

(3,4,5,6-Tetrahydro-2H-[1,4']bipyridinyl-4-ylmethyl)-carbamic acid tBu ester

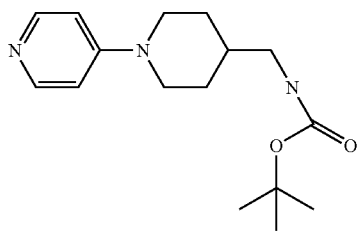

A suspension of 5 g (23.3 mmol) piperidin-4-ylmethyl-carbamic acid tBu ester 3.85 g (25.7 mmol) 4-chloropyridin hydrochloride in 15 ml n-BuOH/H$_2$O/NEt$_3$ 1:1:1 was refluxed for 3 days. After removal of the solvent under reduced pressure the residue was purified by chromatography on silica with CH$_2$Cl$_2$/MeOH 100:1->50:1->10:1–5:1 to yield a white solid.

(ii) C-(3,4,5,6-Tetrahydro-2H-[1,4']bipyridinyl-4-yl)-methylamine tris trifluoroacetate

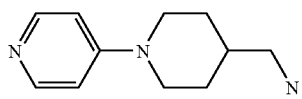

To a solution of 4.58 g (3,4,5,6-Tetrahydro-2H-[1,4'] bipyridinyl-4-ylmethyl)-carbamic acid tBu ester in 12 ml CH$_2$Cl$_2$ 12 ml TFA were added at RT. After stirring for 30 min the solution was diluted with 20 ml of toluene and evaporated under reduced pressure. The residue was codestilled twice with toluene and then used in the subsequent reactions without further purification.

(iii) 4-Bromo-3-hydroxy-benzoic acid methyl ester 1.5 ml of thionyl chloride was added to 40 ml of MeOH at 0° C. The solution was stirred for 10 min and 5 g of 4-Bromo-3-hydroxy-benzoic acid was added. The reaction was stirred for 16 h at RT then heated to 50° C. for 3 h. The solvents were removed under reduced pressure. The residue was used directly in the next step. Yield 5.92 g.

(iv) 4-Bromo-3-[2-(2,4-dichloro-phenyl)-ethoxy]-benzoic acid methyl ester 1.6 g of triphenylphosphine and 1 g of 4-Bromo-3-hydroxy-benzoic acid methyl ester were dissolved in 15 ml of anhydrous THF. The solution was cooled to 0° C. to 10° C. and a solution of 0.88 ml DEAD in 5 ml anhydrous THF was added dropwise over 20 min. The reaction was warmed to RT and stirred for 45 min. A solution of 0.69 ml 2-(2,4-Dichlorophenyl)-ethanol in 2 ml anhydrous THF was added with cooling. The reaction was stirred at RT for 3 h, then the solvents were removed under reduced pressure. The residue was treated with n-heptane:ethyl acetate/1:1. The filtrate was dried under reduced pressure. The product was purified by silica gel chromatography, eluting with n-heptane:ethyl acetate/4:1 to n-heptane:ethyl acetate/1:1. Yield 2 g.

4-Bromo-3-[2-(2,4-dichloro-phenyl)-ethoxy]-benzoic acid 2 g of 4-Bromo-3-[2-(2,4-dichloro-phenyl)-ethoxy]-benzoic acid methyl ester was dissolved in 10 ml of MeOH:water/3:1. 230 mg of lithium hydroxide monohydrate were added to the solution, and the reaction was stirred at RT for 16 h then at 50° C. for 2 h. The solution was cooled to RT, then acidified with half-concentrated hydrochloric acid. The suspension was concentrated under reduced pressure and then extracted with ethyl acetate. The organic layer was dried over Na$_2$SO$_4$ and the solvent was removed under reduced pressure to yield a white solid. Yield 2.2 g.

4-Bromo-3-[2-(2,4-dichloro-phenyl)-ethoxy]-N-(3,4,5,6-tetrahydro-2H-[1,4']bipyridinyl-4-ylmethyl)-benzamide To a solution of 200 mg 4-Bromo-3-[2-(2,4-dichloro-phenyl)-ethoxy]-benzoic acid in 4 ml CH$_2$Cl$_2$ 259 µl N-NEM and subsequently 168 mg TOTU were added. After stirring for 1 h at RT 272 mg C-(3,4,5,6-Tetrahydro-2H-[1,4']bipyridinyl-4-yl)-methylamine tris trifluoroacetate in 1 ml CH$_2$Cl$_2$ were added and the mixture was stirred for additional 2 h followed by removal of the solvent under reduced pressure. The residue was taken up in 3 ml saturated NaHCO$_3$ solution and filtered through a chem elut® cartridge by elution with ethyl acetate. After concentration under reduced pressure and purification by preparative HPLC (C18 reverse phase column, elution with a H$_2$O/MeCN gradient with 0.5% TFA) the fractions containing the product were evaporated and lyophilised. The product was obtained as its trifluoroacetate salt.

| Yield: 178 mg | MS (ESI+): 563, chloro pattern |

Analogously to example 77 the following compounds were prepared by a similar procedure:

| Example | Structure | MS (ESI+) |
|---|---|---|
| 78 | 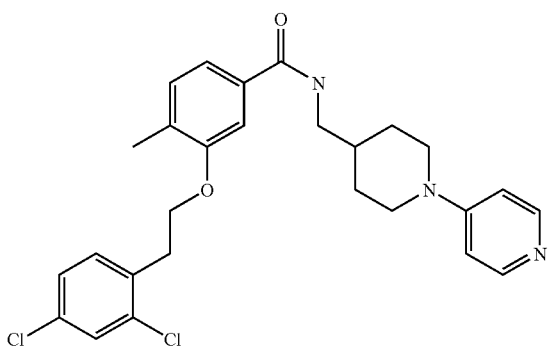 | 498, chloro pattern |
| 79 | 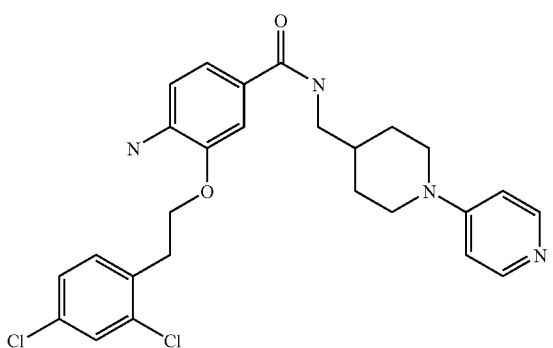 | 499, chloro pattern |
| 80 | 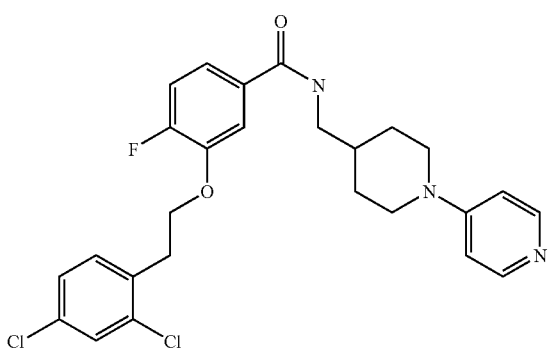 | 502, chloro pattern |
| 81 | 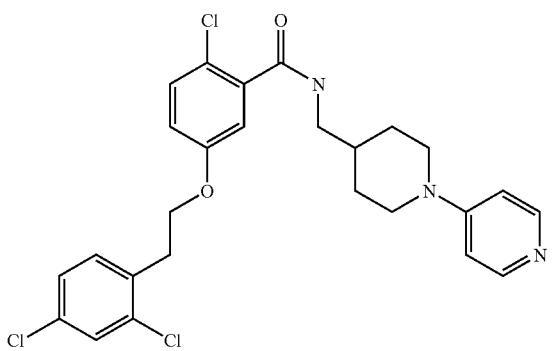 | 518, chloro pattern |

-continued

| Example | Structure | MS (ESI+) |
|---|---|---|
| 82 | 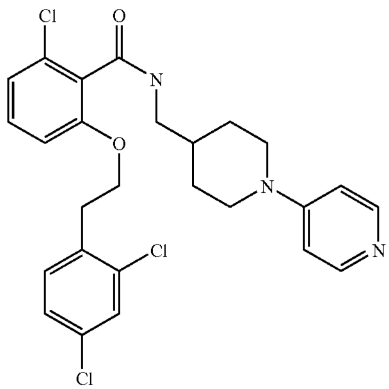 | 518, chloro pattern |
| 83 | 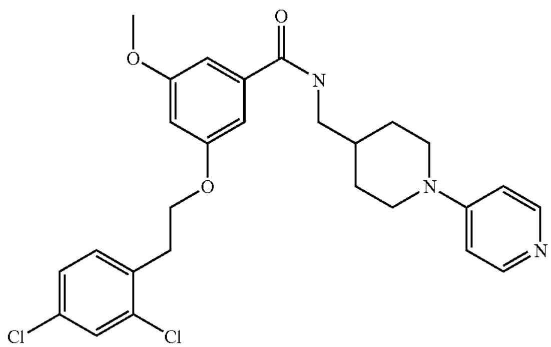 | 514, chloro pattern |
| 84 | 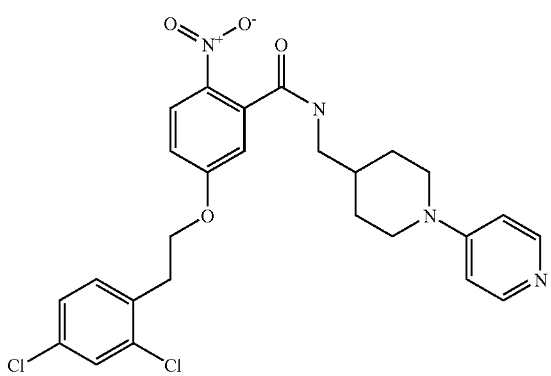 | 529, chloro pattern |
| 85 | 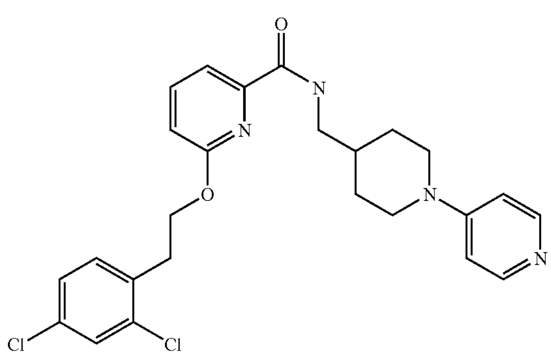 | 485, chloro pattern |

-continued

| Example | Structure | MS (ESI+) |
|---|---|---|
| 86 | 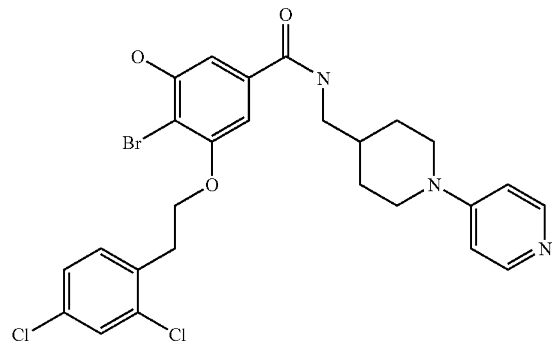 | 579, chloro pattern |
| 87 | 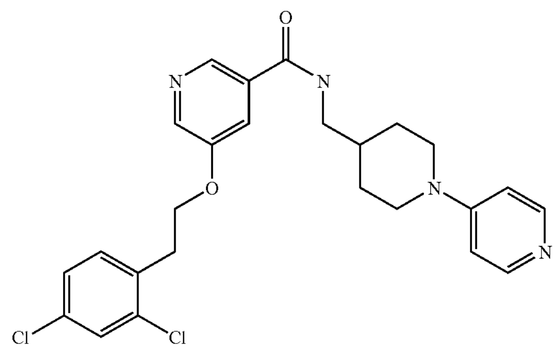 | 485, chloro pattern |

Example 88

3-[2-(2,4-Dichloro-phenyl)-ethoxy]-N-(3,4,5,6-tetrahydro-2H-[1,4']bipyridinyl-4-ylmethyl)-4-trifluoromethyl-benzamide

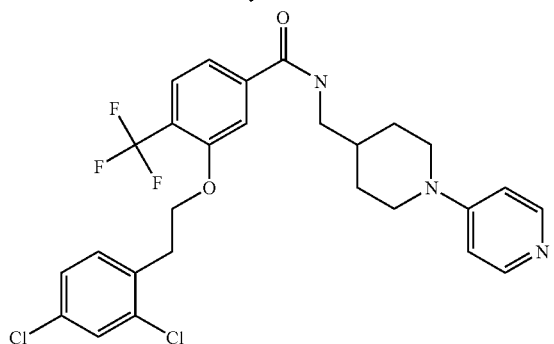

3-Hydroxy-4-iodo-benzoic acid

To a solution of 26 g 3-Hydroxybenzoic acid and 43 g Na₂CO₃ in 45 mg H₂O at 100° C. was added dropwise a solution of 48 g KI and 48 g iodine in 135 ml H₂O. After heating for additional 3 h the mixture was cooled to RT and acidified with concentrated HCl. The title compound precipitated as a white solid and was collected by filtration.
Yield 20 g.

(ii) 3-Hydroxy-4-iodo-benzoic acid methyl ester 5 ml of thionyl chloride was added to 120 ml of MeOH at 0° C. The solution was stirred for 10 min and 20 g of 4-Iodo-3-hydroxy-benzoic acid was added. The reaction was stirred for 16 h at RT then heated to 50° C. for 3 h. The solvents were removed under reduced pressure. The residue was used directly in the next step. Yield 21 g.

(iii) 4-Iodo-3-[2-(2,4-dichloro-phenyl)-ethoxy]-benzoic acid methyl ester 6.6 g of triphenylphosphine and 5 g of 4-Iodo-3-hydroxy-benzoic acid methyl ester were dissolved in 65 ml of anhydrous THF. The solution was cooled to 0° C. to 10° C. and a solution of 3.7 ml DEAD in 7.5 ml anhydrous THF was added dropwise over 20 min. The reaction was warmed to RT and stirred for 45 min. A solution of 2.8 ml 2-(2,4-Dichlorophenyl)-ethanol in 3 ml anhydrous THF was added with cooling. The reaction was stirred at RT for 3 h, then the solvents were removed under reduced pressure. The residue was treated with n-heptane:ethyl acetate/1:1. The filtrate was dried under reduced pressure. The product was purified by silica gel chromatography, eluting with n-heptane:ethyl acetate/4:1 to n-heptane:ethyl acetate/1:1.
Yield 8 g.

(iv) 3-[2-(2,4-Dichloro-phenyl)-ethoxy]-4-trifluoromethyl-benzoic acid methyl ester To suspension of 800 mg 4-Iodo-3-[2-(2,4-dichloro-phenyl)-ethoxy]-benzoic acid methyl ester, 520 mg CuI and 160 mg KF in 5 ml DMF 0.57 ml chloro-difluoro-acetic acid methyl ester were added dropwise at 120° C. and then stirred over night. After addition of 5 ml saturated aqueous NH₄Cl the suspension was filtered through a chem elut® cartridge by elution with ethyl acetate. After concentration under reduced pressure and purification by preparative HPLC (C₁₈ reverse phase column, elution with a H₂O/MeCN gradient with 0.5% TFA) the fractions containing the product were evaporated and lyophilised. The product was obtained as its trifluoroacetate salt.

Yield: 720 mg    MS (ESI+): 451, chloro pattern

3-[2-(2,4-Dichloro-phenyl)-ethoxy]-4-trifluoromethyl-benzoic acid 500 mg of 3-[2-(2,4-Dichloro-phenyl)-ethoxy]-4-trifluoromethyl-benzoic acid methyl ester was dissolved in 10 ml of MeOH:water/3:1. 230 mg of lithium hydroxide monohydrate were added to the solution, and the reaction was stirred at RT for 16 h then at 50° C. for 2 h. The solution was cooled to RT, then acidified with half-concentrated hydrochloric acid. The solution was concentrated under reduced pressure and then extracted with ethyl acetate. The organic layer was dried over $Na_2SO_4$ and the solvent was removed under reduced pressure to yield a white solid.

Yield: 480 mg.

3-[2-(2,4-Dichloro-phenyl)-ethoxy]-N-(3,4,5,6-tetrahydro-2H-[1,4']bipyridinyl-4-ylmethyl)-4-trifluoromethyl-benzamide To a solution of 200 mg 3-[2-(2,4-Dichloro-phenyl)-ethoxy]-4-trifluoromethyl-benzoic acid in 4 ml $CH_2Cl_2$ 1 ml N-NEM were added followed by 237 mg TOTU. After stirring for 1 h at RT 282 mg C-(3,4,5,6-Tetrahydro-2H-[1,4']bipyridinyl-4-yl)-methylamine tris trifluoroacetate in 1 ml $CH_2Cl_2$ was added and the mixture was stirred for additional 2 h followed by removal of the solvent under reduced pressure. The residue was taken up in 3 ml saturated $NaHCO_3$ solution and filtered through a chem elut® cartridge by elution with ethyl acetate. After concentration under reduced pressure and purification by preparative HPLC (C18 reverse phase column, elution with a $H_2O$/MeCN gradient with 0.5% TFA) the fractions containing the product were evaporated and lyophilised. The product was obtained as its trifluoroacetate salt.

| Yield: 180 mg | MS (ESI+): 552, chloro pattern |
| --- | --- |

Example 89

4-Cyano-3-[2-(2,4-dichloro-phenyl)-ethoxy]-N-(3,4,5,6-tetrahydro-2H-[1,4']bipyridinyl-4-ylmethyl)-benzamide

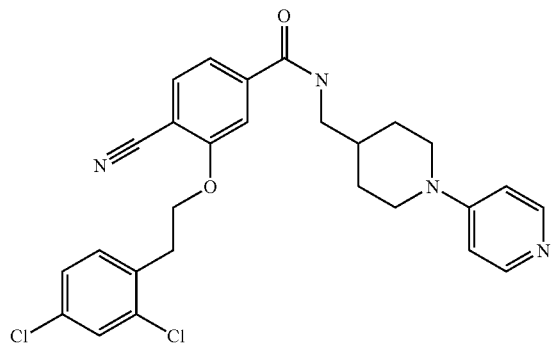

4-Cyano-3-[2-(2,4-dichloro-phenyl)-ethoxy]-benzoic acid methyl ester

A suspension of 800 mg 4-Iodo-3-[2-(2,4-dichloro-phenyl)-ethoxy]-benzoic acid methyl ester, 180 mg CuCN, 312 mg $Et_4NCN$ in 8 ml dioxane were purged with argon for 10 min. Then 91 mg $Pd_2(dba)_3$ and 111 mg dppf were added and the mixture refluxed overnight. After addition of 5 ml saturated aqueous $NH_4Cl$ the suspension was filtered through a chem elut® cartridge by elution with ethyl acetate. After concentration under reduced pressure and purification by preparative HPLC ($C_{18}$ reverse phase column, elution with a $H_2O$/MeCN gradient with 0.5% TFA) the fractions containing the product were evaporated and lyophilised.

| Yield: 500 mg | MS (ESI+): 350, chloro pattern |
| --- | --- |

(ii) 4-Cyano-3-[2-(2,4-dichloro-phenyl)-ethoxy]-benzoic acid 500 mg of 4-Cyano-3-[2-(2,4-dichloro-phenyl)-ethoxy]-benzoic acid methyl ester was dissolved in 50 ml of MeOH:water/3:1. 1 g of lithium hydroxide monohydrate was added to the added to the solution, and the reaction was stirred at RT for 16 h and 2 h at 50° C. The solution was cooled to RT, then acidified with half-concentrated hydrochloric acid. The suspension was concentrated under reduced pressure and then extracted with ethyl acetate. The organic layer was dried over $Na_2SO_4$ and the solvent was removed under reduced pressure to yield a white solid.

Yield: 480 mg.

(iii) 4-Cyano-3-[2-(2,4-dichloro-phenyl)-ethoxy]-N-(3,4,5,6-tetrahydro-2H-[1,4']bipyridinyl-4-ylmethyl)-benzamide To a solution of 200 mg 4-Cyano-3-[2-(2,4-dichloro-phenyl)-ethoxy]-benzoic acid in 4 ml $CH_2Cl_2$ 1 ml N-NEM were added followed by 237 mg TOTU. After stirring for 1 h at RT 282 mg C-(3,4,5,6-Tetrahydro-2H-[1,4']bipyridinyl-4-yl)-methylamine tris trifluoroacetate in 1 ml $CH_2Cl_2$ were added and the mixture was stirred for additional 2 h followed by removal of the solvent under reduced pressure. The residue was taken up in 3 ml saturated $NaHCO_3$ solution and filtered through a chem elut® cartridge by elution with ethyl acetate. After concentration under reduced pressure and purification by preparative HPLC (C18 reverse phase column, elution with a $H_2O$/MeCN gradient with 0.5% TFA) the fractions containing the product were evaporated and lyophilised. The product was obtained as its trifluoroacetate salt.

| Yield: 124 mg | MS (ESI+): 509, chloro pattern |
| --- | --- |

Example 90

3-[3-(2,4-Dichloro-phenyl)-ureido]-N-(3,4,5,6-tetrahydro-2H-[1,4']bipyridinyl-4-ylmethyl)-benzamide

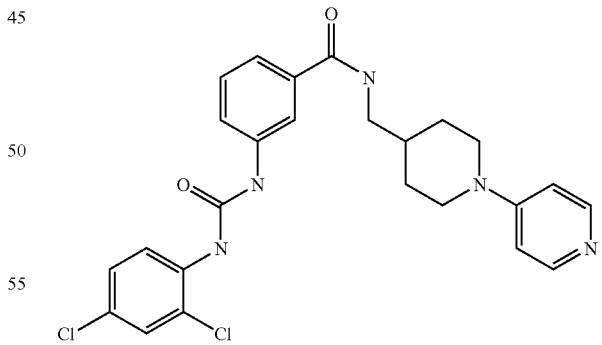

3-[3-(2,4-Dichloro-phenyl)-ureido]-benzoic acid

To a solution of 200 mg 3-Isocyanato-benzoic acid methyl ester in 2 ml ethyl acetate is added dropwise a solution of 162 mg 2,4-dichloroaniline in 1 ml ethyl acetate. After 5 h at RT the solvent was removed under reduced pressure and the residue dissolved in 5 ml MeOH/THF/$H_2O$ 2:2:1. 100 mg lithium hydroxide monohydrate was added and the mixture stirred over night at RT. After removal of the solvent the residue was acidified by addition of 5 ml half concentrated HCl. The precipitating acid was filtered off and dried.

(ii) 3-[3-(2,4-Dichloro-phenyl)-ureido]-N-(3,4,5,6-tetrahydro-2H-[1,4']bipyridinyl-4-ylmethyl)-benzamide To a solution of 100 mg 3-[3-(2,4-Dichloro-phenyl)-ureido]-benzoic acid in 5 ml ethyl acetate 0.5 ml NEt$_3$ and 102 mg BOP-Cl were added. After 10 min 100 mg C-(3,4,5,6-Tetrahydro-2H-[1,4']bipyridinyl-4-yl)-methylamine tris trifluoroacetate in 1 ml CH$_2$Cl$_2$ were added and the mixture stirred for 2 h at RT followed by removal of the solvent under reduced pressure. The residue was taken-up in 3 ml saturated NaHCO$_3$ solution and filtered through a chem elut® cartridge by elution with ethyl acetate. After concentration under reduced pressure and purification by preparative HPLC (C$_{18}$ reverse phase column, elution with a H$_2$O/MeCN gradient with 0.5% TFA) the fractions containing the product were evaporated and lyophilised. The product was obtained as its trifluoroacetate salt.

| Yield: 73 mg | MS (ESI+): 498, chloro pattern |
|---|---|

Example 91

3-[3-(5-Chloro-pyridin-2-yl)-ureido]-N-(3,4,5,6-tetrahydro-2H-[1,4']bipyridinyl-4-ylmethyl)-benzamide

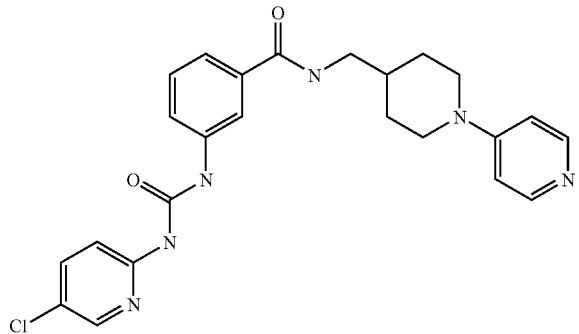

This compound was prepared analogously to example 90 employing 5-Chloro-pyridin-2-ylamine as amine component. MS (ESI+): 465, chloro pattern Example 92

3-[2-(2,4-Dichloro-phenyl)-ethoxy]-4-methylsulfanyl-N-(3,4,5,6-tetrahydro-2H-[1,4']bipyridinyl-4-ylmethyl)-benzamide

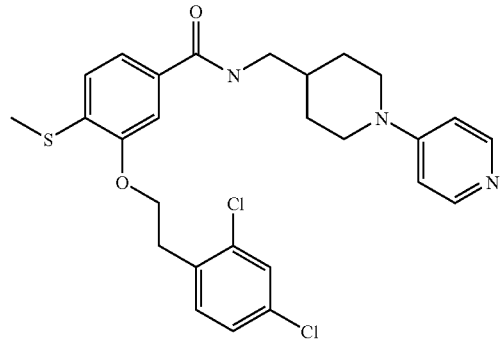

3-[2-(2,4-Dichloro-phenyl)-ethoxy]-4-methylsulfanyl-benzoic acid

To a solution of 300 mg 3-[2-(2,4-Dichloro-phenyl)-ethoxy]-4-fluoro-benzoic acid methyl ester in 0.5 ml DMSO 70 mg NaSMe were added and stirred over night. After addition of 0.3 ml H$_2$O and 20 mg lithium hydroxide monohydrate the solution was stirred for 5 h and then acidified with diluted HCl. The mixture was extracted with ethyl acetate, the organic layer dried over Na$_2$SO$_4$. Removal of the solvent yielded the acid as a yellow solid.

(ii) 3-[2-(2,4-Dichloro-phenyl)-ethoxy]-4-methylsulfanyl-N-(3,4,5,6-tetrahydro-2H-[1,4']bipyridinyl-4-ylmethyl)-benzamide To a solution of 120 mg 3-[2-(2,4-Dichloro-phenyl)-ethoxy]-4-methylsulfanyl-benzoic acid in 5 ml ethyl acetate 0.5 ml NEt$_3$ and 102 mg BOP—Cl were added. After 10 min 100 mg C-(3,4,5,6-Tetrahydro-2H-[1,4']bipyridinyl-4-yl)-methylamine tris trifluoroacetate in 1 ml CH$_2$Cl$_2$ were added and the mixture stirred for 10 h at RT followed by removal of the solvent under reduced pressure. The residue was taken up in 3 ml saturated NaHCO$_3$ solution and filtered through a chem elut® cartridge by elution with ethyl acetate. After concentration under reduced pressure and purification by preparative HPLC (C$_{18}$ reverse phase column, elution with a H$_2$O/MeCN gradient with 0.5% TFA) the fractions containing the product were evaporated and lyophilised. The product was obtained as its trifluoroacetate salt.

| Yield: 57 mg | MS (ESI+): 530, chloro pattern |
|---|---|

Example 93

3-[5-(5-Chloro-thiophen-2-yl)-isoxazol-3-ylmethoxy]-4-methoxy-N-(3,4,5,6-tetrahydro-2H-[1,4']bipyridinyl-4-ylmethyl)-benzamide

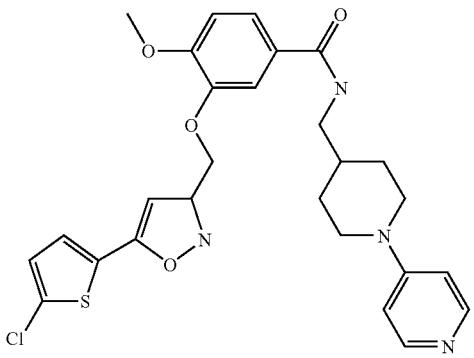

3-[5-(5-Chloro-thiophen-2-yl)-isoxazol-3-ylmethoxy]-4-methoxy-benzoic acid

To a solution of 145 mg 3-Hydroxy-4-methoxy-benzoic acid methyl ester in 2 ml DMF 200 mg 3-Bromomethyl-5-(5-chloro-thiophen-2-yl)-isoxazole [prepared as described in example 30] and 325 mg Cs$_2$CO$_3$ were added. The mixture was stirred for 3 h at RT and then diluted with 1 ml H$_2$O and 1 ml EtOH. After addition of 500 mg lithium hydroxide monohydrate the suspension was stirred over night. Subsequent removal of the solvent under reduced pressure and addition of diluted HCl yielded the acid as a white precipitate that was collected by filtration.

(ii) 3-[5-(5-Chloro-thiophen-2-yl)-isoxazol-3-ylmethoxy]-4-methoxy-N-(3,4,5,6-tetrahydro-2H-[1,4']bipyridinyl-4-ylmethyl)-benzamide To a solution of 180 mg 3-[5-(5-Chloro-thiophen-2-yl)-isoxazol-3-ylmethoxy]-4-methoxy-benzoic acid in 5 ml ethyl acetate 0.5 ml NEt₃ and 250 mg BOP-Cl were added. After 30 min 200 mg C-(3,4,5,6-Tetrahydro-2H-[1,4']bipyridinyl-4-yl)-methylamine tris trifluoro-acetate in 1 ml CH₂Cl₂ were added and the mixture stirred for 10 h at RT followed by removal of the solvent under reduced pressure. The residue was taken up in 3 ml saturated NaHCO₃ solution and filtered through a chem elut® cartridge by elution with ethyl acetate. After concentration under reduced pressure and purification by preparative HPLC (C18 reverse phase column, elution with a H₂O/MeCN gradient with 0.5% TFA) the fractions containing the product were evaporated and lyophilised. The product was obtained as its trifluoroacetate salt.

| Yield: 157 mg | MS (ESI+): 539, chloro pattern |
|---|---|

Analogously to example 93 the following compounds were prepared by a similar procedure:

| Example | Structure | MS (ESI+) |
|---|---|---|
| 94 | 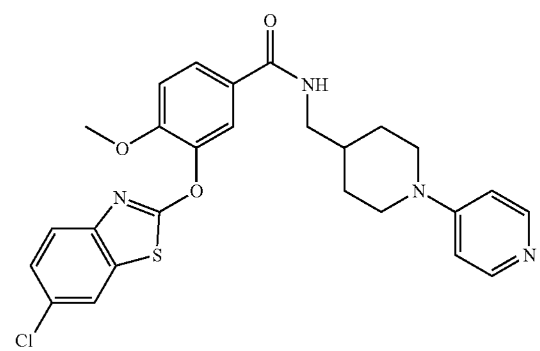 | 509, chloro pattern |
| 95 | 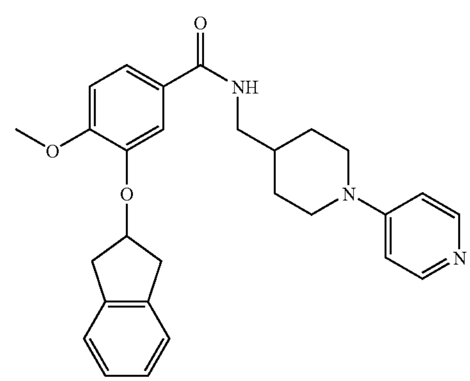 | 558 |
| 96 | 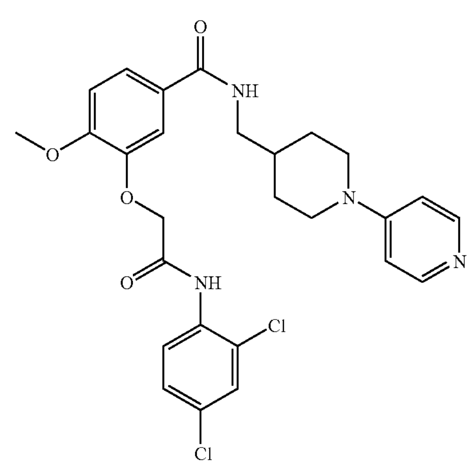 | 543, chloro pattern |

Example 97

3-(6-Chloro-benzo[b]thiophene-2-sulfonylamino)-4-methoxy-N-(3,4,5,6-tetrahydro-2H-[1,4']bipyridinyl-4-ylmethyl)-benzamide

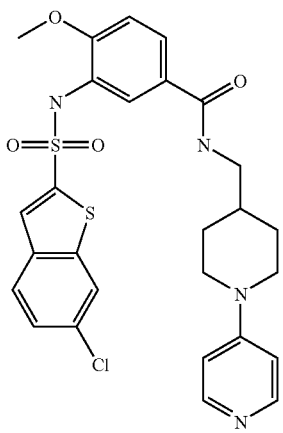

3-(6-Chloro-benzo[b]thiophene-2-sulfonylamino)-4-methoxy-benzoic acid

To a solution of 36 mg 3-Amino-4-methoxy-benzoic acid methyl esterin 1 ml acetonitrile and 0.1 ml NEt₃ 50 mg 6-Chloro-benzo[b]thiophene-2-sulfonyl chloride [prepared by a procedure described by Ewing, William R.; Becker, Michael R.; Choi-Sledeski, Yong Mi; Pauls, Heinz W.; He, Wei; Condon, Stephen M.; Davis, Roderick S.; Hanney, Barbara A.; Spada, Alfred P.; Burns, Christopher J.; Jiang, John Z.; Li, Aiwen; Myers, Michael R.; Lau, Wan F.; Poli, Gregory B., PCT Int. Appl. (1999), 300 pp. WO99/37304] were added at RT. The mixture was stirred at RT for 5 h, then diluted with 2 ml MeOH/THF/H₂O 2:2:1. After addition of 100 mg lithium hydroxide monohydrate the suspension was stirred over night. Subsequent removal of the solvent and addition of diluted HCl yielded the acid as a white precipitate, which was filtered off.

(ii) 3-(6-Chloro-benzo[b]thiophene-2-sulfonylamino)-4-methoxy-N-(3,4,5,6-tetrahydro-2H-[1,4']bipyridinyl-4-ylmethyl)-benzamide To a solution of 80 mg 3-(6-Chloro-benzo[b]thiophene-2-sulfonylamino)-4-methoxy-benzoic acid in 5 ml ethyl acetate 0.1 ml NEt₃ and 100 mg BOP-Cl were added. After 30 min 200 mg C-(3,4,5,6-Tetrahydro-2H-[1,4']bipyridinyl-4-yl)-methylamine tris trifluoroacetate in 1 ml CH₂Cl₂ were added and the mixture stirred for 10 h at RT followed by removal of the solvent under reduced pressure. The residue was taken up in 3 ml saturated NaHCO₃ solution and filtered through a chem elut® cartridge by elution with ethyl acetate. After concentration under reduced pressure and purification by preparative HPLC (C18 reverse phase column, elution with a H₂O/MeCN gradient with 0.5% TFA) the fractions containing the product were evaporated and lyophilised. The product was obtained as its trifluoroacetate salt.

| Yield: 44 mg | MS (ESI+): 571, chloro pattern |
|---|---|

Example 98

3-(2,4-Dichloro-benzylsulfamoyl)-N-(3,4,5,6-tetrahydro-2H-[1,4']bipyridinyl-4-ylmethyl)-benzamide

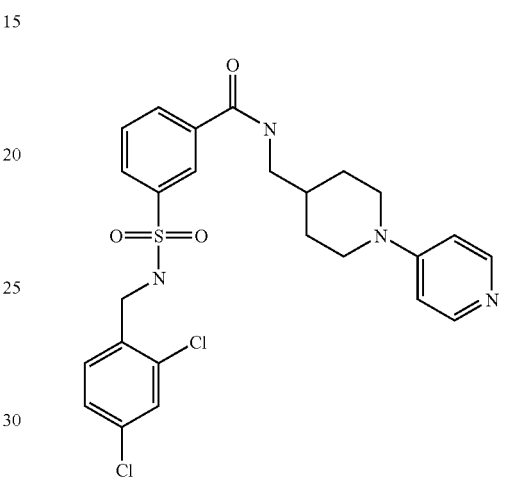

3-(2,4-Dichloro-benzylsulfamoyl)-benzoic acid

To a solution of 1.3 g 2,4-Dichloro-benzylamine and 5 mg DMAP in 10 ml pyridine 1 g 3-Chlorosulfonyl-benzoic acid in 10 ml ethyl acetate was added dropwise. After stirring over night the solvent was removed under reduced pressure and the residue was taken up in 10 ml diluted HCl and extracted with ethyl acetate. The organic layer is dried over Na₂SO₄ and concentrated to yield the acid as a yellow solid.

(ii) 3-(2,4-Dichloro-benzylsulfamoyl)-N-(3,4,5,6-tetrahydro-2H-[1,4']bipyridinyl-4-ylmethyl)-benzamide To a solution of 100 mg 3-(2,4-Dichloro-benzylsulfamoyl)-benzoic acid in 4 ml CH₂Cl₂ 259 µl N-NEM and subsequently 47 mg TOTU were added. After stirring for 1 h at RT 172 mg C-(3,4,5,6-Tetrahydro-2H-[1,4']bipyridinyl-4-yl)-methylamine tris trifluoro-acetate in 1 ml CH₂Cl₂ were added and the mixture was stirred for additional 2 h followed by removal of the solvent under reduced pressure. The residue was taken up in 3 ml saturated NaHCO₃ solution and filtered through a chem elut® cartridge by elution with ethyl acetate. After concentration under reduced pressure and purification by preparative HPLC (C18 reverse phase column, elution with a H₂O/MeCN gradient with 0.5% TFA) the fractions containing the product were evaporated and lyophilised. The product was obtained as its trifluoroacetate salt.

| Yield: 32 mg | MS (ESI+): 533, chloro pattern |
|---|---|

Example 99

3-(5-Chloro-pyridin-2-ylsulfamoyl)-N-(3,4,5,6-tetrahydro-2H-[1,4']bipyridinyl-4-ylmethyl)-benzamide

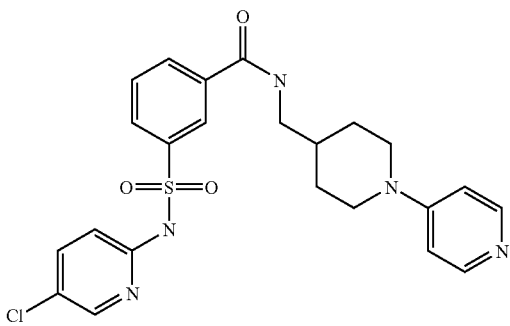

This compound was prepared analogously to example 95 employing 5-Chloro-pyridin-2-ylamineas amine component. MS (ESI+): 486, chloro pattern

Example 100

3-[2-(2,4-Dichloro-phenyl)-acetylamino]-4-methoxy-N-(3,4,5,6-tetrahydro-2H-[1,4']bipyridinyl-4-ylmethyl)-benzamide

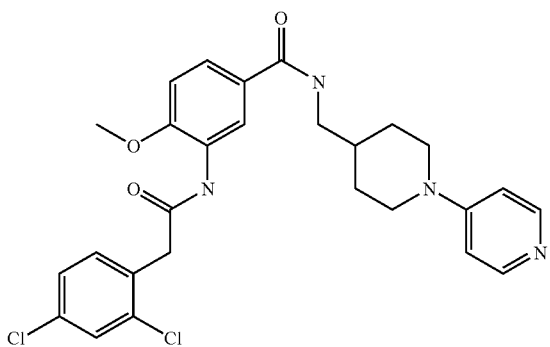

3-[2-(2,4-Dichloro-phenyl)-acetylamino]-4-methoxy-benzoic acid methyl ester

To a solution of 1.1 g 3-Amino-4-methoxy-benzoic acid methyl ester and 1 g (2,4-Dichloro-phenyl)-acetic acid in 15 ml CH$_2$Cl$_2$, 2.7 ml NEt$_3$ and 1.24 g BOP-Cl and 10 mg DMAP were added. After stirring over night the solvent was removed under reduced pressure and the residue directly purified by chromatography on silica with ethyl acetate/heptane 1:5->1:1 to yield the ester as a yellow oil.

(ii) 3-[2-(2,4-Dichloro-phenyl)-acetylamino]-4-methoxy-benzoic acid

To a solution of 400 mg 3-[2-(2,4-Dichloro-phenyl)-acetylamino]-4-methoxy-benzoic acid methyl ester in 5 ml MeOH/H$_2$O 2:1 56 mg lithium hydroxide monohydrate were added and the mixture was stirred over night. The suspension was diluted with 5 ml concentrated HCl to precipitate the acid. After filtration the filter cake was washed twice with water and then dried to yield the acid as a white powder.

(iii) 3-[2-(2,4-Dichloro-phenyl)-acetylamino]-4-methoxy-N-(3,4,5,6-tetrahydro-2H-[1,4']bipyridinyl-4-ylmethyl)-benzamide To a solution of 150 mg 3-[2-(2,4-Dichloro-phenyl)-acetylamino]-4-methoxy-benzoic acid in 4 ml CH$_2$Cl$_2$ 259 µl N-NEM and subsequently 70 mg TOTU were added. After stirring for 1 h at RT 268 mg C-(3,4,5,6-Tetrahydro-2H-[1,4']bipyridinyl-4-yl)-methylamine tris trifluoroacetate in 1 ml CH$_2$Cl$_2$ were added and the mixture was stirred for additional 2 h followed by removal of the solvent under reduced pressure. The residue was taken up in 3 ml saturated NaHCO$_3$ solution and filtered through a chem elut® cartridge by elution with ethyl acetate. After concentration under reduced pressure and purification by preparative HPLC (C18 reverse phase column, elution with a H$_2$O/MeCN gradient with 0.5% TFA) the fractions containing the product were evaporated and lyophilised. The product was obtained as its trifluoroacetate salt.

| Yield: 97 mg | MS (ESI+): 527, chloro pattern |
|---|---|

Example 101

5-[2-(2,4-Dichloro-phenyl)-ethoxy]-N-(3,4,5,6-tetrahydro-2H-[1,4']bipyridinyl-4-ylmethyl)-isophthalamide

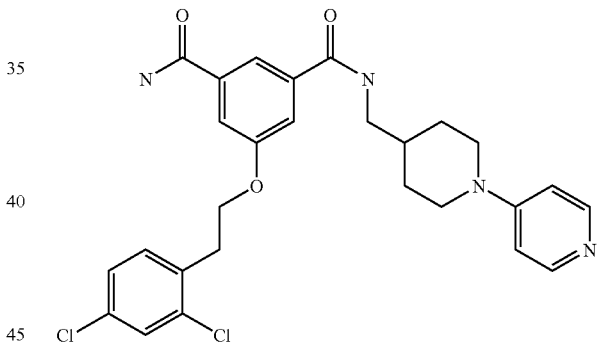

5-[2-(2,4-Dichloro-phenyl)-ethoxy]-isophthalic acid dimethyl ester 1.75 g of triphenylphosphine and 1 g of 5-Hydroxy-isophthalic acid dimethyl ester were dissolved in 17 ml of anhydrous THF. The solution was cooled to 0–10° C. and a solution of 1 ml DEAD in 1 ml anhydrous THF was added dropwise over 20 min. The reaction was warmed to RT and stirred for 45 min. A solution of 11.3 ml 2-(2,4-Dichlorophenyl)-ethanol in 1 ml anhydrous THF was added with cooling. The reaction was stirred at RT for 16 h, then the solvents were removed under reduced pressure. The residue was treated with n-heptane:ethyl acetate/1:1. The filtrate was dried under reduced pressure and the product was purified by silica gel chromatography, eluting with n-heptane:ethyl acetate/4:1 to n-heptane:ethyl acetate/3:1.

(ii) 5-[2-(2,4-Dichloro-phenyl)-ethoxy]-isophthalic acid 500 mg 5-[2-(2,4-Dichloro-phenyl)-ethoxy]-isophthalic acid dimethyl ester were dissolved in 50 ml of MeOH:water/3:1. Then 1 g of lithium hydroxide monohydrate was added the solution, and the reaction was stirred at RT for 16 h and 2 h at 50° C. The solution was cooled to RT and then acidified with half-concentrated hydrochloric acid. The suspension was concentrated under reduced pressure and then extracted with ethylacetate. The organic layer was dried over $Na_2SO_4$ and the solvent was removed under reduced pressure to yield a white solid.

(iii) 5-[2-(2,4-Dichloro-phenyl)-ethoxy]-isophthalamic acid

To a solution of 100 mg 5-[2-(2,4-Dichloro-phenyl)-ethoxy]-isophthalic acid in 3 ml THF 46 mg N,N-carbonyldiimidazole was added at RT. After 1 h 0.5 ml concentrated aqueous $NH_3$ solution were added and the reaction mixture was stirred for further 4 h. Concentration under reduced pressure and purification by preparative HPLC (C18 reverse phase column, elution with a $H_2O$/MeCN gradient with 0.5% TFA) the fractions containing the product were evaporated and lyophilised to yield a white solid. The product was obtained as its trifluoroacetate salt.

(iv) 5-[2-(2,4-Dichloro-phenyl)-ethoxy]-N-(3,4,5,6-tetrahydro-2H-[1,4']bipyridinyl-4-ylmethyl)-isophthalamide To a solution of 40 mg 5-[2-(2,4-Dichloro-phenyl)-ethoxy]-isophthalamic acid in 2 ml $CH_2Cl_2$ 59 µl N-NEM and subsequently 37 mg TOTU were added. After stirring for 1 h at RT 43 mg C-(3,4,5,6-Tetrahydro-2H-[1,4']bipyridinyl-4-yl)-methylamine tris trifluoro-acetate in 1 ml $CH_2Cl_2$ were added and the mixture was stirred for additional 2 h followed by removal of the solvent under reduced pressure. The residue was taken up in 3 ml saturated $NaHCO_3$ solution and filtered through a chem elut® cartridge by elution with ethyl acetate. After concentration under reduced pressure and purification by preparative HPLC (C18 reverse phase column, elution with a $H_2O$/MeCN gradient with 0.5% TFA) the fractions containing the product were evaporated and lyophilised. The product was obtained as its trifluoroacetate salt.

| Yield: 12 mg | MS (ESI+): 527, chloro pattern |

Example 102

5-[2-(2,4-Dichloro-phenyl)-ethoxy]-1-oxy-N-(3,4,5,6-tetrahydro-2H-[1,4']bipyridinyl-4-ylmethyl)-nicotinamide

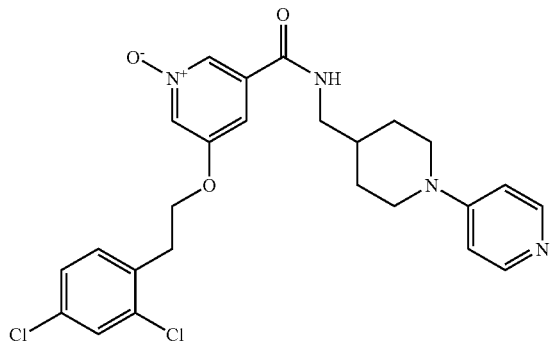

5-Hydroxy-1-oxy-nicotinic acid methyl ester

To a solution of 600 mg 5-Hydroxy-nicotinic acid methyl ester in 8 ml $CH_2Cl_2$ 880 mg MCPBA were added at 0° C. After stirring at RT over night the solvent was removed under reduced pressure. The residue was extracted with ethylacetate/heptane 1:1. The product was isolated after filtration as a white solid and used without further purification in the subsequent reaction.

Yield: 600 mg.

(ii) 5-[2-(2,4-Dichloro-phenyl)-ethoxy]-1-oxy-nicotinic acid methyl ester 1.4 g of diphenyl-2-pyridylphosphine and 600 mg 5-Hydroxy-1-oxy-nicotinic acid methyl ester and 0.5 ml 2-(2,4-dichlorophenyl)-ethanol were dissolved in 16 ml of anhydrous THF. The solution was cooled to 0–10° C. and a solution of 1.22 g di-tert-butyl azodicarboxylate in 1 ml anhydrous THF was added dropwise over 20 min. The reaction was warmed to RT and stirred over night. After addition of 14 ml saturated methanolic HCl the reaction mixture was stirred for 1 h and then the solvent was removed under reduced pressure. The residue was dissolved in $CH_2Cl_2$ and extracted with half-concentrated hydrochloric acid. The organic layer was evaporated and residue subjected to the subsequent reaction without further purification.

Yield: 1.2 g.

(iii) 5-[2-(2,4-Dichloro-phenyl)-ethoxy]-1-oxy-nicotinic acid 1.2 g 5-[2-(2,4-Dichloro-phenyl)-ethoxy]-1-oxy-nicotinic acid methyl ester were dissolved in 15 ml of MeOH/water 3:1. Then 200 mg of lithium hydroxide monohydrate was added the solution, and the reaction was stirred at RT for 16 h. The solution was acidified with half-concentrated hydrochloric acid under precipitation of the product. After filtration a white solid was obtained.

Yield: 900 mg.

(iv) 5-[2-(2,4-Dichloro-phenyl)-ethoxy]-1-oxy-N-(3,4,5,6-tetrahydro-2H-[1,4']bipyridinyl-4-ylmethyl)-nicotinamide To a solution of 100 mg 5-[2-(2,4-Dichloro-phenyl)-ethoxy]-1-oxy-nicotinic acid in 4 ml $CH_2Cl_2$ 150 µl N-NEM and subsequently 50 mg TOTU were added. After stirring for 1 h at RT 223 mg C-(3,4,5,6-Tetrahydro-2H-[1,4']bipyridinyl-4-yl)-methylamine tris trifluoroacetate in 1 ml $CH_2Cl_2$ were added and the mixture was stirred over night followed by removal of the solvent under reduced pressure. The residue was taken up in 3 ml saturated $NaHCO_3$ solution and filtered through a chem elut® cartridge by elution with ethyl acetate. After concentration under reduced pressure and purification by preparative HPLC (C18 reverse phase column, elution with a $H_2O$/MeCN gradient with 0.5% TFA) the fractions containing the product were evaporated and lyophilised. The product was obtained as its trifluoroacetate salt.

| Yield: 55 mg | MS (ESI+): 501, chloro pattern |

Example 103

3-[2-(2,4-Dichloro-phenyl)-ethoxy]-4-methoxy-N-(4-pyridin-4-yl-phenyl)-benzamide

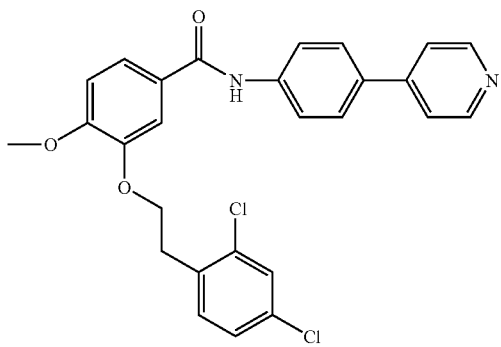

3-[2-(2,4-dichloro-phenyl)-ethoxy]-4-methoxy-benzamidoyl-4-phenyl-boronic acid

To a solution of 3.8 g 3-[2-(2,4-Dichloro-phenyl)-ethoxy]-4-methoxy-benzoic acid in 20 ml $CH_2Cl_2$ 5.6 ml N-NEM and subsequently 3.6 g TOTU were added. After stirring for 1 h at RT 4-aminophenyl boronic acid 10 ml $CH_2Cl_2$ were added and the mixture was over night followed by removal of the solvent under reduced pressure. The residue was taken up in 10 ml saturated $NaHCO_3$ solution and filtered through a chem elut® cartridge by elution with ethyl acetate. After concentration under reduced pressure the residue was subjected to the subsequent reaction without further purification.

(ii) 3-[2-(2,4-Dichloro-phenyl)-ethoxy]-4-methoxy-N-(4-pyridin-4-yl-phenyl)-benzamide A mixture of 100 mg 3-[2-(2,4-dichloro-phenyl)-ethoxy]-4-methoxy-benzamidoyl-4-phenyl-boronic acid, 64 mg 4-Brompyridine hydrochloride, 0.2 ml aqueous $Na_2CO_3$ (10M) in 5 ml dme were purged with argon for 10 min. Then 5 mg $Pd(PPh_3)_3$ were added under argon and the mixture refluxed overnight. The residue was taken up in 3 ml saturated $NaHCO_3$ solution and filtered through a chem elut® cartridge by elution with ethyl acetate. Subsequent removal of the solvent under reduced pressure and purification by preparative HPLC ($C_{18}$ reverse phase column, elution with a $H_2O$/MeCN gradient with 0.5% TFA) the fractions containing the product were evaporated and lyophilised. The product was obtained as its trifluoroacetate salt.

| Yield: 8 mg | MS (ESI–): 493, chloro pattern |
|---|---|

Analogously to example 103 the following compounds were prepared by a similar procedure:

| Example | Structure | MS (ESI+) |
|---|---|---|
| 104 | 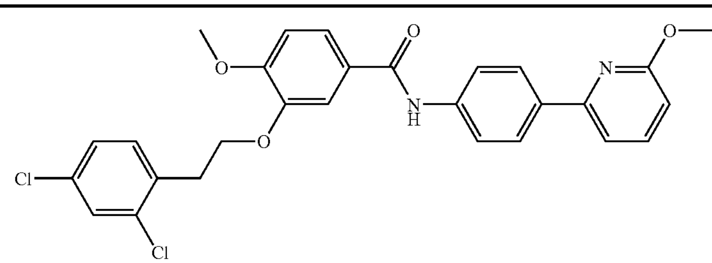 | 523, chloro pattern |
| 105 | 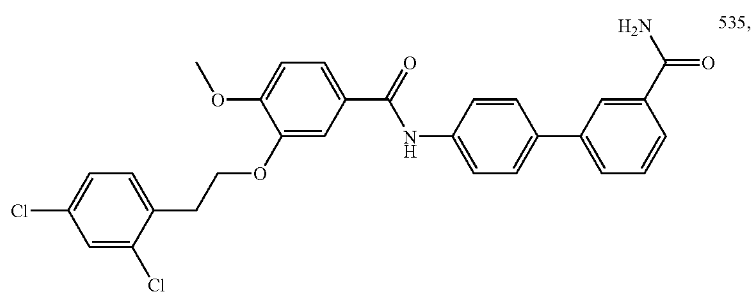 | 535, chloro pattern |
| 106 | 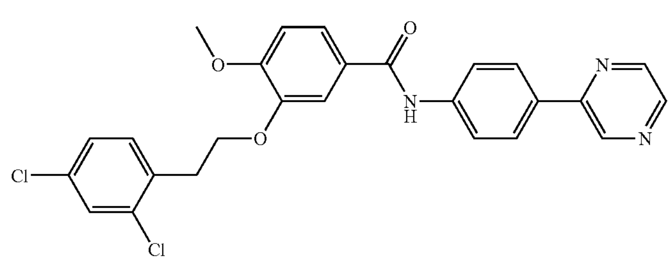 | 494, chloro pattern |

| Example | Structure | MS (ESI+) |
|---|---|---|
| 107 | 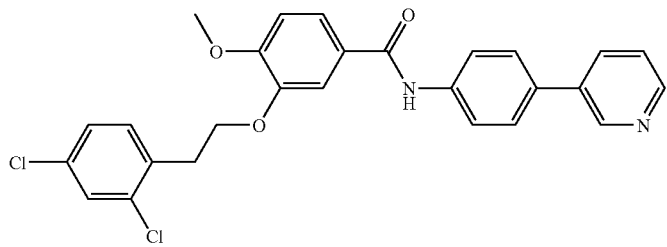 | 493, chloro pattern |
| 108 | 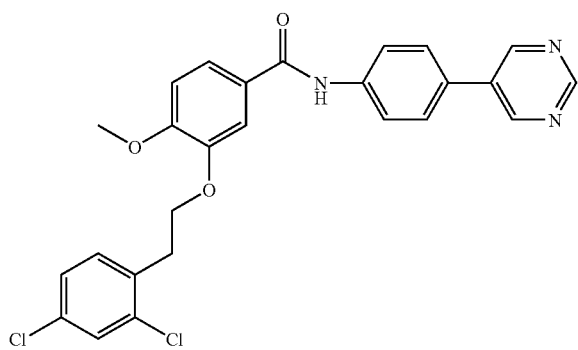 | 494, chloro pattern |
| 109 | 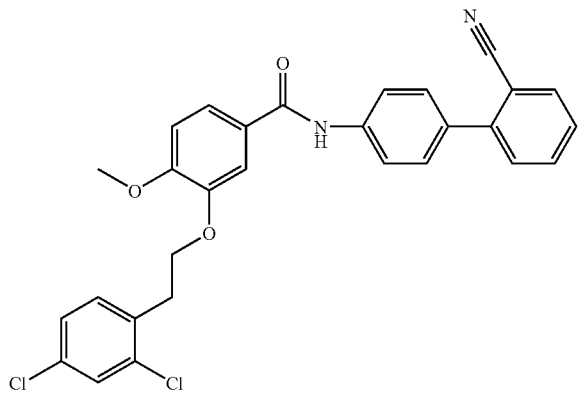 | 517, chloro pattern |
| 110 | 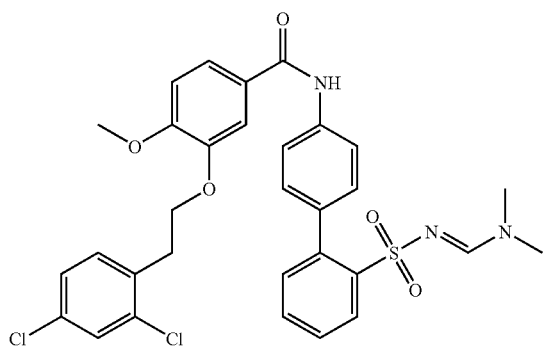 | 626, chloro pattern |

-continued
| Example | Structure | MS (ESI+) |
|---|---|---|
| 111 | 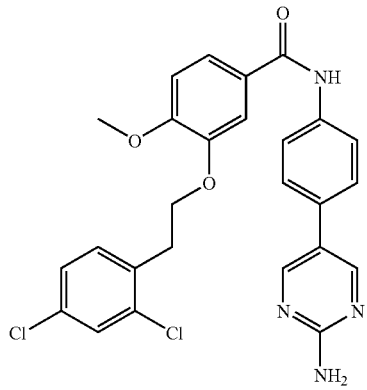 | 508 chloro pattern |
| 112 | 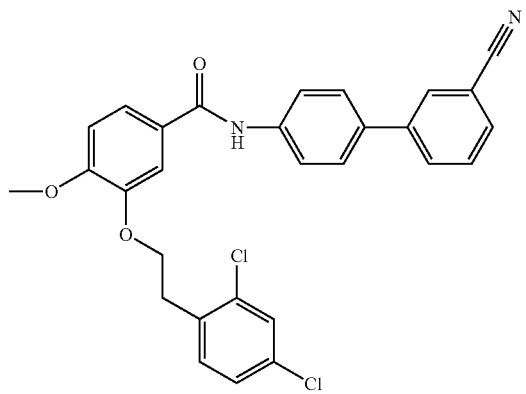 | 517, chloro pattern |
| 113 | 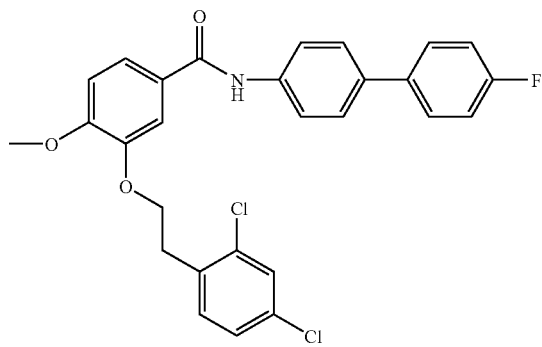 | 510, chloro pattern |
| 114 | 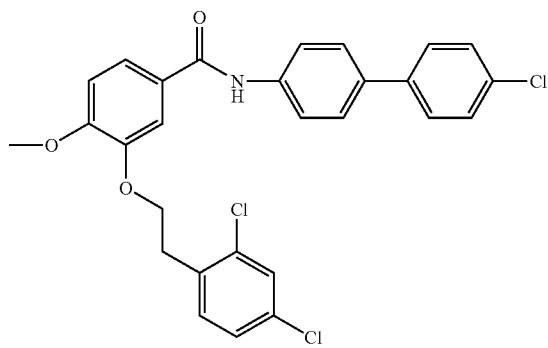 | 528, chloro pattern |

-continued

| Example | Structure | MS (ESI+) |
|---|---|---|
| 115 | 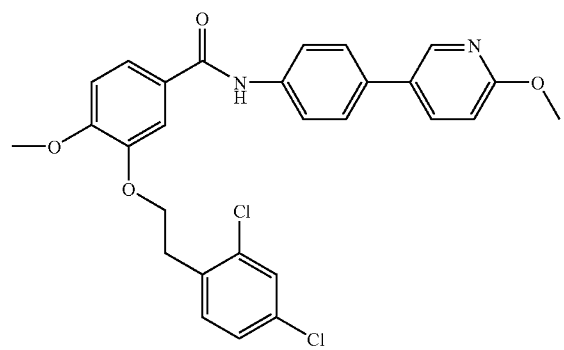 | 523, chloro pattern |
| 116 | 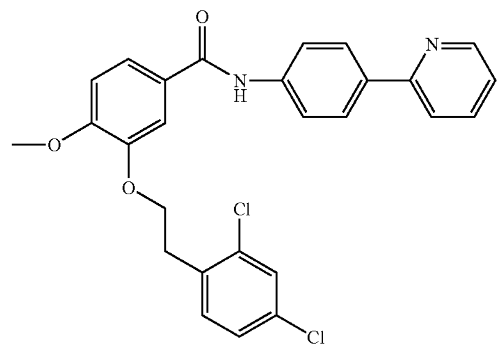 | 493, chloro pattern |

Example 117

2-[2-(2,4-Dichloro-phenyl)-ethoxy]-N4-(3,4,5,6-tetrahydro-2H-[1,4']bipyridinyl-4-ylmethyl)-terephthalamide

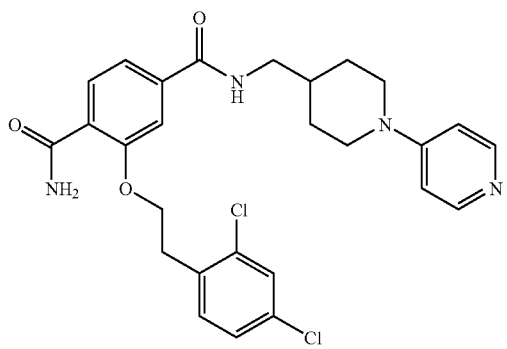

3-[2-(2,4-Dichloro-phenyl)-ethoxy]-terephthalamic acid methyl ester

To a solution of 100 mg 4-Cyano-3-[2-(2,4-dichloro-phenyl)-ethoxy]-benzoic acid methyl ester in 2 ml DMSO 93 mg $K_2CO_3$ and 68 µl $H_2O_2$ (35%) were added at RT. After stirring the reaction over night the mixture was taken up in 5 ml ethyl acetate and 3 ml water and filtered through a chem elut® cartridge by elution with ethyl acetate. After removal of the solvent the crude product was subjected to the subsequent reaction.

Yield: 103 mg.

(ii) 3-[2-(2,4-Dichloro-phenyl)-ethoxy]-terephthalamic acid 103 mg of 3-[2-(2,4-Dichloro-phenyl)-ethoxy]-terephthalamic acid methyl ester were dissolved in 1.2 ml of MeOH/water 3:1. 14 mg of lithium hydroxide monohydrate were added to the added to the solution, and the reaction was stirred at RT for 16 h and 2 h at 50° C. The solution was cooled to RT, then acidified with half-concentrated hydrochloric acid. The suspension was concentrated under reduced pressure and then extracted with ethyl acetate. The organic layer was dried over $Na_2SO_4$ and the solvent was removed under reduced pressure to yield a white solid.

Yield: 50 mg.

(iii) 2-[2-(2,4-Dichloro-phenyl)-ethoxy]-N-4-(3,4,5,6-tetrahydro-2H-[1,4']bipyridinyl-4-ylmethyl)-terephthalamide To a solution of 50 mg 3-[2-(2,4-Dichloro-phenyl)-ethoxy]-terephthalamic acid in 2 ml $CH_2Cl_2$ 100 µl N-NEM and subsequently 27 mg TOTU were added. After stirring for 1 h at RT 82 mg C-(3,4,5,6-Tetrahydro-2H-[1,4']bipyridinyl-4-yl)-methylamine tris trifluoro-acetate in 1 ml $CH_2Cl_2$ were added and the mixture was stirred for additional 2 h followed by removal of the solvent under reduced pressure. The residue was taken up in 3 ml saturated $NaHCO_3$ solution and filtered through a chem elut® cartridge by elution with ethyl acetate. After concentration under reduced pressure and purification by preparative HPLC (C18 reverse phase column, elution with a $H_2O$/MeCN gradient with 0.5% TFA) the fractions containing the product were evaporated and lyophilised. The product was obtained as its trifluoroacetate salt.

| Yield: 8 mg | MS (ESI+): 527, chloro pattern |

Example 118

4-Acetylamino-3-[2-(2,4-dichloro-phenyl)-ethoxy]-N-(3,4,5,6-tetrahydro-2H-[1,4']bipyridinyl-4-ylmethyl)-benzamide

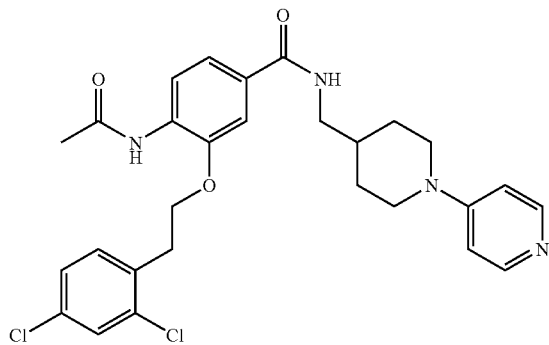

To a solution of 50 mg 4-Amino-3-[2-(2,4-dichloro-phenyl)-ethoxy]-N-(3,4,5,6-tetrahydro-2H-[1,4']bipyridinyl-4-ylmethyl)-benzamide and 42 µl NEt₃ in 1 ml acetonitrile 30 µl acetic acid anhydride were added at RT. After stirring the reaction over night the mixture was taken up in 3 ml saturated NaHCO₃ solution and filtered through a chem elut® cartridge by elution with ethyl acetate. After concentration under reduced pressure and purification by preparative HPLC (C18 reverse phase column, elution with a H₂O/MeCN gradient with 0.5% TFA) the fractions containing the product were evaporated and lyophilised. The product was obtained as its trifluoroacetate salt.

| Yield: 15 mg | MS (ESI+): 541, chloro pattern |

Example 119

3-[2-(2,4-Dichloro-phenyl)-ethoxy]-N-(3,4,5,6-tetrahydro-2H-[1,4']bipyridinyl-4-ylmethyl)-4-ureido-benzamide

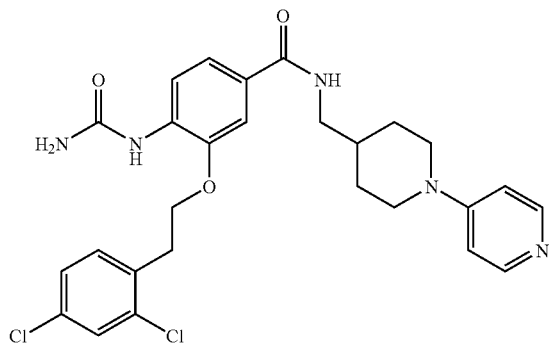

A solution of 50 mg 4-Amino-3-[2-(2,4-dichloro-phenyl)-ethoxy]-N-(3,4,5,6-tetrahydro-2H-[1,4']bipyridinyl-4-ylmethyl)-benzamide and 13 mg KCNO in 2 ml acetic was stirred reaction over night at RT. The mixture was taken up in 5 ml saturated NaHCO₃ solution and filtered through a chem elut® cartridge by elution with ethyl acetate. After concentration under reduced pressure and purification by preparative HPLC (C18 reverse phase column, elution with a H₂O/MeCN gradient with 0.5% TFA) the fractions containing the product were evaporated and lyophilised. The product was obtained as its trifluoroacetate salt.

| Yield: 8 mg | MS (ESI+): 541, chloro pattern |

Example 120

3-[2-(2,4-Dichloro-phenyl)-ethoxy]-4-methylamino-N-(3,4,5,6-tetrahydro-2H-[1,4']bipyridinyl-4-ylmethyl)-benzamide

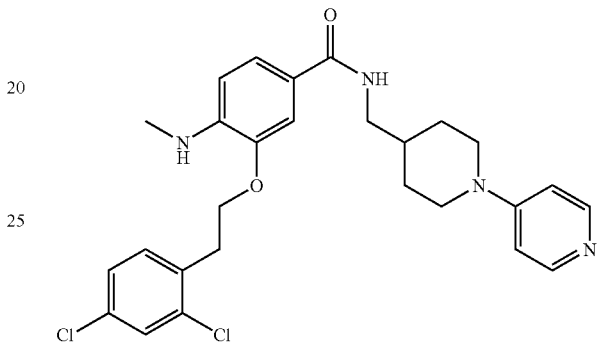

3-[2-(2,4-Dichloro-phenyl)-ethoxy]-4-methylamino-benzoic acid methyl ester

To a solution of 500 mg 4-Amino-3-[2-(2,4-dichloro-phenyl)-ethoxy]-benzoic acid methyl ester in 2.5 ml acetonitrile 0.5 ml MeI were added and stirred over night at RT. After concentration under reduced pressure and purification by preparative HPLC (C18 reverse phase column, elution with a H₂O/MeCN gradient with 0.5% TFA) the fractions containing the product were evaporated and lyophilised. The product was obtained as its trifluoroacetate salt.

(ii) 3-[2-(2,4-Dichloro-phenyl)-ethoxy]-4-methylamino-benzoic acid

To a solution of 100 mg 3-[2-(2,4-Dichloro-phenyl)-ethoxy]-4-methylamino-benzoic acid methyl ester in 3 ml of MeOH:water/3:1, 14 mg of lithium hydroxide monohydrate were added and the reaction was stirred at RT for 16 h. The solution was acidified with half-concentrated hydrochloric acid and the solvent was evaporated. The crude acid was subjected to the subsequent amide coupling without further purification.

(iii) 3-[2-(2,4-Dichloro-phenyl)-ethoxy]-4-methylamino-N-(3,4,5,6-tetrahydro-2H-[1,4']bipyridinyl-4-ylmethyl)-benzamide To a solution of 60 mg 3-[2-(2,4-Dichloro-phenyl)-ethoxy]-4-methylamino-benzoic acid in 1 ml CH₂Cl₂ 100 µl N-NEM and subsequently 30 mg TOTU were added. After stirring for 1 h at RT 106 mg C-(3,4,5,6-Tetrahydro-2H-[1,4']bipyridinyl-4-yl)-methylamine tris trifluoro-acetate in 1 ml CH₂Cl₂ were added and the mixture was stirred over night followed by removal of the solvent under reduced pressure. The residue was taken up in 3 ml saturated NaHCO₃ solution and filtered through a chem elut® cartridge by elution with ethyl acetate. After concentration under reduced pressure and purification by preparative HPLC (C18 reverse phase column, elution with a H₂O/MeCN gradient with 0.5% TFA) the fractions containing the product were evaporated and lyophilised. The product was obtained as its trifluoroacetate salt.

| Yield: 12 mg | MS (ESI+): 513, chloro pattern |

Example 121

3-[2-(2,4-Dichloro-phenyl)-ethoxy]-4-formylamino-N-(3,4,5,6-tetrahydro-2H-[1,4']bipyridinyl-4-ylmethyl)-benzamide

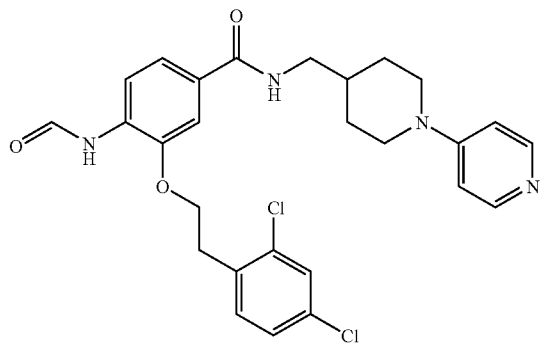

A solution of 50 mg 4-Amino-3-[2-(2,4-dichloro-phenyl)-ethoxy]-N-(3,4,5,6-tetrahydro-2H-[1,4']bipyridinyl-4-ylmethyl)-benzamide in 0.2 ml formic acid were heated to 100° C. for 1 h. The mixture was purified by preparative HPLC (C18 reverse phase column, elution with a $H_2O$/MeCN gradient with 0.5% TFA) and the fractions containing the product were evaporated and lyophilised. The product was obtained as its trifluoroacetate salt.

| Yield: 25 mg | MS (ESI+): 527, chloro pattern |

Example 122

{2-[2-(2,4-Dichloro-phenyl)-ethoxy]-4-[(3,4,5,6-tetrahydro-2H-[1,4']bipyridinyl-4-ylmethyl)-carbamoyl]-phenyl}-carbamic acid methyl ester

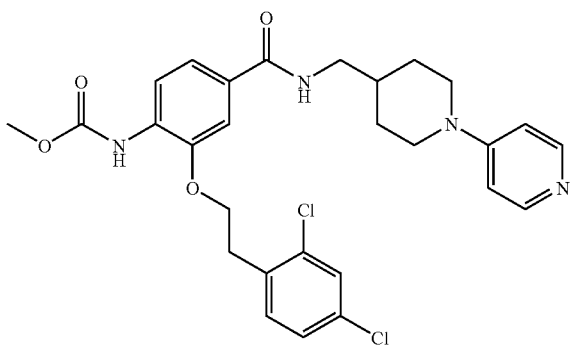

To a solution of 50 mg 4-Amino-3-[2-(2,4-dichloro-phenyl)-ethoxy]-N-(3,4,5,6-tetrahydro-2H-[1,4']bipyridinyl-4-ylmethyl)-benzamide, 20 μl $NEt_3$ in 1 ml $CH_2Cl_2$ 10 μl chloroformic acid methyl ester were added at RT. After stirring over night the mixture was concentrated and purified by preparative HPLC (C18 reverse phase column, elution with a $H_2O$/MeCN gradient with 0.5% TFA) and the fractions containing the product were evaporated and lyophilised. The product was obtained as its trifluoroacetate salt.

| Yield: 25 mg | MS (ESI+): 557, chloro pattern |

Example 123

N-[1-(4-Chloro-phenyl)-piperidin-4-yl]-3-[2-(2,4-dichloro-phenyl)-ethoxy]4-methoxy-benzamide

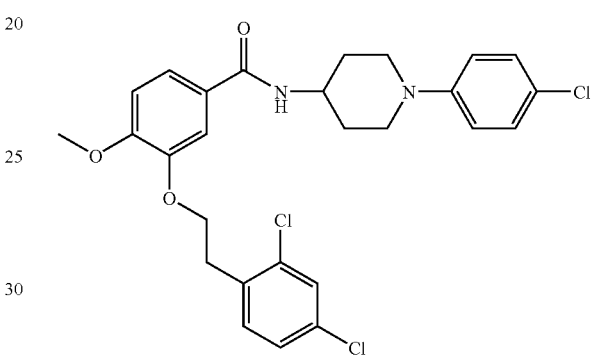

4-{3-[2-(2,4-Dichloro-phenyl)-ethoxy]-4-methoxy-benzoylamino}-piperidine-1-carboxylic acid tert-butyl ester To a solution of 1 g 3-[2-(2,4-Dichloro-phenyl)-ethoxy]-4-methoxy-benzoic acid in 15 ml $CH_2Cl_2$ 1.5 ml N-NEM and subsequently 962 mg TOTU were added. After stirring for 1 h at RT 881 mg Boc-(4-amino)piperidine in 5 ml $CH_2Cl_2$ were added and the mixture was stirred for additional 2 h followed by addition of 20 ml saturated $NaHCO_3$ solution. The organic layer was separated and dried over $Na_2SO_4$ and the solvent evaporated. The residue was recrystallized from ethyl acetate/heptane to afford a white powder.

Yield: 1.4 g.

(ii) 3-[2-(2,4-Dichloro-phenyl)-ethoxy]-4-methoxy-N-piperidin-4-yl-benzamide 1.4 g 4-{3-[2-(2,4-Dichloro-phenyl)-ethoxy]-4-methoxy-benzoylamino}-piperidine-1-carboxylic acid tert-butyl ester was suspended in 20 ml HCl in ethanol at RT. After 2 h a clear solution was obtained. Addition of 50 ml toluene followed by evaporation of the solvent and repeatedly coevaporation of the residue with toluene yielded the product as a white foam.

Yield: 1 g.

(iii) N-[1-(4-Chloro-phenyl)-piperidin-4-yl]-3-[2-(2,4-dichloro-phenyl)-ethoxy]-4-methoxy-benzamide A mixture of 100 mg 3-[2-(2,4-Dichloro-phenyl)-ethoxy]-4-methoxy-N-piperidin-4-yl-benzamide hydrochloride (0.2 mmol), 62 mg (0.33 mmol) 4-Bromochlorobenzene, 73 mg sodium-t-butoxide in 5 ml dioxane were purged with argon for 10 min. Then 37 mg of 2-(Dicyclohexylphosphino) biphenyl and 20 mg $Pd_2(dba)_3$ were added under argon and the mixture refluxed overnight. The residue was taken up in 3 ml saturated NaHCO₃ solution and filtered through a chem elut® cartridge by elution with ethyl acetate. Subsequent removal of the solvent under reduced pressure and purification by preparative HPLC (C18 reverse phase column, elution with a H₂O/MeCN gradient with 0.5% TFA) the fractions containing the product were evaporated and lyophilised. The product was obtained as its trifluoroacetate salt.

| Yield: 3 mg | MS (ESI+): 533, chloro pattern |
|---|---|

Analogously to example 123 the following compounds were prepared by a similar procedure:

| Example | Structure | MS (ESI+) |
|---|---|---|
| 124 | 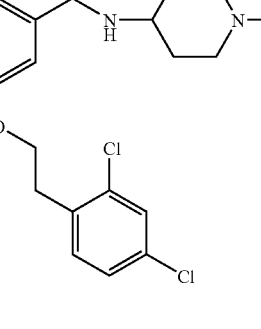 | 530, chloro pattern |
| 125 | 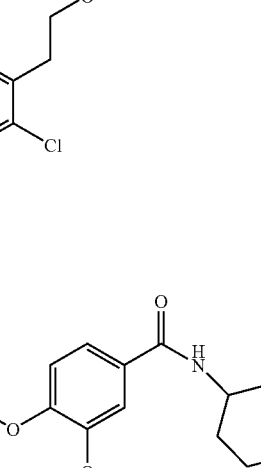 | 516, chloro pattern |
| 126 | 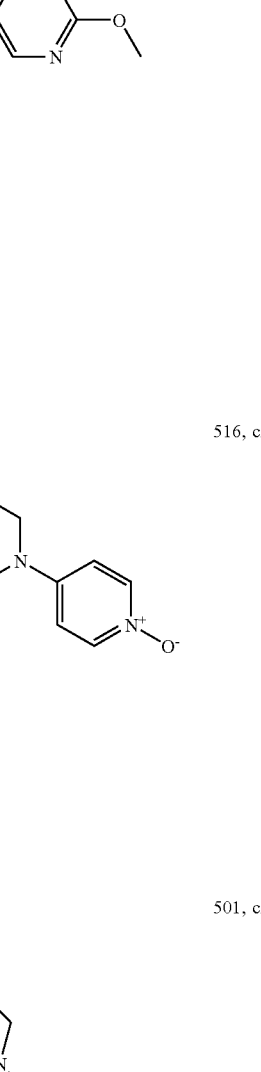 | 501, chloro pattern |

| Example | Structure | MS (ESI+) |
|---|---|---|
| 127 | 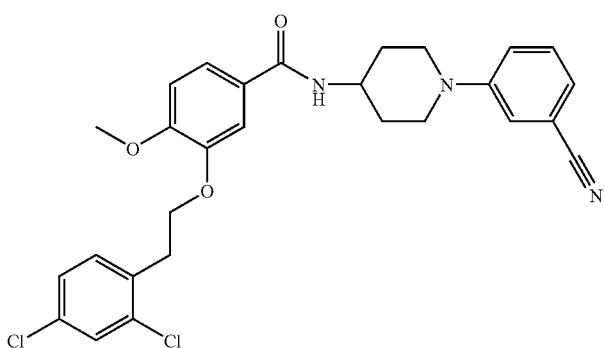 | 524, chloro pattern |

Example 128

N-(1-Cyclohexyl-piperidin-4-yl)-3-[2-(2,4-dichloro-phenyl)-ethoxy]-4-methoxy-benzamide

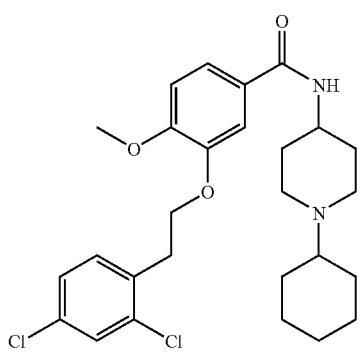

To a solution of 100 mg 3-[2-(2,4-Dichloro-phenyl)-ethoxy]-4-methoxy-N-piperidin-4-yl-benzamide hydrochloride and 43 mg cyclohexanone in 2 ml acetonitrile 27 mg Na(CN)BH$_3$ were introduced. After stirring at RT overnight the reaction mixture was heated to 80° C. for 4 h. After removal of the solvent under reduced pressure and purification by preparative HPLC (C$_{18}$ reverse phase column, elution with a H$_2$O/MeCN gradient with 0.5% TFA) the fractions containing the product were evaporated and lyophilised. The product was obtained as its trifluoroacetate salt.

| Yield: 26 mg | MS (ESI+): 505, chloro pattern |
|---|---|

Analogously to example 128 the following compounds were prepared by a similar procedure:

| Example | Structure | MS (ESI+) |
|---|---|---|
| 129 | 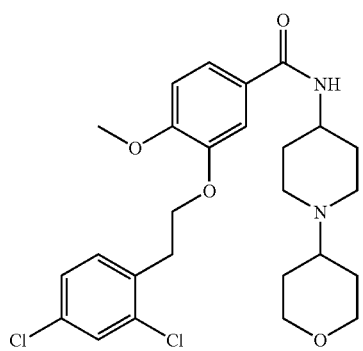 | 507, chloro pattern |

| Example | Structure | MS (ESI+) |
|---|---|---|
| 130 | 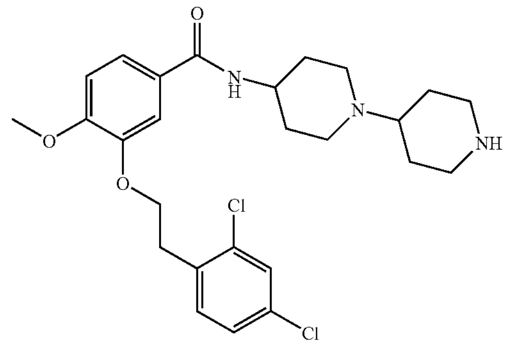 | 506, chloro pattern |
| 131 | 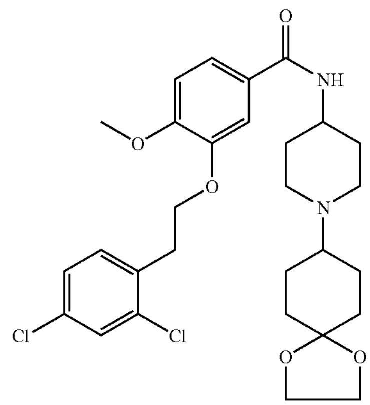 | 563, chloro pattern |

Example 132

3-[2-(5-Chloro-pyridin-2-yl)-ethoxy]-4-methoxy-N-(3,4,5,6-tetrahydro-2H-[1,4']bipyridinyl-4-ylmethyl)-benzamide

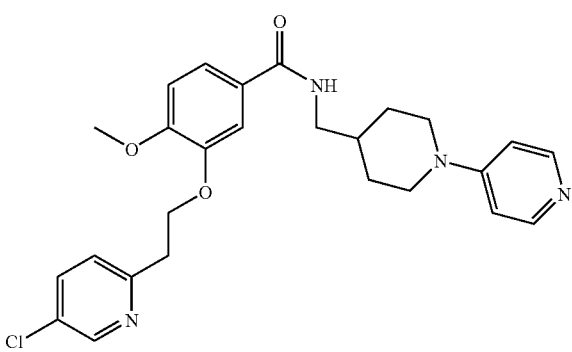

5-Chloro-2-vinyl-pyridine

A solution of 2 g 2,5-dichloropyridine and 4.3 g tributylvinylstannane in 20 ml toluene was purged with argon for 15 min. Then 50 mg Pd(PPh$_3$)$_4$ was added under argon and the reaction mixture was refluxed for 3 h. After removal of the solvent under reduced pressure the residue was taken up in ethyl acetate and saturated aqueous KF solution. Filtration through a chem elut® cartridge by elution with ethyl acetate and evaporation of the solvent yielded a slightly brown oil.

Yield: 2 g.

(ii) 2-(5-Chloro-pyridin-2-yl)-ethanol

To a solution of 2 g 5-Chloro-2-vinyl-pyridine in 10 ml THF was added dropwise 86 ml of a 9-BBN solution in THF (0.5 M) at RT. After 1 h 2.2 ml of a aqueous NaOH solution (10%) were added cautiously followed by the addition of 25 ml H$_2$O$_2$ (35%). This reaction mixture was stirred over night at RT. Then saturated Na$_2$SO$_3$ solution and 20 ml ethylacetate was added and the organic layer was separated. After removal of the solvent under reduced pressure and purification by preparative HPLC (C$_{18}$ reverse phase column, elution with a H$_2$O/MeCN gradient with 0.5% TFA) the fractions containing the product were evaporated and lyophilised. The product was obtained as its trifluoroacetate salt.

Yield: 1.5 g.

(iii) 3-[2-(5-Chloro-pyridin-2-yl)-ethoxy]-4-methoxy-benzoic acid methyl ester

To a solution of 400 mg 3-Hydroxy-4-methoxy-benzoic acid methyl ester, 346 mg 2-(5-Chloro-pyridin-2-yl)-ethanol, 1800 mg polymerbound triphenyl phosphine (Fluka, 3 mmol triphenylphosphine/g resin) and 1015 µl DEAD were introduced and the mixture was shaken over night at RT. After filtration, evaporation of the solvent the residue was purified by preparative HPLC (C$_{18}$ reverse phase column, elution with a H$_2$O/MeCN gradient with 0.5% TFA) and the fractions containing the product were evaporated and lyophilised. The product was obtained as its trifluoroacetate salt.

Yield: 530 mg.

127

(iv) 3-[2-(5-Chloro-pyridin-2-yl)-ethoxy]-4-methoxy-benzoic acid 85 mg 3-[2-(5-Chloro-pyridin-2-yl)-ethoxy]-4-methoxy-benzoic acid methyl ester was dissolved in 1.2 ml of MeOH:water/3:1. 30 mg of lithium hydroxide monohydrate were added to the added to the solution, and the reaction was stirred at RT for 16 h. The reaction mixture was acidified with half-concentrated hydrochloric acid. The suspension was concentrated under reduced pressure, coevaporated twice with toluene (2×10 ml) and then directly subjected to the subsequent amide coupling.

Yield. 50 mg.

3-[2-(5-Chloro-pyridin-2-yl)-ethoxy]-4-methoxy-N-(3,4,5,6-tetrahydro-2H-[1,4']bipyridinyl-4-ylmethyl)-benzamide To a solution of 50 mg 3-[2-(5-Chloro-pyridin-2-yl)-ethoxy]-4-methoxy-benzoic acid in 5 ml ethyl acetate 0.1 ml NEt$_3$ and 100 mg BOP-Cl were added. After 30 min 200 mg C-(3,4,5,6-Tetrahydro-2H-[1,4']bipyridinyl-4-yl)-methylamine tris trifluoro-acetate in 1 ml CH$_2$Cl$_2$ were added and the mixture stirred for 10 h at RT followed by removal of the solvent under reduced pressure. The residue was taken up in 3 ml saturated NaHCO$_3$ solution and filtered through a chem elut® cartridge by elution with ethyl acetate. After concentration under reduced pressure and purification by preparative HPLC (C18 reverse phase column, elution with a H$_2$O/MeCN gradient with 0.5% TFA) the fractions containing the product were evaporated and lyophilised. The product was obtained as its trifluoroacetate salt.

| Yield: 16 mg | MS (ESI+): 480, chloro pattern |

Example 133

4-Chloro-3-[2-(5-chloro-pyridin-2-yl)-ethoxy]-N-(3,4,5,6-tetrahydro-2H-[1,4']bipyridinyl-4-ylmethyl)-benzamide

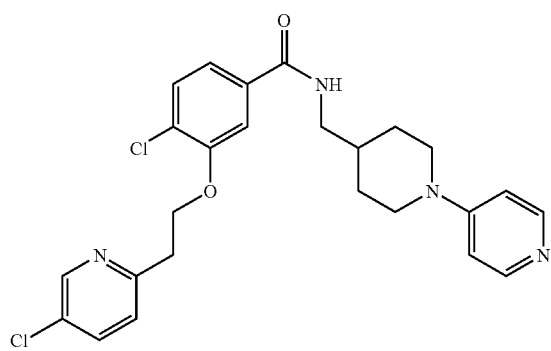

This compound was prepared analogously to example 132 employing 4-Chloro-3-hydroxy-benzoic acid ethyl ester coupling component. MS (ESI+): 485, chloro pattern

128

Example 134

3-[2-(5-Chloro-pyridin-2-yl)-ethoxy]-4-fluoro-N-(3,4,5,6-tetrahydro-2H-[1,4']bipyridinyl-4-ylmethyl)-benzamide

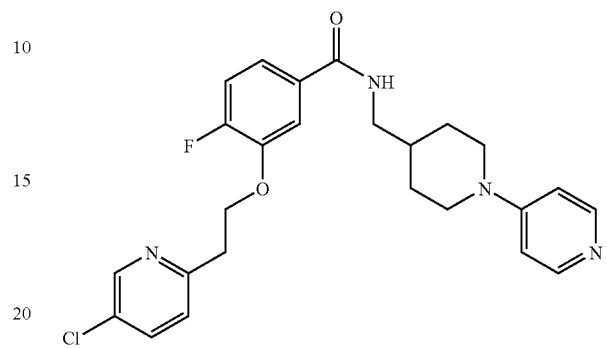

This compound was prepared analogously to example 132 employing 4-Fluoro-3-hydroxy-benzoic acid ethyl ester coupling component. MS (ESI+): 569, chloro pattern Example 135

N-[1-(3-Acetylamino-phenyl)-piperidin-4-ylmethyl]-3-[2-(2,4-dichloro-phenyl)-ethoxy]-4-methoxy-benzamide

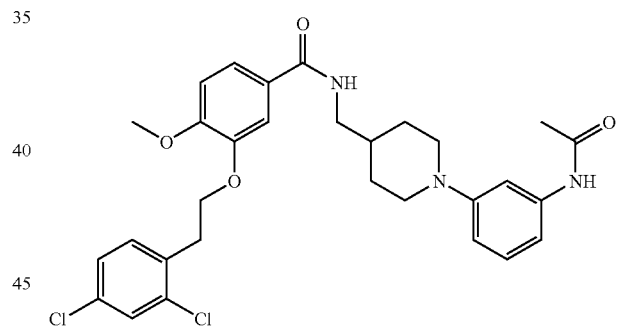

To a solution of 50 mg 3-[2-(2,4-Dichloro-phenyl)-ethoxy]-4-methoxy-N-piperidin-4-ylmethyl-benzamide hydrochloride, 38 mg 3-acetamidoboronic acid in 1 ml CH$_2$Cl$_2$ 100 mg molsieve 3 Å, 38.5 mg Cu(OAc)$_2$ and 25 µl pyridine were added. The suspension was stirred for 3 d, then 3 ml saturated NaHCO$_3$ solution were added and the mixture filtered through a chem elut® cartridge by elution with ethyl acetate. After concentration under reduced pressure and purification by preparative HPLC (C18 reverse phase column, elution with a H$_2$O/MeCN gradient with 0.5% TFA) the fractions containing the product were evaporated and lyophilised. The product was obtained as its trifluoroacetate salt.

| Yield: 2 mg | MS (ESI+):, chloro pattern |

Analogously to example 135 the following compounds were prepared by a similar procedure:

| Example | Structure | MS (ESI+) |
|---|---|---|
| 136 | 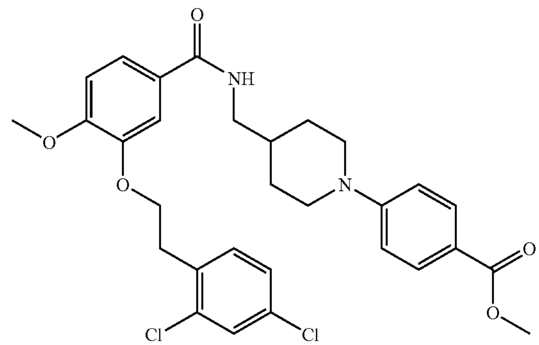 | 571, chloro pattern |
| 137 | 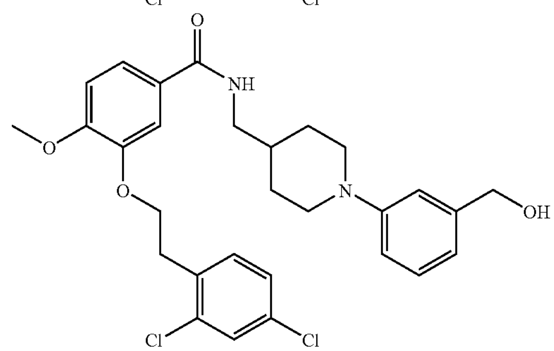 | 543, chloro pattern |
| 138 | 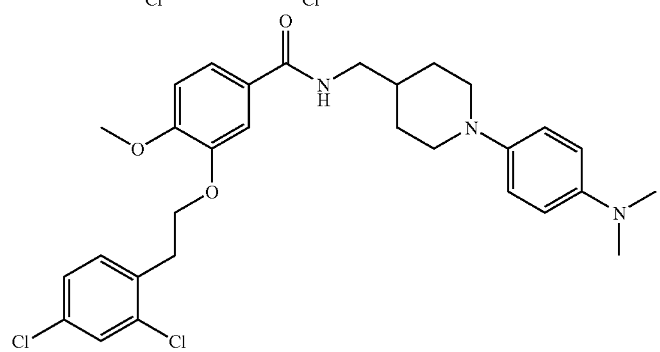 | 556, chloro pattern |

Example 139

3-[1-(4-Chloro-phenyl)-cyclobutylmethoxy]-4-methoxy-N-(3,4,5,6-tetrahydro-2H-[1,4']bipyridinyl-4-ylmethyl)-benzamide

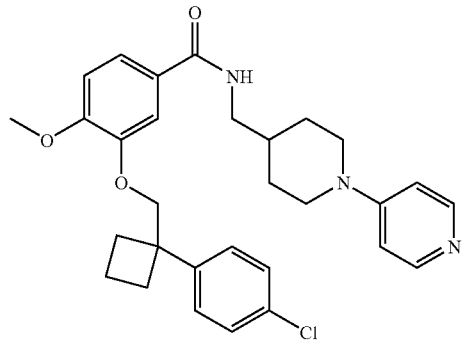

[1-(4-Chloro-phenyl)-cyclobutyl]-methanol

To a solution of 1 g 1-(4-Chloro-phenyl)-cyclobutanecarboxylic acid in 15 ml THF were added dropwise at 0° C. 9.5 ml BH$_3$*THF in THF (1M). Then the reaction mixture was heated at reflux for 2 h and then cooled again to 0° C. followed by cautious addition of 30 ml methanol. After evaporation of the solvents the residue was codestilled twice with toluene. The crude product was subjected to the subsequent reaction without further purification.

(ii) 3-[1-(4-Chloro-phenyl)-cyclobutylmethoxy]-4-methoxy-benzoic acid

To a solution of 300 mg 3-Hydroxy-4-methoxy-benzoic acid methyl ester, 388 mg [1-(4-Chloro-phenyl)-cyclobutyl]-methanol 1645 mg polymerbound triphenyl phosphine (Fluka, 3 mmol triphenyl phosphine/g resin) and 762 µl DEAD were introduced and the mixture was shaken over night at RT. After filtration, evaporation of the solvent the residue was taken up in 5 ml MeOH/H$_2$O 3:1 and 20 mg LiOH monohydrate was added. After heating the mixture at 60° C. for 2 h the mixture was acidified with half concentrated HCl and filtered through a chem elut® cartridge by elution with ethyl acetate. After concentration under reduced pressure the crude product was subjected to the following amide coupling without further purification.

(iii) 3-[1-(4-Chloro-phenyl)-cyclobutylmethoxy]-4-methoxy-N-(3,4,5,6-tetrahydro-2H-[1,4']bipyridinyl-4-ylmethyl)-benzamide To a solution of 50 mg acid in 5 ml ethyl acetate 0.1 ml NEt₃ and 100 mg BOP-Cl were added. After 30 min 111 mg C-(3,4,5,6-Tetrahydro-2H-[1,4']bipyridinyl-4-yl)-methylamine tris trifluoro-acetate in 1 ml CH₂Cl₂ were added and the mixture stirred for 10 h at RT followed by removal of the solvent under reduced pressure. The residue was taken up in 3 ml saturated NaHCO₃ solution and filtered through a chem elut® cartridge by elution with ethyl acetate. After concentration under reduced pressure and purification by preparative HPLC (C18 reverse phase column, elution with a H₂O/MeCN gradient with 0.5% TFA) the fractions containing the product were evaporated and lyophilised. The product was obtained as its trifluoroacetate salt.

| Yield: 10 mg | MS (ESI+): 520, chloro pattern |
|---|---|

Analogously to example 139 the following compounds were prepared by a similar procedure:

| Example | Structure | MS (ESI+) |
|---|---|---|
| 140 | 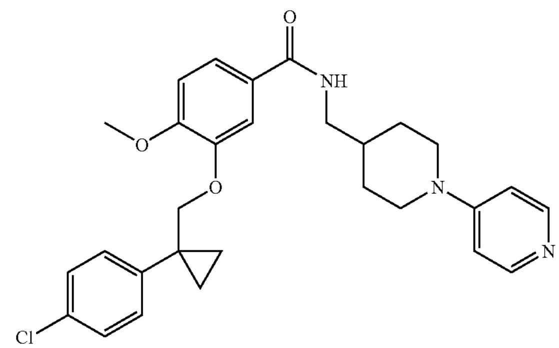 | 506, chloro pattern |
| 141 | 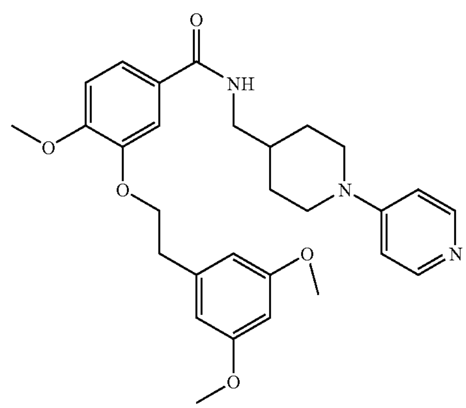 | 505, chloro pattern |
| 142 | 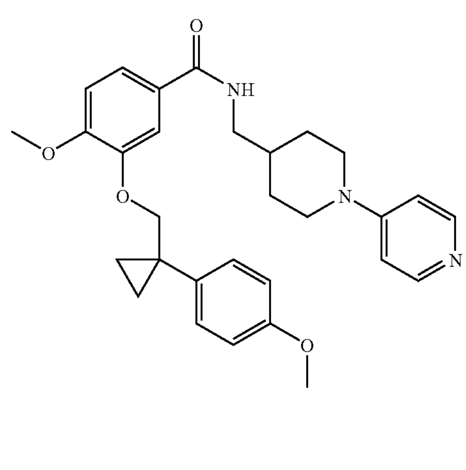 | 502, chloro pattern |

-continued

| Example | Structure | MS (ESI+) |
|---|---|---|
| 143 | 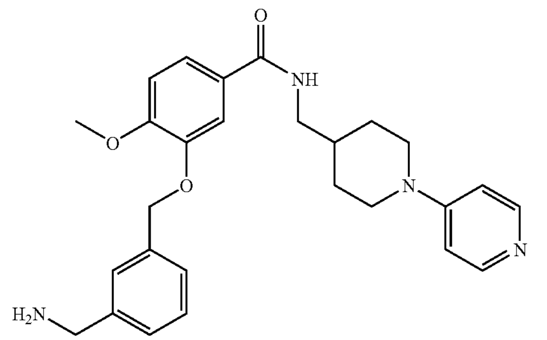 | 460, chloro pattern |
| 144 | 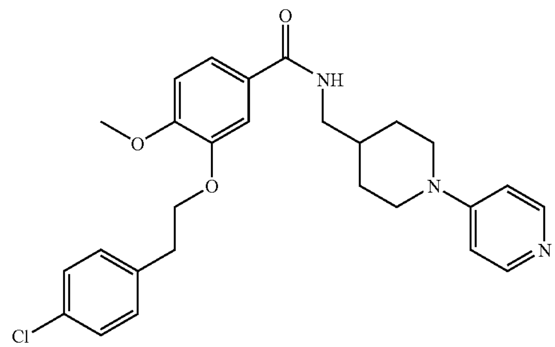 | 480, chloro pattern |
| 145 | 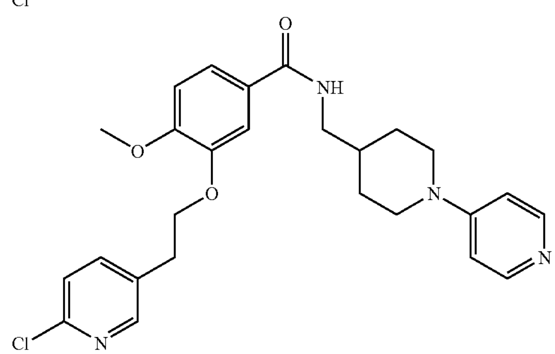 | 480, chloro pattern |

Example 146

3-[2-(2,4-Dichloro-phenyl)-ethoxy]-4-methoxy-N-[1-(2-oxo-2-pyrrolidin-1-yl-ethyl)-piperidin-4-ylmethyl]-benzamide

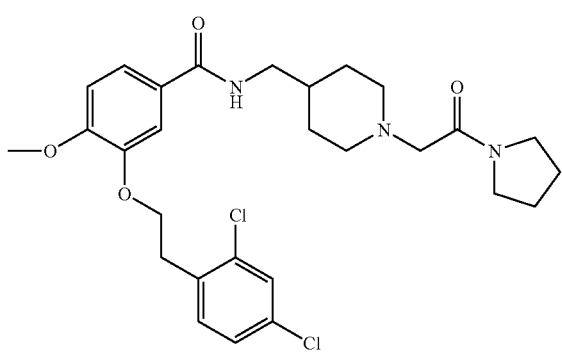

[4-({3-[2-(2,4-Dichloro-phenyl)-ethoxy]-4-methoxy-benzoylamino}-methyl)-piperidin-1-yl]-acetic acid To 1 g 3-[2-(2,4-Dichloro-phenyl)-ethoxy]-4-methoxy-N-piperidin-4-ylmethyl-benzamide hydrochloride and 400 mg NaOH in 50 ml EtOH/H$_2$O 1:1 0.35 g bromo acetic acid were added at RT. After stirring over night the reaction mixture was acidified with half concentrated HCl. After evaporation of the solvent the residue was coevaporated with toluene. The waxy brown solid was subjected to the subsequent reaction without further purification.

Yield: 1.1 g.

(ii) 3-[2-(2,4-Dichloro-phenyl)-ethoxy]-4-methoxy-N-[1-(2-oxo-2-pyrrolidin-1-yl-ethyl)-piperidin-4-ylmethyl]-benzamide To a solution of 60 mg [4-({3-[2-(2,4-Dichloro-phenyl)-ethoxy]-4-methoxy-benzoylamino}-methyl)-piperidin-1-yl]-acetic acid, 100 μl NEt$_3$ in 2 ml THF 30 mg CDI was added and the reaction mixture stirred for 2 h at RT. Then 18 mg pyrrolidine were added and the reaction was stirred for further 16 h. After removal of the solvent the residue was directly purified by preparative HPLC (C18 reverse phase column, elution with a H₂O/MeCN gradient with 0.5% TFA). The fractions containing the product were evaporated and lyophilised. The product was obtained as its trifluoroacetate salt.

| Yield: 12 mg | MS (ESI+): 547, chloro pattern |
|---|---|

Analogously to example 146 the following compounds were prepared by a similar procedure:

| Example | Structure | MS (ESI+) |
|---|---|---|
| 147 | 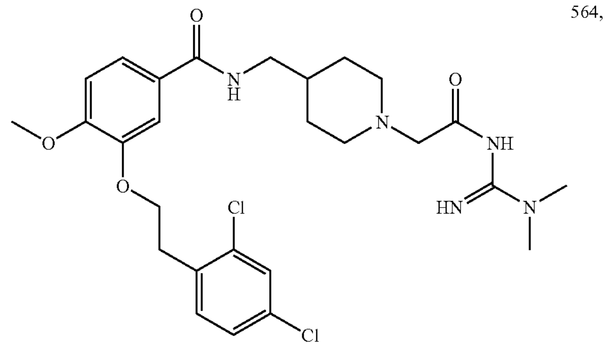 | 564, chloro pattern |
| 148 | 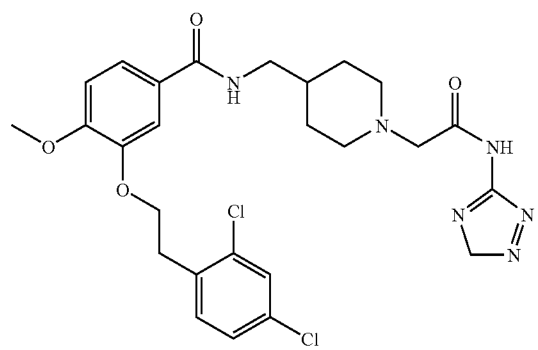 | 564, chloro pattern |
| 149 | 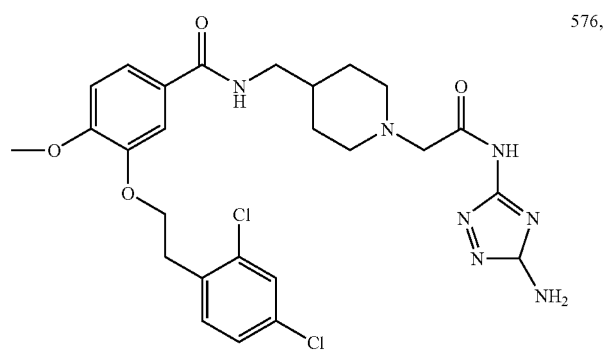 | 576, chloro pattern |
| 150 | 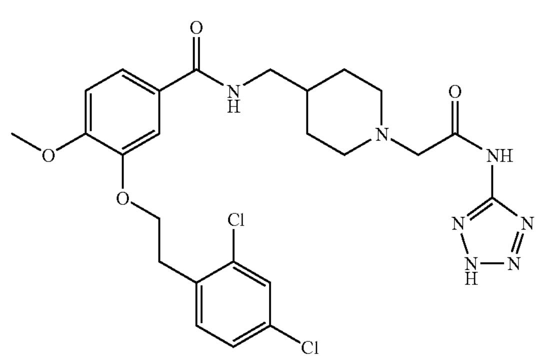 | 562, chloro pattern |

-continued
| Example | Structure | MS (ESI+) |
|---|---|---|
| 151 | 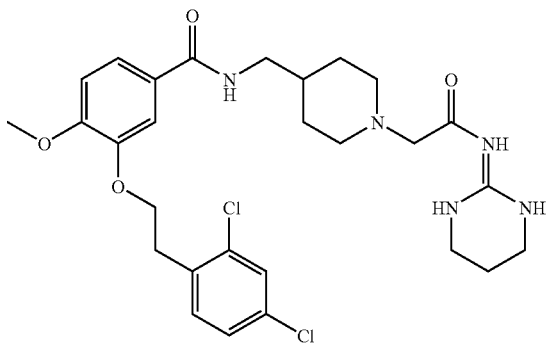 | 576, chloro pattern |
| 152 | 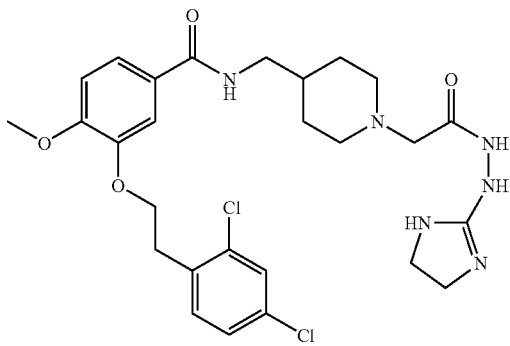 | 577, chloro pattern |
| 153 | 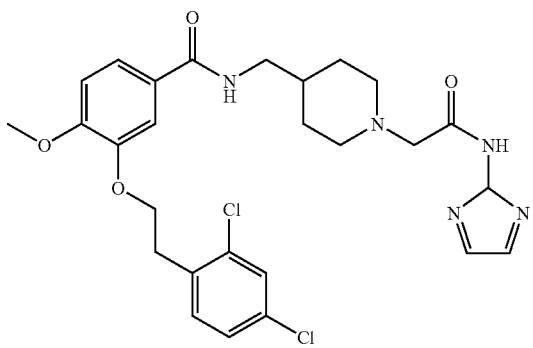 | 560, chloro pattern |
| 154 | 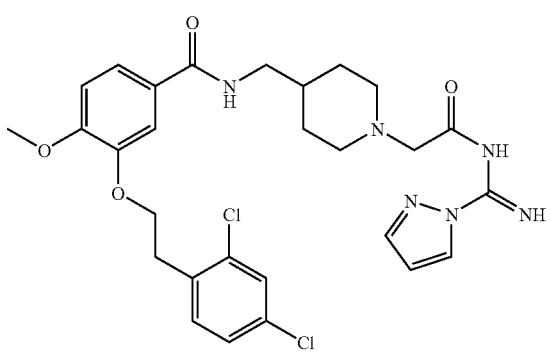 | 587, chloro pattern |

| Example | Structure | MS (ESI+) |
|---|---|---|
| 155 | 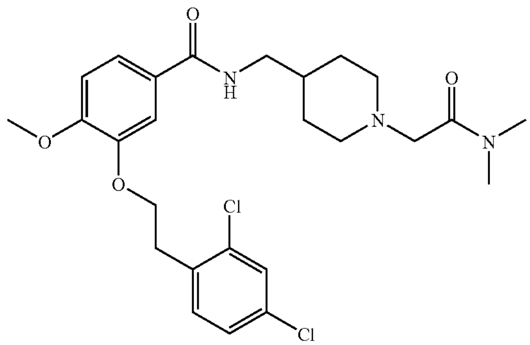 | 522, chloro pattern |
| 156 | 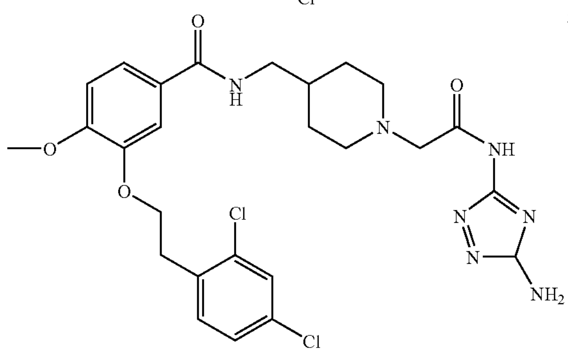 | 576, chloro pattern |
| 157 | 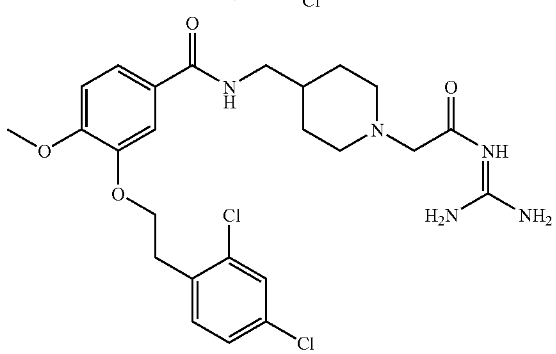 | 536, chloro pattern |

Example 158

3-[2-(2,4-Dichloro-phenyl)-ethoxy]-4-methoxy-N-[1-(2-oxo-2-pyrrolidin-1-yl-ethyl)-piperidin-4-yl]-benzamide

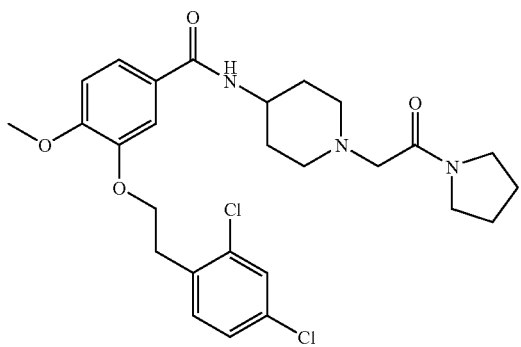

(4-{3-[2-(2,4-Dichloro-phenyl)-ethoxy]-4-methoxy-benzoylamino}-piperidin-1-yl)-acetic acid To 360 mg 3-[2-(2,4-Dichloro-phenyl)-ethoxy]-4-methoxy-N-piperidin-4-yl-benzamide hydrochloride and 162 mg NaOH in 20 ml EtOH/H$_2$O 1:1 142 mg bromo acetic acid was added at RT. After stirring over night the reaction mixture was acidified with half concentrated HCl. After evaporation of the solvent the residue was coevaporated with toluene. The waxy brown solid was subjected to the subsequent reaction without further purification.

Yield: 330 mg.

(iii) 3-[2-(2,4-Dichloro-phenyl)-ethoxy]-4-methoxy-N-[1-(2-oxo-2-pyrrolidin-1-yl-ethy)-piperidin-4-yl]-benzamide To a solution of 60 mg (4-{3-[2-(2,4-Dichloro-phenyl)-ethoxy]-4-methoxy-benzoylamino}-piperidin-1-yl)-acetic acid, 100 µl NEt$_3$ in 2 ml DMF 30 mg CDI was added and the reaction mixture stirred for 2 h at RT. Then 18 mg pyrrolidine were added and the reaction was stirred for further 16 h. After removal of the solvent the residue was directly purified by preparative HPLC (C18 reverse phase column, elution with a H₂O/MeCN gradient with 0.5% TFA). The fractions containing the product were evaporated and lyophilised. The product was obtained as its trifluoroacetate salt.

| Yield: 22 mg | MS (ESI+): 534, chloro pattern |
|---|---|

Analogously to example 158 the following compounds were prepared by a similar procedure:

| Example | Structure | MS (ESI+) |
|---|---|---|
| 159 | 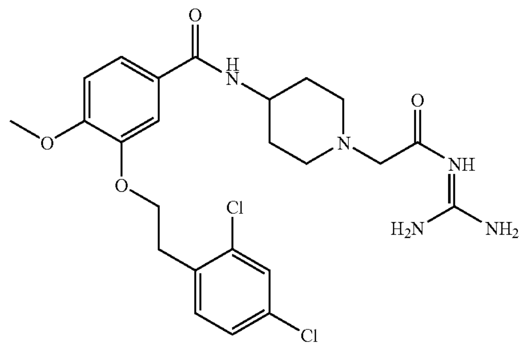 | 522, chloro pattern |
| 160 | 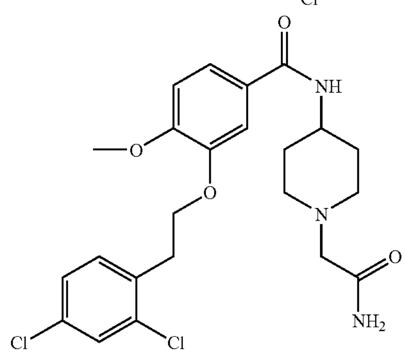 | 563, chloro pattern |
| 161 | 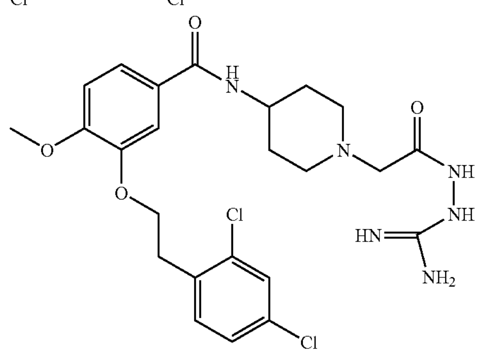 | 537, chloro pattern |
| 162 | 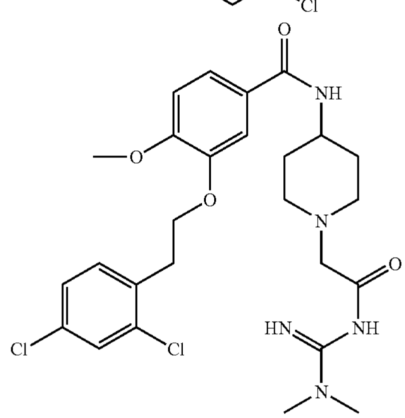 | 550, chloro pattern |

Example 163

2-{3-[2-(2,4-Dichloro-phenyl)-ethoxy]-4-methoxy-benzoylamino}-3-furo[3,2-c]pyridin-2-yl-propionic acid methyl ester

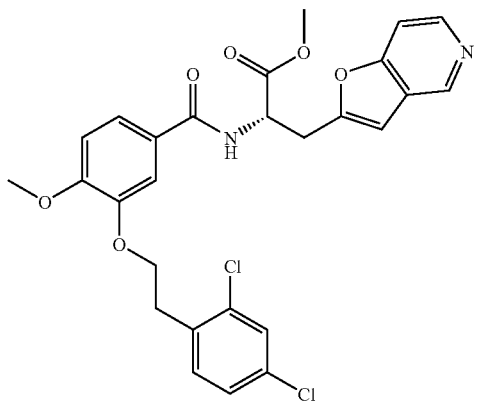

3-Iodo-pyridin-4-ol

A solution of 20 g 4-hydroxypyridine and 13 g Na$_2$SO$_4$ in 50 ml water was heated to 100° C. To this mixture a solution of 27 g I$_2$, 28 g KI was added dropwise. After 3 h the mixture was washed with ethylacetate. Concentration of the aqueous layer led to precipitation of the product, which was isolated by filtration:

Yield: 12.5 g.

(ii) 2-{3-[2-(2,4-Dichloro-phenyl)-ethoxy]-4-methoxy-benzoylamino}-pent-4-ynoic acid methyl ester To a solution of 1 g 3-[2-(2,4-Dichloro-phenyl)-ethoxy]-4-methoxy-benzoic acid in 15 ml CH$_2$Cl$_2$ 1.5 ml N-NEM and subsequently 1.1 g TOTU were added. After stirring for 1 h at RT 500 mg 2-Amino-pent-4-ynoic acid methyl ester hydrochloride in 5 ml CH$_2$Cl$_2$ were added and the mixture was stirred over night followed by addition of 20 ml saturated NaHCO$_3$ solution. The organic layer was separated and dried over Na$_2$SO$_4$ and the solvent evaporated. The residue was purified by preparative HPLC (C18 reverse phase column, elution with a H$_2$O/MeCN gradient with 0.5% TFA) and the fractions containing the product were evaporated and lyophilised. The product was obtained as its trifluoroacetate salt.

Yield: 1.4 g.

(iii) 2-{3-[2-(2,4-Dichloro-phenyl)-ethoxy]-4-methoxy-benzoylamino}-3-furo[3,2-c]pyridin-2-yl-propionic acid methyl ester A solution of 100 mg 2-{3-[2-(2,4-Dichloro-phenyl)-ethoxy]-4-methoxy-benzoylamino}-pent-4-ynoic acid methyl ester, 74 mg 3-Iodo-pyridin-4-ol, 123 µl NEt$_3$, 1 mg CuI in 3 ml DMF was purged with argon for 15 min. Then 8 mg Pd(PPh$_3$)$_2$Cl$_2$, were added under argon and the mixture was heated to 100° C. for 2 h. After cooling to 50° C. 66 µl DBU was added, followed by stirring for 2 h at this temperature. The residue was taken up in 3 ml saturated NaHCO$_3$ solution and filtered through a chem elut® cartridge by elution with ethyl acetate. Subsequent removal of the solvent under reduced pressure and purification by preparative HPLC (C18 reverse phase column, elution with a H$_2$O/MeCN gradient with 0.5% TFA) the fractions containing the product were evaporated and lyophilised. The product was obtained as its trifluoroacetate salt.

Yield: 6 mg.

Example 164

2-{3-[2-(2,4-Dichloro-phenyl)-ethoxy]-4-methoxy-benzoylamino}-3-(1H-pyrrolo[3,2-c]pyridin-2-yl)-propionic acid methyl ester

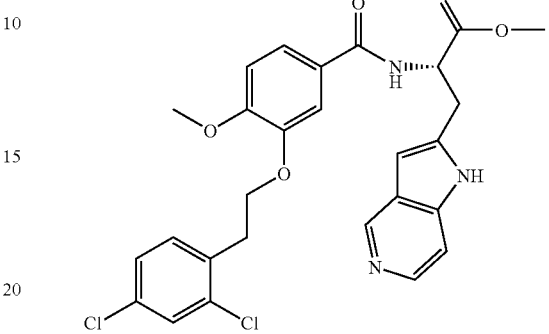

(3-Iodo-pyridin-4-yl)-carbamic acid tert-butyl ester

To a solution of 20 g 4-aminopyridine in 50 ml acetic acid 46 g ICl were added at RT. The reaction mixture was heated to 100° C. for 4 h and then quenched with 100 ml water. The pH was adjusted to 9 by addition of Na$_2$CO$_3$ solution followed by addition of Na$_2$SO$_3$. Extraction of the aqueous solution was done with ethylacetate. The organic layer was dried over Na$_2$SO$_4$ and the solvent removed under reduced pressure. The residue was dissolved in 70 ml CH$_2$Cl$_2$ and 15 ml NEt$_3$. Then 20 g Boc$_2$O were added at RT and the reaction mixture was stirred over night. After removal of the solvent the residue was chromatographied on silica gel with heptane/ethylacetate to yield a brown solid.

Yield: 20 g.

(ii) 2-(2-{3-[2-(2,4-Dichloro-phenyl)-ethoxy]-4-methoxy-benzoylamino}-2-methoxycarbonyl-ethyl)-pyrrolo[3,2-c]pyridine-1-carboxylic acid tert-butyl ester A solution of 100 mg 2-{3-[2-(2,4-Dichloro-phenyl)-ethoxy]-4-methoxy-benzoylamino}-pent-4-ynoic acid methyl ester, 106 mg (3-Iodo-pyridin-4-yl)-carbamic acid tert-butyl ester, 123 µl NEt$_3$, 1 mg CuI in 3 ml DMF was purged with argon for 15 min. Then 8 mg Pd(PPh$_3$)$_2$Cl$_2$ were added under argon and the mixture was heated to 100° C. for 2 h. After cooling to 50° C. 66 µl DBU was added, followed by stirring for 2 h at this temperature. The residue was taken up in 3 ml saturated NaHCO$_3$ solution and filtered through a chem elut® cartridge by elution with ethyl acetate. Subsequent removal of the solvent under reduced pressure and purification by preparative HPLC (C18 reverse phase column, elution with a H$_2$O/MeCN gradient with 0.5% TFA) the fractions containing the product were evaporated and lyophilised. The product was obtained as its trifluoroacetate salt.

Yield: 9 mg.

(iii) 2-{3-[2-(2,4-Dichloro-phenyl)-ethoxy]-4-methoxy-benzoylamino}-3-(1H-pyrrolo[3,2-c]pyridin-2-yl)-propionic acid methyl ester To a solution of 9 mg 2-(2-{3-[2-(2,4-Dichloro-phenyl)-ethoxy]-4-methoxy-benzoylamino}-2-methoxycarbonyl-ethyl)-pyrrolo[3,2-c]pyridine-1-carboxylic acid tert-butyl ester in 1 ml CH$_2$Cl$_2$ 0.5 ml TFA was added dropwise at 0° C. After 1 h 5 ml toluene were added and the solvent removed under reduced pressure to yield a brown foam. The product was obtained as its trifluoroacetate salt. Yield: 5 mg.

Example 165

3-[2-(2,4-Dichloro-phenyl)-ethoxy]-N-(2'-hydroxy-3,4,5,6-tetrahydro-2H-[1,4']bipyridinyl-4-ylmethyl)-4-methoxy-benzamide

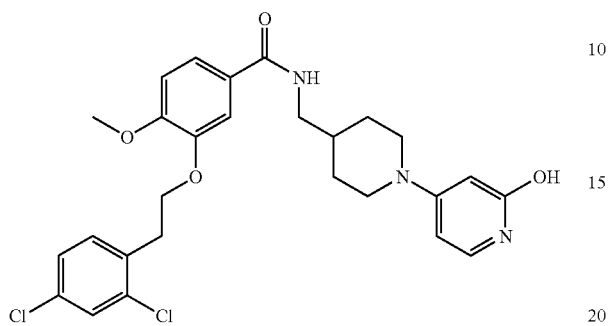

(2'-Hydroxy-3,4,5,6-tetrahydro-2H-[1,4']bipyridinyl-4-ylmethyl)-carbamic acid tert-butyl ester To a solution of 500 mg 2,4 dihydroxypyridine in DMF 216 mg NaH (60% in mineral oil) were added at RT. After 30 min N-phenyltrifluoromethanesulfonamide was added and the mixture stirred for 1 h. Then 960 mg (boc-aminomethyl)piperidine were added and the reaction mixture stirred over night. After of water and extraction with ethylacetate the organic layer was dried over $Na_2SO_4$. Subsequent removal of the solvent under reduced pressure and purification by preparative HPLC (C18 reverse phase column, elution with a $H_2O$/MeCN gradient with 0.5% TFA) the fractions containing the product were evaporated and lyophilised. The product was obtained as its trifluoroacetate salt.

Yield: 1.2 g.

(ii) 4-Aminomethyl-3,4,5,6-tetrahydro-2H-[1,4']bipyridinyl-2'-ol

To a solution of 500 mg (2'-Hydroxy-3,4,5,6-tetrahydro-2H-[1,4']bipyridinyl-4-ylmethyl)-carbamic acid tert-butyl ester in 5 ml $CH_2Cl_2$ 3 ml TFA was added dropwise at 0° C. After 16 h 20 ml toluene were added and the solvent removed under reduced pressure to yield a brown foam.

Yield: 503 mg.

(iii) 3-[2-(2,4-Dichloro-phenyl)-ethoxy]-N-(2'-hydroxy-3,4,5,6-tetrahydro-2H-[1,4']bipyridinyl-4-ylmethyl)-4-methoxy-benzamide To a solution of 200 mg 3-[2-(2,4-Dichloro-phenyl)-ethoxy]-4-methoxy-benzoic acid in 5 ml $CH_2Cl_2$ 300 µl N-NEM and subsequently 192 mg TOTU were added. After stirring for 1 h at RT 243 mg 4-Aminomethyl-3,4,5,6-tetrahydro-2H-[1,4']bipyridinyl-2'-ol tris trifluoroacetate in 1 ml $CH_2Cl_2$ were added and the mixture was stirred for over night followed by removal of the solvent under reduced pressure. The residue was taken up in 5 ml saturated $NaHCO_3$ solution and filtered through a chem elut® cartridge by elution with ethyl acetate. After concentration under reduced pressure and purification by preparative HPLC (C18 reverse phase column, elution with a $H_2O$/MeCN gradient with 0.5% TFA) the fractions containing the product were evaporated and lyophilised. The product was obtained as its trifluoroacetate salt.

Yield: 85 mg    MS (ESI+): 530, chloro pattern

Example 166

3-[2-(2,4-Dichloro-phenyl)-ethoxy]-4-methoxy-N-(1-pyrimidin-4-yl-piperidin-4-ylmethyl)-benzamide

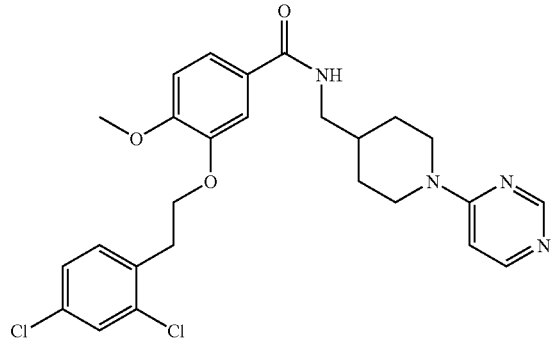

[1-(2-Chloro-pyrimidin-4-yl)-piperidin-4-ylmethyl]-carbamic acid tert-butyl ester

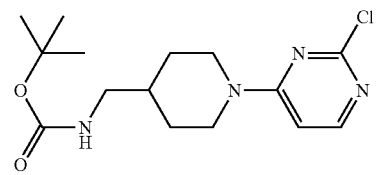

Piperidin-4-ylmethyl-carbamic acid tert-butyl ester (2 g, 9.33 mmol), 2,4-dichloro-pyrimidine (1.67 g, 11.2 mmol) and ethyl-diisopropyl-amine (2,41 g, 18.66 mmol) were heated under reflux in 100 ml of ethanol for 4 hours. The reaction mixture was evaporated, dissolved in ethyl acetate and extracted with aqueous solution (pH4). The organic layer was dried with $MgSO_4$ and evaporated to yield a mixture of the main isomer [1-(2-chloro-pyrimidin-4-yl)-piperidin-4-ylmethyl]-carbamic acid tert-butyl ester and traces of [1-(4-chloro-pyrimidin-2-yl)-piperidin-4-ylmethyl]-carbamic acid tert-butyl ester.

Yield: 2.67 g (87%)    MS: 327.1/329.1 (M + H)+.

(ii) (1-Pyrimidin-4-yl-piperidin-4-ylmethyl)-carbamic acid tert-butyl ester

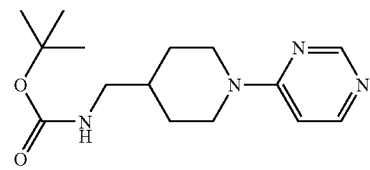

[1-(2-chloro-pyrimidin-4-yl)-piperidin-4-ylmethyl]-carbamic acid tert-butyl (400 mg) was dissolved in 100 ml of methanol. After addition of 50 mg of palladium on charcoal (10%) hydrogen was introduced in a shaking apparatus for 3 hours. After filtration of the catalyst the solution was evaporated.

Yield: 350 mg    MS: 293.2 (M + H)+.

(iii) C-(1-Pyrimidin-4-yl-piperidin-4-yl)-methylamine

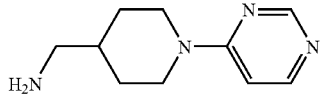

(1-Pyrimidin-4-yl-piperidin-4-ylmethyl)-carbamic acid tert-butyl ester (400 mg) and 50% aqueous trifluoro-acetic acid (5 ml) were stirred 24 hours at room temperature. The mixture was evaporated and lyophilised. The product was obtained as its trifluoroacetate salt.

| Yield: 519 mg, | MS: 193.2 (M + H)+. |
|---|---|

(iv) 3-[2-(2,4-Dichloro-phenyl)-ethoxy]-4-methoxy-N-(1-pyrimidin-4-yl-piperidin-4-ylmethyl)-benzamide To a solution of 70 mg 3-[2-(2,4-Dichloro-phenyl)-ethoxy]-4-methoxy-benzoic acid in 3 ml CH$_2$Cl$_2$ 200 µl N-NEM and subsequently 120 mg TOTU were added. After stirring for 1 h at RT 120 mg C-(1-Pyrimidin-4-yl-piperidin-4-yl)-methylamine tris trifluoro-acetate in 1 ml CH$_2$Cl$_2$ were added and the mixture was stirred for over night followed by removal of the solvent under reduced pressure. The residue was taken up in 5 ml saturated NaHCO$_3$ solution and filtered through a chem elut® cartridge by elution with ethyl acetate. After concentration under reduced pressure and purification by preparative HPLC (C18 reverse phase column, elution with a H$_2$O/MeCN gradient with 0.5% TFA) the fractions containing the product were evaporated and lyophilised. The product was obtained as its trifluoroacetate salt.

| Yield. 8 mg | MS (ESI+): 515, chloro pattern |
|---|---|

Example 167

4-Chloro-3-[2-(6-chloro-pyridin-3-yl)-ethoxy]-N-(2'-methyl-3,4,5,6-tetrahydro-2H-[1,4']bipyridinyl-4-ylmethyl)-benzamide

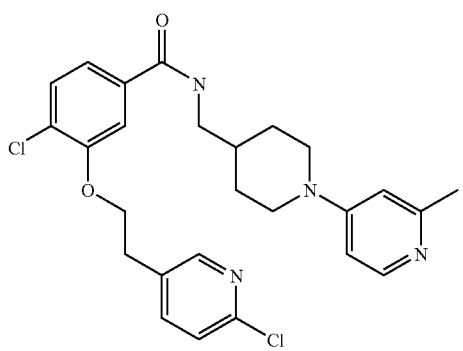

(2'-Methyl-3,4,5,6-tetrahydro-2H-[1,4']bipyridinyl-4-ylmethyl)-carbamic acid tert-butyl ester

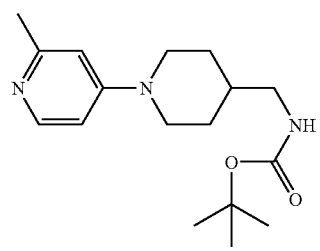

A suspension of 1 g piperidin-4-ylmethyl-carbamic acid tBu ester 0.65 g 4-chloropicoline in 5 ml n-BuOH/H$_2$O/NEt$_3$ 1:1:1 was refluxed for 3 days. After removal of the solvent under reduced pressure the residue was purified by chromatography on silica with CH$_2$Cl$_2$/MeOH 100:1->50:1->10:1–5:1 to yield a white solid.

(ii) C-(2'-Methyl-3,4,5,6-tetrahydro-2H-[1,4']bipyridinyl-4-yl)-methylamine tris trifluoroacetate

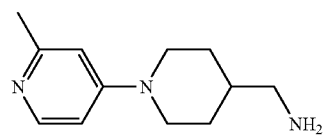

To a solution of 1.24 (2'-Methyl-3,4,5,6-tetrahydro-2H-[1,4']bipyridinyl-4-ylmethyl)-carbamic acid tert-butyl ester in 5 ml CH$_2$Cl$_2$ 2 ml TFA were added at RT. After stirring for 30 min the solution was diluted with 20 ml of toluene and evaporated under reduced pressure. The residue was codestilled twice with toluene and then used in the subsequent reactions without further purification.

(iii) 4-Chloro-3-[2-(6-chloro-pyridin-3-yl)-ethoxy]-N-(2'-methyl-3,4,5,6-tetrahydro-2H-[1,4']bipyridinyl-4-ylmethyl)-benzamide To a solution of 100 mg 3-[2-(5-Chloro-pyridin-2-yl)-ethoxy]-4-methoxy-benzoic acid in 5 ml ethyl acetate 0.1 ml NEt$_3$ and 150 mg BOP-Cl were added. After 30 min 124 mg C-(2'-Methyl-3,4,5,6-tetrahydro-2H-[1,4']bipyridinyl-4-yl)-methylamine tris trifluoroacetate tris trifluoro-acetate in 1 ml CH$_2$Cl$_2$ were added and the mixture stirred for 10 h at RT followed by removal of the solvent under reduced pressure. The residue was taken up in 3 ml saturated NaHCO$_3$ solution and filtered through a chem elut® cartridge by elution with ethyl acetate. After concentration under reduced pressure and purification by preparative HPLC (C18 reverse phase column, elution with a H$_2$O/MeCN gradient with 0.5% TFA) the fractions containing the product were evaporated and lyophilised. The product was obtained as its trifluoroacetate salt.

| Yield: 18 mg | MS (ESI+): 484, chloro pattern |
|---|---|

Analogously to example 167 the following compounds were prepared by a similar procedure:

| Example | Structure | MS (ESI+) |
|---|---|---|
| 168 | 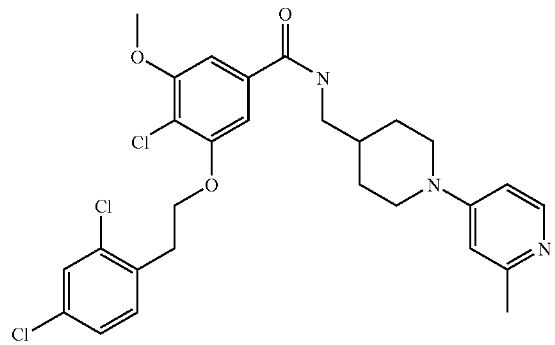 | 562, chloro pattern |
| 169 | 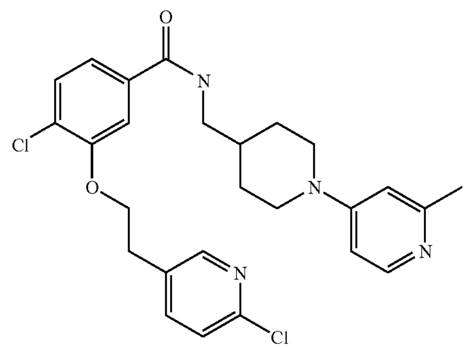 | 484, chloro pattern |
| 170 | 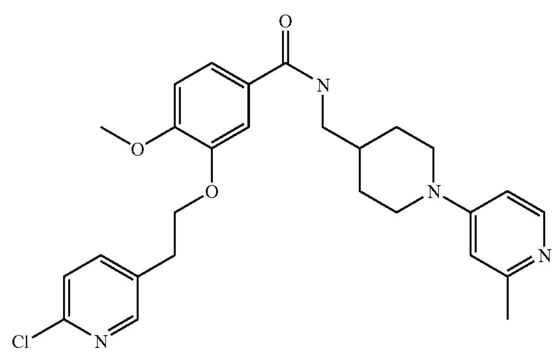 | 499, chloro pattern |
| 171 | 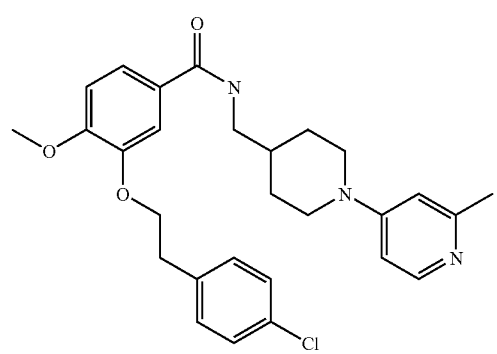 | 494, chloro pattern |

Example 172

N-[1-(2-Chloro-pyrimidin-4-yl)-piperidin-4-ylmethyl]-3-[2-(2,4-dichloro-phenyl)-ethoxy]-4-methyl-benzamide

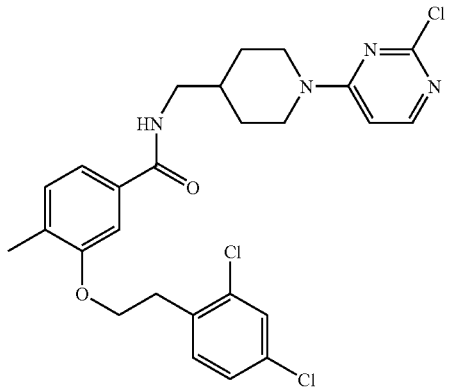

C-[1-(2-Chloro-pyrimidin-4-yl)-piperidin-4-yl]-methylamine

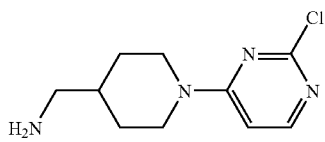

[1-(2-Chloro-pyrimidin-4-yl)-piperidin-4-ylmethyl]-carbamic acid tert-butyl ester (200 mg) was stirred with 50% aqueous trifluoro-acetic acid (5 ml) 24 hours at room temperature. The mixture was evaporated and lyophilized. The product was obtained as its trifluoroacetate salt.

| Yield: 300 mg | MS: 227.2/229.2 (M + H)+. |
|---|---|

(ii) N-[1-(2-Chloro-pyrimidin-4-yl)-piperidin-4-ylmethyl]-3-[2-(2,4-dichloro-phenyl)-ethoxy]-4-methyl-benzamide 3-[2-(2,4-Dichloro-phenyl)-ethoxy]-4-methyl-benzoic acid (50 mg, 0.15 mmol) and triethyl-amine (46.7 mg, 0.46 mmol) were dissolved in 5 ml of dichloro-methane. After cooling to −15° C. ethyl chloroformate (18.4 mg, 0.17 mmol) in 5 ml of dichloro-methane was added and stirred at room temperature for 24 hours. The mixture was evaporated and the solid was washed with dodium bicarbonate solution and water and was dried.

| Yield: 37 mg (37%) | MS: 533.1/535.1 (M + H)+. |
|---|---|

Example 173

N-[1-(5-Amino-[1,2,4]oxadiazol-3-yl)-piperidin-4-ylmethyl]-3-[2-(2,4-dichloro-phenyl)-ethoxy]-4-methyl-benzamide (1-Cyano-piperidin-4-ylmethyl)-carbamic acid tert-butyl ester

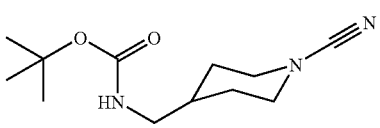

Piperidin-4-ylmethyl-carbamic acid tert-butyl ester (4 g, 18.66 mmol) was suspended in 120 ml of acetonitrile. Dried potassium carbonate (2.837 g, 20.53 mmol) was added. A solution of bromoacetonitrile in (3.72 ml, 5 mmolar solution, 18.66 mmol) was added (argon atmosphere) and the mixture was stirred for 3 hours. After addition of aqueous FeSO$_4$ solution and ethyl acetate, the separated solid was filtered and the organic layer separated, dried and evaporated.

| Yield: 4.04 g (90%) | MS: 240.2 (M + H)+. |
|---|---|

(ii) [1-(N-Hydroxycarbamimidoyl)-piperidin-4-ylmethyl]-carbamic acid tert-butyl ester

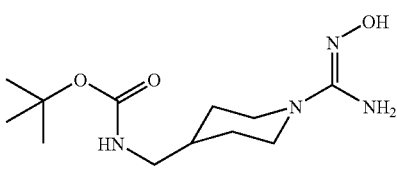

(1-Cyano-piperidin-4-ylmethyl)-carbamic acid tert-butyl ester (2 g, 8.36 mmol), hydroxylamine hydrochloride (3.48 g, 50.14 mmol) and triethylamine (5.92 g, 58.5 mmol) were stirred in 30 ml of isopropanol at room temperature for 4 hours. The mixture was evaporated. After addition of water (pH4) and ethyl acetate, the organic layer was separated and evaporated.

| Yield: 1.3 g (57%) | MS: 273.2 (M + H)+. |
|---|---|

(iii) [1-(5-Trichloromethyl-[1,2,4]oxadiazol-3-yl)-piperidin-4-ylmethyl]-carbamic acid tert-butyl ester

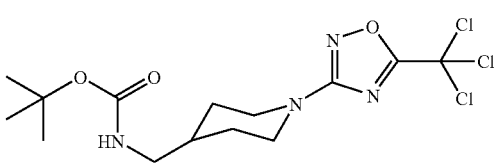

Trichloroaceticacid anhydride (1.24 g, 4 mmol) was added at 0° C. to a solution of [1-(N-Hydroxycarbamimidoyl)-piperidin-4-ylmethyl]-carbamic acid tert-butyl ester (1 g, 3.67 mmol) in 80 ml of tetrahydro-furan. The temperature was raised at room temperature and stirred for 3 hours. After addition of triethylamine (0.74 ml, 7.34 mmol) the mixture was heated at 70° C. for 2 hours and evaporated. The residue was diluted with water and extracted with ethyl acetate. The organic layer was dried with MgSO₄, evaporated and purified by column chromatography (RP18, acetonitrile/water). The product was obtained as its trifluoroacetate salt.

| Yield: 1.07 g (73%) | MS: 399.0/401.1 (M + H)⁺. |
|---|---|

(iv) C-[1-(5-Trichloromethyl-[1,2,4]oxadiazol-3-yl)-piperidin-4-yl]-methylamine; compound with trifluoro-acetic acid

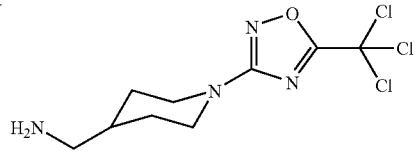

[1-(5-Trichloromethyl-[1,2,4]oxadiazol-3-yl)-piperidin-4-ylmethyl]-carbamic acid tert-butyl ester (500 mg, 1.25 mmol) and 30% aqueous trifluoro-acetic acid (5 ml) were stirred for 24 hours at room temperature. The mixture was evaporated and lyophilised. The product contains excess of trifluoro-acetic acid.

| Yield: 577 mg | MS: 298.9/300.9 (M + H)⁺. |
|---|---|

3-[2-(2,4-Dichloro-phenyl)-ethoxy]-4-methyl-N-[1-(5-trichloromethyl-[1,2,4]oxadiazol-3-yl)-piperidin-4-ylmethyl]-benzamide

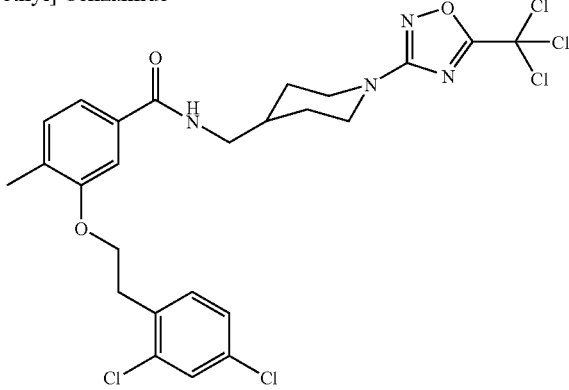

3-[2-(2,4-Dichloro-phenyl)-ethoxy]-4-methyl-benzoic acid (200 mg, 0.615 mmol) was dissolved in 5 ml DMF. After cooling to −15° C. HATU (257.34 mg, 0.676 mmol) and N-ethylmorpholine (283.3 mg, 2.46 mmol) were added. The mixture was stirred at 0° C. for 15 min. and 30 min. at room temperature. C-[1-(5-trichloromethyl-[1,2,4]oxadiazol-3-yl)-piperidin-4-yl]-methylamine; compound with trifluoro-acetic acid (254.4 mg, 0.615 mmol) was added and the mixture stirred for 1 hour and evaporated under reduced pressure. The residue was dissolved in sodium bicarbonate solution and extracted with ethyl acetate. The organic layer was dried with MgSO₄ and evaporated. The crude material was used without further purification.

Yield: 250 mg.

N-[1-(5-Amino-[1,2,4]oxadiazol-3-yl)-piperidin-4-ylmethyl]-3-[2-(2,4-dichloro-phenyl)-ethoxy]-4-methyl-benzamide; compound with trifluoro-acetic acid

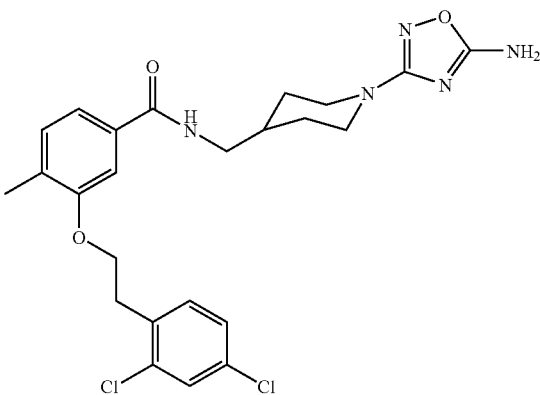

Crude 3-[2-(2,4-dichloro-phenyl)-ethoxy]-4-methyl-N-[1-(5-trichloromethyl-[1,2,4]oxadiazol-3-yl)-piperidin-4-ylmethyl]-benzamide (250 mg) was dissolved in 60 ml of methanol (containing ammonia, 7 molar) in an autoclave at 50 bar pressure and 50° C. for 24 hours. The mixture was evaporated under reduced pressure and purified on RP18 (5 µm) (gradient acetonitrile/water (containing 0.1% trifluoro-acetic acid) 90:10 to 0:100). The fractions containing the product were evaporated and lyophilised. The product was obtained as its trifluoroacetate salt.

| Yield: 18 mg | MS: 504.3/506.3 (M + H)⁺. |
|---|---|

Example 174

3-[2-(2,4-Dichloro-phenyl)-ethoxy]-4-methyl-N-[4-(pyridin-4-yloxy)-3,4,5,6-tetrahydro-2H-[1,4']bipyridinyl-4-ylmethyl]-benzamide

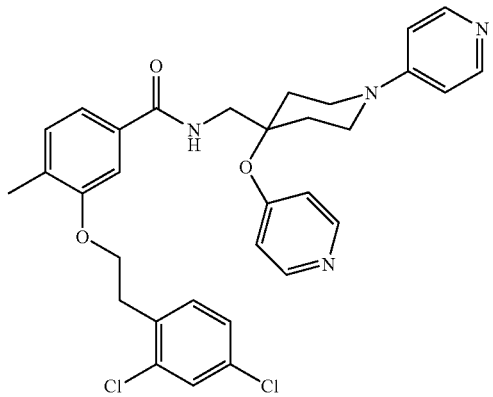

4-Cyano-4-trimethylsilanyloxy-piperidine-1-carboxylic acid tert-butyl ester

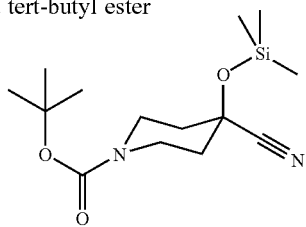

4-Oxo-piperidine-1-carboxylic acid tert-butyl ester (6.48 g, 32.52 mmol) was dissolved in 50 ml of tetrahydro-furan. At 0° C. trimethylsilyl cyanide (5.08 g, 51.38 mmol) and zink iodide (87 mg, 0.27 mmol) were added. The mixture was stirred 3 hours at 0° C. and 3 hours at 60° C. The solid was filtered, the filtrate evaporated and the crude product was used without further purification.

| Yield: 7.54 g | MS: 299.1 (M + H)⁺. |

(ii) 4-Aminomethyl-4-hydroxy-piperidine-1-carboxylic acid tert-butyl ester

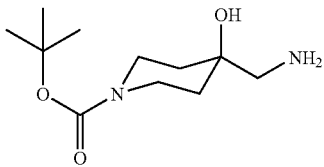

4-Cyano-4-trimethylsilanyloxy-piperidine-1-carboxylic acid tert-butyl ester (7.5 g) was dissolved in 100 ml of tetrahydro-furan under an argon atmosphere. A solution of lithium aluminium hydride in tetrahydro-furan (30 ml, 1 molar) was dropwise added at 0° C. After stirring for 15 hours at room temperature, a sodium hydroxide solution (20%) was slowly added under cooling. The solid was filtered after dilution with ethyl acetate and the organic layer evaporated. The crude material contains a mixture of the desired product (MS: 231.2 (M+H)⁺) and the corresponding trimethylsiliyl ether (MS: 303.1 (M+H)⁺) and was used without further purification.

Yield: 2.1 g.

(iii) 3-{3-[2-(2,4-Dichloro-phenyl)-ethoxy]-4-methyl-benzoyl}-1-oxa-3,8-diaza-spiro[4.5]decane-8-carboxylic acid tert-butyl ester

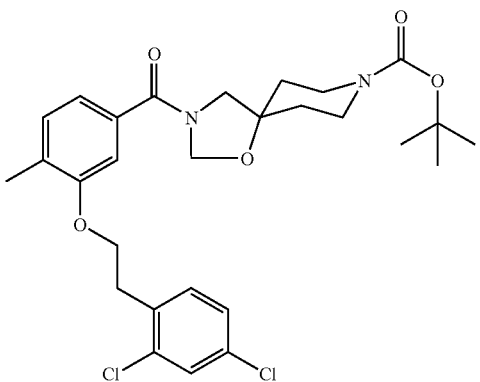

3-[2-(2,4-Dichloro-phenyl)-ethoxy]-4-methyl-benzoic acid (300 mg, 0.922 mmol) and crude 4-aminomethyl-4-hydroxy-piperidine-1-carboxylic acid tert-butyl ester (212.5 mg, 0.922 mmol) was dissolved in 5 ml DMF. After cooling to −15° C. HATU (386 mg, 1 mmol) and N-ethylmorpholine (318.9 mg, 2.77 mmol) were added. The mixture was stirred at 0° C. for 2 hours and at room temperature for 15 hours, evaporated and purified on RP18 (5 μm) (gradient acetonitrile water 90:10 to 0:100). The fractions containing the product were evaporated and lyophilised. The product was obtained as its trifluoroacetate salt.

| Yield: 155 mg (31%) | MS: 549.2 (M + H)⁺. |

(iv) {3-[2-(2,4-Dichloro-phenyl)-ethoxy]-4-methyl-phenyl}-(1-oxa-3,8-diaza-spiro[4.5]dec-3-yl)-methanone

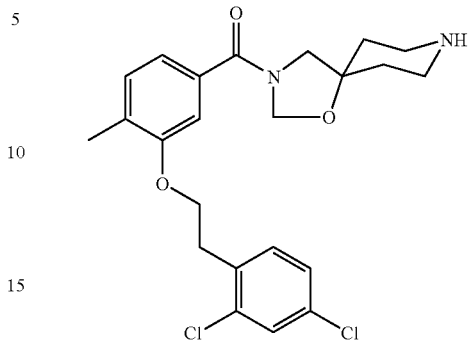

3-{3-[2-(2,4-Dichloro-phenyl)-ethoxy]-4-methyl-benzoyl}-1-oxa-3,8-diaza-spiro[4.5]decane-8-carboxylic acid tert-butyl ester (41 mg, 0.075 mmol) were stirred with 80% aqueous trifluoro-acetic acid (2 ml) for 24 hours at room temperature. The mixture was evaporated and lyophilised. The product was obtained as its trifluoroacetate salt.

| Yield: 42 mg (100%) | MS: 449.1/451.1 (M + H)⁺. |

(v) 3-[2-(2,4-Dichloro-phenyl)-ethoxy]-4-methyl-N-[4-(pyridin-4-yloxy)-3,4,5,6-tetrahydro-2H-[1,4']bipyridinyl-4-ylmethyl]-benzamide {3-[2-(2,4-Dichloro-phenyl)-ethoxy]-4-methyl-phenyl}-(1-oxa-3,8-diaza-spiro[4.5]dec-3-yl)-methanone; compound with trifluoro-acetic acid (42 mg, 0.075 mmol), 4-Chloro-pyridine; hydrochloride (33.5 mg, 0.22 mmol) and triethyl-amine (37.7 mg, 0.37 mmol) were heated in 10 ml of n-butanol under reflux for 7 days. The mixture was evaporated and purified on RP18 (5 μm) (gradient acetonitrile water (containing 0.1% trifluoro-acetic acid) 90:10 to 0:100). The fractions containing the product were evaporated and lyophilised. The product was obtained as its trifluoroacetate salt.

| Yield: 14 mg (23%) | MS: 591.3/593.3 (M + H)⁺. |

Example 175

3-[2-(2,4-Dichloro-phenyl)-ethoxy]-4-methyl-N-{1-[1-(2-oxo-1,2-dihydro-pyrimidin-4-yl)-piperidin-4-yl]-ethyl}-benzamide

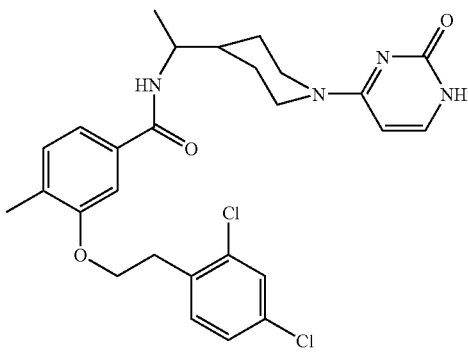

N-(1-Pyridin-4-yl-ethyl)-formamide

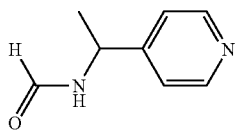

1-Pyridin-4-yl-ethanone (24.2 g, 199.77 mmol) and 10 ml of formic acid were heated to 180° C. and formamide (126 g, 2.797 mol) in 10 ml of formic acid was added within 30 min. The mixture was stirred for 90 min., cooled and poured in 100 ml of water. After addition of conc. sodium hydroxide solution until pH13 the product was extracted with diethyl-ether. The organic layer was dried with MgSO$_4$ and evaporated. Purification by distillation (165° C./4 mbar) yields pure product.

| Yield: 17.9 g (60%) | MS: 151.1 (M + H)$^+$. |
|---|---|

(ii) N-(1-Piperidin-4-yl-ethyl)-formamide

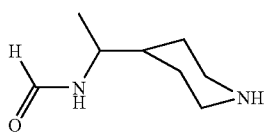

N-(1-Pyridin-4-yl-ethyl)-formamide (1.86 g, 12.38 mmol) was dissolved in 50 ml of acetic acid. After addition of Rh (5% on Al$_2$O$_3$, 307 mg) the mixture was hydrogenated with 10 bar hydrogen and 100° C. for 120 hours. The mixture was evaporated and lyophilised. The crude material was used without purification.

| Yield: 2.52 g | MS: 157.2 (M + H)$^+$. |
|---|---|

(iii) N-{1-[1-(2-Chloro-pyrimidin-4-yl)-piperidin-4-yl]-ethyl}-formamide

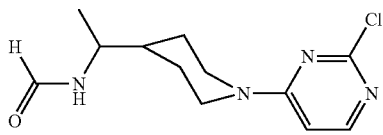

N-(1-Piperidin-4-yl-ethyl)-formamide; compound with acetic acid (350 mg, 1.61 mmol), 2,4-dichloro-pyrimidine (265 mg, 1.78 mmol) and ethyl-diisopropyl-amine (848 mg, 6.56 mmol) in 20 ml of ethanol were heated under reflux for 5 hours. The mixture was evaporated and the residue dissolved in water and extracted with ethyl acetate. The organic layer was dried with MgSO$_4$ and evaporated.

| Yield: 246 mg (46%) | MS: 269.2 (M + H)$^+$. |
|---|---|

4-[4-(1-Amino-ethyl)-piperidin-1-yl]-1H-pyrimidin-2-one

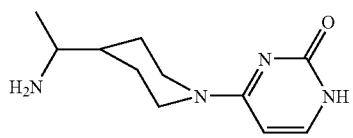

N-{1-[1-(2-Chloro-pyrimidin-4-yl)-piperidin-4-yl]-ethyl}-formamide (240 mg, 0.89 mmol) in 10 ml of 6 N hydrochloric acid was heated under reflux for 1 hour. The mixture was evaporated and lyophilised.

| Yield: 200 mg | MS: 223.3 (M + H)$^+$. |
|---|---|

(v) 3-[2-(2,4-Dichloro-phenyl)-ethoxy]-4-methyl-N-{1-[1-(2-oxo-1,2-dihydro-pyrimidin-4-yl)-piperidin-4-yl]-ethyl}-benzamide

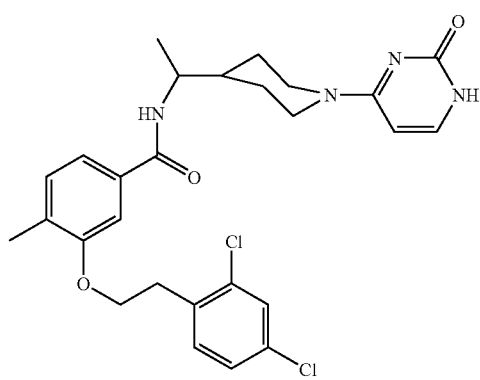

3-[2-(2,4-Dichloro-phenyl)-ethoxy]-4-methyl-benzoic acid (50 mg, 0.15 mmol) and 4-[4-(1-Amino-ethyl)-piperidin-1-yl]-1H-pyrimidin-2-one; hydrochloride (39.8 mg, 0.15 mmol) was dissolved in 3 ml DMF. After cooling to −15° C. HATU (64 mg, 0.17 mmol) and N-ethylmorpholine (53.1 mg, 0.46 mmol) were added. The mixture was stirred at 0° C. for 2 hours and at room temperature for 5 hours, evaporated and purified on RP18 (5 μm) (gradient acetonitrile water 90:10 to 0:100). The fractions containing the product were evaporated and lyophilised. The product was obtained as its trifluoroacetate salt.

| Yield: 33 mg (40%) | MS: 529.3/531.3 (M + H)$^+$. |
|---|---|

Example 176

{4-Bromo-3-[2-(2,4-dichloro-phenyl)-ethoxy]-phenyl}-(4-pyridin-4-ylmethyl-piperazin-1-yl)-methanone

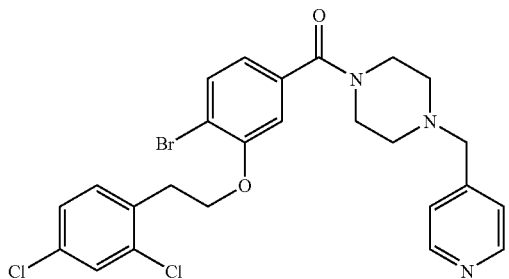

0.05 g (0.13 mmol) of 4-Bromo-3-[2-(2,4-dichloro-phenyl)-ethoxy]-benzoic acid was dissolved in 3 ml of DMF and treated with 0.059 g (0.51 mmol) of NEM and 0.042 g (0.13 mmol) of TOTU and 0.023 g (0.13 mmol) of 1-Pyridin-4-ylmethyl-piperazine. The solution was stirred for 16 h at RT. The solvent was removed under reduced pressure, the residue was taken-up in acetonitrile and the residue was purified by preparative RP-HPLC eluting with a gradient of 0 to 100% acetonitrile in water (+0.01% trifluoroacetic acid). After lyophilization the product was obtained as its trifluoroacetate salt.

| Yield 44.4 mg. | MS (ES$^+$): m/e = 550 (M + H)$^+$. |
|---|---|

Example 177

{3-[2-(2,4-Dichloro-phenyl)-ethoxy]-4,5-diethoxy-phenyl}-(4-pyridin-4-ylmethyl-piperazin-1-yl)-methanone (S0013313)

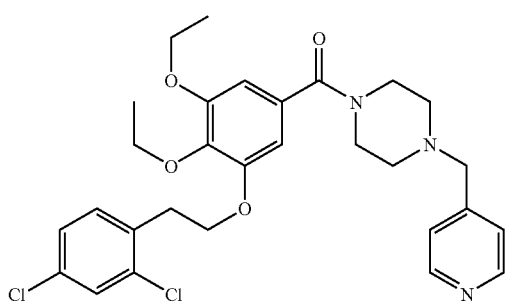

3,4-Diethoxy-5-hydroxy-benzoic acid ethyl ester 5 g (25.2 mmol) of 3,4,5-trihydroxy-benzoic acid ethyl ester was dissolved in 20 ml of DMF and treated at 0° C. with 13.95 g (100.9 mmol) of potassium carbonate and 6.185 g (56.7 mmol) of ethyl bromide. The solution was stirred for 16 h at RT. The solvent was removed under reduced pressure, the residue was taken-up in ethyl acetate and the solution was washed three times with water and twice with saturated aqueous sodium chloride. The organic phase was dried with magnesium sulphate, filtered and the solvent was removed under reduced pressure. The residue was chromatographed on silica gel eluting with n-heptane/ethyl acetate (5/1).

| Yield 1.2 g. | MS (ES$^+$): m/e = 255 (M + H$^+$). |
|---|---|

(ii) 3-[2-(2,4-Dichloro-phenyl)-ethoxy]-4,5-diethoxy-benzoic acid ethyl ester g (3.93 mmol) of 3,4-Diethoxy-5-hydroxy-benzoic acid ethyl ester was dissolved in 20 ml of anhydrous tetrahydrofuran. To this solution was added 0.83 g (4.33 mmol) of 2-(2,4-Dichlorophenyl)-ethanol, 3.93 g (equivalent to 11.8 mmol PPh$_3$) of triphenylphosphine derivatized polystyrene and 2.05 g (11.8 mmol) of DEAD. The solution was shaken for 16 h at RT. The polymer was filtered off and washed with ethyl acetate. The solvent was removed under reduced pressure. The residue was taken-up in ethyl acetate and the solution was washed three times with water and twice with saturated aqueous sodium chloride. The organic phase was dried with magnesium sulphate, filtered and the solvent was removed under reduced pressure. The residue was chromatographed on silica gel eluting with ethyl acetate/n-heptane (1/5).

Yield 660 mg. LC-MS (ES$^+$): m/e=427 (M)$^+$ (iii) 3-[2-(2,4-Dichlorophenyl)-ethoxy]-4,5-diethoxy-benzoic acid 0.66 g (1.54 mmol) of 3-[2-(2,4-Dichlorophenyl)-ethoxy]-4,5-diethoxy-benzoic acid ethyl ester was dissolved in 6 ml of dioxan. 5 ml of water and 2N aqueous NaOH was added to the solution to give a pH of 13. The reaction solution was heated at 60° C. for 4 h and stirred at room temperature for 16 h. The reaction solution was cooled to 0° C. and concentrated hydrochloric acid was added to give a pH of 1–2, whereupon the product precipitated from solution. The suspension was stirred for 30 min, then the product was filtered off and dried under reduced pressure.

Yield 0.571 g. MS (ES$^+$): m/e=399 (M$^+$).

(iv) {3-[2-(2,4-Dichloro-phenyl)-ethoxy]-4,5-diethoxy-phenyl}-(4-pyridin-4-ylmethyl-piperazin-1-yl)-methanone 0.05 g (0.13 mmol) of 3-[2-(2,4-Dichlorophenyl)-ethoxy]-4,5-diethoxy-benzoic acid was dissolved in 2 ml of DMF and treated with 0.059 g (0.51 mmol) of NEM and 0.041 g (0.13 mmol) of TOTU and 0.022 g (0.13 mmol) of 1-Pyridin-4-ylmethyl-piperazine. The solution was stirred for 16 h at RT. The solvent was removed under reduced pressure, the residue was taken-up in acetonitrile and the residue was purified by preparative RP-HPLC eluting with a gradient of 0 to 100% acetonitrile in water (+0.01% trifluoroacetic acid). After lyophilization the product was obtained as its trifluoroacetate salt.

| Yield 17.8 mg. | MS (ES$^+$): m/e = 558 (M + H)$^+$. |
|---|---|

Example 178

3-[2-(2,4-Dichloro-phenyl)-ethoxy]-4,5-diethoxy-N-(3,4,5,6-tetrahydro-2H-[1,4']bipyridinyl-4-ylm-ethyl)-benzamide

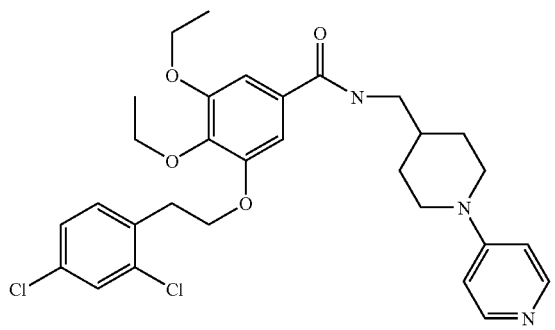

0.050 g (0.13 mmol) of 3-[2-(2,4-Dichlorophenyl)-ethoxy]-4,5-diethoxy-benzoic acid was dissolved in 2 ml of DMF and treated with 0.058 g (0.5 mmol) of NEM and 0.041 g (0.13 mmol) of TOTU and 0.067 g (0.13 mmol) of C-(3,4,5,6-Tetrahydro-2H-[1,4']bipyridinyl-4-yl)-methylamine tris-trifluoroacetate salt. The solution was stirred for 16 h at RT. The solvent was removed under reduced pressure, the residue was taken-up in ethyl acetate and the solution was washed twice with saturated aqueous sodium bicarbonate and once with saturated aqueous sodium chloride. The organic phase was dried with magnesium sulphate, filtered and the solvent was removed under reduced pressure. The residue was purified by preparative RP-HPLC eluting with a gradient of 0 to 100% acetonitrile in water (+0.01% trifluoroacetic acid). After lyophilization the product was obtained as its trifluoroacetate salt. Yield 35.3 mg. MS (ES$^+$): m/e=572 (M$^+$).

Example 179

4-Bromo-3-[2-(2,4-dichloro-phenyl)-ethoxy]-5-ethoxy-N-(3,4,5,6-tetrahydro-2H-[1,4']bipyridinyl-4-ylmethyl)-benzamide (S0013436)

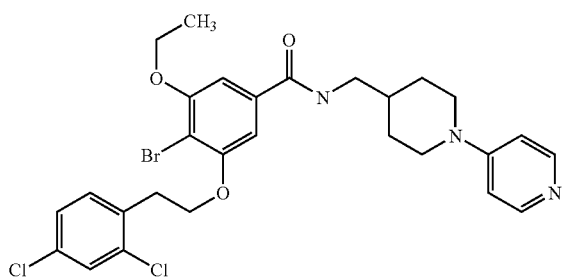

4-Bromo-3-[2-(2,4-dichlorophenyl)-ethoxy]-5-ethoxy-benzoic acid ethyl ester 200 mg (0.49 mmol) of 4-Bromo-3-[2-(2,4-dichloro-phenyl)-ethoxy]-5-hydroxy-benzoic acid was dissolved in 5 ml of DMF and treated at 0° C. with 272 mg (1.97 mmol) of potassium carbonate and 537 mg (4.93 mmol) of ethyl bromide. The solution was stirred for 16 h at RT. The solvent was removed under reduced pressure, the residue was taken-up in ethyl acetate and the solution was washed three times with water and twice with saturated aqueous sodium chloride. The organic phase was dried with magnesium sulphate, filtered and the solvent was removed under reduced pressure.

Yield 219 mg.   MS (ES$^+$): m/e = 463 (M + H$^+$).

(ii) 4-Bromo-3-[2-(2,4-dichlorophenyl)-ethoxy]-5-ethoxy-benzoic acid 0.21 g (0.47 mmol) of 4-Bromo-3-[2-(2,4-dichlorophenyl)-ethoxy]-5-ethoxy-benzoic acid ethyl ester was dissolved in 6 ml of dioxan. 6 ml of water and 2N aqueous NaOH was added to the solution to give a pH of 13. The reaction solution was heated at 60° C. for 4 h and stirred at room temperature for 16 h. The reaction solution was cooled to 0° C. and concentrated hydrochloric acid was added to give a pH of 1–2, whereupon the product precipitated from solution. The suspension was stirred for 30 min, then the product was filtered off and dried under reduced pressure.

Yield 0.175 g.   MS (ES$^+$): m/e = 434 (M$^+$).

(iii) 4-Bromo-3-[2-(2,4-dichlorophenyl)-ethoxy]-5-ethoxy-N-(3,4,5,6-tetrahydro-2H-[1,4']bipyridinyl-4-ylmethyl)-benzamide 0.050 g (0.12 mmol) of 4-Bromo-3-[2-(2,4-dichlorophenyl)-ethoxy]-5-ethoxy-benzoic acid was dissolved in 3 ml of DMF and treated with 0.053 g (0.46 mmol) of NEM and 0.038 g (0.12 mmol) of TOTU and 0.061 g (0.12 mmol) of C-(3,4,5,6-Tetrahydro-2H-[1,4']bipyridinyl-4-yl)-methylamine tris-trifluoroacetate salt. The solution was stirred for 16 h at RT. The solvent was removed under reduced pressure. The residue was purified by preparative RP-HPLC eluting with a gradient of 0 to 100% acetonitrile in water (+0.01% trifluoroacetic acid). After lyophilization the product was obtained as its trifluoroacetate salt.

Yield 42 mg. MS (ES$^+$): m/e=608 (M+H$^+$).

Example 180

{4-Bromo-3-[2-(2,4-dichloro-phenyl)-ethoxy]-5-ethoxy-phenyl}-(4-pyridin-4-ylmethyl-piperazin-1-yl)-methanone (S0013437)

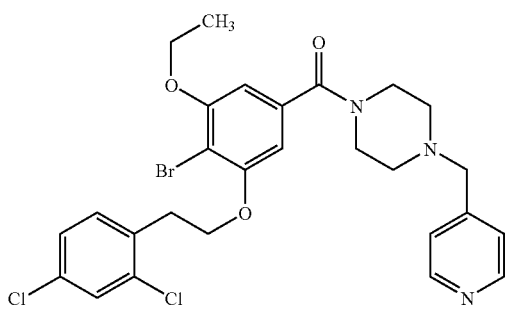

0.050 g (0.12 mmol) of 4-Bromo-3-[2-(2,4-dichlorophenyl)-ethoxy]-5-ethoxy-benzoic acid was dissolved in 3 ml of DMF and treated with 0.053 g (0.46 mmol) of NEM and 0.038 g (0.12 mmol) of TOTU and 0.020 g (0.12 mmol) of 1-Pyridin-4-ylmethyl-piperazine. The solution was stirred for 16 h at RT. The solvent was removed under reduced pressure, the residue was taken-up in acetonitrile and the residue was purified by preparative RP-HPLC eluting with a gradient of 0 to 100% acetonitrile in water (+0.01% trifluoroacetic acid). After lyophilization the product was obtained as its trifluoroacetate salt. Yield 17.8 mg. MS (ES+): m/e=594 (M+H)+.

Example 181

4-Chloro-3-[2-(2,4-dichloro-phenyl)-ethoxy]-N-(3,4,5,6-tetrahydro-2H-[1,4']bipyridinyl-4-ylmethyl)-benzamide (S0013438)

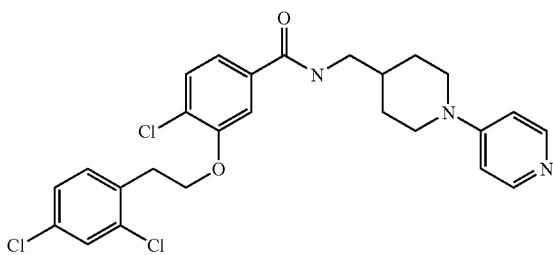

4-Chloro-3-hydroxy-benzoic acid methyl ester 5 g (29 mmol) of 4-Chloro-3-hydroxy-benzoic acid was suspended in 30 ml of saturated methanolic HCl and stirred at room temperature for 16 h. 20 ml of saturated methanolic HCl was added and stirred at room temperature for a further 16 h. The solvent was removed under reduced pressure, and the residue was dried under reduced pressure.

Yield 5.3 g. MS (ES+): m/e=187 (M+H)+.

(ii) 4-Chloro-3-[2-(2,4-dichloro-phenyl)-ethoxy]-benzoic acid methyl ester 2.0 g (10.72 mmol) of 4-Chloro-3-hydroxy-benzoic acid methyl ester was dissolved in 20 ml of anhydrous tetrahydrofuran. To this solution was added 2.25 g (11.79 mmol) of 2-(2,4-Dichlorophenyl)-ethanol, 10.71 g (equivalent to 32.2 mmol PPh$_3$) of triphenylphosphine derivatized polystyrene and 5.6 g (32.2 mmol) of DEAD. The solution was shaken for 16 h at RT. The polymer was filtered off and washed with ethyl acetate. The solvent was removed under reduced pressure. The residue was taken-up in ethyl acetate and the solution was washed three times with water and twice with saturated aqueous sodium chloride. The organic phase was dried with magnesium sulphate, filtered and the solvent was removed under reduced pressure. The residue was chromatographed on silica gel eluting with ethyl acetate/n-heptane (1/6).

Yield 3 g. LC-MS (ES+): m/e=359 (M)+

(iii) 4-Chloro-3-[2-(2,4-dichloro-phenyl)-ethoxy]-benzoic acid g (2.78 mmol) of 4-Chloro-3-[2-(2,4-dichloro-phenyl)-ethoxy]-benzoic acid methyl ester was dissolved in 10 ml of dioxan. 5 ml of water and 2N aqueous NaOH was added to the solution to give a pH of 13. The reaction solution was heated at 60° C. for 4 h and stirred at room temperature for 16 h. The reaction solution was cooled to 0° C. and concentrated hydrochloric acid was added to give a pH of 1–2, whereupon the product precipitated from solution. The suspension was stirred for 30 min, then the product was filtered off and dried under reduced pressure.

Yield 0.910 g. MS (ES+): m/e=345 (M+).

(iv) 4-Chloro-3-[2-(2,4-dichloro-phenyl)-ethoxy]-N-(3,4,5,6-tetrahydro-2H-[1,4']bipyridinyl-4-ylmethyl)-benzamide 0.050 g (0.15 mmol) of 4-Chloro-3-[2-(2,4-dichloro-phenyl)-ethoxy]-benzoic acid was dissolved in 3 ml of DMF and reacted with 0.067 g (0.58 mmol) of NEM and 0.048 g (0.15 mmol) of TOTU and 0.077 g (0.14 mmol) of C-(3,4,5,6-Tetrahydro-2H-[1,4']bipyridinyl-4-yl)-methylamine tris-trifluoroacetate salt. The solution was stirred for 16 h at RT. The solvent was removed under reduced pressure. The residue was purified by preparative RP-HPLC eluting with a gradient of 0 to 100% acetonitrile in water (+0.01% trifluoroacetic acid). After lyophilization the product was obtained as its trifluoroacetate salt. Yield 45.7 mg. MS (ES+): m/e=518 (M+).

Example 182

{4-Chloro-3-[2-(2,4-dichloro-phenyl)-ethoxy]-phenyl}-(4-pyridin-4-ylmethyl-piperazin-1-yl)-methanone (S0013439)

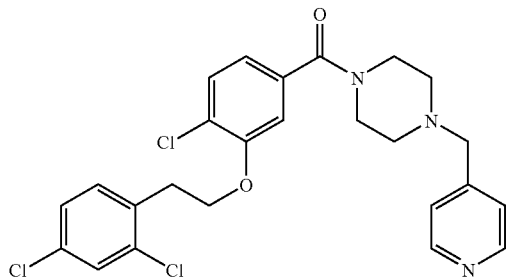

0.050 g (0.15 mmol) of 4-Chloro-3-[2-(2,4-dichloro-phenyl)-ethoxy]-benzoic acid was dissolved in 3 ml of DMF and treated with 0.067 g (0.58 mmol) of NEM and 0.048 g (0.15 mmol) of TOTU and 0.026 g (0.15 mmol) of 1-Pyridin-4-ylmethyl-piperazine. The solution was stirred for 16 h at RT. The solvent was removed under reduced pressure. The residue was purified by preparative RP-HPLC eluting with a gradient of 0 to 100% acetonitrile in water (+0.01% trifluoroacetic acid). After lyophilization the product was obtained as its trifluoroacetate salt.

| Yield 62.6 mg. | MS (ES+): m/e = 504 (M+). |

Example 183

3-[2-(2,4-Dichloro-phenyl)-ethoxy]-4-isopropoxy-N-(3,4,5,6-tetrahydro-2H-[1,4']bipyridinyl-4-ylmethyl)-benzamide (S0013552)

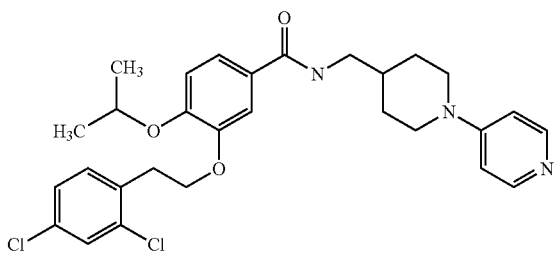

3-Hydroxy-4-isopropoxy-benzoic acid ethyl ester 5 g (27.5 mmol) of 3,4-Dihydroxy-benzoic acid ethyl ester was dissolved in 110 ml of DMF and treated at 0° C.

with 3.8 g (27.5 mmol) of potassium carbonate and 3.38 g (27.5 mmol) of isopropyl bromide. The solution was stirred for 16 h at RT, then a further 1.014 g (8.3 mmol) of isopropyl bromide was added. The reaction solution was heated at 50° C. for 3 h. The solvent was removed under reduced pressure, the residue was taken-up in ethyl acetate and the solution was washed three times with water and twice with saturated aqueous sodium chloride. The organic phase was dried with magnesium sulphate, filtered and the solvent was removed under reduced pressure. The residue was chromatographed on silica gel eluting with n-heptane/ethyl acetate (5/1).

Yield 2.45 g. MS (ES+): m/e=225 (M+H+).

(ii) 3-[2-(2,4-Dichloro-phenyl)-ethoxy]-4-isopropoxy-benzoic acid ethyl ester 1.5 g (6.69 mmol) of 3-Hydroxy-4-isopropoxy-benzoic acid ethyl ester was dissolved in 20 ml of anhydrous tetrahydrofuran. To this solution was added 1.4 g (7.36 mmol) of 2-(2,4-Dichlorophenyl)-ethanol, 6.7 g (equivalent to 20 mmol PPh$_3$) of triphenylphosphine derivatized polystyrene and 3.5 g (20 mmol) of DEAD. The solution was shaken for 16 h at RT. The polymer was filtered off and washed with ethyl acetate. The solvent was removed under reduced pressure. The residue was taken-up in ethyl acetate and the solution was washed three times with water and twice with saturated aqueous sodium chloride. The organic phase was dried with magnesium sulphate, filtered and the solvent was removed under reduced pressure. The residue was chromatographed on silica gel eluting with ethyl acetate/n-heptane (1/6).

| Yield 0.77 g. | LC-MS (ES+): m/e = 397 (M)+ |
|---|---|

(iii) 3-[2-(2,4-Dichloro-phenyl)-ethoxy]-4-isopropoxy-benzoic acid 0.75 g (1.89 mmol) of 3-[2-(2,4-Dichloro-phenyl)-ethoxy]-4-isopropoxy-benzoic acid ethyl ester was dissolved in 15 ml of dioxan. 5 ml of water and 2N aqueous NaOH was added to the solution to give a pH of 13. The reaction solution was heated at 60° C. for 4 h and stirred at room temperature for 16 h. The reaction solution was cooled to 0° C. and concentrated hydrochloric acid was added to give a pH of 1–2, whereupon the product precipitated from solution. The suspension was stirred for 30 min, then the product was filtered off and dried under reduced pressure.

| Yield 0.630 g. | MS (ES+): m/e = 369 (M+). |
|---|---|

(iv) 3-[2-(2,4-Dichloro-phenyl)-ethoxy]-4-isopropoxy-N-(3,4,5,6-tetrahydro-2H-[1,4']bipyridinyl-4-ylmethyl)-benzamide 0.050 g (0.14 mmol) of 3-[2-(2,4-Dichloro-phenyl)-ethoxy]-4-isopropoxy-benzoic acid was dissolved in 3 ml of DMF and treated with 0.062 g (0.54 mmol) of NEM and 0.044 g (0.14 mmol) of TOTU and 0.072 g (0.14 mmol) of C-(3,4,5,6-Tetrahydro-2H-[1,4']bipyridinyl-4-yl)-methylamine tris-trifluoroacetate salt. The solution was stirred for 16 h at RT. The solvent was removed under reduced pressure. The residue was purified by preparative RP-HPLC eluting with a gradient of 0 to 100% acetonitrile in water (+0.01% trifluoroacetic acid). After lyophilization the product was obtained as its trifluoroacetate salt.

| Yield 27.9 mg. | MS (ES+): m/e = 542 (M+). |
|---|---|

Example 184

{3-[2-(2,4-Dichloro-phenyl)-ethoxy]-4-isopropoxy-phenyl}-(4-pyridin-4-ylmethyl-piperazin-1-yl)-methanone

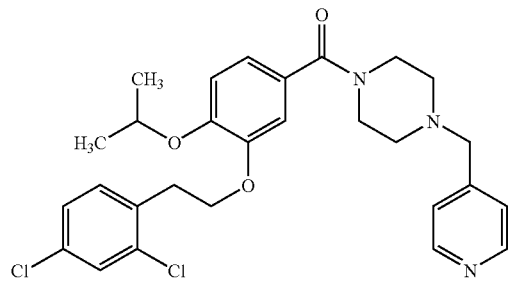

0.050 g (0.14 mmol) of 3-[2-(2,4-Dichloro-phenyl)-ethoxy]-4-isopropoxy-benzoic acid was dissolved in 3 ml of DMF and treated with 0.062 g (0.54 mmol) of NEM and 0.044 g (0.14 mmol) of TOTU and 0.024 g (0.14 mmol) of 1-Pyridin-4-ylmethyl-piperazine. The solution was stirred for 16 h at RT. The solvent was removed under reduced pressure. The residue was purified by preparative RP-HPLC eluting with a gradient of 0 to 100% acetonitrile in water (+0.01% trifluoroacetic acid). After lyophilization the product was obtained as its trifluoroacetate salt.

| Yield 44.3 mg. | MS (ES+): m/e = 528 (M+). |
|---|---|

Example 185

7-[2-(2,4-Dichloro-phenyl)-ethoxy]-benzo[1,3]dioxole-5-carboxylic acid (3,4,5,6-tetrahydro-2H-[1,4']bipyridinyl-4-ylmethyl)-amide

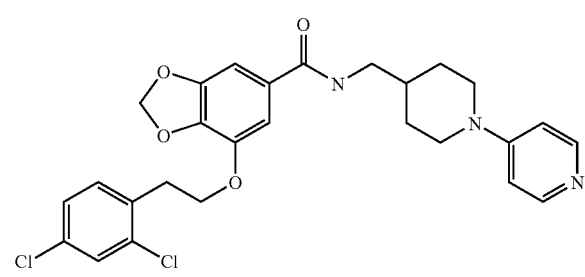

7-Hydroxy-benzo[1,3]dioxole-5-carboxylic acid ethyl ester 5 g (25.2 mmol) of 3,4,5-Trihydroxy-benzoic acid ethyl ester was dissolved in 50 ml of DMF and treated at 0° C. with 13.95 g (101 mmol) of potassium carbonate and 4.39 g (25.2 mmol) of dibromomethane. The reaction solution was heated at 60° C. for 3 h. The solvent was removed under reduced pressure, the residue was taken-up in ethyl acetate and the solution was washed three times with water and twice with saturated aqueous sodium chloride. The organic phase was dried with magnesium sulphate, filtered and the solvent was removed under reduced pressure. The residue was chromatographed on silica gel eluting with n-heptane/ethyl acetate (3/1).

| Yield 0.45 g. | MS (ES$^+$): m/e = 211 (M + H$^+$). |
|---|---|

(ii) 7-[2-(2,4-Dichloro-phenyl)-ethoxy]-benzo[1,3]dioxole-5-carboxylic acid ethyl ester.

410 mg (1.95 mmol) of 7-Hydroxy-benzo[1,3]dioxole-5-carboxylic acid ethyl ester was dissolved in 20 ml of anhydrous tetrahydrofuran. To this solution was added 410 mg (2.15 mmol) of 2-(2,4-Dichlorophenyl)-ethanol, 1.9 g (equivalent to 5.85 mmol PPh$_3$) of triphenylphosphine derivatized polystyrene and 1.0 g (5.85 mmol) of DEAD. The solution was shaken for 16 h at RT. The polymer was filtered off and washed with ethyl acetate. The solvent was removed under reduced pressure. The residue was taken-up in ethyl acetate and the solution was washed three times with water and twice with saturated aqueous sodium chloride. The organic phase was dried with magnesium sulphate, filtered and the solvent was removed under reduced pressure. The residue was chromatographed on silica gel eluting with ethyl acetate/n-heptane (1/5).

| Yield 0.41 g. | LC-MS (ES$^+$): m/e = 383 (M)$^+$ |
|---|---|

(iii) 7-[2-(2,4-Dichloro-phenyl)-ethoxy]-benzo[1,3]dioxole-5-carboxylic acid 0.41 g (1.07 mmol) of 7-[2-(2,4-Dichloro-phenyl)-ethoxy]-benzo[1,3]dioxole-5-carboxylic acid ethyl ester was dissolved in 15 ml of dioxan. 5 ml of water and 2N aqueous NaOH was added to the solution to give a pH of 13. The reaction solution was heated at 60° C. for 4 h and stirred at room temperature for 16 h. The reaction solution was cooled to 0° C. and concentrated hydrochloric acid was added to give a pH of 1–2, whereupon the product precipitated from solution. The suspension was stirred for 30 min, then the product was filtered off and dried under reduced pressure.

| Yield 0.35 g. | MS (ES$^+$): m/e = 355 (M$^+$). |
|---|---|

(iv) 7-[2-(2,4-Dichloro-phenyl)-ethoxy]-benzo[1,3]dioxole-5-carboxylic acid (3,4,5,6-tetrahydro-2H-[1,4']bipyridinyl-4-ylmethyl)-amide 0.050 g (0.14 mmol) of 7-[2-(2,4-Dichloro-phenyl)-ethoxy]-benzo[1,3]dioxole-5-carboxylic acid was dissolved in 3 ml of DMF and treated with 0.065 g (0.56 mmol) of NEM and 0.046 g (0.14 mmol) of TOTU and 0.075 g (0.14 mmol) of C-(3,4,5,6-Tetrahydro-2H-[1,4']bipyridinyl-4-yl)-methylamine tris-trifluoroacetate salt. The solution was stirred for 16 h at RT. The solvent was removed under reduced pressure. The residue was purified by preparative RP-HPLC eluting with a gradient of 0 to 100% acetonitrile in water (+0.01% trifluoroacetic acid). After lyophilization the product was obtained as its trifluoroacetate salt.

| Yield 47.4 mg. | MS (ES$^+$): m/e = 528 (M$^+$). |
|---|---|

Example 186

{7-[2-(2,4-Dichloro-phenyl)-ethoxy]-benzo[1,3]dioxol-5-yl}-(4-pyridin-4-ylmethyl-piperazin-1-yl)-methanone

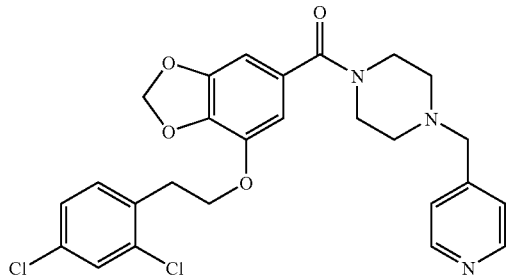

0.050 g (0.14 mmol) of 7-[2-(2,4-Dichloro-phenyl)-ethoxy]-benzo[1,3]dioxole-5-carboxylic acid was dissolved in 3 ml of DMF and treated with 0.065 g (0.56 mmol) of NEM and 0.046 g (0.14 mmol) of TOTU and 0.025 g (0.14 mmol) of 1-Pyridin-4-ylmethyl-piperazine. The solution was stirred for 16 h at RT. The solvent was removed under reduced pressure. The residue was purified by preparative RP-HPLC eluting with a gradient of 0 to 100% acetonitrile in water (+0.01% trifluoroacetic acid). After lyophilization the product was obtained as its trifluoroacetate salt. Yield 74.9 mg. MS (ES$^+$): m/e=514 (M$^+$).

Example 187

{4-Chloro-3-[2-(2,4-dichloro-phenyl)-ethoxy]-phenyl}-[4-(1-oxy-pyridin-4-ylmethyl)-piperazin-1-yl]-methanone

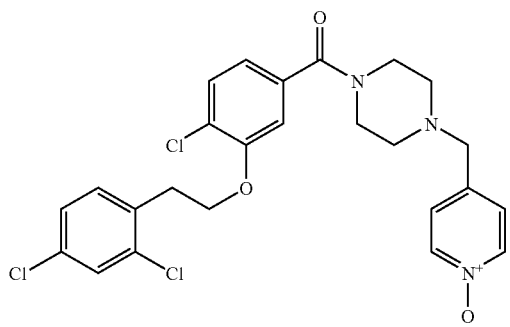

10 mg (0.01 mmol) of {4-Chloro-3-[2-(2,4-dichloro-phenyl)-ethoxy]-phenyl}-(4-pyridin-4-ylmethyl-piperazin-1-yl)-methanone was dissolved in 0.5 ml of dichloromethane and 3.5 mg (0.01 mmol) of 3-chloroperbenzoic acid was added. The solution was allowed to stand for 1 h at RT. The solvent was removed under reduced pressure. The residue was purified by preparative RP-HPLC eluting with a gradient of 0 to 100% acetonitrile in water (+0.01% trifluoroacetic acid). After lyophilization the product was obtained as its trifluoroacetate salt.

| Yield 5.2 mg. | MS (ES$^+$): m/e = 520 (M$^+$). |
|---|---|

Example 188

(4-Cyclohexylmethyl-piperazin-1-yl)-{3-[2-(2,4-dichloro-phenyl)-ethoxy]-4-methoxy-phenyl}-methanone

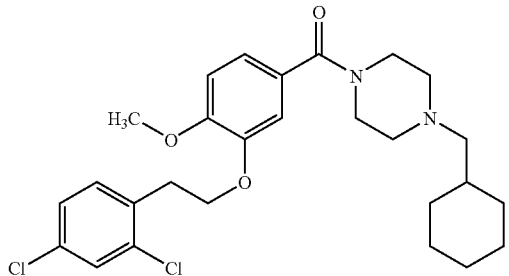

3-[2-(2,4-Dichloro-phenyl)-ethoxy]-4-methoxy-benzoic acid 0.050 g (0.15 mmol) of 3-[2-(2,4-Dichloro-phenyl)-ethoxy]-4-methoxy-benzoic acid was dissolved in 3 ml of DMF and treated with 0.067 g (0.59 mmol) of NEM and 0.048 g (0.15 mmol) of TOTU and 0.027 g (0.15 mmol) of 1-cyclohexylmethyl-piperazine. The solution was stirred for 16 h at RT. The solvent was removed under reduced pressure. The residue was purified by preparative RP-HPLC eluting with a gradient of 0 to 100% acetonitrile in water (+0.01% trifluoroacetic acid). After lyophilization the product was obtained as its trifluoroacetate salt. Yield 66.7 mg. MS (ES$^+$): m/e=505 (M$^+$).

The following examples were prepared analogously to example 188:

| Example | Structure | MS (ES+) |
|---|---|---|
| 189 | 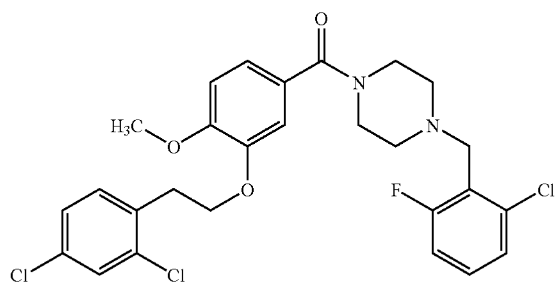 | 551 |
| 190 | 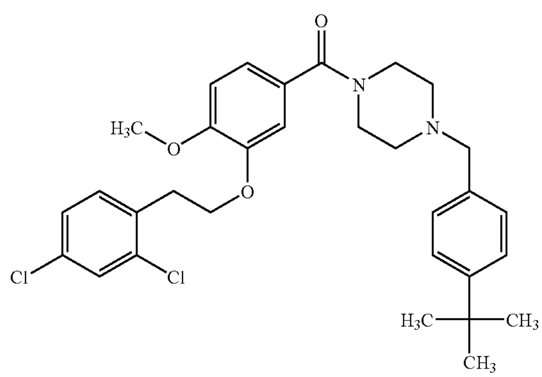 | 555 |
| 191 | 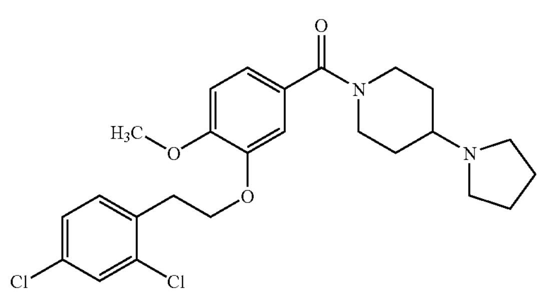 | 477 |

-continued
| Example | Structure | MS (ES+) |
|---|---|---|
| 192 | 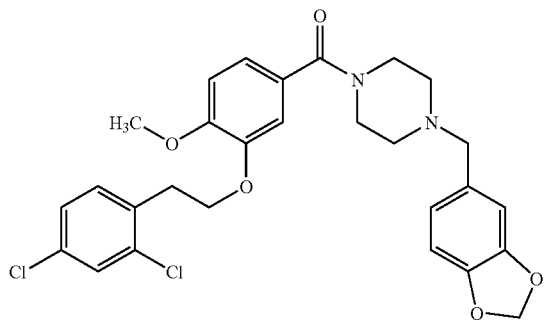 | 543 |
| 193 | 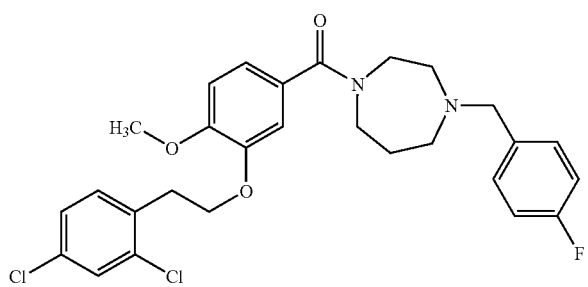 | 531 |
| 194 | 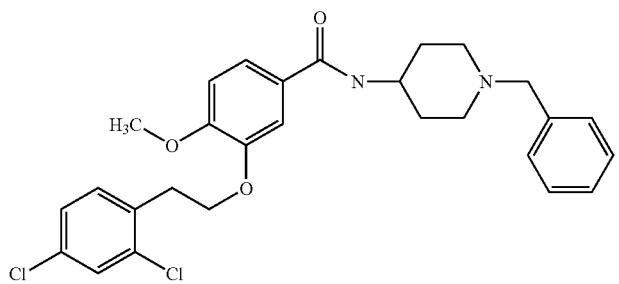 | 513 |
| 195 | 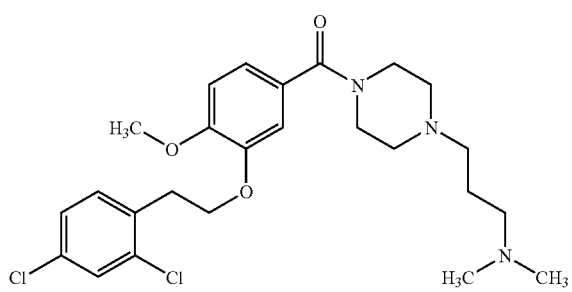 | 494 |
| 196 | 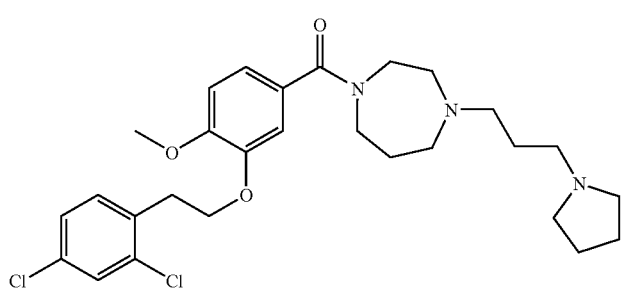 | 534 |

| Example | Structure | MS (ES+) |
|---|---|---|
| 197 | 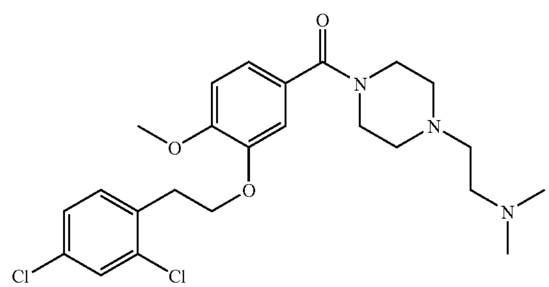 | 480 |
| 198 | 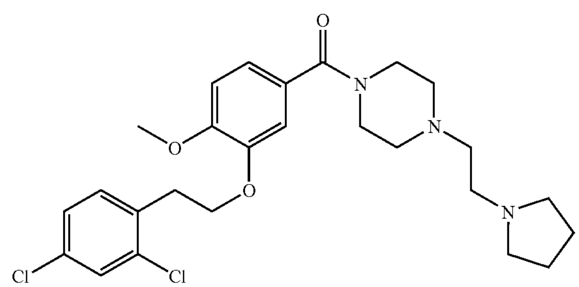 | 506 |

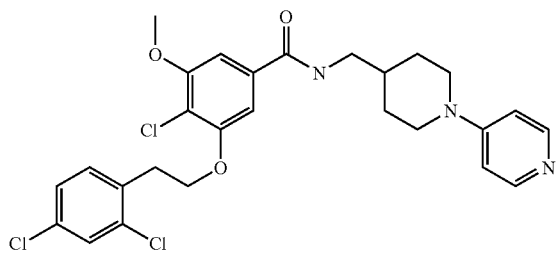

Example 199

4-Chloro-3-[2-(2,4-dichloro-phenyl)-ethoxy]-5-methoxy-N-(3,4,5,6-hydro-2H-[1,4']bipyridinyl-4-ylmethyl)-benzamide

4-Chloro-3,5-dihydroxy-benzoic acid methyl ester 10 g (42.9 mmol) of 4-Bromo-3,5-dihydroxy-benzoic acid was suspended in 40 ml of NMP and treated with 6.37 g (64.3 mmol) of CuCl. The reaction was heated at 205° C. for 2 h. The solution was poured into 1 L of water. The resulting precipitate was filtered off. The product was extracted from the resulting solution with ethyl acetate. The organic phase was washed twice with saturated aqueous sodium chloride. The organic phase was dried with sodium sulphate, filtered and the solvent was removed under reduced pressure. The residue was dissolve in saturated methanolic HCl and stirred at RT for 16 h. The solvent was removed under reduced pressure. The residue was chromatographed on silica gel eluting with dichloromethane/methanol (10/1).

| Yield 3.9 g. | MS (ES+): m/e = 203 (M + H+). |
|---|---|

(ii) 4-Chloro-3-hydroxy-5-methoxy-benzoic acid methyl ester 3.9 g (19.3 mmol) of 4-Chloro-3,5-dihydroxy-benzoic acid methyl ester was dissolved in 250 ml of DMF and treated at 0° C. with 8.6 g (62 mmol) of potassium carbonate and 2.72 g (19.2 mmol) of iodomethane. The reaction solution was stirred at RT for 16 h. The solvent was removed under reduced pressure, the residue was taken-up in ethyl acetate and this solution was washed three times with water and twice with saturated aqueous sodium chloride. The organic phase was dried with sodium sulphate, filtered and the solvent was removed under reduced pressure. The residue was chromatographed on silica gel eluting with n-heptane/ethyl acetate (5/1).

| Yield 1.2 g. | MS (ES+): m/e = 217 (M + H+). |
|---|---|

(iii) 4-Chloro-3-[2-(2,4-dichloro-phenyl)-ethoxy]-5-methoxy-benzoic acid methyl ester 500 mg (2.31 mmol) of 4-Chloro-3-hydroxy-5-methoxy-benzoic acid methyl ester was dissolved in 15 ml of anhydrous tetrahydrofuran. To this solution was added 485 mg (2.54 mmol) of 2-(2,4-Dichlorophenyl)-ethanol, 2.3 g (equivalent to 6.92 mmol PPh₃) of triphenylphosphine derivatized polystyrene and 1.2 g (6.92 mmol) of DEAD. The solution was shaken for 16 h at RT. The polymer was filtered off and washed with ethyl acetate. The solvent was removed under reduced pressure. The residue was chromatographed on silica gel eluting with ethyl acetate/n-heptane (1/5).

| Yield 0.66 g. | LC-MS (ES⁺): m/e = 389 (M)⁺ |

(iii) 4-Chloro-3-[2-(2,4-dichloro-phenyl)-ethoxy]-5-methoxy-benzoic acid 0.51 g (1.31 mmol) of 4-Chloro-3-[2-(2,4-dichloro-phenyl)-ethoxy]-5-methoxy-benzoic acid methyl ester was dissolved in 15 ml of dioxan. 5 ml of water and 2N aqueous NaOH was added to the solution to give a pH of 13. The reaction solution was heated at 60° C. for 4 h and stirred at room temperature for 16 h. The reaction solution was cooled to 0° C. and concentrated hydrochloric acid was added to give a pH of 1–2, whereupon the product precipitated from solution. The suspension was stirred for 30 min, then the product was filtered off and dried under reduced pressure.

| Yield 0.46 g. | MS (ES⁺): m/e = 375 (M⁺). |

(iv) 4-Chloro-3-[2-(2,4-dichloro-phenyl)-ethoxy]-5-methoxy-N-(3,4,5,6-tetrahydro-2H-[1,4']bipyridinyl-4-ylmethyl)-benzamide 0.050 g (0.13 mmol) of 4-Chloro-3-[2-(2,4-dichloro-phenyl)-ethoxy]-5-methoxy-benzoic acid was dissolved in 3 ml of DMF and treated with 0.061 g (0.53 mmol) of NEM and 0.043 g (0.13 mmol) of TOTU and 0.071 g (0.13 mmol) of C-(3,4,5,6-Tetrahydro-2H-[1,4']bipyridinyl-4-yl)-methylamine tris-trifluoroacetate salt. The solution was stirred for 16 h at RT. The solvent was removed under reduced pressure. The residue was purified by preparative RP-HPLC eluting with a gradient of 0 to 100% acetonitrile in water (+0.01% trifluoroacetic acid). After lyophilization the product was obtained as its trifluoroacetate salt.

| Yield 24.8 mg. | MS (ES⁺): m/e = 550 (M + H⁺). |

Example 200

{4-Chloro-3-[2-(2,4-dichloro-phenyl)-ethoxy]-5-methoxy-phenyl}-(4-pyridin-4-ylmethyl-piperazin-1-yl)-methanone

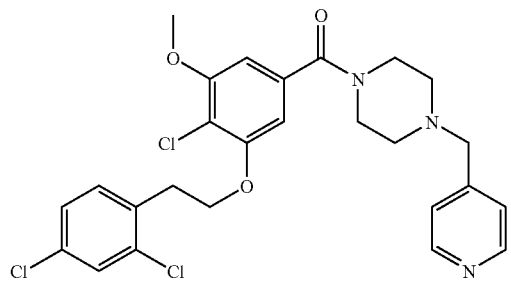

0.050 g (0.13 mmol) of 4-Chloro-3-[2-(2,4-dichloro-phenyl)-ethoxy]-5-methoxy-benzoic acid was dissolved in 3 ml of DMF and treated with 0.061 g (0.53 mmol) of NEM and 0.043 g (0.13 mmol) of TOTU and 0.024 g (0.13 mmol) of 1-Pyridin-4-ylmethyl-piperazine. The solution was stirred for 16 h at RT. The solvent was removed under reduced pressure. The residue was purified by preparative RP-HPLC eluting with a gradient of 0 to 100% acetonitrile in water (+0.01% trifluoroacetic acid). After lyophilization the product was obtained as its trifluoroacetate salt.

| Yield 56.8 mg. | MS (ES⁺): m/e = 536 (M + H⁺). |

Example 201

4-Chloro-3-[2-(4-methoxy-phenyl)-ethoxy]-N-(3,4,5,6-tetrahydro-2H-[1,4']bipyridinyl-4-ylmethyl)-benzamide (S0100717)

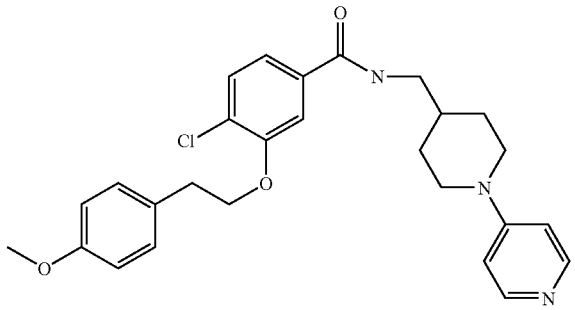

4-Chloro-3-[2-(4-methoxy-phenyl)-ethoxy]-benzoic acid methyl ester g (5.36 mmol) of 4-Chloro-3-hydroxy-benzoic acid methyl ester was dissolved in 40 ml of anhydrous tetrahydrofuran. To this solution was added 0.897 g (5.9 mmol) of 2-(4-Methoxy-phenyl)-ethanol, 5.35 g (equivalent to 16.1 mmol PPh₃) of triphenylphosphine derivatized polystyrene and 2.80 g (16.1 mmol) of DEAD. The solution was shaken for 16 h at RT. The polymer was filtered off and washed with ethyl acetate. The solvent was removed under reduced pressure. The residue was taken-up in ethyl acetate and the solution was washed three times with water and twice with saturated aqueous sodium chloride. The organic phase was dried with magnesium sulphate, filtered and the solvent was removed under reduced pressure. The residue was chromatographed on silica gel eluting with ethyl acetate/n-heptane (1/5).

| Yield 1.27 g. | LC-MS (ES⁺): m/e = 321 (M)⁺ |

(ii) 4-Chloro-3-[2-(4-methoxy-phenyl)-ethoxy]-benzoic acid 1.27 g (3.96 mmol) of 4-Chloro-3-[2-(4-methoxy-phenyl)-ethoxy]-benzoic acid methyl ester was dissolved in 15 ml of dioxan. 5 ml of water and 2N aqueous NaOH was added to the solution to give a pH of 13. The reaction solution was heated at 60° C. for 2 h and stirred at room temperature for 16 h. The reaction solution was cooled to 0° C. and concentrated hydrochloric acid was added to give a pH of 1–2, whereupon the product precipitated from solution. The suspension was stirred for 30 min, then the product was filtered off and dried under reduced pressure.

| Yield 1.10 g. | MS (ES⁺): m/e = 307 (M + H⁺). |

(iii) 4-Chloro-3-[2-(4-methoxy-phenyl)-ethoxy]-N-(3,4,5,6-tetrahydro-2H-[1,4']bipyridinyl-4-ylmethyl)-benzamide 0.050 g (0.16 mmol) of 4-Chloro-3-[2-(4-methoxy-phenyl)-ethoxy]-benzoic acid was dissolved in 3 ml of DMF and treated with 0.188 g (1.63 mmol) of NEM and 0.054 g (0.16 mmol) of TOTU and 0.087 g (0.16 mmol) of C-(3,4,5,6-Tetrahydro-2H-[1,4']bipyridinyl-4-yl)-methylamine tris-trifluoroacetate salt. The solution was stirred for 16 h at RT. The solvent was removed under reduced pressure. The residue was purified by preparative RP-HPLC eluting with a gradient of 0 to 100% acetonitrile in water (+0.01% trifluoroacetic acid). After lyophilization the product was obtained as its trifluoroacetate salt. Yield 40.1 mg.

MS (ES$^+$): m/e=480 (M$^+$).

Example 202

4-Chloro-3-[2-(4-chloro-phenyl)-ethoxy]-5-methoxy-N-(3,4,5,6-tetrahydro-2H-[1,4']bipyridinyl-4-ylmethyl)-benzamide

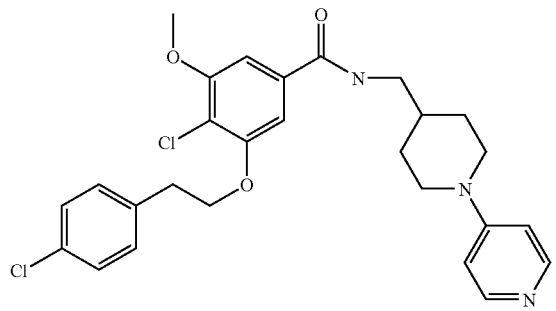

This compound was prepared analogously to Example 199.

| Yield 44.4 mg. | MS (ES$^+$): m/e = 514 (M$^+$). |

Example 203

4-Chloro-3-[2-(4-chloro-phenyl)-ethoxy]-N-(3,4,5,6-tetrahydro-2H-[1,4']bipyridinyl-4-ylmethyl)-benzamide

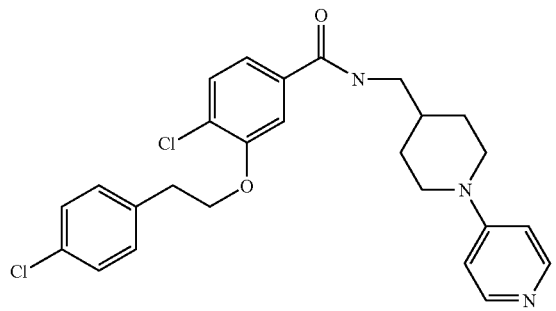

4-Chloro-3-[2-(4-chloro-phenyl)-ethoxy]-benzoic acid methyl ester g (5.36 mmol) of 4-Chloro-3-hydroxy-benzoic acid methyl ester was dissolved in 40 ml of anhydrous tetrahydrofuran. To this solution was added 0.923 g (5.9 mmol) of 2-(4-chloro-phenyl)-ethanol, 5.35 g (equivalent to 16.1 mmol PPh$_3$) of triphenylphosphine derivatized polystyrene and 2.80 g (16.1 mmol) of DEAD. The solution was shaken for 16 h at RT. The polymer was filtered off and washed with ethyl acetate. The solvent was removed under reduced pressure. The residue was taken-up in ethyl acetate and the solution was washed three times with water and twice with saturated aqueous sodium chloride. The organic phase was dried with magnesium sulphate, filtered and the solvent was removed under reduced pressure. The residue was chromatographed on silica gel eluting with ethyl acetate/n-heptane (1/5). Yield 1.6 g. LC-MS (ES$^+$): m/e=325 (M)$^+$ 4-Chloro-3-[2-(4-chloro-phenyl)-ethoxy]-benzoic acid 1.6 g (4.94 mmol) of 4-Chloro-3-[2-(4-chloro-phenyl)-ethoxy]-benzoic acid methyl ester was dissolved in 15 ml of dioxan. 5 ml of water and 2N aqueous NaOH was added to the solution to give a pH of 13. The reaction solution was heated at 60° C. for 2 h. The reaction solution was cooled to 0° C. and concentrated hydrochloric acid was added to give a pH of 1–2, whereupon the product precipitated from solution. The suspension was stirred for 30 min, then the product was filtered off and dried under reduced pressure.

| Yield 1.21 g. | MS (ES$^+$): m/e = 311 (M$^+$). |

(iii) 4-Chloro-3-[2-(4-chloro-phenyl)-ethoxy]-N-(3,4,5,6-tetrahydro-2H-[1,4']bipyridinyl-4-ylmethyl)-benzamide 0.050 g (0.16 mmol) of 4-Chloro-3-[2-(4-chloro-phenyl)-ethoxy]-benzoic acid was dissolved in 3 ml of DMF and treated with 0.185 g (1.61 mmol) of NEM and 0.054 g (0.16 mmol) of TOTU and 0.087 g (0.16 mmol) of C-(3,4,5,6-Tetrahydro-2H-[1,4']bipyridinyl-4-yl)-methylamine tris-trifluoroacetate salt. The solution was stirred for 16 h at RT. The solvent was removed under reduced pressure. The residue was purified by preparative RP-HPLC eluting with a gradient of 0 to 100% acetonitrile in water (+0.01% trifluoroacetic acid). After lyophilization the product was obtained as its trifluoroacetate salt.

| Yield 44 mg. | MS (ES$^+$): m/e = 484 (M$^+$). |

The following examples were prepared analogously to example 203:

| Example | Structure | MS (ES+) |
|---|---|---|
| 204 | 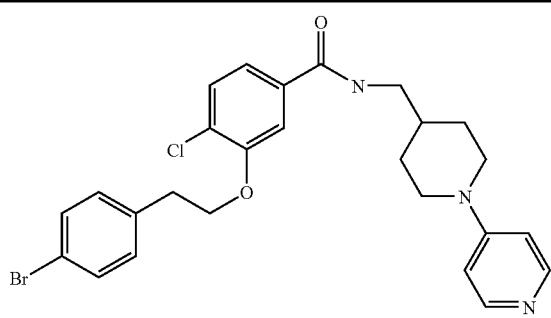 | 528 |

| Example | Structure | MS (ES+) |
|---|---|---|
| 205 | 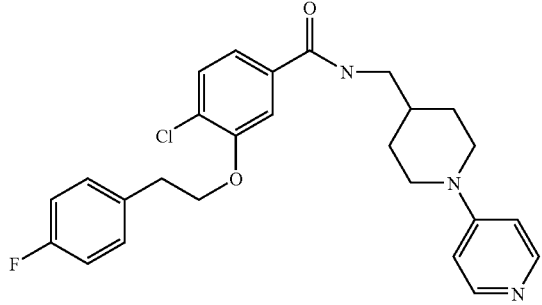 | 468 |
| 206 | 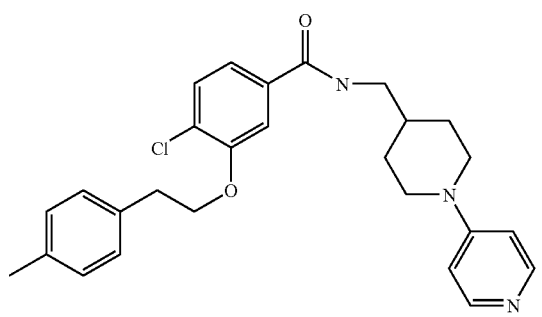 | 464 |
| 207 | 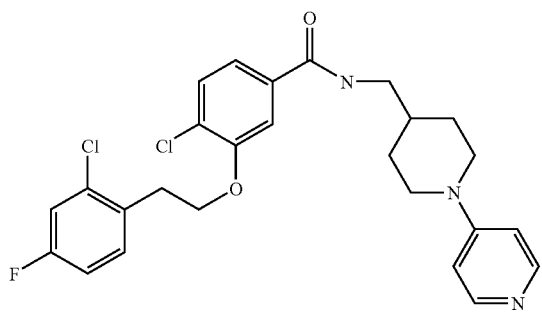 | 502 |
| 208 | 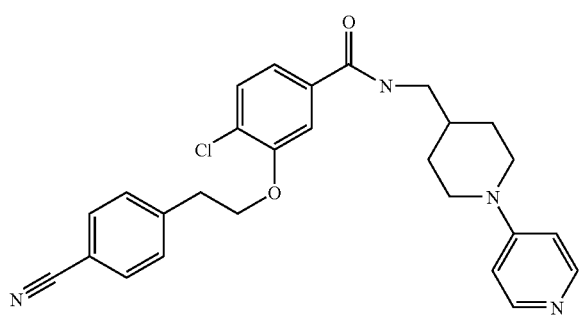 | 475 |
| 209 | 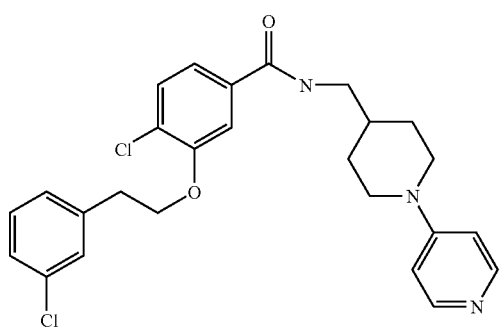 | 484 |

-continued

| Example | Structure | MS (ES+) |
|---|---|---|
| 210 | 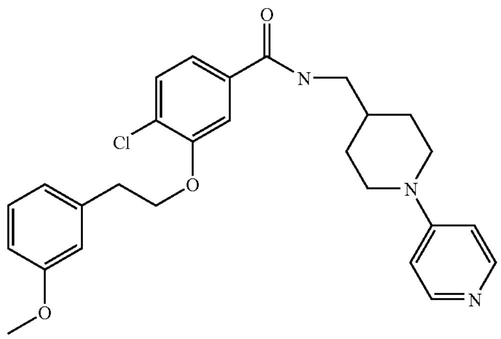 | 480 |
| 211 | 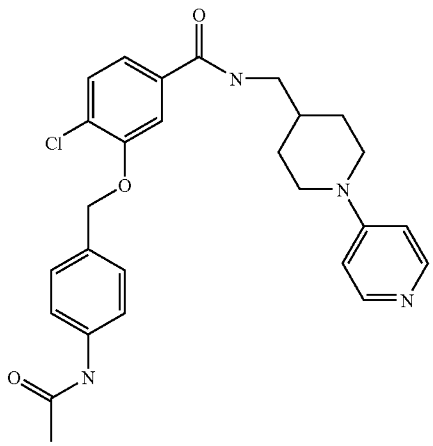 | 493 |

Example 212

3-[2-(4-Chloro-phenyl)-ethoxy]-4-fluoro-N-(3,4,5,6-tetrahydro-2H-[1,4']bipyridinyl-4-ylmethyl)-benzamide

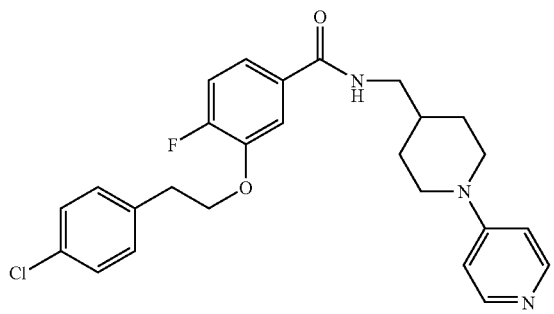

4-Fluoro-3-hydroxy-benzoic acid methyl ester 5.16 g (33 mmol) of 4-Fluoro-3-hydroxy-benzoic acid was suspended in 150 ml of saturated methanolic HCl and stirred at room temperature for 16 h. The solvent was removed under reduced pressure, and the residue was dried under reduced pressure.

Yield 5.5 g. MS (ES+): m/e = 171 (M + H)+.

(ii) 3-[2-(4-Chloro-phenyl)-ethoxy]-4-fluoro-benzoic acid methyl ester 0.5 g (2.94 mmol) of 4-Fluoro-3-hydroxy-benzoic acid methyl ester was dissolved in 30 ml of anhydrous tetrahydrofuran. To this solution was added 0.506 g (3.23 mmol) of 2-(4-chloro-phenyl)-ethanol, 2.93 g (equivalent to 8.8 mmol PPh₃) of triphenylphosphine derivatized polystyrene and 1.53 g (8.8 mmol) of DEAD. The solution was shaken for 16 h at RT. The polymer was filtered off and washed with tetrahydrofuran. The solvent was removed under reduced pressure. The residue was taken-up in ethyl acetate/n-heptane (1/5) and the insoluble residue was removed by filtration. The solvent was removed under reduced pressure. The residue was chromatographed on silica gel eluting with ethyl acetate/n-heptane (1/5).

Yield 0.75 g. LC-MS (ES+): m/e=309 (M+H)+

(iii) 3-[2-(4-Chloro-phenyl)-ethoxy]-4-fluoro-benzoic acid 0.75 g (2.43 mmol) of 3-[2-(4-Chloro-phenyl)-ethoxy]-4-fluoro-benzoic acid methyl ester was dissolved in 25 ml of dioxan. 5 ml of water and 2N aqueous NaOH was added to the solution to give a pH of 13. The reaction solution was heated at 60° C. for 2 h. The reaction solution was cooled to 0° C. and concentrated hydrochloric acid was added to give a pH of 1–2, whereupon the product precipitated from solution. The suspension was stirred for 30 min, then the product was filtered off and dried under reduced pressure.

Yield 0.64 g. MS (ES+): m/e = 295 (M + H+).

(iv) 3-[2-(4-Chloro-phenyl)-ethoxy]-4-fluoro-N-(3,4,5,6-tetrahydro-2H-[1,4']bipyridinyl-4-ylmethyl)-benzamide 0.053 g (0.18 mmol) of 3-[2-(4-Chloro-phenyl)-ethoxy]-4-fluoro-benzoic acid was dissolved in 2 ml of DMF and treated with 0.206 g (1.8 mmol) of NEM and 0.059 g (0.18 mmol) of TOTU and 0.075 g (0.18 mmol) of C-(3,4,5,6-Tetrahydro-2H-[1,4']bipyridinyl-4-yl)-methylamine bis-trifluoroacetate salt. The solution was stirred for 16 h at RT. The solvent was removed under reduced pressure. The residue was purified by preparative RP-HPLC eluting with a gradient of 0 to 100% acetonitrile in water (+0.01% trifluoroacetic acid). After lyophilization the product was obtained as its trifluoroacetate salt. Yield 42 mg.

MS (ES+): m/e=468 (M+).

The following examples were prepared analogously to example 212:

| Example | Structure | MS (ES+) |
| --- | --- | --- |
| 213 | 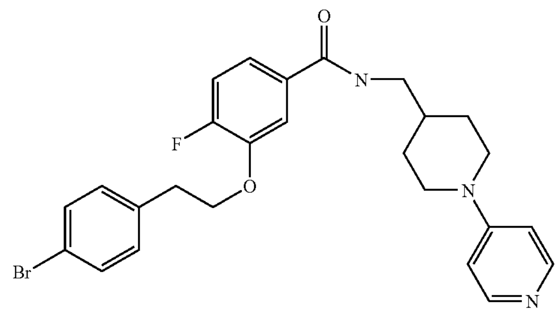 | 512 |
| 214 | 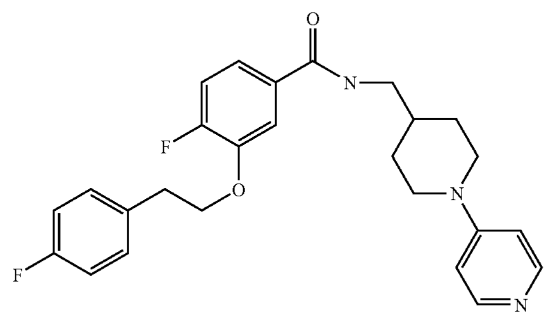 | 452 |
| 215 | 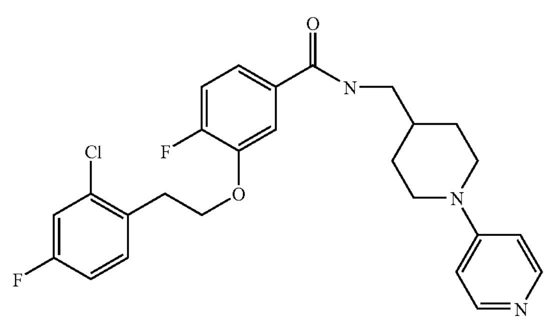 | 485 |
| 216 | 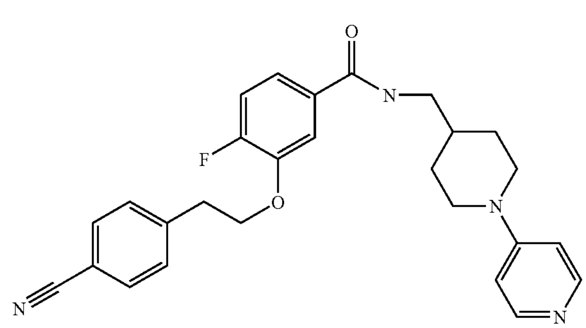 | 459 |

-continued
| Example | Structure | MS (ES+) |
|---|---|---|
| 217 | 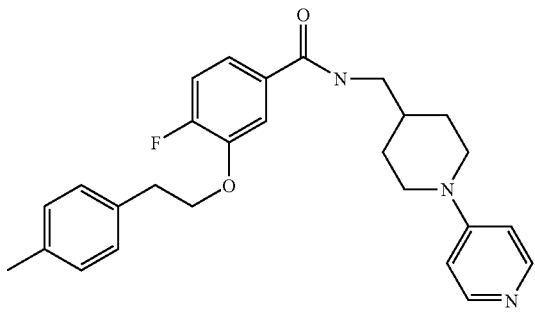 | 447 |
| 218 | 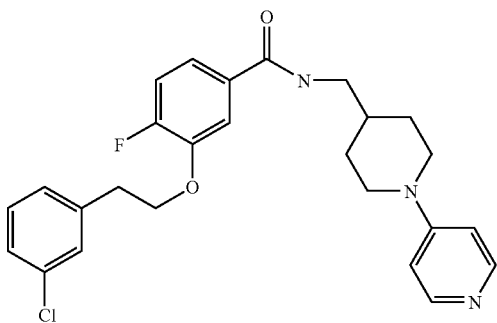 | 468 |
| 219 | 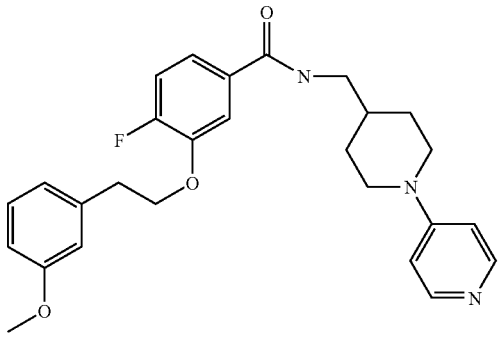 | 464 |
| 220 | 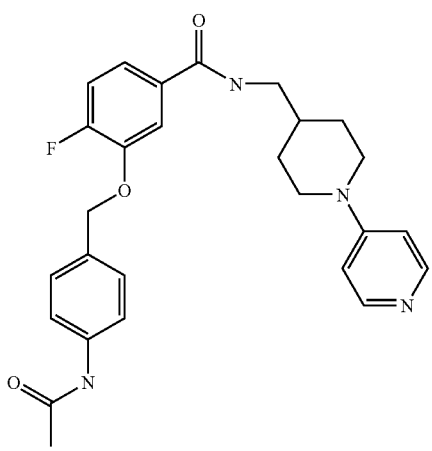 | 477 |

| Example | Structure | MS (ES+) |
|---|---|---|
| 221 | 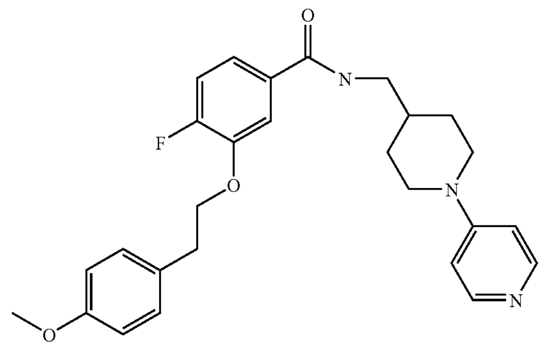 | 448 |

-continued

Example 222

4-Chloro-3-[2-(4-chloro-phenyl)-ethoxy]-5-methoxy-N-(2'-methyl-3,4,5,6-tetrahydro-2H-[1,4']bipyridinyl-4-ylmethyl)-benzamide This compound was prepared analogously to Example 202, using C-(2'-Methyl-3,4,5,6-tetrahydro-2H-[1,4']bipyridinyl-4-yl)-methylamine trifluoroacetate salt.

| Yield 62 mg. | MS (ES+): m/e = 528 (M+). |
|---|---|

Example 223

4-Chloro-3-[2-(4-chloro-phenyl)-ethoxy]-N-(2'-methyl-3,4,5,6-tetrahydro-2H-[1,4']bipyridinyl-4-ylmethyl)-benzamide This compound was prepared analogously to Example 203, using C-(2'-Methyl-3,4,5,6-tetrahydro-2H-[1,4']bipyridinyl-4-yl)-methylamine trifluoroacetate salt.

| Yield 106 mg. | MS (ES+): m/e = 498 (M+). |
|---|---|

Example 224

4-Bromo-3-[2-(4-chloro-phenyl)-ethoxy]-5-methoxy-N-(3,4,5,6-tetrahydro-2H-[1,4']bipyridinyl-4-ylmethyl)-benzamide This compound was prepared analogously to Example 20.

| Yield 88 mg. | MS (ES+): m/e = 558 (M+). |
|---|---|

Example 225

4-Bromo-3-[2-(4-chloro-phenyl)-ethoxy]-5-methoxy-N-(2'-methyl-3,4,5,6-tetrahydro-2H-[1,4']bipyridinyl-4-ylmethyl)-benzamide

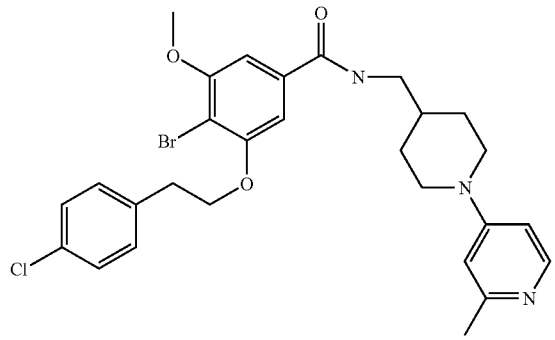

This compound was prepared analogously to Example 224, using C-(2'-Methyl-3,4,5,6-tetrahydro-2H-[1,4']bipyridinyl-4-yl)-methylamine trifluoroacetate salt.

| Yield 86 mg. | MS (ES⁺): m/e = 572 (M⁺). |
|---|---|

Example 226

5-[2-(2,4-Dichlorophenyl)-ethoxy]-N-(3,4,5,6-tetrahydro-2H-[1,4']bipyridinyl-4-ylmethyl)-isophthalamic acid

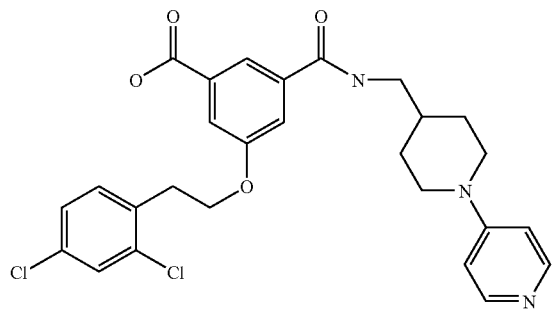

0.2 g (0.56 mmol) of 5-[2-(2,4-Dichlorophenyl)-ethoxy]-isophthalic acid was dissolved in 25 ml of DMF and treated with 0.649 g (5.63 mmol) of NEM and 0.277 g (0.84 mmol) of TOTU and 0.215 g (1.13 mmol) of C-(3,4,5,6-Tetrahydro-2H-[1,4']bipyridinyl-4-yl)-methylamine. The solution was stirred for 16 h at RT. The solvent was removed under reduced pressure. The residue was purified by preparative RP-HPLC eluting with a gradient of 0 to 100% acetonitrile in water (+0.01% trifluoroacetic acid). After lyophilization the product was obtained as its trifluoroacetate salt.

| Yield 65 mg. | MS (ES⁺): m/e = 528 (M⁺). |
|---|---|

Example 227

5-[2-(2,4-Dichloro-phenyl)-ethoxy]-N,N'-bis-(3,4,5,6-tetrahydro-2H-[1,4']bipyridinyl-4-ylmethyl)-isophthalamide

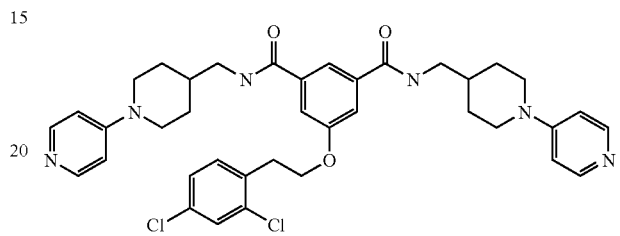

0.2 g (0.56 mmol) of 5-[2-(2,4-Dichlorophenyl)-ethoxy]-isophthalic acid was dissolved in 25 ml of DMF and treated with 0.649 g (5.63 mmol) of NEM and 0.277 g (0.84 mmol) of TOTU and 0.215 g (1.13 mmol) of C-(3,4,5,6-Tetrahydro-2H-[1,4']bipyridinyl-4-yl)-methylamine. The solution was stirred for 16 h at RT. The solvent was removed under reduced pressure. The residue was purified by preparative RP-HPLC eluting with a gradient of 0 to 100% acetonitrile in water (+0.01% trifluoroacetic acid). After lyophilization the product was obtained as its trifluoroacetate salt.

| Yield 4 mg. | MS (ES⁺): m/e = 701 (M⁺). |
|---|---|

Example 228

4-Chloro-3-[2-(2,4-dichloro-phenyl)-ethoxy]-5-methoxy-N-(1'-oxy-3,4,5,6-tetrahydro-2H-[1,4']bipyridinyl-4-ylmethyl)-benzamide

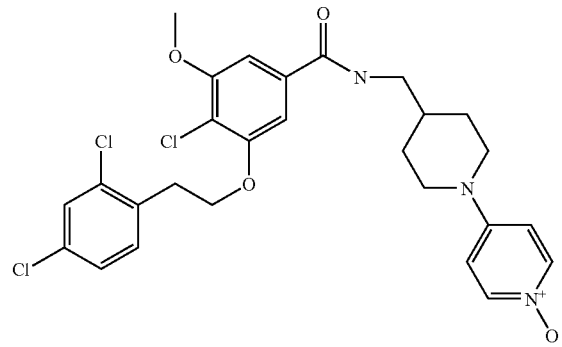

This compound was prepared analogously to Example 199, using C-(1'-Oxy-3,4,5,6-tetrahydro-2H-[1,4']bipyridinyl-4-yl)-methylamine trifluoroacetate salt.

| Yield 12 mg. | MS (ES+): m/e = 565 (M+). |
|---|---|

Example 229

4-Chloro-3-[2-(4-chloro-phenyl)-ethoxy]-5-methoxy-N-(1'-oxy-3,4,5,6-tetrahydro-2H-[1,4']bipyridinyl-4-ylmethyl)-benzamide

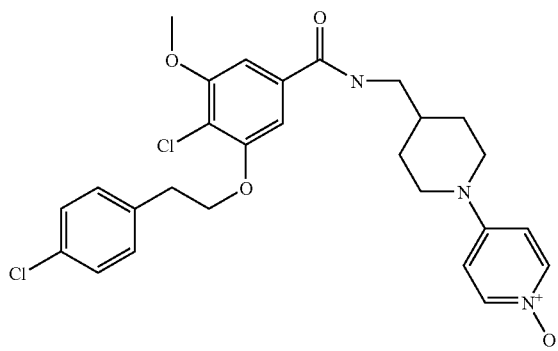

This compound was prepared analogously to Example 202, using C-(1'-Oxy-3,4,5,6-tetrahydro-2H-[1,4']bipyridinyl-4-yl)-methylamine trifluoroacetate salt.

| Yield 8.7 mg. | MS (ES+): m/e = 530 (M+). |
|---|---|

Example 230

4-Chloro-3-[2-(2,4-dichloro-phenyl)-ethoxy]-N-(1'-oxy-3,4,5,6-tetrahydro-2H-[1,4']bipyridinyl-4-ylmethyl)-benzamide

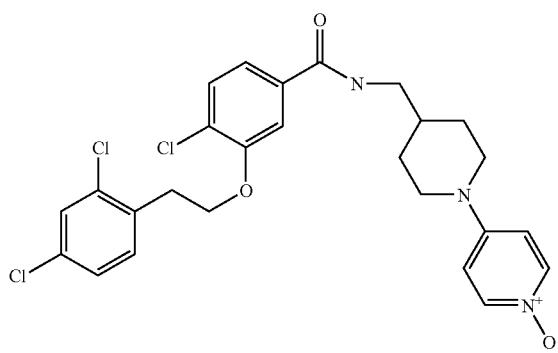

This compound was prepared analogously to Example 281, using C-(1'-Oxy-3,4,5,6-tetrahydro-2H-[1,4']bipyridinyl-4-yl)-methylamine trifluoroacetate salt.

| Yield 11 mg. | MS (ES+): m/e = 535 (M+). |
|---|---|

Example 231

4-Chloro-3-[2-(4-chloro-phenyl)-ethoxy]-N-(1'-oxy-3,4,5,6-tetrahydro-2H-[1,4']bipyridinyl-4-ylmethyl)-benzamide

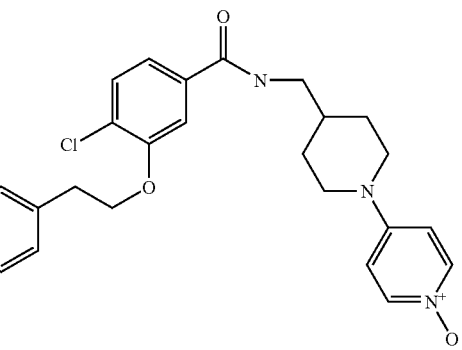

This compound was prepared analogously to Example 203, using C-(1'-Oxy-3,4,5,6-tetrahydro-2H-[1,4']bipyridinyl-4-yl)-methylamine trifluoroacetate salt.

| Yield 16 mg. | MS (ES+): m/e = 500 (M+). |
|---|---|

Example 232

5-[2-(2,4-Dichloro-phenyl)-ethoxy]-N,N-diethyl-N'-(3,4,5,6-tetrahydro-2H-[1,4']bipyridinyl-4-ylmethyl)-isophthalamide

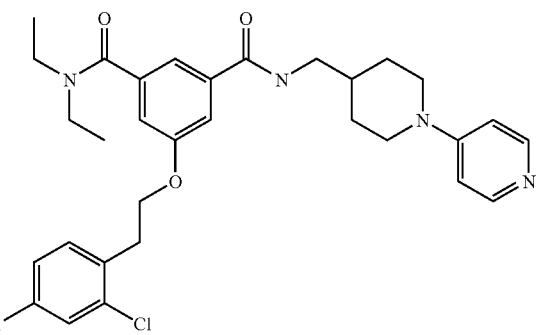

5-[2-(2,4-Dichloro-phenyl)-ethoxy]-N,N-diethyl-isophthalamic acid 0.5 g (1.41 mmol) of 5-[2-(2,4-Dichlorophenyl)-ethoxy]-isophthalic acid was dissolved in 5 ml of DMF and treated with 0.648 g (5.63 mmol) of NEM and 0.461 g (1.41 mmol) of TOTU and 0.103 g (1.41 mmol) of diethylamine. The solution was stirred for 16 h at RT. The compound was purified by preparative RP-HPLC eluting with a gradient of 0 to 100% acetonitrile in water (+0.01% trifluoroacetic acid). After lyophilization the product was obtained as its trifluoroacetate salt.

| Yield 163 mg. | MS (ES$^+$): m/e = 410 (M$^+$). |

(ii): 5-[2-(2,4-Dichloro-phenyl)-ethoxy]-N,N-diethyl-N'-(3,4,5,6-tetrahydro-2H-[1,4']bipyridinyl-4-ylmethyl)-isophthalamide 0.05 g (0.12 mmol) of 5-[2-(2,4-Dichloro-phenyl)-ethoxy]-N,N-diethyl-isophthalamic acid was dissolved in 1 ml of DMF and treated with 0.140 g (1.22 mmol) of NEM and 0.04 g (0.12 mmol) of TOTU and 0.051 g (0.12 mmol) of C-(3,4,5,6-Tetrahydro-2H-[1,4']bipyridinyl-4-yl)-methylamine. The solution was stirred for 16 h at RT. The compound was purified by preparative RP-HPLC eluting with a gradient of 0 to 100% acetonitrile in water (+0.01% trifluoroacetic acid). After lyophilization the product was obtained as its trifluoroacetate salt.

| Yield 20 mg. | MS (ES$^+$): m/e = 583 (M$^+$). |

Example 233

3-[(2,4-Dichloro-benzylamino)-methyl]-N-(3,4,5,6-tetrahydro-2H-[1,4']bipyridinyl-4-ylmethyl)-benzamide

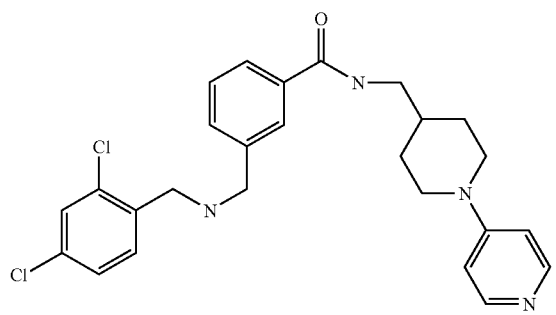

3-[(2,4-Dichloro-benzylamino)-methyl]-benzoic acid methyl ester g (5.68 mmol) of 2,4-dichlorobenzylamine was dissolved in 20 ml of dichloromethane and treated with 2.94 g (22.7 mmol) of diisopropylethylamine and 1.43 g (6.25 mmol) of 3-bromomethyl-benzoic acid methyl ester. The solution was stirred for 16 h at RT. The solvent was removed under reduced pressure. The residue was chromatographed on silica gel eluting with ethyl acetate/n-heptane (1/4).

| Yield 990 mg. | MS (ES$^+$): m/e = 324 (M$^+$). |

(ii) 3-{[tert-Butoxycarbonyl-(2,4-dichloro-benzyl)-amino]-methyl}-benzoic acid methyl ester 0.98 g (3.02 mmol) of 3-[(2,4-Dichloro-benzylamino)-methyl]-benzoic acid methyl ester was dissolved in 20 ml of dioxan and treated with 0.659 g (3.02 mmol) of di-tert-butyl pyrocarbonate. The solution was stirred for 16 h at RT. The solvent was removed under reduced pressure.

| Yield 1.35 g. | MS (ES$^+$): m/e = 368 (M-tBu$^+$). |

(iii) 3-{[tert-Butoxycarbonyl-(2,4-dichloro-benzyl)-amino]-methyl}-benzoic acid 0.85 g (2.00 mmol) of 3{[tert-Butoxycarbonyl-(2,4-dichloro-benzyl)-amino]-methyl}-benzoic acid methyl ester was dissolved in 20 ml of dioxan. 5 ml of water and 2N aqueous NaOH was added to the solution to give a pH of 13. The reaction solution was stirred for 5 h then poured into water. The resulting solution was cooled to 0° C. and concentrated hydrochloric acid was added to give a pH of 3. The product was extracted 3 times with ethyl acetate. The organic phase was dried over magnesium sulphate, filtered and the solvent was removed under reduced pressure.

| Yield 0.77 g. | MS (ES$^+$): m/e = 354 (M-tBu $^+$). |

(iv) (2,4-Dichloro-benzyl)-{3-[(3,4,5,6-tetrahydro-2H-[1,4']bipyridinyl-4-ylmethyl)-carbamoyl]-benzyl}carbamic acid tert-butyl ester 0.15 g (0.37 mmol) of 3{[tert-Butoxycarbonyl-(2,4-dichloro-benzyl)-amino]-methyl}benzoic acid was dissolved in 2 ml of DMF and treated with 0.42 g (3.7 mmol) of NEM and 0.12 g (0.37 mmol) of TOTU and 0.195 g (0.37 mmol) of C-(3,4,5,6-Tetrahydro-2H-[1,4']bipyridinyl-4-yl)-methylamine trifluoroacetate salt. The solution was stirred for 3 h at RT. The compound was purified by preparative RP-HPLC eluting with a gradient of 0 to 100% acetonitrile in water (+0.01% trifluoroacetic acid). After lyophilization the product was obtained as its trifluoroacetate salt.

| Yield 128 mg. | MS (ES$^+$): m/e = 583 (M$^+$). |

3-[(2,4-Dichloro-benzylamino)-methyl]-N-(3,4,5,6-tetrahydro-2H-[1,4']bipyridinyl-4-ylmethyl)-benzamide 60 mg (0.1 mmol) of (2,4-Dichloro-benzyl)-{3-[(3,4,5,6-tetrahydro-2H-[1,4']bipyridinyl)-4-ylmethyl)-carbamoyl]-benzyl}-carbamic acid tert-butyl ester was dissolved in dichloromethane/TFA (1/1) and stirred for 45 min at RT. The solvent was removed under reduced pressure and the residue was dissolve in acetonitrile/water. After lyophilization the product was obtained as its trifluoroacetate salt.

Yield 44 mg. MS (ES$^+$): m/e=483 (M$^+$).

Example 234

[4-(2-{2-Chloro-5-[(3,4,5,6-tetrahydro-2H-[1,4']bipyridinyl-4-ylmethyl)-carbamoyl]-phenoxy}-ethyl)-phenyl]-carbamic acid tert-butyl ester (S0103893)

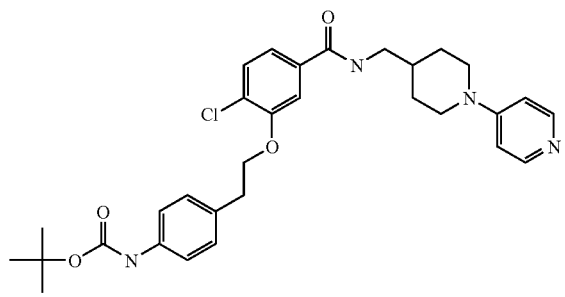

[4-(2-Hydroxy-ethyl)-phenyl]-carbamic acid tert-butyl ester 5 g (36.4 mmol) of 2-(4-Amino-phenyl)-ethanol was dissolved in 25 ml of dioxan and treated with 7.95 g (36.4 mmol) of di-tert-butyl pyrocarbonate. The solution was stirred for 16 h at RT. The solvent was removed under reduced pressure.

| Yield 8.5 g. | MS (ES$^+$): m/e = 238 (M + H$^+$). |
| --- | --- |

(ii) [4-(2-{2-Chloro-5-[(3,4,5,6-tetrahydro-2H-[1,4']bipyridinyl-4-ylmethyl)-carbamoyl]-phenoxy}-ethyl)-phenyl]-carbamic acid tert-butyl ester This compound was prepared analogously to Example 203.

| Yield 65 mg. | MS (ES$^+$): m/e = 565 (M$^+$). |
| --- | --- |

Example 235

[4-(2-{2-Fluoro-5-[(3,4,5,6-tetrahydro-2H-[1,4']bipyridinyl-4-ylmethyl)-carbamoyl]-phenoxy}-ethyl)-phenyl]-carbamic acid tert-butyl ester

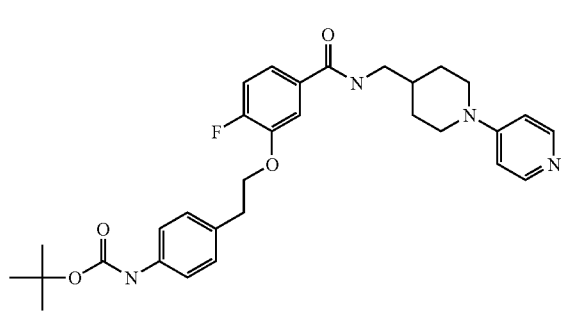

This compound was prepared analogously to Example 212.

| Yield 62 mg. | MS (ES$^+$): m/e = 548 (M$^+$). |
| --- | --- |

Example 236

3-[2-(4-Amino-phenyl)-ethoxy]-4-chloro-N-(3,4,5,6-tetrahydro-2H-[1,4']bipyridinyl-4-ylmethyl)-benzamide 62 mg (0.1 mmol) of [4-(2-{2-Chloro-5-[(3,4,5,6-tetrahydro-2H-[1,4']bipyridinyl-4-ylmethyl)-carbamoyl]-phenoxy}-ethyl)-phenyl]-carbamic acid tert-butyl ester was dissolved in dichloromethane/TFA (1/1) and stirred for 30 min at RT. The solvent was removed under reduced pressure and the residue was dissolve in acetonitrile/water. After lyophilization the product was obtained as its trifluoroacetate salt.

| Yield 36 mg. | MS (ES$^+$): m/e = 465 (M + H$^+$). |
| --- | --- |

Example 237

3-[2-(4-Amino-phenyl)-ethoxy]-4-fluoro-N-(3,4,5,6-tetrahydro-2H-[1,4']bipyridinyl-4-ylmethyl)-benzamide 59 mg (0.1 mmol) of [4-(2-{2-Fluoro-5-[(3,4,5,6-tetrahydro-2H-[1,4']bipyridinyl-4-ylmethyl)-carbamoyl]-phenoxy}-ethyl)-phenyl]-carbamic acid tert-butyl ester was dissolved in dichloromethane/TFA (1/1) and stirred for 30 min at RT. The solvent was removed under reduced pressure and the residue was dissolve in acetonitrile/water. After lyophilization the product was obtained as its trifluoroacetate salt.

Yield 44 mg.   MS (ES+): m/e = 449 (M + H+).

Example 238

3-[2-(2,4-Dichloro-phenyl)-ethoxy]-5-methoxy-4-methyl-N-(3,4,5,6-tetrahydro-2H-[1,4']bipyridinyl-4-ylmethyl)-benzamide

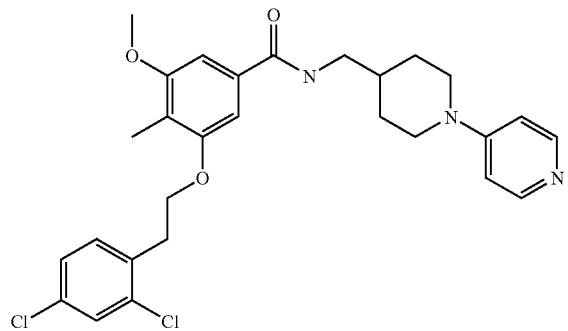

3,5-Dihydroxy-4-methyl-benzoic acid methyl ester
4.8 g (28.6 mmol) of 3,5-Dihydroxy-4-methyl-benzoic acid was suspended in 100 ml of saturated methanolic HCl and stirred at room temperature for 16 h. The solvent was removed under reduced pressure, and the residue was dried under reduced pressure.

Yield 5.1 g.   MS (ES−): m/e = 181 (M)−.

(ii) 3-Hydroxy-5-methoxy-4-methyl-benzoic acid methyl ester 5.1 g (28.2 mmol) of 3,5-Dihydroxy-4-methyl-benzoic acid methyl ester was dissolved in 100 ml of DMF and treated at 0° C. with 7.8 g (56.4 mmol) of potassium carbonate and 4.0 g (28.2 mmol) of methyl iodide. The solution was stirred for 16 h at RT. The solvent was removed under reduced pressure, the residue was taken-up in ethyl acetate and the solution was washed three times with water and twice with saturated aqueous sodium chloride. The organic phase was dried with magnesium sulphate, filtered and the solvent was removed under reduced pressure. The compound was purified by preparative RP-HPLC eluting with a gradient of 0 to 100% acetonitrile in water (+0.01% trifluoroacetic acid).

Yield 0.3 g.   MS (ES−): m/e = 194 (M−).

(iii) 3-[2-(2,4-Dichloro-phenyl)-ethoxy]-5-methoxy-4-methyl-N-(3,4,5,6-tetrahydro-2H-[1,4']bipyridinyl-4-ylmethyl)-benzamide This compound was prepared analogously to Example 199.

Yield 39 mg.   MS (ES+): m/e = 528 (M+).

| Example | Structure | MS (ES+) |
|---------|-----------|----------|
| 239 | 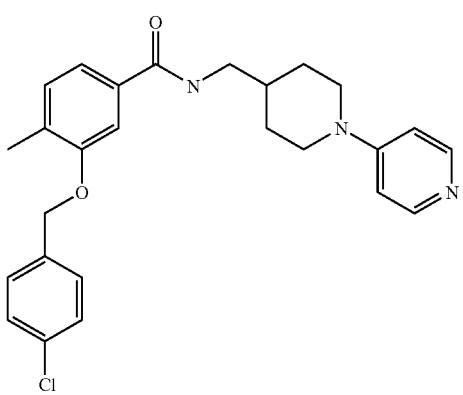 | 450 |

-continued

| Example | Structure | MS (ES+) |
|---|---|---|
| 240 | 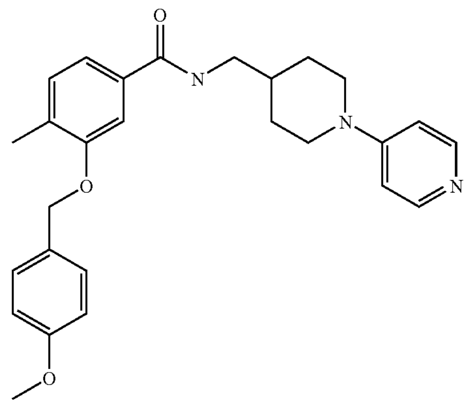 | 446 |
| 241 | 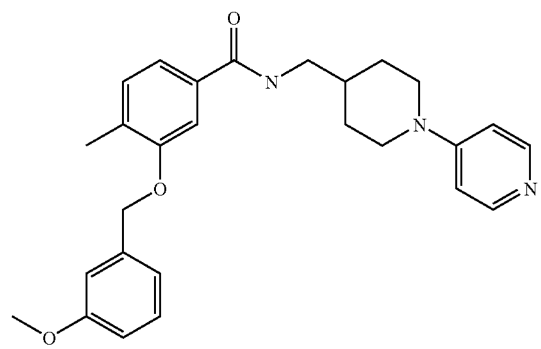 | 446 |
| 242 | 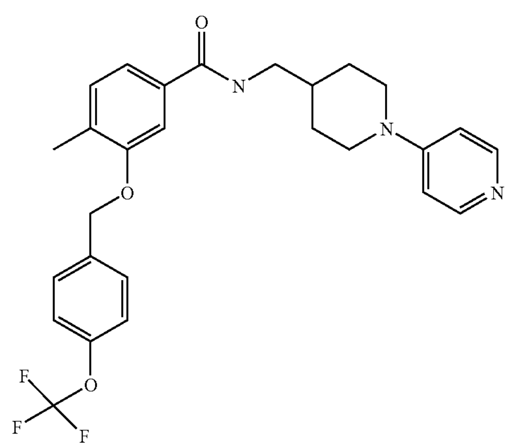 | 500 |
| 243 | 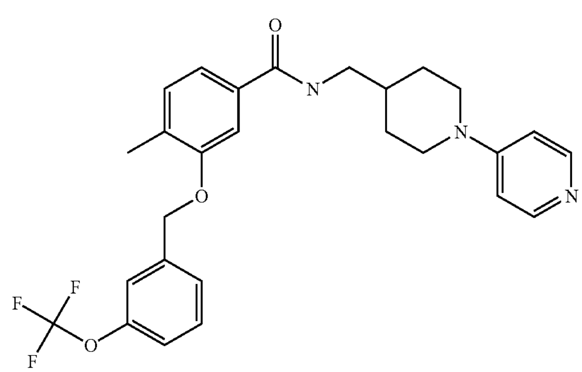 | 500 |

Example 244

3-[2-(4-Cyano-phenyl)-ethoxy]-4-methoxy-N-(3,4,5,
6-tetrahydro-2H-[1,4']bipyridinyl-4-ylmethyl)-benzamide

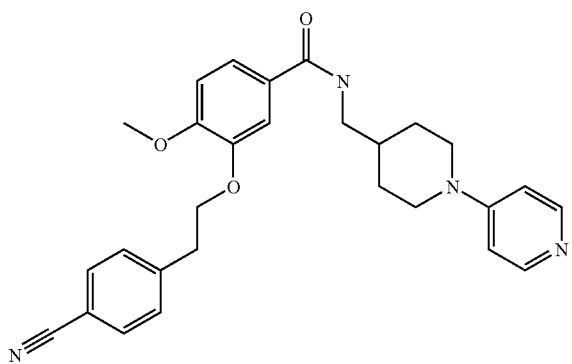

This compound was prepared analogously to Example 139.

| Yield 12 mg. | MS (ES⁺): m/e = 471. |
|---|---|

Pharmacological Testing

The ability of the compounds of the formula I to inhibit factor Xa or factor VIIa or other enzymes like thrombin, plasmin, or trypsin can be assessed by determining the concentration of the compound of the formula I that inhibits enzyme activity by 50%, i.e. the $IC_{50}$ value, which is related to the inhibition constant Ki. Purified enzymes are used in chromogenic assays. The concentration of inhibitor that causes a 50% decrease in the rate of substrate hydrolysis is determined by linear regression after plotting the relative rates of hydrolysis (compared to the uninhibited control) versus the log of the concentration of the compound of formula I. For calculating the inhibition constant Ki, the $IC_{50}$ value is corrected for competition with substrate using the formula $Ki = IC_{50}/\{1+(\text{substrate concentration}/Km)\}$ wherein Km is the Michaelis-Menten constant (Chen and Prusoff, Biochem. Pharmacol. 22 (1973), 3099–3108; I. H. Segal, Enzyme Kinetics, 1975, John Wiley & Sons, New York, 100–125; which are incorporated herein by reference).

Factor Xa Assay

In the assay for determining the inhibition of factor Xa activity TBS-PEG buffer (50 mM Tris-HCl, pH 7.8, 200 mM NaCl, 0.05% (w/v) PEG-8000, 0.02% (w/v) NaN₃) was used. The $IC_{50}$ was determined by combining in appropriate wells of a Costar half-area microtiter plate 25 µl human factor Xa (Enzyme Research Laboratories, Inc.; South Bend, Ind.) in TBS-PEG; 40 µl 10% (v/v) DMSO in TBS-PEG (uninhibited control) or various concentrations of the compound to be tested diluted in 10% (v/v) DMSO in TBS-PEG; and substrate S-2765 (N(α)-benzyloxycarbonyl-D-Arg-Gly-L-Arg-p-nitroanilide; Kabi Pharmacia, Inc.; Franklin, Ohio) in TBS-PEG.

The assay was performed by pre-incubating the compound of formula I plus enzyme for 10 min. Then the assay was initiated by adding substrate to obtain a final volume of 100 µl. The initial velocity of chromogenic substrate hydrolysis was measured by the change in absorbance at 405 nm using a Bio-tek Instruments kinetic plate reader (Ceres UV900HDi) at 25° C. during the linear portion of the time course (usually 1.5 min after addition of substrate). The enzyme concentration was 0.5 nM and substrate concentration was 140 µM.

b) Factor VIIa Assay

The inhibitory activity towards factor VIIa/tissue factor activity was determined using a chromogenic assay essentially as described previously (J. A. Ostrem et al., Biochemistry 37 (1998) 1053–1059, which is incorporated herein by reference). Kinetic assays were conducted at 25° C. in half-area microtiter plates (Costar Corp., Cambridge, Mass.) using a kinetic plate reader (Molecular Devices Spectramax 250). A typical assay consisted of 25 µl human factor VIIa and TF (5 nM and 10 nM, respective final concentration) combined with 40 µl of inhibitor dilutions in 10% DMSO/TBS-PEG buffer (50 mM Tris, 15 mM NaCl, 5 mM CaCl₂, 0.05% PEG 8000, pH 8.15). Following a 15 minute preincubation period, the assay was initiated by the addition of 35 µl of the chromogenic substrate S-2288 (D-Ile-Pro-Arg-p-nitroanilide, Pharmacia Hepar Inc., 500 µM final concentration). The results (inhibition constants Ki (FXa) for inhibition of factor Xa) are shown in Table 1.

TABLE 1

| Example | Ki(FXa) [µM] |
|---|---|
| 1 | 0.600 |
| 2 | 1.540 |
| 3 | 5.410 |
| 4 | 0.298 |
| 5 | 0.167 |
| 6 | 0.050 |
| 7 | 2.820 |
| 8 | 0.106 |
| 9 | 0.306 |
| 10 | 0.061 |
| 11 | 1.378 |
| 12 | 3.005 |
| 13 | 1.412 |
| 14 | 2.184 |
| 15 | 2.221 |
| 16 | 4.219 |
| 17 | 0.407 |
| 18 | 6.200 |
| 19 | 0.095 |
| 20 | 0.020 |
| 24 | 1.128 |
| 28 | 0.960 |
| 31 | 9.340 |
| 32 | 0.970 |
| 54 | 6.515 |
| 55 | 0.650 |
| 56 | 4.327 |
| 57 | 6.217 |
| 60 | 1.051 |
| 61 | 0.057 |
| 66 | 1.484 |
| 67 | 0.018 |
| 68 | 3.040 |
| 77 | 0.076 |
| 78 | 0.037 |
| 79 | 0.029 |
| 80 | 0.050 |
| 81 | 0.241 |
| 83 | 0.125 |
| 84 | 4.883 |
| 85 | 0.304 |
| 86 | 0.026 |
| 87 | 0.070 |
| 88 | 0.140 |

TABLE 1-continued

| Example | Ki(FXa) [µM] |
|---|---|
| 89 | 0.044 |
| 91 | 1.393 |
| 92 | 0.028 |
| 93 | 0.188 |
| 94 | 0.760 |
| 95 | 29.734 |
| 97 | 3.497 |
| 99 | 3.709 |
| 100 | 0.298 |
| 101 | 0.057 |
| 102 | 0.636 |
| 117 | 0.588 |
| 118 | 0.316 |
| 119 | 1763 |
| 120 | 0.048 |
| 121 | 0.075 |
| 128 | 40.95 |
| 129 | 25.18 |
| 132 | 0.054 |
| 133 | 0.020 |
| 134 | 0.037 |
| 140 | 69.50 |
| 143 | 38.79 |
| 144 | 0.041 |
| 145 | 0.591 |
| 165 | 0.950 |
| 166 | 0.110 |
| 167 | 0.277 |
| 168 | 0.024 |
| 169 | 0.277 |
| 170 | 1.796 |
| 171 | 0.130 |
| 172 | 6.450 |
| 176 | 0.365 |
| 177 | 0.226 |
| 178 | 0.263 |
| 179 | 0.086 |
| 180 | 0.255 |
| 181 | 0.041 |
| 182 | 0.312 |
| 183 | 0.233 |
| 184 | 0.617 |
| 185 | 0.039 |
| 186 | 0.401 |
| 187 | 0.964 |
| 195 | 6.737 |
| 196 | 4.265 |
| 197 | 6.028 |
| 198 | 5.004 |
| 199 | 0.01 |
| 200 | 0.108 |
| 201 | 0.314 |
| 202 | 0.025 |
| 203 | 0.013 |
| 204 | 0.036 |
| 205 | 0.102 |
| 206 | 0.124 |
| 207 | 0.068 |
| 208 | 1.552 |
| 209 | 1.931 |
| 210 | 2.494 |
| 212 | 0.040 |
| 213 | 0.071 |
| 214 | 0.203 |
| 215 | 0.059 |
| 216 | 4.605 |
| 217 | 0.206 |
| 218 | 0.712 |
| 219 | 3.348 |
| 221 | 0.307 |
| 222 | 0.072 |
| 223 | 0.044 |
| 224 | 0.020 |
| 225 | 0.065 |
| 226 | 0.082 |
| 227 | 0.058 |
| 228 | 0.220 |
| 229 | 0.285 |
| 230 | 0.649 |
| 231 | 0.227 |
| 232 | 0.192 |
| 233 | 0.275 |
| 234 | 4.531 |
| 236 | 0.420 |
| 237 | 1.554 |
| 238 | 0.013 |
| 239 | 3.839 |
| 240 | 1.345 |
| 241 | 2.168 |
| 242 | 2.939 |

We claim:

1. A compound of formula I, $$R^0\text{-Q-X-Q'-W-U-V-G-M} \quad (I)$$

wherein:
$R^0$ phenyl, wherein phenyl is unsubstituted or mono- or disubstituted independently of one another by $R^2$, or pyridyl, wherein pyridyl is unsubstituted or mono-, disubstituted independently of one another by $R^2$;

Q is a direct bond;

X is ethylenyl;

Q' is —O—;

W is phenyl or pyridyl, wherein W is unsubstituted or mono-, di- or trisubstituted independently of one another by $R^1$;

U is —$(CH_2)_m$—C(O)—$NR^{10}$—$(CH_2)_n$, wherein n is zero, 1 or 2, m is zero or 1, provided that Q' and U are in a 1,3-substitution relationship with respect to each other and the 2-position is unsubstituted;

V is tetrahydropyridine, pyridine, or phenyl wherein said groups are unsubstituted or mono-, di- or trisubstituted independently of one another by $R^{14}$;

G is a direct bond, —$(CH_2)_m$, —$(CH_2)_m$—C(O)—$NR^{10}$—$(CH_2)_n$, —$(CH_2)_m$—C(O)—$(CH_2)_n$, —$(CH_2)_m$—$NR^{10}$—C(O,—$NR^{10}$—$(CH_2)_n$, —$(CH_2)_m$—$NR^{10}$—C(O)—$(CH_2)_n$, —$(CH_2)_m$—$SO_2$—$NR^{10}$—$(CH_2)_n$ or —$(CH_2)_m$—$NR^{10}$—$SO_2$—$(CH_2)_n$, M is a pyrimidinyl group that is unsubstituted or substituted by $R^{14}$, wherein $R^1$, $R^2$, and $R^3$ independent from each other are hydrogen, F, Cl, —O—$CH_3$, —$CH_3$, —C(O)—$N(CH_2$—$CH_3)_2$, —C(O)—$NH_2$, or —C(O)—NH—$CH_2$-piperidine-pyridine;

$R^4$ and $R^5$ are independently of one another identical or different and are hydrogen atom, —$(C_1$–$C_6)$-alkyl, wherein alkyl is unsubstituted or mono-, di- or trisubstituted independently of one another by $R^{13}$, —$(C_6$–$C_{14})$-phenyl-$(C_1$–$C_4)$-alkyl-, wherein alkyl and phenyl independently from one another are unsubstituted or mono-, di- or trisubstituted by $R^{13}$, —$(C_6$–$C_{14})$-phenyl-, wherein phenyl is unsubstituted or mono-, di- or trisubstituted independently of one another by $R^{13}$;

$R^{10}$ hydrogen atom or —$(C_1$–$C_4)$-alkyl;

$R^{13}$ is halogen, —$NO_2$, —CN, —OH, —$(C_1$–$C_8)$-alkyl, —$(C_1$–$C_8)$-alkyloxy, —$CF_3$, —C(O)—$NH_2$, —$NH_2$ or the residue V-G-M, wherein V, G and M are as defined above;

$R^{14}$ is halogen, —OH, —$NR^4R^5$, =O, —($C_1$–$C_4$)-alkyl, —($C_1$–$C_4$)-alkoxyl, —C(O)—OH, —CN, —C(O)—O—($C_1$–$C_4$)-alkyl, —C(O)—$NR^4R^5$, —($C_1$–$C_8$)-alkylsulfonyl, —C(O)—$NH_2$, —$SO_2$—$NR^4R^5$, —C(O)—NH—($C_1$–$C_8$)-alkyl, —C(O)—NH—[($C_1$–$C_8$)-alkyl]$_2$, wherein $R^4$ or $R^5$ are as defined above; and wherein n, m, and $R^{10}$ are as defined above, in all its stereoisomeric forms and mixtures thereof in any ratio, and its physiologically tolerable salts.

2. A compound according to claim 1 comprising the chemical structure

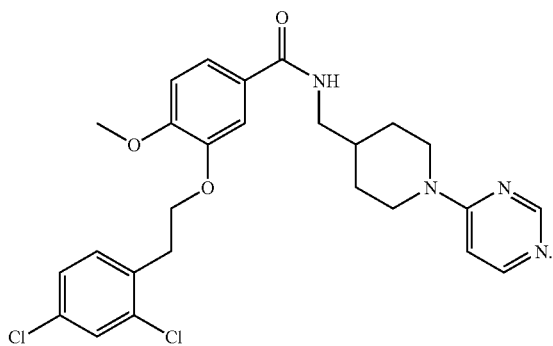

3. A compound according to claim 1 comprising the chemical structure

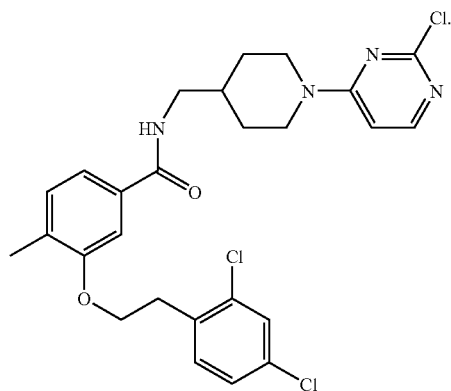

4. A process for the preparation of a compound of claim 1, wherein W is phenyl comprising:

a) linking a compound of the formula XI,

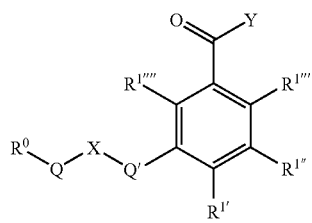

wherein $R^0$, Q, Q' and X are as defined in claim 1, are precursor groups thereof, or are protected by protective groups $R^{1'}$, $R^{1''}$, $R^{1'''}$ and $R^{1''''}$, which protective groups are independently from each other a hydrogen atom; $R^1$, which is as defined in claim 1; a precursor group; or protective group; and Y is a nucleophilically substitutable leaving group or a hydroxyl group, with a compound of the formula XII

H—$NR^{10}$-V-G-M (XII)

wherein $R^{10}$ is a hydrogen atom or —($C_1$–$C_4$)-alkyl, and V, G and M are as defined in claim 1, or are precursor groups thereof; and b) reacting the compound of formula XII with a compound of the formula XIII

$R^0$-Q-X-Q'-W-C(O)-Y (XIII)

wherein $R^0$, Q, Q', X, W and Y are as defined in claim 1, or are precursor groups thereof, and Y is a nucleophilic group or a hydroxyl group.

5. The process of claim 4, wherein $R^{10}$, V, G and M, or the precursor groups thereof, are protected by protective groups.

6. The process of claim 4, wherein $R^0$, Q, Q', X, W and Y, or the precursor groups thereof, are protected by protective groups.

7. The process of claim 4, wherein Y is attached to a polystyrene resin.

8. A pharmaceutical preparation, comprising at least one compound of claim 1.

9. A pharmaceutical preparation, comprising at least one physiologically tolerable salt of a compound of claim 1.

10. A pharmaceutical preparation comprising at least one compound of claim 1, and a pharmaceutically acceptable carrier.

11. A method of modulating blood coagulation of fibrinolysis comprising administering one or more of the compounds of claim 1 in a pharmaceutical preparation to a subject to inhibit factor Xa, factor VIIa, or a combination thereof.

12. The method of claim 11, wherein the compound is administered to treat or prevent blood coagulation, due to inflammatory response, fibrinolysis, cardiovascular disorders, thromboembolic diseases, restenoses, abnormal thrombus formation, acute myocardial infarction, unstable angina, acute vessel closure associated with thrombolytic therapy, thromboembolism, percutaneous, transluminal coronary angioplasty pathologic thrombus formation occurring in the veins of the lower extremities following abdominal, knee and hip surgery, transluminal coronary angioplasty, transient ischemic attacks, stroke, disseminated systemic intravascular coagulatopathy occurring in vascular systems during septic shock, pulmonary thromboembolism, viral infections or cancer, intravascular coagulatopathy occurring in vascular systems during septic shock, coronary heart disease, myocardial infarction, angina pectoris, vascular restenosis, adult respiratory distress syndrome, multi-organ failure, stroke and disseminated intravascular clotting disorder, or thromboses.

13. The method of claim 12, wherein the compound is used to treat restenosis following angioplasty-like PTCA.

14. The method of claim 12, wherein the compound is used to treat deep vein and proximal vein thrombosis occurring following surgery.

15. A pharmaceutical preparation, comprising at least one compound of claim 2.

16. A pharmaceutical preparation, comprising at least one compound of claim 3.

* * * * *